US009388222B2

(12) United States Patent
Pastan et al.

(10) Patent No.: US 9,388,222 B2
(45) Date of Patent: Jul. 12, 2016

(54) MODIFIED *PSEUDOMONAS* EXOTOXIN A

(71) Applicants: The United States of America, as repres

(56) References Cited

U.S. PATENT DOCUMENTS

| | | | |
|---|---|---|---|
| 7,355,012 | B2 | 4/2008 | Pastan et al. |
| 7,368,110 | B2 | 5/2008 | Pastan et al. |
| 7,470,775 | B2 | 12/2008 | Pastan et al. |
| 7,521,054 | B2 | 4/2009 | Pastan et al. |
| 7,541,034 | B1 | 6/2009 | Fitzgerald et al. |
| 2002/0197266 | A1 | 12/2002 | Debinski |
| 2004/0132028 | A1 | 7/2004 | Tumpp et al. |
| 2007/0189962 | A1 | 8/2007 | Pastan et al. |
| 2007/0224633 | A1 | 9/2007 | Skerra et al. |
| 2008/0139791 | A1 | 6/2008 | Lipovsek et al. |

FOREIGN PATENT DOCUMENTS

| | | |
|---|---|---|
| EP | 0 239 400 B1 | 8/1994 |
| EP | 0 972 838 A1 | 1/2000 |
| EP | 1 641 818 A1 | 4/2006 |
| GB | 2 188 638 A | 10/1987 |
| WO | WO 87/02671 A1 | 5/1987 |
| WO | WO 93/11161 A1 | 6/1993 |
| WO | WO 98/45322 A2 | 10/1998 |
| WO | WO 99/51643 A1 | 10/1999 |
| WO | WO 03/027135 A2 | 4/2003 |
| WO | WO 2005/052006 A2 | 6/2005 |
| WO | WO 2005/056764 A2 | 6/2005 |
| WO | WO 2007/014743 A2 | 2/2007 |
| WO | WO 2007/016150 A2 | 2/2007 |
| WO | WO 2007/031741 A1 | 3/2007 |
| WO | WO 2008/098796 A1 | 8/2008 |
| WO | WO 2009/032954 A1 | 3/2009 |
| WO | WO 2011/032022 A1 | 3/2011 |
| WO | WO 2012/154530 A1 | 11/2012 |
| WO | WO 2012/170617 A1 | 12/2012 |
| WO | WO 2013/040141 A1 | 3/2013 |

OTHER PUBLICATIONS

Beck et al., "Nucleotide sequence and genome organisation of filamentous bacteriophages fl and fd," *Gene*, 16(1-3), 35-58 (1981).
Bian et al., "Discovery of promiscuous HLA-II-restricted T cell epitopes with tepitope," *Methods*, 34(4), 468-75 (2004).
Binz et al., "Designing repeat proteins: well-expressed, soluble and stable proteins from combinatorial libraries of consensus ankyrin repeat proteins," *J. Mol. Biol.*, 332(2), 489-503 (2003).
Borghouts et al., "Peptide aptamers: recent developments for cancer therapy," *Expert Opin. Biol. Ther.*, 5(6), 783-97 (2005).
Braddock, M., "11th annual Inflammatory and Immune Diseases Drug Discovery and Development Summit Mar. 12-13, 2007, San Francisco, USA," *Expert Opin. Investig. Drugs*, 16(6), 909-17 (2007).
Bujard et al., "A T5 promoter-based transcription-translation system for the analysis of proteins in vitro and in vivo," Methods Enzymol., 155, 416-33 (1987).
Chowdhury et al., "Improving antibody affinity by mimicking somatic hypermutation in vitro," *Nat. Biotechnol.*, 17(6), 568-572 (1999).
Davies et al., "Antibody VH Domains as Small Recognition Units," *Biotechnology*, 13, 475-9 (1995).
Duckert et al., "Prediction of proprotein convertase cleavage sites," *Protein Eng. Des. Sel.*, 17(1), 107-12 (2004).
Farabaugh, P. J., "Sequence of the lacI gene," *Nature*, 274(5673), 765-69 (1978).
Frankel et al., "Targeted toxins," *Clin. Cancer Res.*, 6(2), 326-34 (2000).
Gebauer et al., "Engineered protein scaffolds as next-generation antibody therapeutics," *Curr. Opin. Chem. Biol.*, 13, 245-55 (2009).
Ghahroudi et al., "Selection and identification of single domain antibody fragments from camel heavy-chain antibodies," *FEBS Lett.*, 414, 521-526 (1997).
Harmsen et al., "Properties, production, and applications of camelid single-domain antibody fragments," *Appl. Microbiol. Biotechnol.*, 77(1), 13-22 (2007).

Haskard et al., "The production of human monoclonal autoantibodies from patients with rheumatoid arthritis by the ebv-hybridoma technique," *J. Immunol. Methods*, 74, 361-7 (1984).
Holliger et al., "Diabodies: small bivalent and bispecific antibody fragments" *PNAS*, 90, 6444-6448 (1993).
Holt et al., "Domain antibodies: proteins for therapy," *Trends Biotechnol.*, 21(11), 484-90 (2003).
Hosse et al., "A new generation of protein display scaffolds for molecular recognition," *Protein Science*, 15(1), 14-27 (2006).
Huse et al., "Generation of a large combinatorial library of the immunoglobulin repertoire in phage lambda," *Science*, 246, 1275-81 (1989).
Hwang et al., "Functional domains of Pseudomonas exotoxin identified by deletion analysis of the gene expressed in *E.coli*," *Cell*, 48(1), 129-36 (1987).
Irving et al., "Ribosome display and affinity maturation: from antibodies to single V-domains and steps towards cancer therapeutics," *J. Immunol. Methods*, 248, 31-45 (2001).
Jones et al., "Replacing the complementarity-determining regions in a human antibody with those from a mouse," *Nature*, 321, 522-525 (1986).
Kohl et al., "Designed to be stable: crystal structure of a consensus ankyrin repeat protein," *PNAS*, 100(4), 1700-5 (2003).
Köhler et al., "Derivation of specific antibody-producing tissue culture and tumor lines by cell fusion," *Eur. J. Immunol.*, 6(7), 511-19 (1976).
Kondo et al., "Activity of immunotoxins constructed with modified pseudomonas exotoxin a lacking the cell recognition domain," *Biol. Chem.*, 263, 9470-9475 (1988).
Kreitman, R. J., "Immunotoxins for targeted cancer therapy," *AAPS J.*, 8(3), E532-51 (2006).
Kreitman et al., "Antibody fusion proteins: anti-CD22 recombinant immunotoxin moxetumomab pasudotox," *Clin. Cancer Res.*, 17(20), 6398-6405 (2011).
Lauwereys et al., "Potent enzyme inhibitors derived from dromedary heavy-chain antibodies," *EMBO J.*, 17(13), 3512-20 (1998).
Leaver-Fay et al., "An object-oriented software suite for the stimulation and design of macromolecules," *Methods in Enzymology*, 487, 545-74 (2011).
Lee et al., "The interpretation of protein structures: estimation of static accessibility," *J. Mol. Biol.*, 55(3), 379-400 (1971).
Liu et al., "A recombinant immunotoxin engineered for increased stability by adding a disulfide bond has decreased immunogenicity," *Protein Eng. Des. Sel.*, 25(1), 1-6 (2012).
Liu et al., "Recombinant immunotoxin engineered for low immunogenicity and antigenicity by identifying and silencing human B-cell epitopes," *PNAS*, 109(29), 11782-7 (2012).
Meissner et al., "Transient gene expression: recombinant protein production with suspension-adapted HEK293-EBNA cells," *Biotechnol. Bioeng.*, 75(2), 197-203 (2001).
Mufson, R. A., "Tumor antigen targets and tumor immunotherapy," *Front Biosci.*, 11, 337-43 (2006).
Pace et al., "How to measure and predict the molar absorption coefficient of a protein," *Protein Sci.*, 4, 2411-23 (1995).
Pai et al., "Anti-tumor activities of immunotoxins made of monoclonal antibody B3 and various forms of pseudomas exotoxin," *PNAS*, 88, 3358-3362 (1991).
Parker et al., "Antibody mimics based on human fibronectin type three domain engineered for thermostability and high-affinity binding to vascular endothelial growth factor receptor two," *Protein Eng. Dec. Sel.*, 18(9), 435-44 (2005).
Pastan et al., "Targeted therapy of cancer with recombinant immunotoxins," *Biochem. Biophys. Acta.*, 1333, C1-C6 (1997).
Pedersen et al., "Comparison of surface accessible residues in human and murine immunoglobulin fv domains," *J. Mol. Biol.*, 235, 959-73 (1994).
Reiter et al., "An antibody single-domain phage display library of a native heavy chain variable region: isolation of functional single-domain VH molecules with a unique interface," *J. Mol. Biol.*, 290, 685-698 (1999).
Riechmann et al., "Reshaping human antibodies for therapy," *Nature*, 332, 323-7 (1988).

(56) References Cited

OTHER PUBLICATIONS

Roder et al., "The EBV-hybridoma technique," *Methods Enzymol.*, 121, 140-167 (1986).
Roscoe et al., "Primate antibody response to immunotoxin: serological and computer-aided analysis of epitopes on a truncated form of pseudomonas exotoxin," *Infect. Immunity*, 62, 5055-65 (1994).
Rose et al., "Structure and function of the yeast URA3 gene: expression in *Escherichia coli*," *Gene*, 29, 113-24 (1984).
Saerens et al., "Single-domain antibodies as building blocks for novel therapeutics," *Curr. Opin. Pharmacol.*, 8(5), 600-8 (2008).
Siegall et al., "Functional analysis of domains II, Ib, and III of Pseudomonas exotoxin," *J. Biol. Chem*, 264(24), 14256-61 (1989).
Silverman et al., "Multivalent avimer proteins evolved by exon shuffling of a family of human receptor domains," *Nat. Biotechnol.*, 23(12), 1556-61 (2005).
Skerra "Lipocalins as a scaffold," *Biochim. Biophys. Acta.*, 1482(1-2), 337-50 (2000).
Stumpp et al., "DARPins: a new generation of protein therapeutics," *Drug Discovery Today*, 13, 695-701 (2008).
Stüber et al., "System for high-level production in *Escherichia coli* and rapid purification of recombinant proteins: Application to epitope mapping, preparation of antibodies, and structure-function analysis," *Immunol. Methods IV*, 121-52 (1990).
Sutcliffe, J. "Complete nucleotide sequence of the *Escherichia coli* plasmid pBR322," *Quant. Biol.*, 43, 77-90 (1979).
Schwarz et al., "Nucleotide sequence of cro, cII and part of the O gene in phage lambda DNA," *Nature*, 272, 410-14 (1978).
Verhoeyen et al., "Reshaping human antibodies: grafting an antilysozyme activity," *Science*, 239, 1534-6 (1988).
Wadhwa et al., "Receptor mediated glycotargeting," *J. Drug Targeting*, 3, 111-27 (1995).
Wang et al., "A systematic assessment of MHC class II peptide binding predictions and evaluation of a consensus approach," *PLoS Comput. Biol.*, 4(4), e1000048 (2008).
Weldon et al., "A protease-resistant immunotoxin against CD22 with greatly increased activity against CLL and diminished animal toxicity," *Blood*, 113, 3792-3800 (2009).
Weldon et al., "A recombinant immunotoxin against the tumor-associated antigen mesothelin reengineered for high activity, low off-target toxicity, and reduced antigenicity," *Mol. Cancer Ther.*, 12, 48-57 (2013).
Wesolowski et al, "Single domain antibodies: promising experimental and therapeutic tools in infection and immunity," *Med. Microbiol. Immunol.*, 198(3), 157-74 (2009).

Wikman et al., "Selection and characterization of HER2/neu-binding affibody ligands," *Protein Eng. Des. Sel.*, 17, 455-62 (2004).
Winter et al., "Man-made antibodies," *Nature*, 349, 293-9 (1991).
Zahnd et al., "A designed ankyrin repeat protein evolved to picomolar affinity to Her2," *J. Mol. Biol.*, 369(4), 1015-29 (2007).
Bera et al., "An improved recombinant Fab-immunotoxin targeting CD22 expressing malignancies," *Leuk. Res.*, 38 (10), 1224-1229 (2014).
GENESEQ Database Accession No. AES70126, date Apr. 5, 2007.
GENESEQ Database Accession No. AES70132, date Apr. 5, 2007.
GENESEQ Database Accession No. AES70135, date Apr. 5, 2007.
GENESEQ Database Accession No. AES70142, date Apr. 5, 2007.
GENESEQ Database Accession No. BAG38720 date Jan. 3, 2013.
GENESEQ Database Accession No. BAI47300, date Jan. 31, 2013.
GENESEQ Database Accession No. BAI47306, date Jan. 31, 2013.
GENESEQ Database Accession No. BAI47368, date Jan. 31, 2013.
GENESEQ Database Accession No. BAI47371, date Jan. 31, 2013.
Hansen et al., "A recombinant immunotoxin targeting CD22 with low immunogenicity, low nonspecific toxicity, and high antitumor activity in mice," *J. Immunother.*, 33 (3), 297-304 (2010).
International Search Report, Application No. PCT/US2014/058941, date mailed Jun. 26, 2015.
Liu et al., "Recombinant immunotoxin engineered for low immunogenicity and antigenicity by identifying and silencing human B-cell epitopes," *Proc. Natl. Acad. Sci.*, 109 (29), 11782-11787 (2012).
Mazor et al., "Recombinant immunotoxin for cancer treatment with low immunogenicity by identification and silencing of human T-cell epitopes," *Proc. Natl. Acad. Sci.*, 111 (23), 8571-8576 (2014).
Nagata et al., "Removal of B cell epitopes as a practical approach for reducing the immunogenicity of foreign protein-based therapeutics," *Adv. Drug Deliv. Rev.*, 61 (11), 977-985 (2009).
Onda et al., "An immunotoxin with greatly reduced immunogenicity by identification and removal of B cell epitopes," *Proc. Natl. Acad. Sci.*, 105 (32), 11311-11316 (2008).
Onda et al., "Characterization of the B cell epitopes associated with a truncated form of Pseudomonas exotoxin (PE38) used to make immunotoxins for the treatment of cancer patients," *J. Immunol.*, 177 (2), 8822-8834 (2006).
Onda et al., "Recombinant immunotoxin against B-cell malignancies with no immunogenicity in mice by removal of B-cell epitopes," *Proc. Natl. Acad. Sci.*, 108 (14), 5742-5747 (2011).
Partial International Search Report, Application No. PCT/US2014/058941, date mailed Feb. 9, 2015.
Weldon et al., "A guide to taming a toxin—recombinant immunotoxins constructed from Pseudomonas exotoxin A for the treatment of cancer," *FEBS J.*, 278 (23), 4683-4700 (2011).
Written Opinion of the International Searching Authority, Application No. PCT/US2014,058941, dated Jun. 26, 2015.

MODIFIED PSEUDOMONAS EXOTOXIN A

CROSS-REFERENCE TO RELATED APPLICATIONS

This patent application claims the benefit of U.S. Provisional Patent Application Nos. 61/887,418, filed Oct. 6, 2013; 61/908,464, filed Nov. 25, 2013; 61/982,051, filed Apr. 21, 2014; and 62/052,665, filed Sep. 19, 2014, each of which is incorporated herein by reference in its entirety.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: one 144,473 Byte ASCII (Text) file named "718352_ST25.txt," dated Oct. 1, 2014.

BACKGROUND OF THE INVENTION

Pseudomonas exotoxin A (PE) is a bacterial toxin with cytotoxic activity that may be effective for destroying or inhibiting the growth of undesirable cells, e.g., cancer cells. Accordingly, PE may be useful for treating or preventing diseases such as, e.g., cancer. However, PE may be highly immunogenic. Accordingly, PE administration may stimulate an anti-PE immune response including, for example, the production of anti-PE antibodies and/or T-cells, that undesirably neutralizes the cytotoxic activity of PE. Such immunogenicity may reduce the amount of PE that can be given to the patient which may, in turn, reduce the effectiveness of the PE for treating the disease, e.g., cancer. Thus, there is a need for improved PE.

Several deimmunized Pseudomonas exotoxins (PE) are known in art. The domain II deleted versions (for example, PE24) may be less immunogenic and may cause fewer side effects (such as, for example, capillary leak syndrome and hepatotoxicity) as compared to PE38, which contains domain II. Without being bound to a particular theory, it is believed that the reduced immunogenicity and fewer side effects of PE24 could, at least in part, be due to the reduced size of PE24, which disadvantageously results in a shorter serum half life. Different furin cleavable linkers may be employed in PE24 variants. PE immunoconjugates have mostly used dsFv fragments as targeting moieties. Such deimmunized Pseudomonas exotoxins (PE) are described in, for example, International Patent Application Publications WO2005052006, WO2007016150, WO2007014743, WO2007031741, WO200932954, WO201132022, WO2012/154530, and WO 2012/170617.

Previous immunotoxins have many disadvantages. For example, deimmunization of previous immunotoxins has been incomplete with respect to the human B-cell epitopes because immunogenic reactions still occurred. In addition, the deimmunization of previous immunotoxins was accompanied by a reduced cytotoxic potency. For example, a LO10 deimmunized PE variant described in WO 2012/170617 provided a loss of potency of at least 40% compared to wild type (WT) PE and other PE variants. In International Patent Application Publication WO2013/040141, Pseudomonas exotoxins with less immunogenic B-cell epitopes have been described. In the PE variant LRO10, all B-cell epitopes were removed. This, however, also led to a reduction of cytotoxicity towards tumor cells.

In addition, fusion of a dsFv with domain II deleted versions of PE (PE24) have a shorter serum half life due to their reduced overall size as compared to dsFv fusions with PE38. The linkers of previous immunoxins also contained T-cell epitopes and poor developability such as, for example, a poor stability at 37° C. In addition, previous anti-mesothelin (MSLN) immunotoxins have only used mouse-derived dsFv fragments fused to PE, which may further contribute to immunogenicity. International Patent Application Publication WO 2012/154530 refers to Pseudomonas exotoxin variant chimeric molecules with short flexible linkers which improve the cytotoxicity towards tumor cells.

BRIEF SUMMARY OF THE INVENTION

The invention relates to deimmunized Pseudomonas exotoxins and Fab fusions thereof (e.g., humanized anti-MSLN), methods for the treatment of cancer, stabilized pharmaceutical formulations, methods for the reduction of side effects and methods for enhancing the serum half life and optimizing treatment schedule.

An embodiment of the invention provides a Pseudomonas exotoxin A (PE) comprising a PE amino acid sequence, wherein one or more of amino acid residues F443, R456, L477, R494, and L552 as defined by reference to SEQ ID NO: 1 are, independently, substituted, wherein the PE optionally has:

(i) a further substitution of one or more amino acid residues within one or more B cell epitopes, and the further substitution for an amino acid within one or more B-cell epitopes is a substitution of, independently, one or more of amino acid residues D403, D406, R412, R427, E431, R432, D461, R463, R467, R490, R505, R513, E522, R538, E548, R551, R576, Q592, and L597 as defined by reference to SEQ ID NO: 1, (ii) a further substitution of one or more amino acid residues within one or more T-cell epitopes, (iii) a deletion of one or more continuous amino acid residues of residues 1-273 and 285-394 as defined by SEQ ID NO: 1, or (iv) a combination of any one, two, or three of (i)-(iii).

Another embodiment of the invention provides an isolated, mutated Pseudomonas exotoxin A (PE), comprising a sequence of the following formula:

$$R^1_n\text{-FCS-}R^2_n\text{-}R^3_n\text{-PE functional domain III}$$

wherein:
n=0 or 1 independently for each of $R^1$, $R^2$ and $R^3$,
$R^1$=1 to 10 amino acid residues
FCS=a furin cleavage sequence of amino acid residues, which sequence is cleavable by furin and has an amino end and a carboxyl end,
$R^2$=1 to 10 amino acid residues;
$R^3$=1 or more contiguous residues of residues 365-394 of SEQ ID NO:1; and,
PE functional domain III=residues 395-613 of SEQ ID NO:1, wherein one or more of amino acid residues F443, R456, L477, R494, and L552 as defined by reference to SEQ ID NO: 1 are, independently, substituted, wherein the PE optionally has:

(i) a further substitution of one or more amino acid residues within one or more B cell epitopes, and the further substitution for an amino acid within one or more B-cell epitopes is a substitution of, independently, one or more of amino acid residues D403, D406, R412, R427, E431, R432, D461, R463, R467, R490, R505, R513, E522, R538, E548, R551, R576, Q592, and L597 as defined by reference to SEQ ID NO: 1, (ii) a further substitution of one or more amino acid residues within one or more T-cell epitopes, or (iii) both (i) and (ii).

Another embodiment of the invention provides an isolated, mutated *Pseudomonas* exotoxin A (PE), comprising a sequence of the following formula:

$$R^1_n\text{-FCS-}R^2_n\text{-}R^3_n\text{-PE functional domain III}$$

wherein:

n=0 or 1 independently for each of $R^1$, $R^2$ and $R^3$, $R^1$=1 to 10 amino acid residues FCS=a furin cleavage sequence of amino acid residues, which sequence is cleavable by furin and has an amino end and a carboxyl end, $R^2$=1 to 10 amino acid residues;

$R^3$=1 or more contiguous residues of residues 365-394 of SEQ ID NO:1; and,

PE functional domain III=residues 395-613 of SEQ ID NO:1, wherein the PE includes an arginine at position 458, as defined by reference to SEQ ID NO: 1, and wherein the PE has:

(a) a substitution of alanine for amino acid residue R427;
(b) a substitution of alanine for amino acid residue R463;
(c) a substitution of alanine for amino acid residue R467;
(d) a substitution of alanine for amino acid residue R490;
(e) a substitution of alanine for amino acid residue R505; and
(f) a substitution of alanine for amino acid residue R538.

Additional embodiments of the invention provide related chimeric molecules, as well as related nucleic acids, recombinant expression vectors, host cells, populations of cells, and pharmaceutical compositions.

Still another embodiment of the invention provides a method of treating or preventing cancer in a mammal comprising administering to the mammal the inventive PE, chimeric molecule, nucleic acid, recombinant expression vector, host cell, population of cells, or pharmaceutical composition, in an amount effective to treat or prevent cancer in the mammal.

Another embodiment of the invention provides a method of inhibiting the growth of a target cell comprising contacting the cell with the inventive PE, chimeric molecule, nucleic acid, recombinant expression vector, host cell, population of cells, or pharmaceutical composition, in an amount effective to inhibit growth of the target cell.

Additional embodiments of the invention provide methods of producing the inventive PE and methods of producing the inventive chimeric molecule.

DETAILED DESCRIPTION OF THE INVENTION

Figures 1A, 1B:
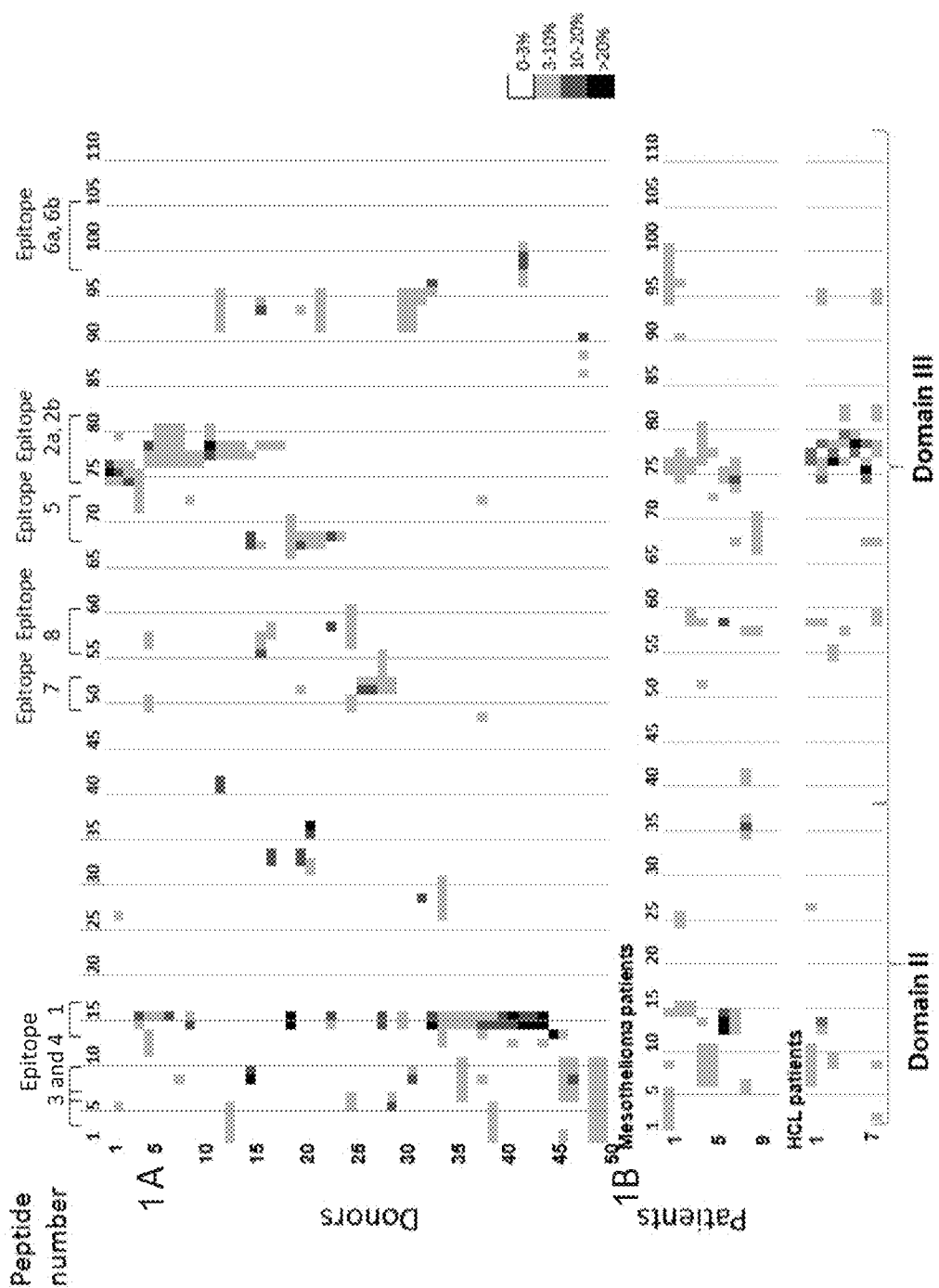
FIGS. 1A and 1B are T cell epitope heat maps showing the strongest (>20%, black squares), medium (10-20%, dark grey squares), weak (3%-10%, light grey squares) and negative (absence of response; <3%, white squares) responses for naïve donors (n=50) (A) and previously treated patients (n=16) (B). The responses are shown as a percentage of responsive spots for each donor. Responses were clustered using automatic sorting based on the responsiveness of the pools.
Figures 2A, 2B, 2C:
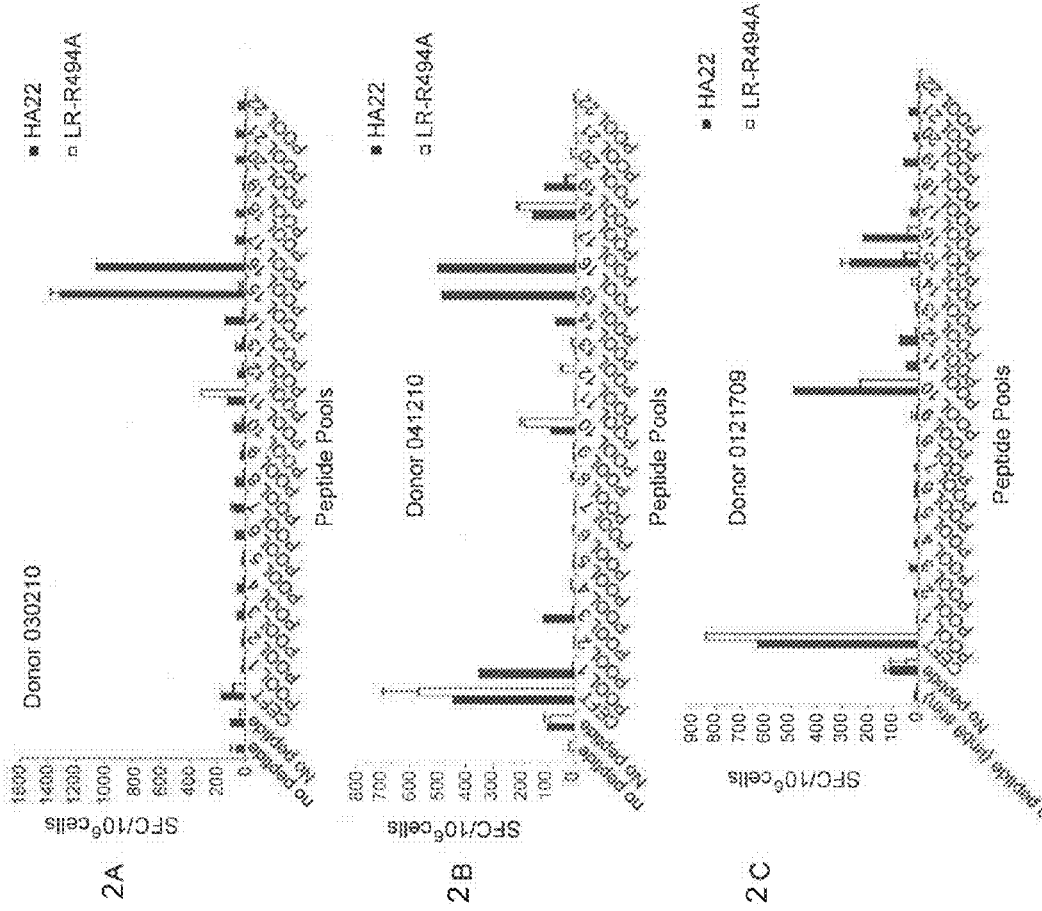
FIGS. 2A-2D are graphs showing the response of three donor samples (A-C) and one HCL patient sample (D) to one of 22 peptide pools, control pool (CEFT), or no peptide after stimulation with HA22 (shaded bars) or LR-R494A (unshaded bars) as measured in spot-forming cells (SFCs) per $10 \times 10^6$ cells. * indicates statistical significance between HA22 and LR-R494A (p<0.01).
Figure 2D:
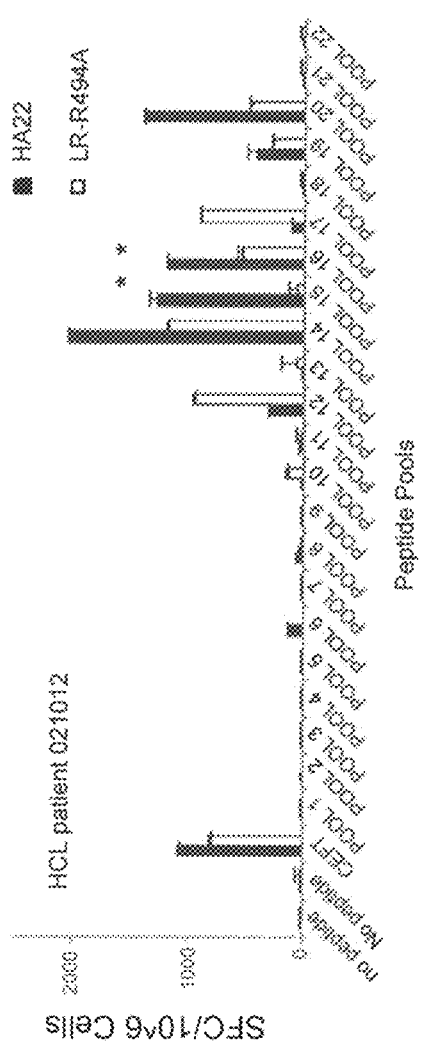

*Pseudomonas* exotoxin A ("PE") is a bacterial toxin (molecular weight 66 kD) secreted by *Pseudomonas aeruginosa*. The native, wild-type PE sequence (SEQ ID NO: 1) is set forth in U.S. Pat. No. 5,602,095, which is incorporated herein by reference. Native, wild-type PE includes three structural domains that contribute to cytotoxicity. Domain Ia (amino acids 1-252) mediates cell binding, domain II (amino acids 253-364) mediates translocation into the cytosol, and domain III (amino acids 400-613) mediates ADP ribosylation of elongation factor 2. While the structural boundary of domain III of PE is considered to start at residue 400, it is contemplated that domain III may require a segment of domain Ib to retain ADP-ribosylating activity. Accordingly, functional domain III is defined as residues 395-613 of PE. The function of domain Ib (amino acids 365-399) remains undefined. Without being bound by a particular theory or mechanism, it is believed that the cytotoxic activity of PE occurs through the inhibition of protein synthesis in eukaryotic cells, e.g., by the inactivation of the ADP-ribosylation of elongation factor 2 (EF-2).

Substitutions of PE are defined herein by reference to the amino acid sequence of PE. Thus, substitutions of PE are described herein by reference to the amino acid residue present at a particular position, followed by the amino acid with which that residue has been replaced in the particular substitution under discussion. In this regard, the positions of the amino acid sequence of a particular embodiment of a PE are referred to herein as the positions of the amino acid sequence of the particular embodiment or as the positions as defined by SEQ ID NO: 1. When the positions are as defined by SEQ ID NO: 1, then the actual positions of the amino acid sequence of a particular embodiment of a PE are defined relative to the corresponding positions of SEQ ID NO: 1 and may represent different residue position numbers than the residue position numbers of SEQ ID NO: 1. Thus, for example, substitutions refer to a replacement of an amino acid residue in the amino acid sequence of a particular embodiment of a PE corresponding to the indicated position of the 613-amino acid sequence of SEQ ID NO: 1 with the understanding that the actual positions in the respective amino acid sequences may be different. For example, when the positions are as defined by SEQ ID NO: 1, the term "R490" refers to the arginine normally present at position 490 of SEQ ID NO: 1, "R490A" indicates that the arginine normally present at position 490 of SEQ ID NO: 1 is replaced by an alanine, while "K590Q" indicates that the lysine normally present at position 590 of SEQ ID NO: 1 has been replaced with a glutamine. In the event of multiple substitutions at two or more positions, the two or more substitutions may be the same or different, i.e., each amino acid residue of the two or more amino acid residues being substituted can be substituted with the same or different amino acid residue unless explicitly indicated otherwise.

The terms "*Pseudomonas* exotoxin" and "PE" as used herein include PE that has been modified from the native protein to reduce or to eliminate immunogenicity. Such modifications may include, but are not limited to, elimination of domain Ia, various amino acid deletions in domains Ib, II, and III, single amino acid substitutions and the addition of one or more sequences at the carboxyl terminus such as DEL and REDL (SEQ ID NO: 7). See Siegall et al., *J. Biol. Chem.*, 264: 14256-14261 (1989). Such modified PEs may be further modified to include any of the inventive substitution(s) for one or more amino acid residues within one or more T-cell and/or B-cell epitopes described herein. In an embodiment, the modified PE may be a cytotoxic fragment of native, wild-type PE. Cytotoxic fragments of PE may include those which are cytotoxic with or without subsequent proteolytic or other processing in the target cell (e.g., as a protein or pre-protein). In a preferred embodiment, the cytotoxic fragment of PE retains at least about 20%, preferably at least about 40%, more preferably at least about 50%, even more preferably at least about 75%, more preferably at least about 90%, and still more preferably at least about 95% of the cytotoxicity of native PE. In particularly preferred embodiments, the cytotoxic fragment has at least the cytotoxicity of native PE, and preferably has increased cytotoxicity as compared to native PE.

Modified PE that reduces or eliminates immunogenicity includes, for example, PE4E, PE40, PE38, PE25, PE38QQR, PE38KDEL, and PE35. In an embodiment, the PE may be any of PE4E, PE40, PE38, PE25, PE38QQR (in which PE38 has the sequence QQR added at the C-terminus), PE38KDEL (in which PE38 has the sequence KDEL (SEQ ID NO: 5) added at the C-terminus), PE-LR (resistance to lysosomal degradation)(also referred to as PE24), PE24-LO10, and PE35.

In an embodiment, the PE has been modified to reduce immunogenicity by deleting domain Ia as described in U.S. Pat. No. 4,892,827, which is incorporated herein by reference. The PE may also be modified by substituting certain residues of domain Ia. In an embodiment, the PE may be PE4E, which is a substituted PE in which domain Ia is present but in which the basic residues of domain Ia at positions 57, 246, 247, and 249 are replaced with acidic residues (e.g., glutamic acid), as disclosed in U.S. Pat. No. 5,512,658, which is incorporated herein by reference.

PE40 is a truncated derivative of PE (Pai et al., *Proc. Nat'l. Acad. Sci. USA,* 88: 3358-62 (1991) and Kondo et al., *Biol. Chem.,* 263: 9470-9475 (1988)). PE35 is a 35 kD carboxyl-terminal fragment of PE in which amino acid residues 1-279 have been deleted and the molecule commences with a Met at position 280 followed by amino acids 281-364 and 381-613 of native PE. PE35 and PE40 are disclosed, for example, in U.S. Pat. Nos. 5,602,095 and 4,892,827, each of which is incorporated herein by reference. PE25 contains the 11-residue fragment from domain II and all of domain III. In some embodiments, the PE contains only domain III.

In a preferred embodiment, the PE is PE38. PE38 contains the translocating and ADP ribosylating domains of PE but not the cell-binding portion (Hwang J. et al., *Cell,* 48: 129-136 (1987)). PE38 is a truncated PE pro-protein composed of amino acids 253-364 and 381-613 which is activated to its cytotoxic form upon processing within a cell (see e.g., U.S. Pat. No. 5,608,039, which is incorporated herein by reference, and Pastan et al., *Biochim. Biophys. Acta,* 1333: C1-C6 (1997)).

In another preferred embodiment, the PE is PE-LR. PE-LR contains a deletion of domain II except for a furin cleavage sequence (FCS) corresponding to amino acid residues 274-284 of SEQ ID NO: 1 (RHRQPRGWEQL (SEQ ID NO: 8)) and a deletion of amino acid residues 365-394 of domain Ib. Thus, PE-LR contains amino acid residues 274-284 and 395-613 of SEQ ID NO: 1. PE-LR is described in International Patent Application Publication WO 2009/032954, which is incorporated herein by reference. The PE-LR may, optionally, additionally comprise a GGS (SEQ ID NO: 283) linking peptide between the FCS and amino acid residues 395-613 of SEQ ID NO: 1.

As noted above, alternatively or additionally, some or all of domain Ib may be deleted with the remaining portions joined by a bridge or directly by a peptide bond. Alternatively or additionally, some of the amino portion of domain II may be deleted. Alternatively or additionally, the C-terminal end may contain the native sequence of residues 609-613 (REDLK) (SEQ ID NO: 6), or may contain a variation that may maintain the ability of the PE to translocate into the cytosol, such as KDEL (SEQ ID NO: 5) or REDL (SEQ ID NO: 7), and repeats of these sequences. See, e.g., U.S. Pat. Nos. 5,854,044; 5,821,238; and 5,602,095 and International Patent Application Publication WO 1999/051643, which are incorporated herein by reference. Any form of PE in which immunogenicity has been eliminated or reduced can be used in combination with any of the inventive substitution(s) for one or more amino acid residues within one or more T-cell and/or B-cell epitopes described herein so long as it remains capable of cytotoxicity to targeted cells, e.g., by translocation and EF-2 ribosylation in a targeted cell.

An embodiment of the invention provides a *Pseudomonas* exotoxin A (PE) comprising a PE amino acid sequence wherein one or more of amino acid residues F443, R456, L477, R494, and L552 as defined by reference to SEQ ID NO: 1 are, independently, substituted, wherein the PE optionally has:

(i) a further substitution of one or more amino acid residues within one or more B cell epitopes, and the further substitution for an amino acid within one or more B-cell epitopes is a substitution of, independently, one or more of amino acid residues D403, D406, R412, R427, E431, R432, D461, R463, R467, R490, R505, R513, E522, R538, E548, R551, R576, Q592, and L597 as defined by reference to SEQ ID NO: 1, (ii) a further substitution of one or more amino acid residues within one or more T-cell epitopes, (iii) a deletion of one or more continuous amino acid residues of residues 1-273 and 285-394 as defined by SEQ ID NO: 1, or (iv) a combination of any one, two, or three of (i)-(iii).

It has been discovered that amino acid residues F443, L477, R494, and L552 are located within one or more T-cell epitopes of PE. Thus, a substitution of one or more of amino acid residues F443, L477, R494, and L552 may, advantageously, remove one or more T cell epitope(s). Accordingly, the inventive PEs may, advantageously, be less immunogenic than an unsubstituted (e.g., wild-type) PE.

A preferred embodiment of the invention provides an isolated, mutated *Pseudomonas* exotoxin A (PE), comprising a sequence of the following formula:

$$R^1_n\text{-FCS-}R^2_n\text{-}R^3_n\text{-PE functional domain III}$$

wherein:

n=0 or 1 independently for each of $R^1$, $R^2$ and $R^3$ $R^1$=1 to 10 amino acid residues FCS=a furin cleavage sequence of amino acid residues, which sequence is cleavable by furin and has an amino end and a carboxyl end, $R^2$=1 to 10 amino acid residues;

$R^3$=1 or more contiguous residues of residues 365-394 of SEQ ID NO: 1; and,

PE functional domain III=residues 395-613 of SEQ ID NO: 1, wherein one or more of amino acid residues F443, L477, R494, and L552 as defined by reference to SEQ ID NO: 1 are, independently substituted;

and the PE comprises optionally a further substitution of an amino acid within one or more B-cell epitopes.

The substitution of one or more of amino acid residues F443, L477, R494, and L552 may be a substitution of any amino acid residue for one or more of amino acid residues F443, L477, R494, and L552. In an embodiment of the invention, the substitution of one or more of amino acid residues F443, L477, R494, and L552 is a substitution of, independently, alanine, glutamic acid, histidine, or asparagine in place of one or more of amino acid residues F443, L477, R494, and L552. In an embodiment of the invention, the substitution of L552 is a substitution of glutamic acid or asparagine in place of L552 and the substitution of L477 is a substitution of histidine in place of L477.

In an embodiment of the invention, the substitution of one or more of amino acid residues F443, L477, R494, and L552 is a substitution of alanine in place of amino acid residue F443; a substitution of histidine in place of amino acid residue L477; a substitution of alanine in place of amino acid residue R494; and a substitution of glutamic acid or asparagine in place of amino acid residue L552.

In addition to the substitution(s) for one or more amino acid residues within one or more PE T-cell epitopes described herein, the inventive PE may, optionally, also include additional substitution(s) for one or more amino acid residues within one or more B-cell epitopes of SEQ ID NO: 1. In this regard, in an embodiment of the invention, the PE has a substitution of one or more amino acids within one or more B-cell epitopes of SEQ ID NO: 1. In a preferred embodiment of the invention, the substitution of one or more amino acid residues within one or more B-cell epitopes of SEQ ID NO: 1 includes a substitution of alanine, glycine, serine, or glutamine for one or more amino acids within one or more B-cell epitopes of SEQ ID NO: 1. The substitution(s) within one or more B-cell epitopes may, advantageously, further reduce immunogenicity by the removal of one or more B-cell epitopes. The substitution(s) may be located within any suitable PE B-cell epitope. Exemplary B-cell epitopes are disclosed in, for example, International Patent Application Publications WO 2007/016150, WO 2009/032954, and WO 2011/032022, each of which is incorporated herein by reference. In a preferred embodiment, the substitution of one or more amino acids within one or more B-cell epitopes of SEQ ID NO: 1 is a substitution of alanine, glycine, serine, or glutamine, independently, in place of one or more of amino acid residues E282, E285, P290, R313, N314, P319, D324, E327, E331, Q332, D403, D406, R412, R427, E431, R432, D461, D463, R467, Y481, R490, R505, R513, L516, E522, R538, E548, R551, R576, K590, Q592, and L597, wherein the amino acid residues E282, E285, P290, R313, N314, P319, D324, E327, E331, Q332, D403, D406, R412, R427, E431, R432, D461, D463, R467, Y481, R490, R505, R513, L516, E522, R538, E548, R551, R576, K590, Q592, and L597 are defined by reference to SEQ ID NO: 1.

In an embodiment of the invention, the further substitution of an amino acid within one or more B-cell epitopes is a substitution of, independently, alanine, glycine, serine, or glutamine in place of one or more of amino acid residues E282, E285, P290, R313, N314, P319, D324, E327, E331, Q332, D403, D406, R412, R427, E431, R432, D461, D463, R467, R490, R505, R513, E522, R538, E548, R551, R576, K590, Q592, and L597, as defined by reference to SEQ ID NO: 1. Preferably, the further substitution of an amino acid within one or more B-cell epitopes is a substitution of, independently, alanine, glycine, or serine in place of one or more of amino acid residues R427, R505, and R551. In an especially preferred embodiment, the substitution of one or more of amino acid residues F443, R456, L477, R494, and L552 is a substitution of alanine in place of amino acid residue F443, a substitution of histidine in place of L477, a substitution of alanine in place of R494, and a substitution of glutamic acid in place of L552, and the further substitution of an amino acid within one or more B-cell epitopes is: (a) a substitution of alanine for amino acid residue R427; and (b) a substitution of alanine for amino acid residue R505, as defined by reference to SEQ ID NO: 1.

In an embodiment of the invention, any of the PEs described herein may have an arginine at position 458, with reference to SEQ ID NO: 1. Without being bound to a particular theory or mechanism, it is believed that an arginine at position 458 provides enhanced cytotoxicity.

In an embodiment of the invention, the PE has an arginine residue at position 458, as defined by reference to SEQ ID NO: 1. In a preferred embodiment, the substitution of one or more of amino acid residues F443, R456, L477, R494, and L552 is a substitution of alanine in place of amino acid residue R456, the PE has an arginine residue at position 458, and the further substitution of an amino acid within one or more B-cell epitopes is: (a) a substitution of alanine for amino acid residue R427; (b) a substitution of alanine for amino acid residue R463; (c) a substitution of alanine for amino acid residue R467; (d) a substitution of alanine for amino acid residue R490; and (e) a substitution of alanine for amino acid residue R505; (f) a substitution of alanine for amino acid residue R538; as defined by reference to SEQ ID NO: 1.

In an embodiment of the invention, the substitution of one or more of amino acid residues F443, R456, L477, R494, and L552 is a substitution of alanine in place of amino acid residue F443; a substitution of alanine in place of amino acid residue R456; a substitution of histidine in place of amino acid residue L477; a substitution of alanine in place of amino acid residue R494; and a substitution of glutamic acid in place of amino acid residue L552, the PE has an arginine residue at position 458, and the further substitution of an amino acid within one or more B-cell epitopes is: (a) a substitution of alanine for amino acid residue R427; (b) a substitution of alanine for amino acid residue R463; (c) a substitution of alanine for amino acid residue R467; (d) a substitution of alanine for amino acid residue R490; (e) a substitution of alanine for amino acid residue R505; and (f) a substitution of alanine for amino acid residue R538; as defined by reference to SEQ ID NO: 1.

In an embodiment of the invention, the substitution of one or more of amino acid residues F443, R456, L477, R494, and L552 is a substitution of alanine in place of amino acid residue R456, the PE has an arginine residue at position 458, and the further substitution of an amino acid within one or more B-cell epitopes is: (a) a substitution of alanine for amino acid residue R427; (b) a substitution of alanine for amino acid residue R463; (c) a substitution of alanine for amino acid residue R467; (d) a substitution of alanine for amino acid residue R490; (e) a substitution of alanine for amino acid residue R505; and (f) a substitution of alanine for amino acid residue R538; as defined by reference to SEQ ID NO: 1.

In another embodiment of the invention, the substitution of one or more of amino acid residues F443, R456, L477, R494, and L552 is a substitution of alanine in place of amino acid residue F443; a substitution of alanine in place of amino acid residue R456; a substitution of histidine in place of amino acid residue L477; a substitution of alanine in place of amino acid residue R494; and a substitution of asparagine in place of amino acid residue L552, the PE has an arginine residue at position 458, and the further substitution of an amino acid within one or more B-cell epitopes is: (a) a substitution of alanine for amino acid residue R427; (b) a substitution of alanine for amino acid residue R463; (c) a substitution of alanine for amino acid residue R467; (d) a substitution of alanine for amino acid residue R490; (e) a substitution of alanine for amino acid residue R505; and (f) a substitution of alanine for amino acid residue R538; as defined by reference to SEQ ID NO: 1.

In a preferred embodiment of the invention, the substitution of one or more of amino acid residues F443, L477, R494, and L552 is a substitution of alanine in place of amino acid residue F443; a substitution of histidine in place of amino acid residue L477; a substitution of alanine in place of amino acid residue R494; and a substitution of glutamic acid in place of amino acid residue L552, the PE has an arginine residue at position 458, and the further substitution of an amino acid within one or more B-cell epitopes is: (a) a substitution of alanine for amino acid residue R427; (b) a substitution of alanine for amino acid residue R456; (c) a substitution of alanine for amino acid residue R463; (d) a substitution of alanine for amino acid residue R467; (e) a substitution of alanine for amino acid residue R490; (f) a substitution of alanine for amino acid residue R505; and (g) a substitution of alanine for amino acid residue R538; as defined by reference to SEQ ID NO: 1. A preferred embodiment is a PE comprising SEQ ID NO: 285 (T14-L010R+456A).

In a preferred embodiment of the invention, the substitution of one or more of amino acid residues F443, L477, R494, and L552 is a substitution of alanine in place of amino acid residue F443; a substitution of histidine in place of amino acid residue L477; a substitution of alanine in place of amino acid residue R494; and a substitution of asparagine in place of amino acid residue L552, the PE has an arginine residue at position 458, and the further substitution of an amino acid within one or more B-cell epitopes is: (a) a substitution of alanine for amino acid residue R427; (b) a substitution of alanine for amino acid residue R456; (c) a substitution of alanine for amino acid residue R463; (d) a substitution of alanine for amino acid residue R467; (e) a substitution of alanine for amino acid residue R490; (f) a substitution of alanine for amino acid residue R505; and (g) a substitution of alanine for amino acid residue R538; as defined by reference to SEQ ID NO: 1. A preferred embodiment is a PE comprising SEQ ID NO: 286 (T15-L010R+456A).

In a preferred embodiment of the invention, the substitution of one or more of amino acid residues F443, L477, R494, and L552 is a substitution of alanine in place of amino acid residue F443; a substitution of histidine in place of amino acid residue L477; a substitution of alanine in place of amino acid residue R494; and a substitution of glutamic acid in place of amino acid residue L552, the PE has an arginine residue at position 458, and the further substitution of an amino acid within one or more B-cell epitopes is: (a) a substitution of alanine for amino acid residue R427; (b) a substitution of alanine for amino acid residue R463; (c) a substitution of alanine for amino acid residue R467; (d) a substitution of alanine for amino acid residue R490; (e) a substitution of alanine for amino acid residue R505; and (f) a substitution of alanine for amino acid residue R538; as defined by reference to SEQ ID NO: 1. A preferred embodiment is a PE comprising SEQ ID NO: 287 (T14-L010R).

In a preferred embodiment of the invention, the substitution of one or more of amino acid residues F443, L477, R494, and L552 is a substitution of alanine in place of amino acid residue F443; a substitution of histidine in place of amino acid residue L477; a substitution of alanine in place of amino acid residue R494; and a substitution of asparagine in place of amino acid residue L552, the PE has an arginine residue at position 458, and the further substitution of an amino acid within one or more B-cell epitopes is: (a) a substitution of alanine for amino acid residue R427; (b) a substitution of alanine for amino acid residue R463; (c) a substitution of alanine for amino acid residue R467; (d) a substitution of alanine for amino acid residue R490; (e) a substitution of alanine for amino acid residue R505; and (f) a substitution of alanine for amino acid residue R538; as defined by reference to SEQ ID NO: 1. A preferred embodiment is a PE comprising SEQ ID NO: 288 (T15-L010R).

In a preferred embodiment, the FCS is a furin cleavage sequence (FCS) corresponding to amino acid residues 274-284 of SEQ ID NO: 1 (RHRQPRGWEQL (SEQ ID NO: 8)).

In a preferred embodiment,
n=1 for $R^1$ and $R^2$,
$R^1$=a linker of the amino acid sequence of SEQ ID NO: 282 (DKTHKASGG),
$R^2$=a linker of the amino acid sequence of SEQ ID NO: 284 (GGGGGS), and
FCS=furin cleavage sequence (FCS) corresponding to amino acid residues 274-284 of SEQ ID NO: 1 (RHRQPRG-WEQL (SEQ ID NO: 8)). In an especially preferred embodiment, n is 0 for $R^3$.

In an embodiment of the invention, the PE has the further substitution of an amino acid within one or more T-cell epitopes. In this regard, the PE may comprise an amino acid sequence having a further substitution of any amino acid in place of one or more amino acid residues at positions R421, L422, L423, A425, R427, L429, Y439, H440, F443, L444, A446, A447, I450, 463-519, R551, L552, T554, I555, L556, and W558 as defined by reference to SEQ ID NO: 1. In an embodiment of the invention, the further substitution of any amino acid in place of one or more amino acid residues at positions R421, L422, L423, A425, R427, L429, Y439, H440, F443, L444, A446, A447, I450, 463-519, R551, L552, T554, I555, L556, and W558 is a substitution of one or more amino acid residues at positions R421, L422, L423, A425, R427, L429, Y439, H440, F443, L444, A446, A447, I450, Y470, I471, A472, P475, A476, L477, I493, R494, N495, L498, L499, R500, V501, Y502, V503, R505, L508, P509, R551, L552, T554, I555, L556, and W558.

The substitution of one or more amino acid residues at positions R421, L422, L423, A425, R427, L429, Y439, H440, F443, L444, A446, A447, I450, 463-519, R551, L552, T554, I555, L556, and W558 of SEQ ID NO: 1 may be a substitution of any amino acid residue in place of an amino acid residue at any one or more of positions R421, L422, L423, A425, R427, L429, Y439, H440, F443, L444, A446, A447, I450, 463-519, R551, L552, T554, I555, L556, and W558 of SEQ ID NO: 1. The substitution of one or more amino acid residues at positions R421, L422, L423, A425, R427, L429, Y439, H440, F443, L444, A446, A447, I450, 463-519, R551, L552, T554, I555, L556, and W558 of SEQ ID NO: 1 may include, e.g., a substitution of alanine, glycine, serine, or glutamine in place of one or more amino acid residues at position 421, 422, 423, 425, 427, 429, 439, 440, 443, 444, 446, 447, 450, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 551, 552, 554, 555, 556, and 558 of SEQ ID NO: 1. In a preferred embodiment, the substitution of one or more amino acid residues at positions R421, L422, L423, A425, R427, L429, Y439, H440, F443, L444, A446, A447, I450, 463-519, R551, L552, T554, I555, L556, and W558 of SEQ ID NO: 1 is a substitution of alanine, glycine, serine, or glutamine in place of one or more of amino acid residues R421, L422, L423, A425, R427, L429, Y439, H440, F443, L444, A446, A447, I450, Y470, I471, A472, P475, A476, L477, I493, R494, N495, L498, L499, R500, V501, Y502, V503, R505, L508, P509, R551, L552, T554, I555, L556, and W558. One or more substitutions in one or more T cell epitopes located at positions R421, L422, L423, A425, R427, L429, Y439, H440, F443, L444, A446, A447, I450, 463-519, R551, L552, T554, I555, L556, and W558 of PE as defined by reference to SEQ ID NO: 1 may further reduce immunogenicity of PE. In an embodiment, the amino acid sequence does not have a substitution of one or more amino acid residues at positions 427, 467, 485, 490, 505, 513, 516, and 551.

Preferably, the PE comprises one or more substitutions that increase cytotoxicity as disclosed, for example, in International Patent Application Publication WO 2007/016150, which is incorporated herein by reference. In this regard, an embodiment of the invention provides PE with a substitution of an amino acid within one or more B-cell epitopes of SEQ ID NO: 1 and the substitution of an amino acid within one or more B-cell epitopes of SEQ ID NO: 1 is a substitution of valine, leucine, or isoleucine in place of amino acid residue R490, wherein the amino acid residue R490 is defined by reference to SEQ ID NO: 1. In an embodiment of the invention, substitution of one or more amino acid residues at positions 313, 327, 331, 332, 431, 432, 505, 516, 538, and 590 defined by reference to SEQ ID NO: 1 with alanine or glutamine may provide a PE with an increased cytotoxicity as disclosed, for example, in International Patent Application Publication WO 2007/016150, which is incorporated herein by reference. Increased cytotoxic activity and decreased immunogenicity can occur simultaneously, and are not mutually exclusive. Substitutions that both increase cytotoxic activity and decrease immunogenicity, such as substitutions of R490 to glycine or, more preferably, alanine, are especially preferred.

In an embodiment of the invention, another embodiment of the invention provides an isolated, mutated *Pseudomonas* exotoxin A (PE), comprising a sequence of the following formula:

$R^1_n$-FCS-$R^2_n$-$R^3_n$-PE functional domain III wherein:
n=0 or 1 independently for each of $R^1$, $R^2$ and $R^3$,
$R^1$=1 to 10 amino acid residues FCS=a furin cleavage sequence of amino acid residues, which sequence is cleavable by furin and has an amino end and a carboxyl end,
$R^2$=1 to 10 amino acid residues;
$R^3$=1 or more contiguous residues of residues 365-394 of SEQ ID NO: 1; and, PE functional domain III=residues 395-613 of SEQ ID NO:1, wherein one or more of amino acid residues F443, R456, L477, R494, and L552 as defined by reference to SEQ ID NO: 1 are, independently, substituted, wherein the PE optionally has:

(i) a further substitution of one or more amino acid residues within one or more B cell epitopes, and the further substitution for an amino acid within one or more B-cell epitopes is a substitution of, independently, one or more of amino acid residues D403, D406, R412, R427, E431, R432, D461, R463, R467, R490, R505, R513, E522, R538, E548, R551, R576, Q592, and L597 as defined by reference to SEQ ID NO: 1, (ii) a further substitution of one or more amino acid residues within one or more T-cell epitopes, or (iii) both (i) and (ii).

Another embodiment of the invention provides an isolated, mutated *Pseudomonas* exotoxin A (PE), comprising a sequence of the following formula:

$R^1_n$-FCS-$R^2_n$-$R^3_n$-PE functional domain III wherein:
n=0 or 1 independently for each of $R^1$, $R^2$ and $R^3$,
$R^1$=1 to 10 amino acid residues
FCS=a furin cleavage sequence of amino acid residues, which sequence is cleavable by furin and has an amino end and a carboxyl end,
$R^2$=1 to 10 amino acid residues;
$R^3$=1 or more contiguous residues of residues 365-394 of SEQ ID NO: 1; and,
PE functional domain III=residues 395-613 of SEQ ID NO:1, wherein the PE includes an arginine residue at position 458, as defined by reference to SEQ ID NO: 1, and
wherein the PE has:
(a) a substitution of alanine for amino acid residue R427;
(b) a substitution of alanine for amino acid residue R463;
(c) a substitution of alanine for amino acid residue R467;
(d) a substitution of alanine for amino acid residue R490;
(e) a substitution of alanine for amino acid residue R505; and
(f) a substitution of alanine for amino acid residue R538.

In an embodiment of the invention, n is 0 for $R^1$ and $R^2$ of Formula I. In another embodiment of the invention, n is 1 for $R^1$ and $R^2$. In an embodiment of the invention, when n is 0 for $R^1$ and $R^2$, the PE of Formula I may further comprise a GGS (SEQ ID NO: 283) linking peptide between the furin cleavage sequence (FCS) and PE functional domain III.

Without being bound by a particular theory or mechanism, it is believed that PEs containing the FCS undergo proteolytic processing inside target cells, thereby activating the cytotoxic activity of the toxin. The FCS of the inventive PEs may comprise any suitable furin cleavage sequence of amino acid residues, which sequence is cleavable by furin. Exemplary furin cleavage sequences are described in Duckert et al., *Protein Engineering, Design & Selection*, 17(1): 107-112 (2004) and International Patent Application Publication WO 2009/032954, each of which is incorporated herein by reference. In an embodiment of the invention, FCS comprises residues 274-284 of SEQ ID NO: 1 (i.e., RHRQPRGWEQL (SEQ ID NO: 8)), wherein the substitution of an amino acid within one or more B-cell epitopes of SEQ ID NO: 1 is a substitution of alanine, glycine, serine, or glutamine for amino acid residue E282 of SEQ ID NO: 1. Other suitable FCS amino acid sequences include, but are not limited to: R-X$_1$-X$_2$-R, wherein X$_1$ is any naturally occurring amino acid and X$_2$ is any naturally occurring amino acid (SEQ ID NO: 9), RKKR (SEQ ID NO: 10), RRRR (SEQ ID NO: 11), RKAR (SEQ ID NO: 12), SRVARS (SEQ ID NO: 13), TSSRKRRFW (SEQ ID NO: 14), ASRRKARSW (SEQ ID NO: 15), RRVKKRFW (SEQ ID NO: 16), RNVVRRDW (SEQ ID NO: 17), TRAVRRRSW (SEQ ID NO: 18), RQPR (SEQ ID NO: 19), RHRQPRGW (SEQ ID NO: 20), RHRQPRGWE (SEQ ID NO: 21), HRQPRGWEQ (SEQ ID NO: 22), RQPRGWE (SEQ ID NO: 23), RHRSKRGWEQL (SEQ ID NO: 24), RSKR (SEQ ID NO: 25), RHRSKRGW (SEQ ID NO: 26), HRSKRGWE (SEQ ID NO: 27), RSKRGWEQL (SEQ ID NO: 28), HRSKRGWEQL (SEQ ID NO: 29), RHRSKR (SEQ ID NO: 30), and R-X$_1$-X$_2$-R, wherein X$_1$ is any naturally occurring amino acid and X$_2$ is arginine or lysine (SEQ ID NO: 4).

In still another embodiment of the invention, PE functional domain III comprises residues 395-613 of SEQ ID NO: 1, wherein one or more of amino acid residues F443, R456, L477, R494, and L552 as defined by reference to SEQ ID NO: 1 are, independently, substituted. Amino acid residues F443, R456, L477, R494, and L552 may be substituted as described herein with respect to other aspects of the invention.

In an embodiment of the invention, the FCS is represented by the formula P4-P3-P2-P1, wherein P4 is an amino acid residue at the amino end, P1 is an amino acid residue at the carboxyl end, P1 is an arginine or a lysine residue, and the sequence is cleavable at the carboxyl end of P1 by furin.

In another embodiment of the invention, the FCS (i) further comprises amino acid residues represented by P6-P5 at the amino end, (ii) further comprises amino acid residues represented by P1'-P2' at the carboxyl end, (iii) wherein if P1 is an arginine or a lysine residue, P2' is tryptophan, and P4 is arginine, valine or lysine, provided that if P4 is not arginine, then P6 and P2 are basic residues, and (iv) the sequence is cleavable at the carboxyl end of P1 by furin.

In still another embodiment of the invention, the PE functional domain III consists of the sequence of residues 395 to 613 of SEQ ID NO: 1.

In still another embodiment of the invention, the mutated PE comprises one or more contiguous residues of residues 365-394 of SEQ ID NO: 1 between the FCS and the PE domain III.

Aspects for the development of *Pseudomonas* exotoxin chimeric molecules as anti-cancer agents include their cytotoxicity towards tumor cells, their immunogenicity towards human B-cells and human T-cells, and their thermal stability. Thermal stability may be useful for the development of pharmaceutical formulations or compositions.

Therefore, in one aspect of the invention, it has been discovered that by introducing the mutation R456A instead of R458A, it may be possible to remove all B-cell epitopes from a PE without substantially reducing their cytotoxicity towards tumor cells (in case no further T-cell epitopes are removed by further substitutions). Thus, for the first time, a PE is provided in which all B-cell epitopes have been fully removed and which retains its cytotoxic activity.

An embodiment of the invention provides an isolated, mutated *Pseudomonas* exotoxin A (PE), comprising a sequence of the following formula:

R$^1_n$-FCS-R$^2_n$-R$^3_n$-PE functional domain III wherein:
n=0 or 1 independently for each of R$^1$, R$^2$ and R$^3$
R$^1$=1 to 10 amino acid residues
FCS=a furin cleavage sequence of amino acid residues, which sequence is cleavable by furin and has an amino end and a carboxyl end,
R$^2$=1 to 10 amino acid residues;
R$^3$=1 or more contiguous residues of residues 365-394 of SEQ ID NO: 1; and,
PE functional domain III=residues 395-613 of SEQ ID NO: 1, wherein the PE includes an arginine at position 458, as defined by reference to SEQ ID NO: 1, and wherein the PE has:
(a) a substitution of alanine for amino acid residue R427;
(b) a substitution of alanine for amino acid residue R463;
(c) a substitution of alanine for amino acid residue R467;
(d) a substitution of alanine for amino acid residue R490;
(e) a substitution of alanine for amino acid residue R505;
(f) a substitution of alanine for amino acid residue R538; and
(g) a substitution of alanine for amino acid residue R456.

In a preferred embodiment, the FCS=a furin cleavage sequence (FCS) corresponding to amino acid residues 274-284 of SEQ ID NO: 1 (RHRQPRGWEQL (SEQ ID NO: 8)).

In a preferred embodiment,
n=1 for R$^1$ and R$^2$,
R$^1$=a linker of the amino acid sequence of SEQ ID NO: 282 (DKTHKASGG),
R$^2$=a linker of the amino acid sequence of SEQ ID NO: 284 (GGGGGS), and
FCS=furin cleavage sequence (FCS) corresponding to amino acid residues 274-284 of SEQ ID NO: 1 (RHRQPRGWEQL (SEQ ID NO: 8)). In an especially preferred embodiment, n is 0 for R$^3$.

In a preferred embodiment, PE functional domain III comprises the amino acid sequence of SEQ ID NO: 37.

An embodiment of the invention provides an isolated, mutated *Pseudomonas* exotoxin A (PE), comprising a sequence of the following formula:

R$^1_n$-FCS-R$^2_n$-R$^3_n$-PE functional domain III wherein:
n=0 or 1 independently for each of R$^1$, R$^2$ and R$^3$
R$^1$=1 to 10 amino acid residues
FCS=a furin cleavage sequence of amino acid residues, which sequence is cleavable by furin and has an amino end and a carboxyl end,
R$^2$=1 to 10 amino acid residues;
R$^3$=1 or more contiguous residues of residues 365-394 of SEQ ID NO: 1; and,
PE functional domain III=residues 395-613 of SEQ ID NO: 1, wherein the PE includes an arginine at position 458, as defined by reference to SEQ ID NO: 1.

The inventive PE may be less immunogenic than an unsubstituted PE in accordance with the invention if the immune response to the inventive PE is diminished, quantitatively or qualitatively, as compared to the immune response to an unsubstituted PE. A quantitative decrease in immunogenicity encompasses a decrease in the magnitude or degree of the immune response. The magnitude or degree of immunogenicity can be measured on the basis of any number of known parameters, such as a decrease in the level of cytokine (e.g., antigen-specific cytokine) production (cytokine concentration), a decrease in the number of lymphocytes activated (e.g., proliferation of lymphocytes (e.g., antigen-specific lymphocytes)) or recruited, and/or a decrease in the production of antibodies (antigen-specific antibodies), etc. A qualitative decrease in immunogenicity encompasses any change in the nature of the immune response that renders the immune response less effective at mediating the reduction of the cytotoxic activity of the PE. Methods of measuring immunogenicity are known in the art. For example, measuring the types and levels of cytokines produced can measure immunogenicity. Alternatively or additionally, measuring the binding of PE to antibodies (e.g., antibodies previously exposed to PE) and/or measuring the ability of the PE to induce antibodies when administered to a mammal (e.g., humans, mice, and/or mice in which the mouse immune system is replaced with a human immune system) can measure immunogenicity. A less immunogenic PE may be characterized by a decrease in the production of cytokines such as any one or more of IFN-γ, TNF-α, and granzyme B, and/or a reduced stimulation of a cell-mediated immune response, such as a decrease in the proliferation and activation of T-cells and/or macrophages specific for PE as compared to that obtained with an unsubstituted PE. Alternatively or additionally, less immunogenic PE may be characterized by an increase in the production of TGF-beta and/or IL-10 as compared to that obtained with an unsubstituted PE. In a preferred embodiment, reduced immunogenicity is characterized by any one or more of a decrease in T cell stimulation, a decrease in T cell proliferation, and a decrease in T cell IFNγ and/or granzyme B secretion. Alternatively or additionally, a less immunogenic PE may be characterized by a decrease in the stimulation and/or activation of B-cells specific for PE as compared to that obtained with an unsubstituted PE. For example, less immunogenic PE may be characterized by a decrease in the differentiation of B cells into antibody-secreting plasma cells and/or memory cells as compared to that obtained with an unsubstituted PE. Reduced immunogenicity may be characterized by any one or more of a decrease in B cell stimulation, a decrease in B cell proliferation, and a decrease in anti-PE antibody secretion. Qualitative and quantitative diminishment of immunogenicity can occur simultaneously and are not mutually exclusive.

One of ordinary skill in the art will readily appreciate that the inventive PEs can be modified in any number of ways, such that the therapeutic or prophylactic efficacy of the inventive PEs is increased through the modification. For instance, the inventive PEs can be conjugated or fused either directly or indirectly through a linker to a targeting moiety. In this regard, an embodiment of the invention provides a chimeric molecule comprising (a) a targeting moiety conjugated or fused to (b) any of the inventive PEs described herein. The practice of conjugating compounds, e.g., inventive PEs, to targeting moieties is known in the art. See, for instance, Wadwa et al., *J. Drug Targeting*, 3: 111 (1995), and U.S. Pat. No. 5,087,616. In an embodiment, any of the inventive PEs described herein may lack a targeting moiety. In an embodiment, any of the inventive PEs described herein may have any of the targeting moieties having any of the sequences described herein.

The term "targeting moiety" as used herein, refers to any molecule or agent that specifically recognizes and binds to a cell-surface marker, such that the targeting moiety directs the delivery of the inventive PE to a population of cells on which surface the receptor is expressed. Targeting moieties include, but are not limited to, antibodies (e.g., monoclonal antibodies), or fragments thereof, peptides, hormones, growth factors, cytokines, and any other natural or non-natural ligands such as, e.g., scaffold antigen binding proteins.

Scaffold antigen binding proteins are known in the art. For example, fibronectin and designed ankyrin-repeat proteins (DARPins) have been used as alternative scaffolds for antigen-binding domains, see, e.g., Gebauer and Skerra, *Curr. Opin. Chem. Biol.*, 13:245-255 (2009) and Stumpp et al., *Drug Discov. Today*, 13:695-701 (2008), both of which are incorporated herein by reference in their entirety.

In an embodiment, a scaffold antigen binding protein is selected from the group consisting of CTLA-4 (Evibody); lipocalin; Protein A-derived molecules such as the Z-domain of Protein A (Affibody, SpA), A-domain (Avimer/Maxibody); heat shock proteins such as GroEI and GroES; transferrin (trans-body); ankyrin repeat protein (DARPin); peptide aptamer; C-type lectin domain (Tetranectin); human γ-crystallin and human ubiquitin (affilins); PDZ domains; scorpion toxinkunitz-type domains of human protease inhibitors; and fibronectin (adnectin), which has been subjected to protein engineering in order to obtain binding to a ligand other than the natural ligand.

CTLA-4 (Cytotoxic T Lymphocyte-associated Antigen 4) is a CD28-family receptor expressed mainly by CD4+ T-cells. Its extracellular domain has a variable domain-like Ig fold. Loops corresponding to CDRs of antibodies can be substituted with a heterologous sequence to confer different binding properties. CTLA-4 molecules engineered to have different binding specificities are also referred to as Evibodies. For further details, see *J. Immunol. Methods*, 248(1-2): 31-45 (2001).

Lipocalins are a family of extracellular proteins which transport small hydrophobic molecules such as steroids, bilins, retinoids and lipids. They have a rigid beta-sheet secondary structure with a number of loops at the open end of the conical structure which can be engineered to bind to different target antigens. Anticalins are between 160-180 amino acids in size, and are derived from lipocalins. For further details, see *Biochim. Biophys. Acta.*, 1482: 337-350 (2000), US7250297B1 and US20070224633.

An affibody is a scaffold derived from Protein A of *Staphylococcus aureus* which can be engineered to bind to an antigen. The domain includes a three-helical bundle of approximately 58 amino acids. Libraries have been generated by the randomization of surface residues. For further details, see *Protein Eng. Des. Sel.*, 17: 455-462 (2004) and EP1641818A1. Avimers are multidomain proteins derived from the A-domain scaffold family. The native domains of approximately 35 amino acids adopt a defined disulphide bonded structure. Diversity is generated by shuffling the natural variation exhibited by the family of A-domains. For further details, see *Nature Biotechnology*, 23(12): 1556-1561 (2005) and *Expert Opinion on Investigational Drugs*, 16(6): 909-917 (2007).

A transferrin is a monomeric serum transport glycoprotein. Transferrins can be engineered to bind to different target antigens by the insertion of peptide sequences in a permissive surface loop. Examples of engineered transferrin scaffolds include the Trans-body. For further details, see *J. Biol. Chem.*, 274: 24066-24073 (1999).

Designed Ankyrin Repeat Proteins (DARPins) are derived from Ankyrin which is a family of proteins that mediate attachment of integral membrane proteins to the cytoskeleton. A single ankyrin repeat is a 33 residue motif consisting of two alpha-helices and a beta-turn. They can be engineered to bind to different target antigens by randomizing residues in the first alpha-helix and a beta-turn of each repeat. Their binding interface can be increased by increasing the number of modules (a method of affinity maturation). For further details, see *J. Mol. Biol.*, 332: 489-503 (2003); *PNAS*, 100(4): 1700-1705 (2003); *J. Mol. Biol.*, 369, 1015-1028 (2007); and U.S. Patent Application Publication 20040132028A1.

Fibronectin is a scaffold which can be engineered to bind to antigen. Adnectins contain a backbone of the natural amino acid sequence of the 10th domain of the 15 repeating units of human fibronectin type III (FN3). Three loops at one end of the beta-sandwich can be engineered to enable an Adnectin to specifically recognize a therapeutic target of interest. For further details see *Protein Eng. Des. Sel.,* 18: 435-444 (2005), U.S. Patent Application Publication 20080139791, International Patent Application Publication WO 2005056764 and U.S. Pat. No. 6,818,418B1.

Peptide aptamers are combinatorial recognition molecules that include a constant scaffold protein, typically thioredoxin (TrxA), which contains a constrained variable peptide loop inserted at the active site. For further details, see *Expert Opin. Biol. Ther.,* 5: 783-797 (2005).

Microbodies are derived from naturally occurring microproteins of 25-50 amino acids in length which contain 3-4 cysteine bridges. Examples of microproteins include KalataBI, conotoxin, and knottins. The microproteins have a loop which can be engineered to include up to 25 amino acids without affecting the overall fold of the microprotein. For further details of engineered knottin domains, see International Patent Application Publication WO 2008098796.

Other antigen binding proteins include proteins which have been used as a scaffold to engineer different target antigen binding properties, including human gamma-crystallin and human ubiquitin (affilins), kunitz type domains of human protease inhibitors, PDZ-domains of the Ras-binding protein AF-6, scorpion toxins (charybdotoxin), and C-type lectin domain (tetranectins). See Chapter 7—Non-Antibody Scaffolds from *Handbook of Therapeutic Antibodies* (2007, edited by Stefan Dubel) and *Protein Science,* 15:14-27 (2006). Epitope binding domains of the present invention could be derived from any of these alternative protein domains.

The term "antibody," as used herein, refers to whole (also known as "intact") antibodies or antigen binding portions thereof that retain antigen recognition and binding capability. The antibody or antigen binding portions thereof can be a naturally-occurring antibody or antigen binding portion thereof, e.g., an antibody or antigen binding portion thereof isolated and/or purified from a mammal, e.g., mouse, rabbit, goat, horse, chicken, hamster, human, etc. The antibody or antigen binding portion thereof can be in monomeric or polymeric form. Also, the antibody or antigen binding portion thereof can have any level of affinity or avidity for the cell surface marker. Desirably, the antibody or antigen binding portion thereof is specific for the cell surface marker, such that there is minimal cross-reaction with other peptides or proteins.

The antibody may be monoclonal or polyclonal and of any isotype, e.g., IgM, IgG (e.g. IgG, IgG2, IgG3 or IgG4), IgD, IgA or IgE. Complementarity determining regions (CDRs) of an antibody or single chain variable fragments (Fvs) of an antibody against a target cell surface marker can be grafted or engineered into an antibody of choice to confer specificity for the target cell surface marker upon that antibody. For example, the CDRs of an antibody against a target cell surface marker can be grafted onto a human antibody framework of a known three dimensional structure (see, e.g., International Patent Application Publications WO 1998/045322 and WO 1987/002671; U.S. Pat. Nos. 5,859,205; 5,585,089; and 4,816,567; European Patent Application Publication 0173494; Jones et al., *Nature,* 321:522 (1986); Verhoeyen et al., *Science,* 239: 1534 (1988), Riechmann et al., *Nature,* 332:323 (1988); and Winter & Milstein, *Nature,* 349: 293 (1991)) to form an antibody that may raise little or no immunogenic response when administered to a human. In a preferred embodiment, the targeting moiety is a monoclonal antibody or an antigen binding portion of the monoclonal antibody.

The antigen binding portion can be any portion that has at least one antigen binding site, such as, e.g., the variable regions or CDRs of the intact antibody. Examples of antigen binding portions of antibodies include, but are not limited to, a heavy chain, a light chain, a variable or constant region of a heavy or light chain, a single chain variable fragment (scFv), or an Fc, Fab, Fab', Fv, or F(ab)$_2$' fragment; single domain antibodies (see, e.g., Wesolowski, *Med Microbiol Immunol.,* 198(3): 157-74 (2009); Saerens et al., *Curr. Opin. Pharmacol.,* 8(5):600-8 (2008); Harmsen and de Haard, *Appl. Microbiol. Biotechnol.,* 77(1): 13-22 (2007), helix-stabilized antibodies (see, e.g., Arndt et al., *J. Mol. Biol.,* 312: 221-228 (2001); triabodies; diabodies (European Patent Application Publication 0404097; International Patent Application Publication WO 1993/011161; and Hollinger et al., *Proc. Natl. Acad. Sci. USA,* 90: 6444-6448 (1993)); single-chain antibody molecules ("scFvs," see, e.g., U.S. Pat. No. 5,888,773); disulfide stabilized antibodies ("dsFvs," see, e.g., U.S. Pat. Nos. 5,747,654 and 6,558,672), and domain antibodies ("dAbs," see, e.g., Holt et al., *Trends Biotech,* 21(11):484-490 (2003), Ghahroudi et al., *FEBS Lett.,* 414:521-526 (1997), Lauwereys et al., *EMBO J* 17:3512-3520 (1998), Reiter et al., *J. Mol. Biol.* 290:685-698 (1999); and Davies and Riechmann, *Biotechnology,* 13:475-479 (2001)).

Methods of testing antibodies or antigen binding portions thereof for the ability to bind to any cell surface marker are known in the art and include any antibody-antigen binding assay, such as, for example, radioimmunoassay (RIA), ELISA, Western blot, immunoprecipitation, and competitive inhibition assays (see, e.g., Janeway et al., infra, and U.S. Patent Application Publication 2002/0197266 A1).

Suitable methods of making antibodies are known in the art. For instance, standard hybridoma methods are described in, e.g., Köhler and Milstein, *Eur. J. Immunol.,* 5, 511-519 (1976), Harlow and Lane (eds.), *Antibodies: A Laboratory Manual,* CSH Press (1988), and C. A. Janeway et al. (eds.), *Immunobiology,* 5$^{th}$ Ed., Garland Publishing, New York, N.Y. (2001)). Alternatively, other methods, such as EBV-hybridoma methods (Haskard and Archer, *J. Immunol. Methods,* 74(2), 361-67 (1984), and Roder et al., *Methods Enzymol.,* 121, 140-67 (1986)), and bacteriophage vector expression systems (see, e.g., Huse et al., *Science,* 246, 1275-81 (1989)) are known in the art. Further, methods of producing antibodies in non-human animals are described in, e.g., U.S. Pat. Nos. 5,545,806, 5,569,825, and 5,714,352, and U.S. Patent Application Publication 2002/0197266 A1.

Phage display also can be used to generate the antibody that may be used in the chimeric molecules of the invention. In this regard, phage libraries encoding antigen-binding variable (V) domains of antibodies can be generated using standard molecular biology and recombinant DNA techniques (see, e.g., Sambrook et al. (eds.), *Molecular Cloning, A Laboratory Manual,* 3$^{rd}$ Edition, Cold Spring Harbor Laboratory Press, New York (2001)). Phage encoding a variable region with the desired specificity are selected for specific binding to the desired antigen, and a complete or partial antibody is reconstituted comprising the selected variable domain. Nucleic acid sequences encoding the reconstituted antibody are introduced into a suitable cell line, such as a myeloma cell used for hybridoma production, such that antibodies having the characteristics of monoclonal antibodies are secreted by the cell (see, e.g., Janeway et al., supra, Huse et al., supra, and U.S. Pat. No. 6,265,150).

Alternatively, antibodies can be produced by transgenic mice that are transgenic for specific heavy and light chain immunoglobulin genes. Such methods are known in the art and described in, for example U.S. Pat. Nos. 5,545,806 and 5,569,825, and Janeway et al., supra.

Alternatively, the antibody can be a genetically-engineered antibody, e.g., a humanized antibody or a chimeric antibody. Humanized antibodies advantageously provide a lower risk of side effects and can remain in the circulation longer. Methods for generating humanized antibodies are known in the art and are described in detail in, for example, Janeway et al., supra, U.S. Pat. Nos. 5,225,539, 5,585,089 and 5,693,761, European Patent 0239400 B1, and United Kingdom Patent 2188638. Humanized antibodies can also be generated using the antibody resurfacing technology described in, for example, U.S. Pat. No. 5,639,641 and Pedersen et al., *J. Mol. Biol.*, 235, 959-973 (1994).

The targeting moiety may specifically bind to any suitable cell surface marker. The choice of a particular targeting moiety and/or cell surface marker may be chosen depending on the particular cell population to be targeted. Cell surface markers are known in the art (see, e.g., Mufson et al., *Front. Biosci.*, 11:337-43 (2006); Frankel et al., *Clin. Cancer Res.*, 6:326-334 (2000); and Kreitman et al., *AAPS Journal*, 8(3): E532-E551 (2006)) and may be, for example, a protein or a carbohydrate. In an embodiment of the invention, the targeting moiety is a ligand that specifically binds to a receptor on a cell surface. Exemplary ligands include, but are not limited to, vascular endothelial growth factor (VEGF), Fas, TNF-related apoptosis-inducing ligand (TRAIL), a cytokine (e.g., IL-2, IL-15, IL-4, IL-13), a lymphokine, a hormone, and a growth factor (e.g., transforming growth factor (TGFa), neuronal growth factor, epidermal growth factor).

The cell surface marker can be, for example, a cancer antigen. The term "cancer antigen" as used herein refers to any molecule (e.g., protein, peptide, lipid, carbohydrate, etc.) solely or predominantly expressed or over-expressed by a tumor cell or cancer cell, such that the antigen is associated with the tumor or cancer. The cancer antigen can additionally be expressed by normal, non-tumor, or non-cancerous cells. However, in such cases, the expression of the cancer antigen by normal, non-tumor, or non-cancerous cells is not as robust as the expression by tumor or cancer cells. In this regard, the tumor or cancer cells can over-express the antigen or express the antigen at a significantly higher level, as compared to the expression of the antigen by normal, non-tumor, or non-cancerous cells. Also, the cancer antigen can additionally be expressed by cells of a different state of development or maturation. For instance, the cancer antigen can be additionally expressed by cells of the embryonic or fetal stage, which cells are not normally found in an adult host. Alternatively, the cancer antigen can be additionally expressed by stem cells or precursor cells, which cells are not normally found in an adult host.

The cancer antigen can be an antigen expressed by any cell of any cancer or tumor, including the cancers and tumors described herein. The cancer antigen may be a cancer antigen of only one type of cancer or tumor, such that the cancer antigen is associated with or characteristic of only one type of cancer or tumor. Alternatively, the cancer antigen may be a cancer antigen (e.g., may be characteristic) of more than one type of cancer or tumor. For example, the cancer antigen may be expressed by both breast and prostate cancer cells and not expressed at all by normal, non-tumor, or non-cancer cells.

Exemplary cancer antigens to which the targeting moiety may specifically bind include, but are not limited to mucin 1 (MUC1; tumor-associated epithelial mucin), melanoma associated antigen (MAGE), preferentially expressed antigen of melanoma (PRAME), carcinoembryonic antigen (CEA), prostate-specific antigen (PSA), prostate specific membrane antigen (PSMA), granulocyte-macrophage colony-stimulating factor receptor (GM-CSFR), CD56, human epidermal growth factor receptor 2 (HER2/neu) (also known as erbB-2), CD5, CD7, tyrosinase tumor antigen, tyrosinase related protein (TRP)1, TRP2, NY-ESO-1, telomerase, and p53. In a preferred embodiment, the cell surface marker, to which the targeting moiety specifically binds, is selected from the group consisting of cluster of differentiation (CD) 19, CD21, CD22, CD25, CD30, CD33 (sialic acid binding Ig-like lectin 3, myeloid cell surface antigen), CD79b, CD123 (interleukin 3 receptor alpha), transferrin receptor, EGF receptor, mesothelin, cadherin, Lewis Y, Glypican-3, FAP (fibroblast activation protein alpha), PSMA (prostate specific membrane antigen), CA9=CAIX (carbonic anhydrase IX), L1CAM (neural cell adhesion molecule L1), Endosialin, HER3 (activated conformation of epidermal growth factor receptor family member 3), Alk1/BMP9 complex (anaplastic lymphoma kinase 1/bone morphogenetic protein 9), TPBG=5T4 (trophoblast glycoprotein), ROR1 (receptor tyrosine kinase-like surface antigen), HER1 (activated conformation of epidermal growth factor receptor), and CLL1 (C-type lectin domain family 12, member A). Mesothelin is expressed in, e.g., ovarian cancer, mesothelioma, non-small cell lung cancer, lung adenocarcinoma, fallopian tube cancer, head and neck cancer, cervical cancer, and pancreatic cancer. CD22 is expressed in, e.g., hairy cell leukemia, chronic lymphocytic leukemia (CLL), prolymphocytic leukemia (PLL), non-Hodgkin's lymphoma, small lymphocytic lymphoma (SLL), and acute lymphatic leukemia (ALL). CD25 is expressed in, e.g., leukemias and lymphomas, including hairy cell leukemia and Hodgkin's lymphoma. Lewis Y antigen is expressed in, e.g., bladder cancer, breast cancer, ovarian cancer, colorectal cancer, esophageal cancer, gastric cancer, lung cancer, and pancreatic cancer. CD33 is expressed in, e.g., acute myeloid leukemia (AML), chronic myelomonocytic leukemia (CML), and myeloproliferative disorders.

In an embodiment of the invention, the targeting moiety is an antibody that specifically binds to a cancer antigen. Exemplary antibodies that specifically bind to cancer antigens include, but are not limited to, antibodies against the transferrin receptor (e.g., HB21 and variants thereof), antibodies against CD22 (e.g., RFB4 and variants thereof), antibodies against CD25 (e.g., anti-Tac and variants thereof), antibodies against mesothelin (e.g., SS1, MORAb-009, SS, HN1, HN2, MN, MB, and variants thereof) and antibodies against Lewis Y antigen (e.g., B3 and variants thereof). In this regard, the targeting moiety may be an antibody selected from the group consisting of B3, RFB4, SS, SS1, MN, MB, HN1, HN2, HB21, and MORAb-009, and antigen binding portions thereof. Further exemplary targeting moieties suitable for use in the inventive chimeric molecules are disclosed e.g., in U.S. Pat. No. 5,242,824 (anti-transferrin receptor); U.S. Pat. No. 5,846,535 (anti-CD25); U.S. Pat. No. 5,889,157 (anti-Lewis Y); U.S. Pat. No. 5,981,726 (anti-Lewis Y); U.S. Pat. No. 5,990,296 (anti-Lewis Y); U.S. Pat. No. 7,081,518 (anti-mesothelin); U.S. Pat. No. 7,355,012 (anti-CD22 and anti-CD25); U.S. Pat. No. 7,368,110 (anti-mesothelin); U.S. Pat. No. 7,470,775 (anti-CD30); U.S. Pat. No. 7,521,054 (anti-CD25); and U.S. Pat. No. 7,541,034 (anti-CD22); U.S. Patent Application Publication 2007/0189962 (anti-CD22); Frankel et al., *Clin. Cancer Res.*, 6: 326-334 (2000), and Kreitman et al., *AAPS Journal*, 8(3): E532-E551 (2006), each of which is incorporated herein by reference. In another embodiment, the targeting moiety may include the targeting moiety of immunotoxins known in the art. Exemplary immunotoxins include, but are not limited to, LMB-2 (Anti-Tac(Fv)-PE38), BL22 and HA22 (RFB4(dsFv)-PE38), SS1P (SS1 (dsFv)-PE38), HB21-PE40, and variants thereof. In a preferred embodiment, the targeting moiety is the antigen binding portion of HA22. HA22 comprises a disulfide-linked Fv anti-CD22 antibody fragment conjugated to PE38. HA22 and variants thereof are disclosed in International Patent Application Publications WO 2003/027135 and WO 2009/032954, which are incorporated herein by reference.

The antigen binding portion of the targeting moiety may comprise a light chain variable region and/or a heavy chain variable region. In an embodiment of the invention, the heavy chain variable region comprises a heavy chain CDR1 region, a heavy chain CDR2 region, and a heavy chain CDR3 region. In this regard, the antigen binding domain may comprise one or more of a heavy chain CDR1 region comprising SEQ ID NO: 49, 65, 81, 97, 113, 129, 145, 161, or 177; a heavy chain CDR2 region comprising SEQ ID NO: 53, 69, 85, 101, 117, 133, 149, 165, or 181; and a heavy chain CDR3 region comprising SEQ ID NO: 57, 73, 89, 105, 121, 137, 153, 169, or 185. Preferably, the heavy chain comprises all of SEQ ID NOs: (a) 49, 53, and 57 (anti-mesothelin heavy chain CDR1-CDR3, respectively); (b) SEQ ID NOs: 65, 69, and 73 (anti-glypican-3 gc33 heavy chain CDR1-CDR3, respectively); (c) SEQ ID NOs: 81, 85, and 89 (anti-glypican 3 ab acidic heavy chain CDR1-CDR3, respectively); (d) SEQ ID NOs: 97, 101, and 105 (anti-Fap heavy chain CDR1-CDR3, respectively); (e) SEQ ID NOs: 113, 117, 121 (anti-PSMA heavy chain CDR1-CDR3, respectively); (f) SEQ ID NOs: 129, 133, and 137 (anti-CAIX heavy chain CDR1-CDR3, respectively); (g) SEQ ID NOs: 145, 149, and 153 (anti-L1CAM-(1) heavy chain CDR1-CDR3, respectively); (h) SEQ ID NOs: 161, 165, 169 (anti-L1CAM (2) heavy chain CDR1-CDR3, respectively); or (i) SEQ ID NOs: 177, 181, and 185 (anti-L1CAM(3) heavy chain CDR1-CDR3, respectively).

In an embodiment of the invention, the light chain variable region may comprise a light chain CDR1 region, a light chain CDR2 region, and a light chain CDR3 region. In this regard, the antigen binding domain may comprise one or more of a light chain CDR1 region comprising SEQ ID NO: 50, 66, 82, 98, 114, 130, 146, 162, or 178; a light chain CDR2 region comprising SEQ ID NO: 54, 70, 86, 102, 118, 134, 150, 166, or 182; and a light chain CDR3 region comprising SEQ ID NO: 58, 74, 90, 106, 122, 138, 154, 170, or 186. Preferably, the light chain comprises all of (a) SEQ ID NOs: 50, 54, and 58 (anti-mesothelin light chain CDR1-CDR3, respectively); (b) SEQ ID NOs: 66, 70, and 74 (anti-glypican-3 ab gc33 light chain CDR1-CDR-3, respectively); (c) SEQ ID NOs: 82, 86, and 90 (anti-glypican 3 ab acidic light chain CDR1-CDR3, respectively); (d) SEQ ID NOs: 98, 102, and 106 (anti-FAP light chain CDR1-CDR3, respectively); (e) SEQ ID NOs: 114, 118, and 122 (anti-PSMA light chain CDR1-3, respectively); (f) SEQ ID NOs: 130, 134, and 138 (anti-CAIX light chain CDR1-CDR3, respectively); (g) SEQ ID NOs: 146, 150, and 154 (anti-L1CAM-(1) light chain CDR1-CDR3, respectively); (h) SEQ ID NOs: 162, 166, and 170 (anti-L1CAM-(2) light chain CDR1-CDR3, respectively); or (i) SEQ ID NOs: 178, 182, and 186 (anti-L1CAM-(3) light chain CDR1-CDR3, respectively).

In an especially preferred embodiment, the antigen binding portion comprises the CDR1, CDR2, CDR3 regions of the light chain and the CDR1, CDR2, CDR3 regions of the heavy chain. In this regard, the antigen binding portion comprises (a) SEQ ID NOs: 49, 50, 53, 54, 57, and 58; (b) SEQ ID NOs: 65, 66, 69, 70, 73, and 74; (c) SEQ ID NOs: 81, 82, 85, 86, 89, and 90; (d) SEQ ID NOs: 97, 98, 101, 102, 105, and 106; (e) SEQ ID NOs: 113, 114, 117, 118, 121, and 122; (f) SEQ ID NOs: 129, 130, 133, 134, 137, and 138; (g) SEQ ID NOs: 145, 146, 149, 150, 153, and 154; (h) SEQ ID NOs: 161, 162, 165, 166, 169, and 170; or (i) SEQ ID NOs: 177, 178, 181, 182, 185, and 186.

In an embodiment, the antigen binding portion comprises framework regions FR1, FR2, FR3, FR4 of the heavy chain and FR1, FR2, FR3, FR4 of the light chain in addition to the CDR regions described above. In this regard, the antigen binding portion may comprise a heavy chain FR1 region comprising SEQ ID NO: 47, 63, 79, 95, 111, 127, 143, 159, or 175; a heavy chain FR2 region comprising SEQ ID NO: 51, 67, 83, 99, 115, 131, 147, 163, or 179; a heavy chain FR3 region comprising SEQ ID NO: 55, 71, 87, 103, 119, 135, 151, 167, 183; and a heavy chain FR4 region comprising SEQ ID NO: 59, 75, 91, 107, 123, 139, 155, 171, or 187. The antigen binding portion may comprise a light chain FR1 region comprising SEQ ID NO: 48, 64, 80, 96, 112, 128, 144, 160, 176; a light chain FR2 region comprising SEQ ID NO: 52, 68, 84, 100, 116, 132, 148, 164, or 180; a FR3 region comprising SEQ ID NO: 56, 72, 88, 104, 120, 136, 152, 168, or 184; and a FR4 region comprising SEQ ID NO: 60, 76, 92, 108, 124, 140, 156, 172, or 188. Preferably, the antigen binding portion comprises the FR1, FR2, FR3, F4, CDR1, CDR2, and CDR3 regions of the light chain and the FR1, FR2, FR3, F4, CDR1, CDR2, and CDR3 regions of the heavy chain. In this regard, the antigen binding portion comprises (a) SEQ ID NOs: 47-60 (anti-mesothelin); (b) SEQ ID NOs: 63-76 (anti-glypican-3 ab gc33); (c) SEQ ID NOs: 79-92 (anti-glypican 3 ab acidic); (d) SEQ ID NOs: 95-108 (anti-FAP); (e) SEQ ID NOs: 111-124 (anti-PSMA); (f) SEQ ID NOs: 127-140 (anti-CAIX); (g) SEQ ID NOs: 143-156 (anti-L1CAM(1)); (h) SEQ ID NOs: 159-172 (anti-L1 CAM(2)); or (i) SEQ ID NOs: 175-188 (anti-L1CAM(3)).

In an embodiment, the light chain variable region of the antigen binding domain may comprise SEQ ID NO: 46, 62, 78, 94, 110, 126, 142, 158, or 174. In an embodiment, the heavy chain variable region of the antigen binding domain may comprise SEQ ID NO: 45, 61, 77, 93, 109, 125, 141, 157, or 173. In a preferred embodiment, the antigen binding domain comprises both (a) SEQ ID NOs: 45 and 46 (anti-mesothelin); (b) SEQ ID NOs: 61 and 62 (anti-glypican-3 ab gc33); (c) SEQ ID NOs: 77 and 78 (anti-gc33 acidic); (d) SEQ ID NOs: 93 and 94 (anti-FAP); (e) SEQ ID NOs: 109 and 110 (anti-PSMA); (f) SEQ ID NOs: 125 and 126 (anti-CAIX); (g) SEQ ID NOs: 141 and 142 (anti-L1CAM(1)); (h) SEQ ID NOs: 157 and 158 (anti-L1CAM(2)); (i) SEQ ID NOs: 173 and 174 (anti-L1CAM(3)); or (j) SEQ ID NOs: 93 and 290 (anti-FAP).

Another aspect of the invention is a humanized anti-mesothelin antibody comprising the comprising the variable heavy chain domain VH of SEQ ID NO: 45 and the variable light chain domain of SEQ ID NO: 46. The humanized antibody was generated by using mouse anti-mesothelin antibody SS1 as a starting material and generating specific combinations of certain framework regions with the CDR regions of mouse SS1 antibody. The humanized antibody advantageously provides good binding properties, stability, and developability.

In an embodiment of the invention, the targeting moiety may be humanized. In an embodiment of the invention, the targeting moiety is a humanized SS1 or an antigen binding portion of the humanized SS1. In this regard, the targeting moiety may comprise a light chain comprising SEQ ID NO: 33 (cFp-0199) and a heavy chain comprising SEQ ID NO: 38 (cFp-0200). In another embodiment, the targeting moiety may comprise a light chain comprising SEQ ID NOs: 31 (cFp-0199 humanized variable light chain domain VL) and SEQ ID NO: 32 (cFp-0199 kappa constant light chain domain). In an embodiment, the targeting moiety may comprise a heavy chain comprising SEQ ID NOs: 34 (cFp-0200 humanized variable heavy chain domain VH) and SEQ ID NO: 35 (cFp-0200 constant heavy chain domain CH1). In an embodiment, the targeting moiety comprises all of SEQ ID NOs: 31, 32, 34, and 35.

In an embodiment of the invention, the chimeric molecule comprises a linker. The term "linker" as used herein, refers to any agent or molecule that connects the inventive PE to the targeting moiety. One of ordinary skill in the art recognizes that sites on the inventive PE, which are not necessary for the function of the inventive PE, are ideal sites for attaching a linker and/or a targeting moiety, provided that the linker and/or targeting moiety, once attached to the inventive PE, do(es) not interfere with the function of the inventive PE, i.e., cytotoxic activity, inhibit growth of a target cell, or to treat or prevent cancer. The linker may be capable of forming covalent bonds to both the PE and the targeting moiety. Suitable linkers are known in the art and include, but are not limited to, straight or branched-chain carbon linkers, heterocyclic carbon linkers, and peptide linkers. Where the PE and the targeting moiety are polypeptides, the linker may be joined to the amino acids through side groups (e.g., through a disulfide linkage to cysteine). Preferably, the linkers will be joined to the alpha carbon of the amino and carboxyl groups of the terminal amino acids.

In another aspect of the invention, it has been discovered that by introducing specific amino acids at both sides of the furin cleavage sequence (FCS), a more stable chimeric molecule of the *Pseudomonas* exotoxin with a targeting moiety has been provided. In addition, further potential T-cell epitopes in the linker region have been removed, which may be particularly advantageous when using Fab fragments of an antibody as a targeting moiety. These chimeric molecules provide improved thermodynamic stability compared to chimeric molecules without these elongated linkers and retain their cytotoxicity towards tumor cells. Accordingly, in an embodiment of the invention, the linker is an elongated linker. The elongated linker may comprise SEQ ID NO: 36.

In a preferred embodiment, $R^1_n$-FCS-$R^2_n$=a linker of the amino acid sequence of SEQ ID NO: 36. The furin cleavage site is located between amino acid residues 15 and 16 of SEQ ID NO: 36.

An embodiment of the invention provides a chimeric molecule comprising (a) a targeting moiety conjugated or fused to (b) any of the PEs described herein.

An embodiment of the invention provides an isolated chimeric molecule comprising (a) a targeting moiety conjugated or fused to (b) a mutated *Pseudomonas* exotoxin A (PE), comprising a sequence of the following formula:

$$R^1_n\text{-FCS-}R^2_n\text{-}R^3_n\text{-PE functional domain III}$$

wherein:
n=0 or 1 independently for each of $R^1$, $R^2$ and $R^3$
$R^1$=1 to 10 amino acid residues
FCS=a furin cleavage sequence of amino acid residues, which sequence is cleavable by furin and has an amino end and a carboxyl end,
$R^2$=1 to 10 amino acid residues;
$R^3$=1 or more contiguous residues of residues 365-394 of SEQ ID NO: 1; and,
PE functional domain III=residues 395-613 of SEQ ID NO: 1, wherein the PE includes an arginine at position 458, as defined by reference to SEQ ID NO: 1, and wherein the PE has:
  (a) a substitution of alanine for amino acid residue R427;
  (b) a substitution of alanine for amino acid residue R463;
  (c) a substitution of alanine for amino acid residue R467;
  (d) a substitution of alanine for amino acid residue R490;
  (e) a substitution of alanine for amino acid residue R505;
  (f) a substitution of alanine for amino acid residue R538; and
  (g) a substitution of alanine for amino acid residue R456.

In a preferred embodiment of the chimeric molecule, the FCS=furin cleavage sequence (FCS) corresponding to amino acid residues 274-284 of SEQ ID NO: 1 (RHRQPRGWEQL (SEQ ID NO: 8)).

In a preferred embodiment of the chimeric molecule,
n=1 for $R^1$ and $R^2$,
$R^1$=a linker of the amino acid sequence of SEQ ID NO: 282 (DKTHKASGG),
$R^2$=a linker of the amino acid sequence of SEQ ID NO: 284 (GGGGGS), and
FCS=furin cleavage sequence (FCS) corresponding to amino acid residues 274-284 of SEQ ID NO: 1 (RHRQPRG-WEQL (SEQ ID NO: 8)). In an especially preferred embodiment, n is 0 for $R^3$.

In a preferred embodiment of the chimeric molecule, $R^1_n$-FCS-$R^2_n$=a linker of the amino acid sequence of SEQ ID NO: 36 and the targeting moiety comprises the Fab fragment of an antibody.

In a preferred embodiment, the chimeric molecule comprises the antigen binding portion of an anti-mesothelin antibody, a linker comprising the amino acid sequence of SEQ ID NO: 36, and a PE comprising SEQ ID NO: 37 (L010R-456A). In one preferred embodiment, the antigen binding portion is the Fab fragment of an anti-mesothelin antibody comprising the variable heavy chain domain VH of SEQ ID NO: 45 and the variable light chain domain of SEQ ID NO: 46. In this regard, the chimeric molecule may comprise (a) SEQ ID NOs: 39 and 40; (b) SEQ ID NOs: 41 and 42; or (c) SEQ ID NOs: 43 and 44.

In a preferred embodiment, the chimeric molecule comprises the antigen binding portion of an anti-glypican-3 antibody, a linker comprising the amino acid sequence of SEQ ID NO: 36, and a PE comprising SEQ ID NO: 37 (L010R-456A). In a preferred embodiment, the antigen binding portion is the Fab fragment of an anti-glypican-3 antibody comprising the variable heavy chain domain VH of SEQ ID NO: 61 and the variable light chain domain of SEQ ID NO: 62.

In a preferred embodiment, the chimeric molecule comprises the antigen binding portion of an anti-glypican-3 antibody, a linker comprising the amino acid sequence of SEQ ID NO: 36, and a PE comprising SEQ ID NO: 37 (L010R-456A). In a preferred embodiment, the antigen binding portion is the Fab fragment of an anti-glypican-3 antibody comprising the variable heavy chain domain VH of SEQ ID NO: 77 and the variable light chain domain of SEQ ID NO: 78.

In a preferred embodiment, the chimeric molecule comprises the antigen binding portion of an anti-FAP antibody, a FCS corresponding to amino acid residues 274-284 of SEQ ID NO: 1 (RHRQPRGWEQL (SEQ ID NO: 8)) and a PE comprising SEQ ID NO: 37 (L010R-456A). In a preferred embodiment, the chimeric molecule comprises the antigen binding portion of an anti-FAP antibody, a linker comprising the amino acid sequence of SEQ ID NO: 36, and a PE comprising SEQ ID NO: 37 (L010R-456A). In a preferred embodiment, the antigen binding portion is the Fab fragment of an anti-FAP antibody comprising the CDR1, CDR2 and CDR3 of the variable heavy chain domain VH of SEQ ID NO: 93 (SEQ ID NOs: 97, 101, and 105, respectively) and the CDR1, CDR2 and CDR3 of the variable light chain domain of SEQ ID NO: 94 (SEQ ID NOs: 98, 102, and 106, respectively). In one preferred embodiment, the antigen binding portion is the Fab fragment of an anti-FAP antibody comprising the variable heavy chain domain VH of SEQ ID NO: 93 and the variable light chain domain of SEQ ID NO: 94. In another preferred embodiment, the antigen binding portion is the Fab fragment of an anti-FAP antibody comprising the variable heavy chain domain VH of SEQ ID NO: 93 and the variable light chain domain VL of SEQ ID NO: 290. In this regard, the chimeric molecule may comprise (a) SEQ ID NOs: 291 and 293; (b) SEQ ID NOs: 291 and 294; or (c) SEQ ID NOs: 292 and 294.

In a preferred embodiment, the chimeric molecule comprises the antigen binding portion of an anti-PSMA antibody, a FCS corresponding to amino acid residues 274-284 of SEQ ID NO: 1 (RHRQPRGWEQL (SEQ ID NO: 8)) and a PE comprising SEQ ID NO: 37 (L010R-456A). In a preferred embodiment, the chimeric molecule comprises the antigen binding portion of an anti-PSMA antibody, a linker comprising the amino acid sequence of SEQ ID NO: 36, and a PE comprising SEQ ID NO: 37 (L010R-456A). In s preferred embodiment, the antigen binding portion is the Fab fragment of an anti-PSMA antibody comprising the CDR1, CDR2 and CDR3 of the variable heavy chain domain VH of SEQ ID NO: 109 (SEQ ID NOs: 113, 117, and 121, respectively) and the CDR1, CDR2 and CDR3 of the variable light chain domain of SEQ ID NO: 110 (SEQ ID NOs: 114, 118, and 122, respectively).

In a preferred embodiment, the chimeric molecule comprises the antigen binding portion of an anti-CAIX antibody, a FCS corresponding to amino acid residues 274-284 of SEQ ID NO: 1 (RHRQPRGWEQL (SEQ ID NO: 8)) and a PE comprising SEQ ID NO: 37 (L010R-456A). In a preferred embodiment, the chimeric molecule comprises the antigen binding portion of an anti-CAIX antibody, a linker comprising the amino acid sequence of SEQ ID NO: 36, and a PE comprising SEQ ID NO: 37 (L010R-456A). In a preferred embodiment, the antigen binding portion is the Fab fragment of an anti-CAIX antibody comprising the CDR1, CDR2 and CDR3 of the variable heavy chain domain VH of SEQ ID NO: 125 (SEQ ID NOs: 129, 133, and 137, respectively) and the CDR1, CDR2 and CDR3 of the variable light chain domain of SEQ ID NO: 126 (SEQ ID NOs: 130, 134, and 138, respectively). In this regard, the chimeric molecule may comprise (a) SEQ ID NOs: 295 and 297 or (b) SEQ ID NOs: 296 and 297.

In a preferred embodiment, the chimeric molecule comprises the antigen binding portion of an anti-L1CAM antibody, a FCS corresponding to amino acid residues 274-284 of SEQ ID NO: 1 (RHRQPRGWEQL (SEQ ID NO: 8)) and a PE comprising SEQ ID NO: 37 (L010R-456A). In a preferred embodiment, the chimeric molecule comprises the antigen binding portion of an anti-L1CAM antibody, a linker comprising the amino acid sequence of SEQ ID NO: 36, and a PE comprising SEQ ID NO: 37 (L010R-456A). In a preferred embodiment, the antigen binding portion is the Fab fragment of an anti-L1CAM antibody comprising the CDR1, CDR2 and CDR3 of the variable heavy chain domain VH of SEQ ID NO: 141 (SEQ ID NOs: 145, 149, and 153, respectively) and the CDR1, CDR2 and CDR3 of the variable light chain domain of SEQ ID NO: 142 (SEQ ID NOs: 146, 150, and 154, respectively). In a preferred embodiment, the antigen binding portion is the Fab fragment of an anti-L1CAM antibody comprising the variable heavy chain domain VH of SEQ ID NO: 157 and the variable light chain domain of SEQ ID NO: 158. In a preferred embodiment, the antigen binding portion is the Fab fragment of an anti-L1CAM antibody comprising the variable heavy chain domain VH of SEQ ID NO: 173 and the variable light chain domain of SEQ ID NO: 174.

In a preferred embodiment, the invention provides an isolated chimeric molecule comprising (a) a targeting moiety conjugated or fused to (b) a mutated *Pseudomonas* exotoxin A (PE), comprising a sequence of the following formula:

$$R^1_n\text{-FCS-}R^2_n\text{-}R^3_n\text{-PE functional domain III}$$

wherein:
n=0 or 1 independently for each of $R^1$, $R^2$ and $R^3$
$R^1$=1 to 10 amino acid residues
FCS=a furin cleavage sequence of amino acid residues, which sequence is cleavable by furin and has an amino end and a carboxyl end,
$R^2$=1 to 10 amino acid residues;
$R^3$=1 or more contiguous residues of residues 365-394 of SEQ ID NO: 1; and,
PE functional domain III=residues 395-613 of SEQ ID NO: 1,
wherein one or more of amino acid residues F443, L477, R494, and L552 as defined by reference to SEQ ID NO: 1 are, independently substituted;
and the PE comprises optionally a further substitution of an amino acid within one or more B-cell epitopes.

It has been discovered that a substitution of histidine in place of amino acid residue L477 leads to a strong reduction of T cell responses compared to substitutions with other amino acids (see, for example, Example 4) while at the same time improving the cytotoxic efficacy of the PE compared to substitutions with other amino acids (see, for example, Examples 3, 5 and 6). Therefore, in a preferred embodiment of the invention with respect to the chimeric molecule, the substitution of one or more of amino acid residues F443, L477, R494, and L552 is a substitution of histidine in place of amino acid residue L477. The substitution of glutamic acid or asparagine in place of amino acid residue L552 also leads to further improved toxicity while reducing T cell responses. In a preferred embodiment of the invention with respect to the chimeric molecule, the substitution of one or more of amino acid residues F443, L477, R494, and L552 is a substitution of histidine in place of amino acid residue L477 and a substitution of glutamic acid or asparagine in place of amino acid residue L552. In an embodiment of the invention with respect to the chimeric molecule, the substitution of one or more of amino acid residues F443, L477, R494, and L552 is a substitution of alanine in place of amino acid residue F443; a substitution of histidine in place of amino acid residue L477; a substitution of alanine in place of amino acid residue R494; and a substitution of glutamic acid or asparagine in place of amino acid residue L552.

In a preferred embodiment of the invention with respect to the chimeric molecule, the substitution of one or more of amino acid residues F443, L477, R494, and L552 is a substitution of alanine in place of amino acid residue F443; a substitution of histidine in place of amino acid residue L477; a substitution of alanine in place of amino acid residue R494; and a substitution of glutamic acid in place of amino acid residue L552, the PE has an arginine residue at position 458, and the further substitution of an amino acid within one or more B-cell epitopes is: (a) a substitution of alanine for amino acid residue R427 and (b) a substitution of alanine for amino acid residue R505 as defined by reference to SEQ ID NO: 1. In a preferred embodiment of the invention, the PE of the chimeric molecule comprises the amino acid sequence of SEQ ID NO: 289 (T18/T20).

In a preferred embodiment of the invention with respect to the chimeric molecule, the substitution of one or more of amino acid residues F443, L477, R494, and L552 is a substitution of alanine in place of amino acid residue F443; a substitution of histidine in place of amino acid residue L477; a substitution of alanine in place of amino acid residue R494; and a substitution of glutamic acid in place of amino acid residue L552, the PE has an arginine residue at position 458, and the further substitution of an amino acid within one or more B-cell epitopes is: (a) a substitution of alanine for amino acid residue R427; (b) a substitution of alanine for amino acid residue R456; (c) a substitution of alanine for amino acid residue R463; (d) a substitution of alanine for amino acid residue R467; (e) a substitution of alanine for amino acid residue R490; (f) a substitution of alanine for amino acid residue R505; and (g) a substitution of alanine for amino acid residue R538; as defined by reference to SEQ ID NO: 1. In a preferred embodiment, the PE of the chimeric molecule comprises the amino acid sequence of SEQ ID NO: 285 (T14-L010R+456A).

In a preferred embodiment of the invention with respect to the chimeric molecule, the substitution of one or more of amino acid residues F443, L477, R494, and L552 is a substitution of alanine in place of amino acid residue F443; a substitution of histidine in place of amino acid residue L477; a substitution of alanine in place of amino acid residue R494; and a substitution of asparagine in place of amino acid residue L552, the PE has an arginine residue at position 458, and the further substitution of an amino acid within one or more B-cell epitopes is: (a) a substitution of alanine for amino acid residue R427; (b) a substitution of alanine for amino acid residue R456; (c) a substitution of alanine for amino acid residue R463; (d) a substitution of alanine for amino acid residue R467; (e) a substitution of alanine for amino acid residue R490; (f) a substitution of alanine for amino acid residue R505; and (g) a substitution of alanine for amino acid residue R538; as defined by reference to SEQ ID NO: 1. In a preferred embodiment, the PE of the chimeric molecule comprises the amino acid sequence of SEQ ID NO: 286 (T15-L010R+456A).

In a preferred embodiment of the invention with respect to the chimeric molecule, the substitution of one or more of amino acid residues F443, L477, R494, and L552 is a substitution of alanine in place of amino acid residue F443; a substitution of histidine in place of amino acid residue L477; a substitution of alanine in place of amino acid residue R494; and a substitution of glutamic acid in place of amino acid residue L552, the PE has an arginine residue at position 458, and the further substitution of an amino acid within one or more B-cell epitopes is: (a) a substitution of alanine for amino acid residue R427; (b) a substitution of alanine for amino acid residue R463; (c) a substitution of alanine for amino acid residue R467; (d) a substitution of alanine for amino acid residue R490; (e) a substitution of alanine for amino acid residue R505; and (f) a substitution of alanine for amino acid residue R538; as defined by reference to SEQ ID NO: 1. In a preferred embodiment, the PE of the chimeric molecule comprises the amino acid sequence of SEQ ID NO: 287 (T14-L010R).

In a preferred embodiment of the invention within the chimeric molecule, the substitution of one or more of amino acid residues F443, L477, R494, and L552 is a substitution of alanine in place of amino acid residue F443; a substitution of histidine in place of amino acid residue L477; a substitution of alanine in place of amino acid residue R494; and a substitution of asparagine in place of amino acid residue L552, the PE has an arginine residue at position 458, and the further substitution of an amino acid within one or more B-cell epitopes is: (a) a substitution of alanine for amino acid residue R427; (b) a substitution of alanine for amino acid residue R463; (c) a substitution of alanine for amino acid residue R467; (d) a substitution of alanine for amino acid residue R490; (e) a substitution of alanine for amino acid residue R505; and (f) a substitution of alanine for amino acid residue R538; as defined by reference to SEQ ID NO: 1. In a preferred embodiment, the PE of the chimeric molecule comprises the amino acid sequence of SEQ ID NO: 288 (T15-L010R).

In a preferred embodiment with respect to the chimeric molecule, the FCS=furin cleavage sequence (FCS) corresponding to amino acid residues 274-284 of SEQ ID NO: 1 (RHRQPRGWEQL (SEQ ID NO: 8)).

In a preferred embodiment with respect to the chimeric molecule, n=1 for $R^1$ and $R^2$, $R^1$=a linker of the amino acid sequence of SEQ ID NO: 282 (DKTHKASGG), $R^2$=a linker of the amino acid sequence of SEQ ID NO: 284 (GGGGGS), and FCS=furin cleavage sequence (FCS) corresponding to amino acid residues 274-284 of SEQ ID NO: 1 (RHRQPRGWEQL (SEQ ID NO: 8)). In an especially preferred embodiment, n is 0 for $R^3$.

In a preferred embodiment with respect to the chimeric molecule, $R^1_n$-FCS-$R^2_n$=a linker of the amino acid sequence of SEQ ID NO: 36 and the targeting moiety comprises the Fab fragment of an antibody.

In a preferred embodiment, the chimeric molecule comprises the antigen binding portion of an anti-mesothelin antibody, a linker comprising the amino acid sequence of SEQ ID NO: 36, and a PE comprising SEQ ID NO: 285 (T14-L010R+456A). In a preferred embodiment, the antigen binding portion is the Fab fragment of an anti-mesothelin antibody comprising the variable heavy chain domain VH of SEQ ID NO: 45 and the variable light chain domain of SEQ ID NO: 46.

In a preferred embodiment, the chimeric molecule comprises the antigen binding portion of an anti-mesothelin antibody, a linker comprising the amino acid sequence of SEQ ID NO: 36, and a PE comprising SEQ ID NO: 286 (T15-L010R+456A). In a preferred embodiment, the antigen binding portion is the Fab fragment of an anti-mesothelin antibody comprising the variable heavy chain domain VH of SEQ ID NO: 45 and the variable light chain domain of SEQ ID NO: 46.

In a preferred embodiment, the chimeric molecule comprises the antigen binding portion of an anti-mesothelin antibody, a linker comprising the amino acid sequence of SEQ ID NO: 36, and a PE comprising SEQ ID NO: 287 (T14-L010R). In a preferred embodiment, the antigen binding portion is the Fab fragment of an anti-mesothelin antibody comprising the variable heavy chain domain VH of SEQ ID NO: 45 and the variable light chain domain of SEQ ID NO: 46.

In a preferred embodiment, the chimeric molecule comprises the antigen binding portion of an anti-mesothelin antibody, a linker comprising the amino acid sequence of SEQ ID NO: 36, and a PE comprising SEQ ID NO: 288 (T15-L010R). In a preferred embodiment, the antigen binding portion is the Fab fragment of an anti-mesothelin antibody comprising the variable heavy chain domain VH of SEQ ID NO: 45 and the variable light chain domain of SEQ ID NO: 46.

In a preferred embodiment, the chimeric molecule comprises the antigen binding portion of an anti-glypican-3 antibody, a furin cleavage sequence (FCS) corresponding to amino acid residues 274-284 of SEQ ID NO: 1 (RHRQPRG-WEQL (SEQ ID NO: 8)) and a PE comprising SEQ ID NO: 289 (T18/T20). In a preferred embodiment, the chimeric molecule comprises the antigen binding portion of an anti-glypican-3 antibody, a linker comprising the amino acid sequence of SEQ ID NO: 36, and a PE comprising SEQ ID NO: 289 (T18/T20). In a preferred embodiment, the antigen binding portion is the Fab fragment of an anti-glypican-3 antibody comprising the CDR1, CDR2 and CDR3 of the variable heavy chain domain VH of SEQ ID NO: 61 (SEQ ID NOs: 65, 69, and 73, respectively) and the CDR1, CDR2 and CDR3 of the variable light chain domain of SEQ ID NO: 62 (SEQ ID NOs: 66, 70, and 74, respectively). In a preferred embodiment, the antigen binding portion is the Fab fragment of an anti-glypican-3 antibody comprising the CDR1, CDR2 and CDR3 of the variable heavy chain domain VH of SEQ ID NO: 77 (SEQ ID NO: 81, 85, and 89, respectively) and the CDR1, CDR2 and CDR3 of the variable light chain domain of SEQ ID NO: 78 (SEQ ID NOs: 82, 86, and 90, respectively). In a preferred embodiment, the antigen binding portion is the Fab fragment of an anti-glypican-3 antibody comprising the variable heavy chain domain VH of SEQ ID NO: 61 and the variable light chain domain of SEQ ID NO: 62. In a preferred embodiment, the antigen binding portion is the Fab fragment of an anti-glypican-3 antibody comprising the variable heavy chain domain VH of SEQ ID NO: 77 and the variable light chain domain of SEQ ID NO: 78.

In a preferred embodiment, the chimeric molecule comprises the antigen binding portion of an anti-glypican-3 antibody, a furin cleavage sequence (FCS) corresponding to amino acid residues 274-284 of SEQ ID NO: 1 (RHRQPRG-WEQL (SEQ ID NO: 8)) and a PE comprising SEQ ID NO: 285 (T14-LO10R+456A). In a preferred embodiment, the chimeric molecule comprises the antigen binding portion of an anti-glypican-3 antibody, a linker comprising the amino acid sequence of SEQ ID NO: 36, and a PE comprising SEQ ID NO: 285 (T14-L010R+456A). In a preferred embodiment, the antigen binding portion is the Fab fragment of an anti-glypican-3 antibody comprising the CDR1, CDR2 and CDR3 of the variable heavy chain domain VH of SEQ ID NO: 61 (SEQ ID NO: 65, 69, and 73, respectively) and the CDR1, CDR2 and CDR3 of the variable light chain domain of SEQ ID NO: 62 (SEQ ID NOs: 66, 70, and 74, respectively). In a preferred embodiment, the antigen binding portion is the Fab fragment of an anti-glypican-3 antibody comprising the CDR1, CDR2 and CDR3 of the variable heavy chain domain VH of SEQ ID NO: 77 (SEQ ID NOs: 81, 85, and 89, respectively) and the CDR1, CDR2 and CDR3 of the variable light chain domain of SEQ ID NO: 78 (SEQ ID NOs: 82, 86, and 90, respectively). In a preferred embodiment, the antigen binding portion is the Fab fragment of an anti-glypican-3 antibody comprising the variable heavy chain domain VH of SEQ ID NO: 61 and the variable light chain domain of SEQ ID NO: 62. In a preferred embodiment, the antigen binding portion is the Fab fragment of an anti-glypican-3 antibody comprising the variable heavy chain domain VH of SEQ ID NO: 77 and the variable light chain domain of SEQ ID NO: 78.

In a preferred embodiment, the chimeric molecule comprises the antigen binding portion of an anti-glypican-3 antibody, a furin cleavage sequence (FCS) corresponding to amino acid residues 274-284 of SEQ ID NO: 1 (RHRQPRG-WEQL (SEQ ID NO: 8)) and a PE comprising SEQ ID NO: 286 (T15-LO10R+456A). In a preferred embodiment, the chimeric molecule comprises the antigen binding portion of an anti-glypican-3 antibody, a linker comprising the amino acid sequence of SEQ ID NO: 36, and a PE comprising SEQ ID NO: 286 (T15-L010R+456A). In a preferred embodiment, the antigen binding portion is the Fab fragment of an anti-glypican-3 antibody comprising the CDR1, CDR2 and CDR3 of the variable heavy chain domain VH of SEQ ID NO: 61 (SEQ ID NO: 65, 69, and 73, respectively) and the CDR1, CDR2 and CDR3 of the variable light chain domain of SEQ ID NO: 62 (SEQ ID NOs: 66, 70, and 74, respectively). In a preferred embodiment, the antigen binding portion is the Fab fragment of an anti-glypican-3 antibody comprising the CDR1, CDR2 and CDR3 of the variable heavy chain domain VH of SEQ ID NO: 77 (SEQ ID NOs: 81, 85, and 89, respectively) and the CDR1, CDR2 and CDR3 of the variable light chain domain of SEQ ID NO: 78 (SEQ ID NOs: 82, 86, and 90, respectively). In a preferred embodiment, the antigen binding portion is the Fab fragment of an anti-glypican-3 antibody comprising the variable heavy chain domain VH of SEQ ID NO: 61 and the variable light chain domain of SEQ ID NO: 62. In a preferred embodiment, the antigen binding portion is the Fab fragment of an anti-glypican-3 antibody comprising the variable heavy chain domain VH of SEQ ID NO: 77 and the variable light chain domain of SEQ ID NO: 78.

In a preferred embodiment, the chimeric molecule comprises the antigen binding portion of an anti-glypican-3 antibody, a furin cleavage sequence (FCS) corresponding to amino acid residues 274-284 of SEQ ID NO: 1 (RHRQPRG-WEQL (SEQ ID NO: 8)) and a PE comprising SEQ ID NO: 287 (T14-LO10R). In a preferred embodiment, the chimeric molecule comprises the antigen binding portion of an anti-glypican-3 antibody, a linker comprising the amino acid sequence of SEQ ID NO: 36, and a PE comprising SEQ ID NO: 287 (T14-LO-1OR). In a preferred embodiment, the antigen binding portion is the Fab fragment of an anti-glypican-3 antibody comprising the CDR1, CDR2 and CDR3 of the variable heavy chain domain VH of SEQ ID NO: 61 (SEQ ID NOs: 65, 69, and 73, respectively) and the CDR1, CDR2 and CDR3 of the variable light chain domain of SEQ ID NO: 62 (SEQ ID NOs: 66, 70, and 74, respectively). In a preferred embodiment, the antigen binding portion is the Fab fragment of an anti-glypican-3 antibody comprising the CDR1, CDR2 and CDR3 of the variable heavy chain domain VH of SEQ ID NO: 77 (SEQ ID NOs: 81, 85, and 89, respectively) and the CDR1, CDR2 and CDR3 of the variable light chain domain of SEQ ID NO: 78 (SEQ ID NOs: 82, 86, and 90, respectively). In a preferred embodiment, the antigen binding portion is the Fab fragment of an anti-glypican-3 antibody comprising the variable heavy chain domain VH of SEQ ID NO: 61 and the variable light chain domain of SEQ ID NO: 62. In a preferred embodiment, the antigen binding portion is the Fab fragment of an anti-glypican-3 antibody comprising the variable heavy chain domain VH of SEQ ID NO: 77 and the variable light chain domain of SEQ ID NO: 78.

In a preferred embodiment, the chimeric molecule comprises the antigen binding portion of an anti-glypican-3 antibody, a furin cleavage sequence (FCS) corresponding to amino acid residues 274-284 of SEQ ID NO: 1 (RHRQPRG-WEQL (SEQ ID NO: 8)) and a PE comprising SEQ ID NO: 288 (T15-LO10R). In a preferred embodiment, the chimeric molecule comprises the antigen binding portion of an anti-glypican-3 antibody, a linker comprising the amino acid sequence of SEQ ID NO: 36, and a PE comprising SEQ ID NO: 288 (T15-L010R). In a preferred embodiment, the antigen binding portion is the Fab fragment of an anti-glypican-3 antibody comprising the CDR1, CDR2 and CDR3 of the variable heavy chain domain VH of SEQ ID NO: 61 (SEQ ID NOs: 65, 69, and 73, respectively) and the CDR1, CDR2 and CDR3 of the variable light chain domain of SEQ ID NO: 62 (SEQ ID NOs: 66, 70, and 74, respectively). In a preferred embodiment, the antigen binding portion is the Fab fragment of an anti-glypican-3 antibody comprising the CDR1, CDR2 and CDR3 of the variable heavy chain domain VH of SEQ ID NO: 77 (SEQ ID NOs: 81, 85, and 89, respectively) and the CDR1, CDR2 and CDR3 of the variable light chain domain of SEQ ID NO: 78 (SEQ ID NOs: 82, 86, and 90, respectively).

In a preferred embodiment, the antigen binding portion is the Fab fragment of an anti-glypican-3 antibody comprising the variable heavy chain domain VH of SEQ ID NO: 61 and the variable light chain domain of SEQ ID NO: 62. In a preferred embodiment, the antigen binding portion is the Fab fragment of an anti-glypican-3 antibody comprising the variable heavy chain domain VH of SEQ ID NO: 77 and the variable light chain domain of SEQ ID NO: 78.

In a preferred embodiment, the chimeric molecule comprises the antigen binding portion of an anti-FAP antibody, a furin cleavage sequence (FCS) corresponding to amino acid residues 274-284 of SEQ ID NO: 1 (RHRQPRGWEQL (SEQ ID NO: 8)) and a PE comprising SEQ ID NO: 289 (T18/T20). In a preferred embodiment, the chimeric molecule comprises the antigen binding portion of an anti-FAP antibody, a linker comprising the amino acid sequence of SEQ ID NO: 36, and a PE comprising SEQ ID NO: 289 (T18/T20). In a preferred embodiment, the antigen binding portion is the Fab fragment of an anti-FAP antibody comprising the CDR1, CDR2 and CDR3 of the variable heavy chain domain VH of SEQ ID NO: 93 (SEQ ID NOs: 97, 101, and 105, respectively) and the CDR1, CDR2 and CDR3 of the variable light chain domain of SEQ ID NO: 94 (SEQ ID NOs: 98, 102, and 106, respectively). In a preferred embodiment, the antigen binding portion is the Fab fragment of an anti-FAP antibody comprising the variable heavy chain domain VH of SEQ ID NO: 93 and the variable light chain domain of SEQ ID NO: 94. In another preferred embodiment, the antigen binding portion is the Fab fragment of an anti-FAP antibody comprising the variable heavy chain domain VH of SEQ ID NO: 93 and the variable light chain domain of SEQ ID NO: 290.

In a preferred embodiment, the chimeric molecule comprises the antigen binding portion of an anti-FAP antibody, a furin cleavage sequence (FCS) corresponding to amino acid residues 274-284 of SEQ ID NO: 1 (RHRQPRGWEQL (SEQ ID NO: 8)) and a PE comprising SEQ ID NO: 285 (T14-L010R+456A). In a preferred embodiment, the chimeric molecule comprises the antigen binding portion of an anti-FAP antibody, a linker comprising the amino acid sequence of SEQ ID NO: 36, and a PE comprising SEQ ID NO: 285 (T14-L010R+456A). In a preferred embodiment, the antigen binding portion is the Fab fragment of an anti-FAP antibody comprising the CDR1, CDR2 and CDR3 of the variable heavy chain domain VH of SEQ ID NO: 93 (SEQ ID NOs: 97, 101, and 105, respectively) and the CDR1, CDR2 and CDR3 of the variable light chain domain of SEQ ID NO: 94 (SEQ ID NOs: 98, 102, and 106, respectively). In a preferred embodiment, the antigen binding portion is the Fab fragment of an anti-FAP antibody comprising the variable heavy chain domain VH of SEQ ID NO: 93 and the variable light chain domain of SEQ ID NO: 94. In another preferred embodiment, the antigen binding portion is the Fab fragment of an anti-FAP antibody comprising the variable heavy chain domain VH of SEQ ID NO: 93 and the variable light chain domain of SEQ ID NO: 290.

In a preferred embodiment, the chimeric molecule comprises the antigen binding portion of an anti-FAP antibody, a furin cleavage sequence (FCS) corresponding to amino acid residues 274-284 of SEQ ID NO: 1 (RHRQPRGWEQL (SEQ ID NO: 8)) and a PE comprising SEQ ID NO: 286 (T15-L010R+456A). In a preferred embodiment, the chimeric molecule comprises the antigen binding portion of an anti-FAP antibody, a linker comprising the amino acid sequence of SEQ ID NO: 36, and a PE comprising SEQ ID NO: 286 (T15-L010R+456A). In a preferred embodiment, the antigen binding portion is the Fab fragment of an anti-FAP antibody comprising the CDR1, CDR2 and CDR3 of the variable heavy chain domain VH of SEQ ID NO: 93 (SEQ ID NOs: 97, 101, and 105, respectively) and the CDR1, CDR2 and CDR3 of the variable light chain domain of SEQ ID NO: 94 (SEQ ID NOs: 98, 102, and 106, respectively). In a preferred embodiment, the antigen binding portion is the Fab fragment of an anti-FAP antibody comprising the variable heavy chain domain VH of SEQ ID NO: 93 and the variable light chain domain of SEQ ID NO: 94. In another preferred embodiment, the antigen binding portion is the Fab fragment of an anti-FAP antibody comprising the variable heavy chain domain VH of SEQ ID NO: 93 and the variable light chain domain of SEQ ID NO: 290.

In a preferred embodiment, the chimeric molecule comprises the antigen binding portion of an anti-FAP antibody, a furin cleavage sequence (FCS) corresponding to amino acid residues 274-284 of SEQ ID NO: 1 (RHRQPRGWEQL (SEQ ID NO: 8)) and a PE comprising SEQ ID NO: 287 (T14-L010R). In a preferred embodiment, the chimeric molecule comprises the antigen binding portion of an anti-FAP antibody, a linker comprising the amino acid sequence of SEQ ID NO: 36, and a PE comprising SEQ ID NO: 287 (T14-L010R). In a preferred embodiment, the antigen binding portion is the Fab fragment of an anti-FAP antibody comprising the CDR1, CDR2 and CDR3 of the variable heavy chain domain VH of SEQ ID NO: 93 (SEQ ID NOs: 97, 101, and 105, respectively) and the CDR1, CDR2 and CDR3 of the variable light chain domain of SEQ ID NO: 94 (SEQ ID NOs: 98, 102, and 106). In a preferred embodiment, the antigen binding portion is the Fab fragment of an anti-FAP antibody comprising the variable heavy chain domain VH of SEQ ID NO: 93 and the variable light chain domain of SEQ ID NO: 94. In another preferred embodiment, the antigen binding portion is the Fab fragment of an anti-FAP antibody comprising the variable heavy chain domain VH of SEQ ID NO: 93 and the variable light chain domain of SEQ ID NO: 290.

In a preferred embodiment, the chimeric molecule comprises the antigen binding portion of an anti-FAP antibody, a furin cleavage sequence (FCS) corresponding to amino acid residues 274-284 of SEQ ID NO: 1 (RHRQPRGWEQL (SEQ ID NO: 8)) and a PE comprising SEQ ID NO: 288 (T15-L010R). In a preferred embodiment, the chimeric molecule comprises the antigen binding portion of an anti-FAP antibody, a linker comprising the amino acid sequence of SEQ ID NO: 36, and a PE comprising SEQ ID NO: 288 (T15-L010R). In a preferred embodiment, the antigen binding portion is the Fab fragment of an anti-FAP antibody comprising the CDR1, CDR2 and CDR3 of the variable heavy chain domain VH of SEQ ID NO: 93 (SEQ ID NOs: 97, 101, and 105, respectively) and the CDR1, CDR2 and CDR3 of the variable light chain domain of SEQ ID NO: 94 (SEQ ID NOs: 98, 102, and 106, respectively). In a preferred embodiment, the antigen binding portion is the Fab fragment of an anti-FAP antibody comprising the variable heavy chain domain VH of SEQ ID NO: 93 and the variable light chain domain of SEQ ID NO: 94. In another preferred embodiment, the antigen binding portion is the Fab fragment of an anti-FAP antibody comprising the variable heavy chain domain VH of SEQ ID NO: 93 and the variable light chain domain of SEQ ID NO: 290. In a preferred embodiment, the chimeric molecule comprises the antigen binding portion of an anti-PSMA antibody, a furin cleavage sequence (FCS) corresponding to amino acid residues 274-284 of SEQ ID NO: 1 (RHRQPRGWEQL (SEQ ID NO: 8)) and a PE comprising SEQ ID NO: 289 (T18/T20). In a preferred embodiment, the chimeric molecule comprises the antigen binding portion of an anti-PSMA antibody, a linker comprising the amino acid sequence of SEQ ID NO: 36, and a PE comprising SEQ ID NO: 289 (T18/T20). In a preferred embodiment, the antigen binding portion is the Fab fragment of an anti-PSMA antibody comprising the CDR1, CDR2 and CDR3 of the variable heavy chain domain VH of SEQ ID NO: 109 (SEQ ID NOs: 113, 117, and 121, respectively) and the CDR1, CDR2 and CDR3 of the variable light chain domain of SEQ ID NO: 110 (SEQ ID NOs: 114, 118, and 122, respectively).

In a preferred embodiment, the chimeric molecule comprises the antigen binding portion of an anti-PSMA antibody, a furin cleavage sequence (FCS) corresponding to amino acid residues 274-284 of SEQ ID NO: 1 (RHRQPRGWEQL (SEQ ID NO: 8)) and a PE comprising SEQ ID NO: 285 (T14-L010R+456A). In a preferred embodiment, the chimeric molecule comprises the antigen binding portion of an anti-PSMA antibody, a linker comprising the amino acid sequence of SEQ ID NO: 36, and a PE comprising SEQ ID NO: 285 (T14-L010R+456A). In a preferred embodiment, the antigen binding portion is the Fab fragment of an anti-PSMA antibody comprising the CDR1, CDR2 and CDR3 of the variable heavy chain domain VH of SEQ ID NO: 109 (SEQ ID NOs: 113, 117, and 121, respectively) and the CDR1, CDR2 and CDR3 of the variable light chain domain of SEQ ID NO: 110 (SEQ ID NOs: 114, 118, and 122, respectively).

In a preferred embodiment, the chimeric molecule comprises the antigen binding portion of an anti-PSMA antibody, a furin cleavage sequence (FCS) corresponding to amino acid residues 274-284 of SEQ ID NO: 1 (RHRQPRGWEQL (SEQ ID NO: 8)) and a PE comprising SEQ ID NO: 286 (T15-L010R+456A). In a preferred embodiment, the chimeric molecule comprises the antigen binding portion of an anti-PSMA antibody, a linker comprising the amino acid sequence of SEQ ID NO: 36, and a PE comprising SEQ ID NO: 286 (T15-L010R+456A). In a preferred embodiment, the antigen binding portion is the Fab fragment of an anti-PSMA antibody comprising the CDR1, CDR2 and CDR3 of the variable heavy chain domain VH of SEQ ID NO: 109 (SEQ ID NOs: 113, 117, and 121, respectively) and the CDR1, CDR2 and CDR3 of the variable light chain domain of SEQ ID NO: 110 (SEQ ID NOs: 114, 118, and 122, respectively).

In a preferred embodiment, the chimeric molecule comprises the antigen binding portion of an anti-PSMA antibody, a furin cleavage sequence (FCS) corresponding to amino acid residues 274-284 of SEQ ID NO: 1 (RHRQPRGWEQL (SEQ ID NO: 8)) and a PE comprising SEQ ID NO: 287 (T14-L010R). In a preferred embodiment, the chimeric molecule comprises the antigen binding portion of an anti-PSMA antibody, a linker comprising the amino acid sequence of SEQ ID NO: 36, and a PE comprising SEQ ID NO: 287 (T14-L010R). In a preferred embodiment, the antigen binding portion is the Fab fragment of an anti-PSMA antibody comprising the CDR1, CDR2 and CDR3 of the variable heavy chain domain VH of SEQ ID NO: 109 (SEQ ID NOs: 113, 117, and 121, respectively) and the CDR1, CDR2 and CDR3 of the variable light chain domain of SEQ ID NO: 110 (SEQ ID NOs: 114, 118, and 122, respectively).

In a preferred embodiment, the chimeric molecule comprises the antigen binding portion of an anti-PSMA antibody, a furin cleavage sequence (FCS) corresponding to amino acid residues 274-284 of SEQ ID NO: 1 (RHRQPRGWEQL (SEQ ID NO: 8)) and a PE comprising SEQ ID NO: 288 (T15-L010R). In a preferred embodiment, the chimeric molecule comprises the antigen binding portion of an anti-PSMA antibody, a linker comprising the amino acid sequence of SEQ ID NO: 36, and a PE comprising SEQ ID NO: 288 (T15-L010R). In a preferred embodiment, the antigen binding portion is the Fab fragment of an anti-PSMA antibody comprising the CDR1, CDR2 and CDR3 of the variable heavy chain domain VH of SEQ ID NO: 109 (SEQ ID NOs: 113, 117, and 121, respectively) and the CDR1, CDR2 and CDR3 of the variable light chain domain of SEQ ID NO: 110 (SEQ ID NOs: 114, 118, and 122, respectively).

In a preferred embodiment, the chimeric molecule comprises the antigen binding portion of an anti-CAIX antibody, a furin cleavage sequence (FCS) corresponding to amino acid residues 274-284 of SEQ ID NO: 1 (RHRQPRGWEQL (SEQ ID NO: 8)) and a PE comprising SEQ ID NO: 289 (T18/T20). In a preferred embodiment, the chimeric molecule comprises the antigen binding portion of an anti-CAIX antibody, a linker comprising the amino acid sequence of SEQ ID NO: 36, and a PE comprising SEQ ID NO: 289 (T18/T20). In a preferred embodiment, the antigen binding portion is the Fab fragment of an anti-CAIX antibody comprising the CDR1, CDR2 and CDR3 of the variable heavy chain domain VH of SEQ ID NO: 125 (SEQ ID NOs: 129, 133, and 137, respectively) and the CDR1, CDR2 and CDR3 of the variable light chain domain of SEQ ID NO: 126 (SEQ ID NOs: 130, 134, and 138).

In a preferred embodiment, the chimeric molecule comprises the antigen binding portion of an anti-CAIX antibody, a furin cleavage sequence (FCS) corresponding to amino acid residues 274-284 of SEQ ID NO: 1 (RHRQPRGWEQL (SEQ ID NO: 8)) and a PE comprising SEQ ID NO: 285 (T14-L010R+456A). In a preferred embodiment, the chimeric molecule comprises the antigen binding portion of an anti-CAIX antibody, a linker comprising the amino acid sequence of SEQ ID NO: 36, and a PE comprising SEQ ID NO: 285 (T14-L010R+456A). In a preferred embodiment, the antigen binding portion is the Fab fragment of an anti-CAIX antibody comprising the CDR1, CDR2 and CDR3 of the variable heavy chain domain VH of SEQ ID NO: 125 (SEQ ID NOs: 129, 133, and 137, respectively) and the CDR1, CDR2 and CDR3 of the variable light chain domain of SEQ ID NO: 126 (SEQ ID NOs: 130, 134, and 138, respectively).

In a preferred embodiment, the chimeric molecule comprises the antigen binding portion of an anti-CAIX antibody, a furin cleavage sequence (FCS) corresponding to amino acid residues 274-284 of SEQ ID NO: 1 (RHRQPRGWEQL (SEQ ID NO: 8)) and a PE comprising SEQ ID NO: 286 (T15-L010R+456A). In a preferred embodiment, the chimeric molecule comprises the antigen binding portion of an anti-CAIX antibody, a linker comprising the amino acid sequence of SEQ ID NO: 36, and a PE comprising SEQ ID NO: 286 (T15-L010R+456A). In a preferred embodiment, the antigen binding portion is the Fab fragment of an anti-CAIX antibody comprising the CDR1, CDR2 and CDR3 of the variable heavy chain domain VH of SEQ ID NO: 125 (SEQ ID NOs: 129, 133, and 137, respectively) and the CDR1, CDR2 and CDR3 of the variable light chain domain of SEQ ID NO: 126 (SEQ ID NOs: 130, 134, and 138, respectively).

In a preferred embodiment, the chimeric molecule comprises the antigen binding portion of an anti-CAIX antibody, a furin cleavage sequence (FCS) corresponding to amino acid residues 274-284 of SEQ ID NO: 1 (RHRQPRGWEQL (SEQ ID NO: 8)) and a PE comprising SEQ ID NO: 287 (T14-L010R). In a preferred embodiment, the chimeric molecule comprises the antigen binding portion of an anti-CAIX antibody, a linker comprising the amino acid sequence of SEQ ID NO: 36, and a PE comprising SEQ ID NO: 287 (T14-L010R). In a preferred embodiment, the antigen binding portion is the Fab fragment of an anti-CAIX antibody comprising the CDR1, CDR2 and CDR3 of the variable heavy chain domain VH of SEQ ID NO: 125 (SEQ ID NOs: 129, 133, and 137, respectively) and the CDR1, CDR2 and CDR3 of the variable light chain domain of SEQ ID NO: 126 (SEQ ID NOs: 130, 134, and 138, respectively).

In a preferred embodiment, the chimeric molecule comprises the antigen binding portion of an anti-CAIX antibody, a furin cleavage sequence (FCS) corresponding to amino acid residues 274-284 of SEQ ID NO: 1 (RHRQPRGWEQL (SEQ ID NO: 8)) and a PE comprising SEQ ID NO: 288 (T15-LO10R). In a preferred embodiment, the chimeric molecule comprises the antigen binding portion of an anti-CAIX antibody, a linker comprising the amino acid sequence of SEQ ID NO: 36, and a PE comprising SEQ ID NO: 288 (T15-L010R). In a preferred embodiment, the antigen binding portion is the Fab fragment of an anti-CAIX antibody comprising the CDR1, CDR2 and CDR3 of the variable heavy chain domain VH of SEQ ID NO: 125 (SEQ ID NOs: 129, 133, and 137, respectively) and the CDR1, CDR2 and CDR3 of the variable light chain domain of SEQ ID NO: 126 (SEQ ID NOs: 130, 134, and 138, respectively). In a preferred embodiment, the chimeric molecule comprises the antigen binding portion of an anti-L1CAM antibody, a furin cleavage sequence (FCS) corresponding to amino acid residues 274-284 of SEQ ID NO: 1 (RHRQPRGWEQL (SEQ ID NO: 8)) and a PE comprising SEQ ID NO: 289 (T18/T20). In a preferred embodiment, the chimeric molecule comprises the antigen binding portion of an anti-L1CAM antibody, a linker comprising the amino acid sequence of SEQ ID NO: 36, and aPE comprising. In a preferred embodiment, the antigen binding portion is the Fab fragment of an anti-L1CAM antibody comprising the CDR1, CDR2 and CDR3 of the variable heavy chain domain VH of SEQ ID NO: 141 (SEQ ID NOs: 145, 149, and 153, respectively) and the CDR1, CDR2 and CDR3 of the variable light chain domain of SEQ ID NO: 142 (SEQ ID NOs: 146, 150, and 154, respectively). In a preferred embodiment, the antigen binding portion is the Fab fragment of an anti-L1CAM antibody comprising the variable heavy chain domain VH of SEQ ID NO: 157 and the variable light chain domain of SEQ ID NO: 158. In a preferred embodiment, the antigen binding portion is the Fab fragment of an anti-L1CAM antibody comprising the variable heavy chain domain VH of SEQ ID NO: 173 and the variable light chain domain of SEQ ID NO: 174.

In a preferred embodiment, the chimeric molecule comprises the antigen binding portion of an anti-L1CAM antibody, a furin cleavage sequence (FCS) corresponding to amino acid residues 274-284 of SEQ ID NO: 1 (RHRQPRGWEQL (SEQ ID NO: 8)) and a PE comprising SEQ ID NO: 285 (T14-LO10R+456A). In a preferred embodiment, the chimeric molecule comprises the antigen binding portion of an anti-L1CAM antibody, a linker comprising the amino acid sequence of SEQ ID NO: 36, and a PE comprising SEQ ID NO: 285 (T14-L010R+456A). In a preferred embodiment, the antigen binding portion is the Fab fragment of an anti-L1CAM antibody comprising the CDR1, CDR2 and CDR3 of the variable heavy chain domain VH of SEQ ID NO: 141 (SEQ ID NOs: 145, 149, and 153, respectively) and the CDR1, CDR2 and CDR3 of the variable light chain domain of SEQ ID NO: 142 (SEQ ID NOs: 146, 150, and 154, respectively). In a preferred embodiment, the antigen binding portion is the Fab fragment of an anti-L1CAM antibody comprising the variable heavy chain domain VH of SEQ ID NO: 157 and the variable light chain domain of SEQ ID NO: 158. In a preferred embodiment, the antigen binding portion is the Fab fragment of an anti-L1CAM antibody comprising the variable heavy chain domain VH of SEQ ID NO: 173 and the variable light chain domain of SEQ ID NO: 174.

In a preferred embodiment, the chimeric molecule comprises the antigen binding portion of an anti-L1CAM antibody, a furin cleavage sequence (FCS) corresponding to amino acid residues 274-284 of SEQ ID NO: 1 (RHRQPRG-WEQL (SEQ ID NO: 8)) and a PE comprising SEQ ID NO: 286 (T15-LO10R+456A). In a preferred embodiment, the chimeric molecule comprises the antigen binding portion of an anti-L1CAM antibody, a linker comprising the amino acid sequence of SEQ ID NO: 36, and a PE comprising SEQ ID NO: 286 (T15-L010R+456A). In a preferred embodiment, the antigen binding portion is the Fab fragment of an anti-L1CAM antibody comprising the CDR1, CDR2 and CDR3 of the variable heavy chain domain VH of SEQ ID NO: 141 (SEQ ID NOs: 145, 149, and 153, respectively) and the CDR1, CDR2 and CDR3 of the variable light chain domain of SEQ ID NO: 142 (SEQ ID NOs: 146, 150, and 154, respectively). In a preferred embodiment, the antigen binding portion is the Fab fragment of an anti-L1CAM antibody comprising the variable heavy chain domain VH of SEQ ID NO: 157 and the variable light chain domain of SEQ ID NO: 158. In a preferred embodiment, the antigen binding portion is the Fab fragment of an anti-L1CAM antibody comprising the variable heavy chain domain VH of SEQ ID NO: 173 and the variable light chain domain of SEQ ID NO: 174.

In a preferred embodiment, the chimeric molecule comprises the antigen binding portion of an anti-L1CAM antibody, a furin cleavage sequence (FCS) corresponding to amino acid residues 274-284 of SEQ ID NO: 1 (RHRQPRG-WEQL (SEQ ID NO: 8)) and a PE comprising SEQ ID NO: 287 (T14-LO10R). In a preferred embodiment, the chimeric molecule comprises the antigen binding portion of an anti-L1CAM antibody, a linker comprising the amino acid sequence of SEQ ID NO: 36, and a PE comprising SEQ ID NO: 287 (T14-L010R). In a preferred embodiment, the antigen binding portion is the Fab fragment of an anti-L1CAM antibody comprising the CDR1, CDR2 and CDR3 of the variable heavy chain domain VH of SEQ ID NO: 141 (SEQ ID NOs: 145, 149, and 153, respectively) and the CDR1, CDR2 and CDR3 of the variable light chain domain of SEQ ID NO: 142 (SEQ ID NOs: 146, 150, and 154, respectively). In a preferred embodiment, the antigen binding portion is the Fab fragment of an anti-L1CAM antibody comprising the variable heavy chain domain VH of SEQ ID NO: 157 and the variable light chain domain of SEQ ID NO: 158. In a preferred embodiment, the antigen binding portion is the Fab fragment of an anti-L1CAM antibody comprising the variable heavy chain domain VH of SEQ ID NO: 173 and the variable light chain domain of SEQ ID NO: 174.

In a preferred embodiment, the chimeric molecule comprises the antigen binding portion of an anti-L1CAM antibody, a furin cleavage sequence (FCS) corresponding to amino acid residues 274-284 of SEQ ID NO: 1 (RHRQPRG-WEQL (SEQ ID NO: 8)) and a PE comprising SEQ ID NO: 288 (T15-LO10R). In a preferred embodiment, the chimeric molecule comprises the antigen binding portion of an anti-L1CAM antibody, a linker comprising the amino acid sequence of SEQ ID NO: 36, and a PE comprising SEQ ID NO: 288 (T15-L010R). In a preferred embodiment, the antigen binding portion is the Fab fragment of an anti-L1CAM antibody comprising the CDR1, CDR2 and CDR3 of the variable heavy chain domain VH of SEQ ID NO: 141 (SEQ ID NOs: 145, 149, and 153, respectively) and the CDR1, CDR2 and CDR3 of the variable light chain domain of SEQ ID NO: 142 (SEQ ID NOs: 146, 150, and 154, respectively). In a preferred embodiment, the antigen binding portion is the Fab fragment of an anti-L1CAM antibody comprising the variable heavy chain domain VH of SEQ ID NO: 157 and the variable light chain domain of SEQ ID NO: 158. In a preferred embodiment, the antigen binding portion is the Fab fragment of an anti-L1CAM antibody comprising the variable heavy chain domain VH of SEQ ID NO: 173 and the variable light chain domain of SEQ ID NO: 174. Included in the scope of the invention are functional portions of the inventive PEs and chimeric molecules described herein. The term "functional portion" when used in reference to a PE or chimeric molecule refers to any part or fragment of the PE or chimeric molecule of the invention, which part or fragment retains the biological activity of the PE or chimeric molecule of which it is a part (the parent PE or chimeric molecule). Functional portions encompass, for example, those parts of a PE or chimeric molecule that retain the ability to specifically bind to and destroy or inhibit the growth of target cells or treat or prevent cancer, to a similar extent, the same extent, or to a higher extent, as the parent PE or chimeric molecule. In reference to the parent PE or chimeric molecule, the functional portion can comprise, for instance, about 10% or more, about 25% or more, about 30% or more, about 50% or more, about 68% or more, about 80% or more, about 90% or more, or about 95% or more, of the parent PE or chimeric molecule.

The functional portion can comprise additional amino acids at the amino or carboxy terminus of the portion, or at both termini, which additional amino acids are not found in the amino acid sequence of the parent PE or chimeric molecule. Desirably, the additional amino acids do not interfere with the biological function of the functional portion, e.g., specifically binding to and destroying or inhibiting the growth of target cells, having the ability to treat or prevent cancer, etc. More desirably, the additional amino acids enhance the biological activity, as compared to the biological activity of the parent PE or chimeric molecule.

Included in the scope of the invention are functional variants of the inventive PEs and chimeric molecules described herein. The term "functional variant" as used herein refers to a PE or chimeric molecule having substantial or significant sequence identity or similarity to a parent PE or chimeric molecule, which functional variant retains the biological activity of the PE or chimeric molecule of which it is a variant. Functional variants encompass, for example, those variants of the PE or chimeric molecule described herein (the parent PE or chimeric molecule) that retain the ability to specifically bind to and destroy or inhibit the growth of target cells to a similar extent, the same extent, or to a higher extent, as the parent PE or chimeric molecule. In reference to the parent PE or chimeric molecule, the functional variant can, for instance, be about 30% or more, about 50% or more, about 75% or more, about 80% or more, about 90% or more, about 95% or more, about 96% or more, about 97% or more, about 98% or more, or about 99% or more identical in amino acid sequence to the parent PE or chimeric molecule.

The functional variant can, for example, comprise the amino acid sequence of the parent PE or chimeric molecule with at least one conservative amino acid substitution. Conservative amino acid substitutions are known in the art and include amino acid substitutions in which one amino acid having certain chemical and/or physical properties is exchanged for another amino acid that has the same chemical or physical properties. For instance, the conservative amino acid substitution can be an acidic amino acid substituted for another acidic amino acid (e.g., Asp or Glu), an amino acid with a nonpolar side chain substituted for another amino acid with a nonpolar side chain (e.g., Ala, Gly, Val, Ile, Leu, Met, Phe, Pro, Trp, Val, etc.), a basic amino acid substituted for another basic amino acid (Lys, Arg, etc.), an amino acid with a polar side chain substituted for another amino acid with a polar side chain (Asn, Cys, Gln, Ser, Thr, Tyr, etc.), etc.

Alternatively or additionally, the functional variants can comprise the amino acid sequence of the parent PE or chimeric molecule with at least one non-conservative amino acid substitution. In this case, it is preferable for the non-conservative amino acid substitution to not interfere with or inhibit the biological activity of the functional variant. Preferably, the non-conservative amino acid substitution enhances the biological activity of the functional variant, such that the biological activity of the functional variant is increased as compared to the parent PE or chimeric molecule.

The PE or chimeric molecule of the invention can consist essentially of the specified amino acid sequence or sequences described herein, such that other components of the functional variant, e.g., other amino acids, do not materially change the biological activity of the functional variant.

The PE or chimeric molecule of the invention (including functional portions and functional variants) of the invention can comprise synthetic amino acids in place of one or more naturally-occurring amino acids. Such synthetic amino acids are known in the art and include, for example, aminocyclohexane carboxylic acid, norleucine, α-amino n-decanoic acid, homoserine, S-acetylaminomethyl-cysteine, trans-3- and trans-4-hydroxyproline, 4-aminophenylalanine, 4-nitrophenylalanine, 4-chlorophenylalanine, 4-carboxyphenylalanine, β-phenylserine β-hydroxyphenylalanine, phenylglycine, α-naphthylalanine, cyclohexylalanine, cyclohexylglycine, indoline-2-carboxylic acid, 1,2,3,4-tetrahydroisoquinoline-3-carboxylic acid, aminomalonic acid, aminomalonic acid monoamide, N'-benzyl-N'-methyl-lysine, N',N'-dibenzyl-lysine, 6-hydroxylysine, ornithine, α-aminocyclopentane carboxylic acid, α-aminocyclohexane carboxylic acid, α-aminocycloheptane carboxylic acid, α-(2-amino-2-norbornane)-carboxylic acid, α,γ-diaminobutyric acid, α,β-diaminopropionic acid, homophenylalanine, and α-tert-butylglycine.

The PE or chimeric molecule of the invention (including functional portions and functional variants) can be glycosylated, amidated, carboxylated, phosphorylated, esterified, N-acylated, cyclized via, e.g., a disulfide bridge, or converted into an acid addition salt and/or optionally dimerized or polymerized, or conjugated.

An embodiment of the invention provides a method of producing the inventive PE comprising (a) recombinantly expressing the PE and (b) purifying the PE. The PEs and chimeric molecules of the invention (including functional portions and functional variants) can be obtained by methods of producing proteins and polypeptides known in the art. Suitable methods of de novo synthesizing polypeptides and proteins are described in references, such as Chan et al., *Fmoc Solid Phase Peptide Synthesis*, Oxford University Press, Oxford, United Kingdom, 2005; *Peptide and Protein Drug Analysis*, ed. Reid, R., Marcel Dekker, Inc., 2000; *Epitope Mapping*, ed. Westwood et al., Oxford University Press, Oxford, United Kingdom, 2000; and U.S. Pat. No. 5,449,752. Also, the PEs and chimeric molecules of the invention can be recombinantly expressed using the nucleic acids described herein using standard recombinant methods. See, for instance, Sambrook et al., *Molecular Cloning: A Laboratory Manual*, 3$^{rd}$ ed., Cold Spring Harbor Press, Cold Spring Harbor, N.Y. 2001; and Ausubel et al., *Current Protocols in Molecular Biology*, Greene Publishing Associates and John Wiley & Sons, NY, 1994.

The method further comprises purifying the PE. Once expressed, the inventive PEs may be purified in accordance with purification techniques known in the art. Exemplary purification techniques include, but are not limited to, ammonium sulfate precipitation, affinity columns, and column chromatography, or by procedures described in, e.g., R. Scopes, *Protein Purification*, Springer-Verlag, NY (1982).

Another embodiment of the invention provides a method of producing the inventive chimeric molecule comprising (a) recombinantly expressing the chimeric molecule and (b) purifying the chimeric molecule. The chimeric molecule may be recombinantly expressed and purified as described herein with respect to other aspects of the invention. In an embodiment of the invention, recombinantly expressing the chimeric molecule comprises inserting a nucleotide sequence encoding a targeting moiety and a nucleotide sequence encoding a PE into a vector. The method may comprise inserting the nucleotide sequence encoding the targeting moiety and the nucleotide sequence encoding the PE in frame so that it encodes one continuous polypeptide including a functional targeting moiety region and a functional PE region. In an embodiment of the invention, the method comprises ligating a nucleotide sequence encoding the PE to a nucleotide sequence encoding a targeting moiety so that, upon expression, the PE is located at the carboxyl terminus of the targeting moiety. In an alternative embodiment, the method comprises ligating a nucleotide sequence encoding the PE to a nucleotide sequence encoding a targeting moiety so that, upon expression, the PE is located at the amino terminus of the targeting moiety.

Still another embodiment of the invention provides a method of producing the inventive chimeric molecule comprising (a) recombinantly expressing the inventive PE, (b) purifying the PE, and (c) covalently linking a targeting moiety to the purified PE. The inventive PE may be recombinantly expressed as described herein with respect to other aspects of the invention. The method further comprises covalently linking a targeting moiety to the purified PE. The method of attaching a PE to a targeting moiety may vary according to the chemical structure of the targeting moiety. For example, the method may comprise reacting any one or more of a variety of functional groups e.g., carboxylic acid (COOH), free amine (—$NH_2$), or sulfhydryl (—SH) groups present on the PE with a suitable functional group on the targeting moiety, thereby forming a covalent bind between the PE and the targeting moiety. Alternatively or additionally, the method may comprise derivatizing the targeting moiety or PE to expose or to attach additional reactive functional groups. Derivatizing may also include attaching one or more linkers to the targeting moiety or PE.

In another embodiment of the invention, the inventive PEs and chimeric molecules may be produced using non-recombinant methods. For example, the inventive PEs and chimeric molecules described herein (including functional portions and functional variants) can be commercially synthesized by companies, such as Synpep (Dublin, Calif.), Peptide Technologies Corp. (Gaithersburg, Md.), and Multiple Peptide Systems (San Diego, Calif.). In this respect, the inventive PEs and chimeric molecules can be synthetic, recombinant, isolated, and/or purified.

It may be desirable, in some circumstances, to free the PE from the targeting moiety when the chimeric molecule has reached one or more target cells. In this regard, the inventive chimeric molecules may comprise a cleavable linker. The linker may be cleavable by any suitable means, e.g., enzymatically. For example, when the target cell is a cancer (e.g., tumor) cell, the chimeric molecule may include a linker cleavable under conditions present at the tumor site (e.g., when exposed to tumor-associated enzymes or acidic pH).

An embodiment of the invention provides a nucleic acid comprising a nucleotide sequence encoding any of the inventive PEs or the inventive chimeric molecules described herein. The term "nucleic acid," as used herein, includes "polynucleotide," "oligonucleotide," and "nucleic acid molecule," and generally means a polymer of DNA or RNA, which can be single-stranded or double-stranded, which can be synthesized or obtained (e.g., isolated and/or purified) from natural sources, which can contain natural, non-natural or altered nucleotides, and which can contain a natural, non-natural, or altered internucleotide linkage, such as a phosphoroamidate linkage or a phosphorothioate linkage, instead of the phosphodiester found between the nucleotides of an unmodified oligonucleotide. It is generally preferred that the nucleic acid does not comprise any insertions, deletions, inversions, and/or substitutions. However, it may be suitable in some instances, as discussed herein, for the nucleic acid to comprise one or more insertions, deletions, inversions, and/or substitutions.

Preferably, the nucleic acids of the invention are recombinant. As used herein, the term "recombinant" refers to (i) molecules that are constructed outside living cells by joining natural or synthetic nucleic acid segments, or (ii) molecules that result from the replication of those described in (i) above. For purposes herein, the replication can be in vitro replication or in vivo replication.

The nucleic acids can be constructed based on chemical synthesis and/or enzymatic ligation reactions using procedures known in the art. See, for example, Sambrook et al., supra, and Ausubel et al., supra. For example, a nucleic acid can be chemically synthesized using naturally occurring nucleotides or variously modified nucleotides designed to increase the biological stability of the molecules or to increase the physical stability of the duplex formed upon hybridization (e.g., phosphorothioate derivatives and acridine substituted nucleotides). Examples of modified nucleotides that can be used to generate the nucleic acids include, but are not limited to, 5-fluorouracil, 5-bromouracil, 5-chlorouracil, 5-iodouracil, hypoxanthine, xanthine, 4-acetylcytosine, 5-(carboxyhydroxymethyl) uracil, 5-carboxymethylaminomethyl-2-thiouridine, 5-carboxymethylaminomethyluracil, dihydrouracil, beta-D-galactosylqueosine, inosine, $N^6$-isopentenyladenine, 1-methylguanine, 1-methylinosine, 2,2-dimethylguanine, 2-methyladenine, 2-methylguanine, 3-methylcytosine, 5-methylcytosine, $N^6$-substituted adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-$N^6$-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, and 2,6-diaminopurine. Alternatively, one or more of the nucleic acids of the invention can be purchased from companies, such as Macromolecular Resources (Fort Collins, Colo.) and Synthegen (Houston, Tex.).

The invention also provides a nucleic acid comprising a nucleotide sequence which is complementary to the nucleotide sequence of any of the nucleic acids described herein or a nucleotide sequence which hybridizes under stringent conditions to the nucleotide sequence of any of the nucleic acids described herein.

The nucleotide sequence which hybridizes under stringent conditions preferably hybridizes under high stringency conditions. By "high stringency conditions" is meant that the nucleotide sequence specifically hybridizes to a target sequence (the nucleotide sequence of any of the nucleic acids described herein) in an amount that is detectably stronger than non-specific hybridization. High stringency conditions include conditions which would distinguish a polynucleotide with an exact complementary sequence, or one containing only a few scattered mismatches, from a random sequence that happened to have only a few small regions (e.g., 3-10 bases) that matched the nucleotide sequence. Such small regions of complementarity are more easily melted than a full-length complement of 14-17 or more bases, and high stringency hybridization makes them easily distinguishable. Relatively high stringency conditions would include, for example, low salt and/or high temperature conditions, such as provided by about 0.02-0.1 M NaCl or the equivalent, at temperatures of about 50-70° C. Such high stringency conditions tolerate little, if any, mismatch between the nucleotide sequence and the template or target strand, and are particularly suitable for detecting expression of any of the inventive PEs or chimeric molecules. It is generally appreciated that conditions can be rendered more stringent by the addition of increasing amounts of formamide.

The invention also provides a nucleic acid comprising a nucleotide sequence that is about 70% or more, e.g., about 80% or more, about 90% or more, about 91% or more, about 92% or more, about 93% or more, about 94% or more, about 95% or more, about 96% or more, about 97% or more, about 98% or more, or about 99% or more identical to any of the nucleic acids described herein.

The nucleic acids of the invention can be incorporated into a recombinant expression vector. In this regard, the invention provides recombinant expression vectors comprising any of the nucleic acids of the invention. For purposes herein, the term "recombinant expression vector" means a genetically-modified oligonucleotide or polynucleotide construct that permits the expression of an mRNA, protein, polypeptide, or peptide by a host cell, when the construct comprises a nucleotide sequence encoding the mRNA, protein, polypeptide, or peptide, and the vector is contacted with the cell under conditions sufficient to have the mRNA, protein, polypeptide, or peptide expressed within the cell. The vectors of the invention are not naturally-occurring as a whole. However, parts of the vectors can be naturally-occurring. The inventive recombinant expression vectors can comprise any type of nucleotides, including, but not limited to DNA and RNA, which can be single-stranded or double-stranded, which can be synthesized or obtained in part from natural sources, and which can contain natural, non-natural or altered nucleotides. The recombinant expression vectors can comprise naturally-occurring, non-naturally-occurring internucleotide linkages, or both types of linkages. Preferably, the non-naturally occurring or altered nucleotides or internucleotide linkages does not hinder the transcription or replication of the vector.

The recombinant expression vector of the invention can be any suitable recombinant expression vector, and can be used to transform or transfect any suitable host cell. Suitable vectors include those designed for propagation and expansion or for expression or for both, such as plasmids and viruses. The vector can be selected from the group consisting of the pUC series (Fermentas Life Sciences), the pBluescript series (Stratagene, LaJolla, Calif.), the pET series (Novagen, Madison, Wis.), the pGEX series (Pharmacia Biotech, Uppsala, Sweden), and the pEX series (Clontech, Palo Alto, Calif.). Bacteriophage vectors, such as λGT10, λGT11, λZapII (Stratagene), λEMBL4, and λNM1149, also can be used. Examples of plant expression vectors include pBI01, pBI101.2, pBI101.3, pBI121 and pBIN19 (Clontech). Examples of animal expression vectors include pEUK-Cl, pMAM, and pMAMneo (Clontech). Preferably, the recombinant expression vector is a viral vector, e.g., a retroviral vector.

The recombinant expression vectors of the invention can be prepared using standard recombinant DNA techniques described in, for example, Sambrook et al., supra, and Ausubel et al., supra. Constructs of expression vectors, which are circular or linear, can be prepared to contain a replication system functional in a prokaryotic or eukaryotic host cell. Replication systems can be derived, e.g., from ColEl, 2μ plasmid, λ, SV40, bovine papilloma virus, and the like.

Desirably, the recombinant expression vector comprises regulatory sequences, such as transcription and translation initiation and termination codons, which are specific to the type of host (e.g., bacterium, fungus, plant, or animal) into which the vector is to be introduced, as appropriate and taking into consideration whether the vector is DNA- or RNA-based.

The recombinant expression vector can include one or more marker genes, which allow for selection of transformed or transfected hosts. Marker genes include biocide resistance, e.g., resistance to antibiotics, heavy metals, etc., complementation in an auxotrophic host to provide prototrophy, and the like. Suitable marker genes for the inventive expression vectors include, for instance, neomycin/G418 resistance genes, hygromycin resistance genes, histidinol resistance genes, tetracycline resistance genes, and ampicillin resistance genes.

The recombinant expression vector can comprise a native or nonnative promoter operably linked to the nucleotide sequence encoding the inventive PE or chimeric molecule (including functional portions and functional variants), or to the nucleotide sequence which is complementary to or which hybridizes to the nucleotide sequence encoding the PE or chimeric molecule. The selection of promoters, e.g., strong, weak, inducible, tissue-specific, and developmental-specific, is within the ordinary skill of the artisan. Similarly, the combining of a nucleotide sequence with a promoter is also within the ordinary skill of the artisan. The promoter can be a non-viral promoter or a viral promoter, e.g., a cytomegalovirus (CMV) promoter, an SV40 promoter, an RSV promoter, or a promoter found in the long-terminal repeat of the murine stem cell virus.

The inventive recombinant expression vectors can be designed for either transient expression, for stable expression, or for both. Also, the recombinant expression vectors can be made for constitutive expression or for inducible expression.

Another embodiment of the invention further provides a host cell comprising any of the recombinant expression vectors described herein. As used herein, the term "host cell" refers to any type of cell that can contain the inventive recombinant expression vector. The host cell can be a eukaryotic cell, e.g., plant, animal, fungi, or algae, or can be a prokaryotic cell, e.g., bacteria or protozoa. The host cell can be a cultured cell, an adherent cell or a suspended cell, i.e., a cell that grows in suspension. For purposes of producing a recombinant inventive PE or chimeric molecule, the host cell is preferably a prokaryotic cell, e.g., an *E. coli* cell.

Also provided by the invention is a population of cells comprising at least one host cell described herein. The population of cells can be a heterogeneous population comprising the host cell comprising any of the recombinant expression vectors described, in addition to at least one other cell, e.g., a host cell which does not comprise any of the recombinant expression vectors. Alternatively, the population of cells can be a substantially homogeneous population, in which the population comprises mainly (e.g., consisting essentially of) host cells comprising the recombinant expression vector. The population also can be a clonal population of cells, in which all cells of the population are clones of a single host cell comprising a recombinant expression vector, such that all cells of the population comprise the recombinant expression vector. In one embodiment of the invention, the population of cells is a clonal population of host cells comprising a recombinant expression vector as described herein.

The inventive PEs, chimeric molecules (including functional portions and functional variants), nucleic acids, recombinant expression vectors, host cells (including populations thereof), and populations of cells can be isolated and/or purified. The term "isolated" as used herein means having been removed from its natural environment. The term "purified" as used herein means having been increased in purity, wherein "purity" is a relative term, and not to be necessarily construed as absolute purity. For example, the purity can be about 50% or more, about 60% or more, about 70% or more, about 80% or more, about 90% or more, or about 100%. The purity preferably is about 90% or more (e.g., about 90% to about 95%) and more preferably about 98% or more (e.g., about 98% to about 99%).

The inventive PEs, chimeric molecules (including functional portions and functional variants), nucleic acids, recombinant expression vectors, host cells (including populations thereof), and populations of cells, all of which are collectively referred to as "inventive PE materials" hereinafter, can be formulated into a composition, such as a pharmaceutical composition. In this regard, the invention provides a pharmaceutical composition comprising any of the PEs, chimeric molecules (including functional portions and functional variants), nucleic acids, recombinant expression vectors, host cells (including populations thereof), and populations of cells, and a pharmaceutically acceptable carrier. The inventive pharmaceutical composition containing any of the inventive PE materials can comprise more than one inventive PE material, e.g., a polypeptide and a nucleic acid, or two or more different PEs. Alternatively, the pharmaceutical composition can comprise an inventive PE material in combination with one or more other pharmaceutically active agents or drugs, such as a chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, vincristine, etc.

Preferably, the carrier is a pharmaceutically acceptable carrier. With respect to pharmaceutical compositions, the carrier can be any of those conventionally used and is limited only by chemico-physical considerations, such as solubility and lack of reactivity with the active compound(s), and by the route of administration. The pharmaceutically acceptable carriers described herein, for example, vehicles, adjuvants, excipients, and diluents, are well-known to those skilled in the art and are readily available to the public. It is preferred that the pharmaceutically acceptable carrier be one which is chemically inert to the active agent(s) and one which has no detrimental side effects or toxicity under the conditions of use.

The choice of carrier will be determined in part by the particular inventive PE material, as well as by the particular method used to administer the inventive PE material. Accordingly, there are a variety of suitable formulations of the pharmaceutical composition of the invention. The following formulations for parenteral (e.g., subcutaneous, intravenous, intraarterial, intramuscular, intradermal, interperitoneal, and intrathecal), oral, and aerosol administration are exemplary and are in no way limiting. More than one route can be used to administer the inventive PE materials, and in certain instances, a particular route can provide a more immediate and more effective response than another route.

Topical formulations are well-known to those of skill in the art. Such formulations are particularly suitable in the context of the invention for application to the skin.

Formulations suitable for oral administration can include (a) liquid solutions, such as an effective amount of the inventive PE material dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and other pharmacologically compatible excipients. Lozenge forms can comprise the inventive PE material in a flavor, usually sucrose and acacia or tragacanth, as well as pastilles comprising the inventive PE material in an inert base, such as gelatin and glycerin, or sucrose and acacia, emulsions, gels, and the like additionally containing such excipients as are known in the art.

The inventive PE material, alone or in combination with other suitable components, can be made into aerosol formulations to be administered via inhalation. These aerosol formulations can be placed into pressurized acceptable propellants, such as dichlorodifluoromethane, propane, nitrogen, and the like. The aerosol formulations also may be formulated as pharmaceuticals for non-pressured preparations, such as in a nebulizer or an atomizer. Such spray formulations also may be used to spray mucosa.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The inventive PE material can be administered in a physiologically acceptable diluent in a pharmaceutical carrier, such as a sterile liquid or mixture of liquids, including water, saline, aqueous dextrose and related sugar solutions, an alcohol, such as ethanol or hexadecyl alcohol, a glycol, such as propylene glycol or polyethylene glycol, dimethylsulfoxide, glycerol, ketals such as 2,2-dimethyl-1,3-dioxolane-4-methanol, ethers, poly(ethyleneglycol) 400, oils, fatty acids, fatty acid esters or glycerides, or acetylated fatty acid glycerides with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-β-aminopropionates, and 2-alkyl-imidazoline quaternary ammonium salts, and (e) mixtures thereof.

The parenteral formulations will typically contain from about 0.5% to about 25% by weight of the inventive PE material in solution. Preservatives and buffers may be used. In order to minimize or eliminate irritation at the site of injection, such compositions may contain one or more nonionic surfactants having a hydrophile-lipophile balance (HLB) of from about 12 to about 17. The quantity of surfactant in such formulations will typically range from about 5% to about 15% by weight. Suitable surfactants include polyethylene glycol sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described. The requirements for effective pharmaceutical carriers for parenteral compositions are well-known to those of ordinary skill in the art (see, e.g., *Pharmaceutics and Pharmacy Practice*, J.B. Lippincott Company, Philadelphia, Pa., Banker and Chalmers, eds., pages 238-250 (1982), and *ASHP Handbook on Injectable Drugs*, Toissel, 4th ed., pages 622-630 (1986)).

It will be appreciated by one of skill in the art that, in addition to the above-described pharmaceutical compositions, the inventive PE materials of the invention can be formulated as inclusion complexes, such as cyclodextrin inclusion complexes, or liposomes.

For purposes of the invention, the amount or dose of the inventive PE material administered should be sufficient to effect a desired response, e.g., a therapeutic or prophylactic response, in the mammal over a reasonable time frame. For example, the dose of the inventive PE material should be sufficient to inhibit growth of a target cell or treat or prevent cancer in a period of from about 2 hours or longer, e.g., 12 to 24 or more hours, from the time of administration. In certain embodiments, the time period could be even longer. The dose will be determined by the efficacy of the particular inventive PE material and the condition of the mammal (e.g., human), as well as the body weight of the mammal (e.g., human) to be treated.

Many assays for determining an administered dose are known in the art. An administered dose may be determined in vitro (e.g., cell cultures) or in vivo (e.g., animal studies). For example, an administered dose may be determined by determining the $IC_{50}$ (the dose that achieves a half-maximal inhibition of symptoms), $LD_{50}$ (the dose lethal to 50% of the population), the $ED_{50}$ (the dose therapeutically effective in 50% of the population), and the therapeutic index in cell culture and/or animal studies. The therapeutic index is the ratio of $LD_{50}$ to $ED_{50}$ (i.e., $LD_{50}/ED_{50}$).

The dose of the inventive PE material also will be determined by the existence, nature, and extent of any adverse side effects that might accompany the administration of a particular inventive PE material. Typically, the attending physician will decide the dosage of the inventive PE material with which to treat each individual patient, taking into consideration a variety of factors, such as age, body weight, general health, diet, sex, inventive PE material to be administered, route of administration, and the severity of the condition being treated. By way of example and not intending to limit the invention, the dose of the inventive PE material can be about 0.001 to about 1000 mg/kg body weight of the subject being treated/day, from about 0.01 to about 10 mg/kg body weight/day, about 0.01 mg to about 1 mg/kg body weight/day, from about 1 to about to about 1000 mg/kg body weight/day, from about 5 to about 500 mg/kg body weight/day, from about 10 to about 250 mg/kg body weight/day, about 25 to about 150 mg/kg body weight/day, or about 10 mg/kg body weight/day.

Alternatively, the inventive PE materials can be modified into a depot form, such that the manner in which the inventive PE material is released into the body to which it is administered is controlled with respect to time and location within the body (see, for example, U.S. Pat. No. 4,450,150). Depot foams of inventive PE materials can be, for example, an implantable composition comprising the inventive PE materials and a porous or non-porous material, such as a polymer, wherein the inventive PE materials is encapsulated by or diffused throughout the material and/or degradation of the non-porous material. The depot is then implanted into the desired location within the body and the inventive PE materials are released from the implant at a predetermined rate.

The inventive PE materials may be assayed for cytotoxicity by assays known in the art. Examples of cytotoxicity assays include a WST assay, which measures cell proliferation using the tetrazolium salt WST-1 (reagents and kits available from Roche Applied Sciences), as described in International Patent Application Publication WO 2011/032022.

It is contemplated that the inventive pharmaceutical compositions, PEs, chimeric molecules, nucleic acids, recombinant expression vectors, host cells, or populations of cells can be used in methods of treating or preventing cancer. Without being bound by a particular theory or mechanism, it is believed that the inventive PEs destroy or inhibit the growth of cells through the inhibition of protein synthesis in eukaryotic cells, e.g., by the inactivation of the ADP-ribosylation of elongation factor 2 (EF-2). Without being bound to a particular theory or mechanism, the inventive chimeric molecules recognize and specifically bind to cell surface markers, thereby delivering the cytotoxic PE to the population of cells expressing the cell surface marker with minimal or no cross-reactivity with cells that do not express the cell surface marker. In this way, the cytotoxicity of PE can be targeted to destroy or inhibit the growth of a particular population of cells, e.g., cancer cells. In this regard, the invention provides a method of treating or preventing cancer in a mammal comprising administering to the mammal any of the PEs, chimeric molecules, nucleic acids, recombinant expression vectors, host cell, population of cells, or pharmaceutical compositions described herein, in an amount effective to treat or prevent cancer in the mammal.

The terms "treat" and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the inventive methods can provide any amount of any level of treatment or prevention of cancer in a mammal. Furthermore, the treatment or prevention provided by the inventive method can include treatment or prevention of one or more conditions or symptoms of the disease, e.g., cancer, being treated or prevented. Also, for purposes herein, "prevention" can encompass delaying the onset of the disease, or a symptom or condition thereof.

For purposes of the inventive methods, wherein host cells or populations of cells are administered, the cells can be cells that are allogeneic or autologous to the host. Preferably, the cells are autologous to the host.

With respect to the inventive methods, the cancer can be any cancer, including any of adrenal gland cancer, sarcomas (e.g., synovial sarcoma, osteogenic sarcoma, leiomyosarcoma uteri, angiosarcoma, fibrosarcoma, rhabdomyosarcoma, liposarcoma, myxoma, rhabdomyoma, fibroma, lipoma, and teratoma), lymphomas (e.g., small lymphocytic lymphoma, Hodgkin lymphoma, and non-Hodgkin lymphoma), hepatocellular carcinoma, glioma, head cancers (e.g., squamous cell carcinoma), neck cancers (e.g., squamous cell carcinoma), acute lymphocytic cancer, leukemias (e.g., hairy cell leukemia, myeloid leukemia (acute and chronic), lymphatic leukemia (acute and chronic), prolymphocytic leukemia (PLL), myelomonocytic leukemia (acute and chronic), and lymphocytic leukemia (acute and chronic)), bone cancer (osteogenic sarcoma, fibrosarcoma, malignant fibrous histiocytoma, chondrosarcoma, Ewing's sarcoma, malignant lymphoma (reticulum cell sarcoma), multiple myeloma, malignant giant cell tumor, chordoma, osteochondroma (osteocartilaginous exostoses), benign chondroma, chondroblastoma, chondromyxoid fibroma, osteoid osteoma, and giant cell tumors), brain cancer (astrocytoma, medulloblastoma, glioma, ependymoma, germinoma (pinealoma), glioblastoma multiforme, oligodendroglioma, schwannoma, and retinoblastoma), fallopian tube cancer, breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vulva (e.g., squamous cell carcinoma, intraepithelial carcinoma, adenocarcinoma, and fibrosarcoma), myeloproliferative disorders (e.g., chronic myeloid cancer), colon cancers (e.g., colon carcinoma), esophageal cancer (e.g., squamous cell carcinoma, adenocarcinoma, leiomyosarcoma, and lymphoma), cervical cancer (cervical carcinoma and pre-invasive cervical dysplasia), gastric cancer, gastrointestinal carcinoid tumor, hypopharynx cancer, larynx cancer, liver cancers (e.g., hepatocellular carcinoma, cholangiocarcinoma, hepatoblastoma, angiosarcoma, hepatocellular adenoma, and hemangioma), lung cancers (e.g., bronchogenic carcinoma (squamous cell, undifferentiated small cell, undifferentiated large cell, and adenocarcinoma), alveolar (bronchiolar) carcinoma, bronchial adenoma, chondromatous hamartoma, small cell lung cancer, non-small cell lung cancer, and lung adenocarcinoma), mesothelioma, skin cancer (e.g., melanoma, basal cell carcinoma, squamous cell carcinoma, Kaposi's sarcoma, nevi, dysplastic nevi, lipoma, angioma, dermatofibroma, and keloids), multiple myeloma, nasopharynx cancer, ovarian cancer (e.g., ovarian carcinoma (serous cystadenocarcinoma, mucinous cystadenocarcinoma, endometrioid carcinoma, and clear cell adenocarcinoma), granulosa-theca cell tumors, Sertoli-Leydig cell tumors, dysgerminoma, and malignant teratoma), pancreatic cancer (e.g., ductal adenocarcinoma, insulinoma, glucagonoma, gastrinoma, carcinoid tumors, and VIPoma), peritoneum, omentum, mesentery cancer, pharynx cancer, prostate cancer (e.g., adenocarcinoma and sarcoma), rectal cancer, kidney cancer (e.g., adenocarcinoma, Wilms tumor (nephroblastoma), and renal cell carcinoma), small intestine cancer (adenocarcinoma, lymphoma, carcinoid tumors, Kaposi's sarcoma, leiomyoma, hemangioma, lipoma, neurofibroma, and fibroma), soft tissue cancer, stomach cancer (e.g., carcinoma, lymphoma, and leiomyosarcoma), testicular cancer (e.g., seminoma, teratoma, embryonal carcinoma, teratocarcinoma, choriocarcinoma, sarcoma, Leydig cell tumor, fibroma, fibroadenoma, adenomatoid tumors, and lipoma), cancer of the uterus (e.g., endometrial carcinoma), thyroid cancer, and urothelial cancers (e.g., squamous cell carcinoma, transitional cell carcinoma, adenocarcinoma, ureter cancer, and urinary bladder cancer).

As used herein, the term "mammal" refers to any mammal, including, but not limited to, mammals of the order Rodentia, such as mice and hamsters, and mammals of the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simoids (monkeys) or of the order Anthropoids (humans and apes). An especially preferred mammal is the human.

Also provided is a method of inhibiting the growth of a target cell comprising contacting the cell with the PE of any of the PEs, chimeric molecules, nucleic acids, recombinant expression vectors, host cell, population of cells, or pharmaceutical compositions described herein, in an amount effective to inhibit growth of the target cell. The growth of the target cell may be inhibited by any amount, e.g., by about 10% or more, about 15% or more, about 20% or more, about 25% or more, about 30% or more, about 35% or more, about 40% or more, about 45% or more, about 50% or more, about 55% or more, about 60% or more, about 65% or more, about 70% or more, about 75% or more, about 80% or more, about 85% or more, about 90% or more, about 95% or more, or about 100%. The target cell may be provided in a biological sample. A biological sample may be obtained from a mammal in any suitable manner and from any suitable source. The biological sample may, for example, be obtained by a blood draw, leukapheresis, and/or tumor biopsy or necropsy. The contacting can take place in vitro or in vivo with respect to the mammal. Preferably, the contacting is in vitro.

In an embodiment of the invention, the target cell is a cancer cell. The target cell may be a cancer cell of any of the cancers described herein. In an embodiment of the invention, the target may express a cell surface marker. The cell surface marker may be any cell surface marker described herein with respect to other aspects of the invention. The cell surface marker may be, for example, selected from the group consisting of CD19, CD21, CD22, CD25, CD30, CD33, CD79b, transferrin receptor, EGF receptor, mesothelin, cadherin, and Lewis Y.

The following examples further illustrate the invention but, of course, should not be construed as in any way limiting its scope.

Example 1

This example demonstrates the identification of T cell epitopes in domain III of PE38.

To identify the T cell epitopes in PE38, peripheral blood mononuclear cells (PBMCs) were first incubated with a recombinant immunotoxin (RIT) for 14 days to allow the RIT to be processed by donor APCs to relevant peptides to be presented to T cells. The enriched PBMCs were subsequently exposed to a peptide library composed of 111 partially overlapping peptides spanning the sequence of PE38 and T cell activation was measured using an ELISpot assay for interleukin-2 (IL-2).

Samples from 50 normal donors with no recorded previous exposure to PE38 and with a broad distribution of human leukocyte antigen (HLA) alleles were analyzed. The cells of this population contained naïve T cell epitope. Samples from nine mesothelioma and seven hairy cell leukemia (HCL) patients that were previously treated with PE-based RIT and who had developed high levels of neutralizing antibodies were also analyzed. The cells of this population contained memory T cell epitopes. The responses of the naïve donors and the previously treated patients are shown in a heat map format in FIGS. 1A-1B.

FIG. 1A presents the positive and negative responses of the 50 naïve donors. The responses are shown as a percentage of responsive spots for each donor. The strongest positive response is shown as >20%, medium responses are shown as 10%-20%, weak responses are shown as 3%-10%, and the absence of a response (negative) is shown as <3%. The results included a total of 258 positive responses, and 201 of those were weak (3-10%), 44 were medium (10-20%), and 13 were strong (>20%), leaving a total of 5292 negative responses (<3%). There were 122 responses in domain II (peptides 1-38) including 11 strong, 24 medium, and 87 weak responses. There were 136 responses in domain III (peptides 39-111) including two strong, 20 medium and 114 weak responses.

Peptides 15 and 14 (in pool 3) provided the strongest and most frequent responses in the study with 21 and 18 positive responses, respectively. A total of 36 peptides did not provide any response. Sixteen of the 50 naïve donors had a single epitope giving a response, as indicated by one, two, or three responses in overlapping consecutive peptides. Fifteen donors had two separate epitopes, 14 had three epitopes, and five had four epitopes. On 22 occasions, a fine screen of a positive pool did not provide a specific peptide response or was not done, resulting in five consecutive positive responses in the heat map.

FIG. 1B illustrates the positive and negative responses of the nine mesothelioma and the seven HCL patients. It was found that the mesothelioma patients provided 919 negative responses and 80 responses, including two strong responses (>20%), four medium responses (10-20%), and 74 weak responses (3-10%). The two strong responses were in peptides 13 and 14, and the medium responses were in peptides 15, 35, 57 and 74. Thirty-five of the responses were in domain II (peptides 1-38) and 45 in domain III (peptides 38-111). The hot spot pattern created in the map is similar to the hot spot pattern in the naïve donors map. The responsiveness (meaning how many epitopes were found for each patient) was higher than the donor's pattern with one patient having two epitopes, four patients having three epitopes, two patients having four epitopes and two more patients having five epitopes.

Moreover, it was found that the seven HCL patients provided three strong responses (>20%), nine medium responses (10-20%), 37 weak responses (3-10%), and 728 negative responses (<3%). The strong responses were all in the consecutive peptides 75, 76 and 77. Twenty-two of the responses were in domain II and 37 responses were in domain III. Interestingly, the immunodominant epitope in peptides 14 and 15 that was identified in more than 40% of the naïve donors and 55% of the mesothelioma patients (five out of nine samples) did not have a single response in the HCL patients. One patient responded to peptides 12 and 13 that have amino acids in common with peptides 14 and 15. However, no responses were found directly to peptides 14 and 15. This may be attributed to the biased HLA distribution of those patients' samples or to the nature of the disease.

Overall, eight major epitopes were identified in PE38 that account for 93% of the responses. Because all T cell epitopes in domain II could be eliminated using the LR deletion, the five epitopes remaining in domain III were the focus of subsequent study. Table 1A summarizes the epitopes' locations, sequences, response rates, and the mutation that diminishes each with minimal disturbance to cytotoxic activity. The epitope ranking was composed of a number of factors, including the number of naïve donors responding to the epitope, the relative strength of the response, the number of mesothelioma patients that responded, and, to a lesser extent, the HCL patients' responses. The epitopes from HCL patients were evaluated to a lesser extent in this analysis because of the HLA bias of the patient cohort and in the HCL patient population, in which HCL patients have an enrichment of BRB1_11 (Annino et al., *Leuk. Lymphoma,* 14 (Suppl.) 1:63-5 (1994)). Epitope 2 spans five peptides. To simplify analysis, it was divided into two sub-epitopes: peptides 77-78 (2A) and peptides 75-76 (2B). Some donors responded to both 2A and 2B epitopes, while others responded to only one. Epitope 6 (peptides 93-96) and epitope 8 (peptides 56-59) were also divided into two sub-epitopes.

TABLE 1A

| Epitope ranking | | Peptide # | Sequence | Responses Donors (n = 50) | Mesothelioma (n = 9) | HCL (n = 7) | Mutations | Relative cytotoxic Activity* |
|---|---|---|---|---|---|---|---|---|
| 1 | | 13-15 | LVALYLAARLSWNQV SEQ ID NO: 189 | 21 | 6 | 1 | Domain II deletion | 100% |
| 2 | A | 77-78 | GALLRVYVPRSSLPG SEQ ID NO: 190 | 14[a] | 3[a] | 6[a] | R505A | 100% |
| | B | 74-76 | IRNGALLRVYVPRSS SEQ ID NO: 191 | 10[a] | 6[a] | 5[a] | R494A | 21-36% |
| 3 | | 8-9 | RQPRGWEQLEQCGYP SEQ ID NO: 192 | 9 | 3 | 3 | Domain II deletion | 100% |
| 4 | | 5-6 | LPLETFTRHRQPRGW SEQ ID NO: 193 | 10 | 2 | 0 | Domain II deletion | 100% |
| 5 | | 67-68 | WRGFYIAGDPALAYG SEQ ID NO: 194 | 8 | 2 | 2 | L477H | 100% |

TABLE 1A-continued

| Epitope ranking | Peptide # | Sequence | Donors (n = 50) | Responses Mesothelioma (n = 9) | HCL (n = 7) | Mutations | Relative cytotoxic Activity* |
|---|---|---|---|---|---|---|---|
| 6A + B | 93-96 | GPEEEGGRLETILGWPLA SEQ ID NO: 195 | 8 | 1 | 2 | L552E | 100% |
| 7 | 51-52 | TVERLLQAHRQLEER SEQ ID NO: 196 | 5 | 1 | 0 | R427A | 100% |
| 8A + B | 56-59 | FVGYHGTFLEAAQSIVFG SEQ ID NO: 197 | 5 | 5 | 4 | F443A | >100% |

*Activity for a single point mutation in HA22 RIT and evaluated in CA46 cell line.
<sup>a</sup>Donors and patients that responded to epitope 2A overlap with the patients and donors that responded to 2B.

To compare the results from naïve donors to immunotoxin-treated patients, two patient cohorts that made neutralizing antibodies against the RIT were studied. The patients' DRB1 HLA alleles are shown in Table 1B. The same epitopes identified in the donor cohort were also present in the patient cohorts. One cohort was from mesothelioma patients treated with SS1P (anti-mesothelin Fv fused to P38) (Chowdhury et al., *Nat. Biotechnol.*, 17: 568-572 (1999)); the other from leukemia patients treated with moxetumomab pasudotox (MP), a RIT including PE38 fused to an anti-CD22 Fv (Kreitman et al., *Clin. Cancer Res.*, 17: 6398-6405 (2011)). The naïve donor epitope responses ranged from 1-4 epitopes per donor, with an average of 2.1, and the patient responses ranged from 1-7 per patient, with a higher average of 3.4 (P<0.001 in Student T test). This suggests that some responses in the naïve population were too weak to be detected by this method, and were amplified after exposure to immunotoxin. The patient samples did not identify any major epitopes that were not identified using the donor cohort.

TABLE 1B

| Donor | Diagnosis | HLA haplotype DRB1 |
|---|---|---|
| 71509WBp | HCL | 04, 11 |
| 102609aph | HCL | 1103, 1303 |
| 112309aph | HCL | 0404, 0701 |
| 121809aph | HCL | 07, 11 |
| 050710aph | HCL | 01, 07 |
| 021012baph | HCL | 04, 07 |
| 071912aph | HCL | 07, 11 |
| 120909aph | Mesothelioma | 0410, 1501 |
| 011410aph | Mesothelioma | 0101, 0801 |
| 012810aph | Mesothelioma | 0301, 1501 |
| 050510aph | Mesothelioma | 0401, 1302 |
| 091510aph | Mesothelioma | 07, 15 |
| 022811aph | Mesothelioma | 1301, 1302 |
| 100711aph | Mesothelioma | 0103, 03 |
| 021012aph | Mesothelioma | 0101, 0101 |
| 031612aph | Mesothelioma | 0401, 12 |

Example 2

This example demonstrates the elimination of T cell epitopes in domain III.

For each one of the epitopes in domain III that are described in Table 1, alanine scanning mutagenesis was performed. The alanine mutant was incorporated into the RIT according to the following 11 steps: (1) a list was made of all alanine peptide variants for each epitope; (2) in silico prediction was performed to rule out alanine variants that had increased binding to at least six HLA alleles using an HLA binding algorithm (Immune Epitope Database, IEDB) (Wang et al., *PLoS Comput. Biol.*, 4:e1000048 (2008)) that measured their ability to bind to 13 major HLA groups; (3) alanine variants were assayed using 8-15 donors and patient samples with in vitro expansion and ELIspot; (4) an alanine mutation with diminished T cell activation was identified; (5) the alanine mutation was cloned into the HA22-LR plasmid, and a RIT was constructed with a single point mutation; (6) activity was studied using the WST8 assay.

If the protein was aggregated or has low cytotoxic activity, (7) in silico prediction and crystal structure was used to identify alternative amino acids to alanine and (8) the new mutation was cloned into an HA22-LR plasmid, and a RIT was constructed with a single point mutation and activity was studied. If the protein was aggregated or had low cytotoxic activity, then the next best alanine mutant was identified as in step 4 and step 5 was carried out. If the protein was active, step 10 was carried out.

If the protein was active, (10) validation was carried out to determine whether the epitope was diminished and that no new epitopes were created due to the mutation; and (11) the successful point mutations were combined into a single RIT.

The results for all epitopes are shown in Tables 2-7. In Tables 2-7, underlined values represent <10%, D=Donor, Pt=patient, "Meso"=mesothelioma, the position where the amino acid was replaced with alanine is underlined, and the average values are bolded. Alanine variants were assayed using 8-15 donor and patient samples with in vitro expansion and ELIspot.

TABLE 2

| CD4+ T cell response to alanine variant peptides and WT76. | | | | | | | | | | | |
|---|---|---|---|---|---|---|---|---|---|---|---|
| donor/ patient | HCL Pt | Meso Pt | HCL Pt | Meso Pt | Meso Pt | D1 | D2 | D3 | D4 | D5 | Mean n = 16 |
| No peptide | 3% | 0% | 0% | 1% | 0% | 0% | 9% | 0% | 17% | 1% | 0% |

TABLE 2-continued

CD4+ T cell response to alanine variant peptides and WT76.

| donor/patient | | HCL Pt | Meso Pt | HCL Pt | Meso Pt | Meso Pt | D1 | D2 | D3 | D4 | D5 | Mean n = 16 |
|---|---|---|---|---|---|---|---|---|---|---|---|---|
| WT76 | IRNGALLRVYVPRSS SEQ ID NO: 198 | 100% | 100% | 100% | 100 | 100% | 100% | 100% | 100% | 100% | 100% | 100% |
| I493A | ARNGALLRVYVPRSS SEQ ID NO: 199 | 2% | 13% | 0% | 36% | 52% | 6% | 20% | 110% | 71% | 76% | 25% |
| R494A | IANGALLRVYVPRSS SEQ ID NO: 200 | 1% | 0% | 2% | 2% | 0% | 12% | 26% | 111% | 88% | 94% | 24% |
| N495A | IRAGALLRVYVPRSS SEQ ID NO: 201 | 95% | 25% | 2% | 31% | 12% | 35% | 40% | 102% | 72% | 72% | 34% |
| G496A | IRNAALLRVYVPRSS SEQ ID NO: 202 | 107% | 58% | 18% | 63% | 34% | 18% | 37% | 96% | 44% | 99% | 42% |
| L498A | IRNGAALRVYVPRSS SEQ ID NO: 203 | 4% | 4% | 0% | 4% | 27% | 0% | 80% | 6% | 16% | 31% | 5% |
| L499A | IRNGALARVYVPRSS SEQ ID NO: 204 | 7% | 0% | 0% | 1% | 2% | 6% | 31% | 30% | 15% | 57% | 3% |
| R500A | IRNGALLAVYVPRSS SEQ ID NO: 205 | 5% | 4% | 24% | 2% | 0% | 24% | 26% | 1% | 20% | 6% | 4% |
| V501A | IRNGALLRAYVPRSS SEQ ID NO: 206 | 5% | 0% | 7% | 13% | 29% | 0% | 46% | 25% | 27% | 48% | 11% |
| Y502A | IRNGALLRVAVPRSS SEQ ID NO: 207 | 29% | 4% | 18% | 23% | 70% | 12% | 23% | 5% | 20% | 0% | 19% |
| V503A | IRNGALLRVYAPRSS SEQ ID NO: 208 | 54% | 58% | 47% | 68% | 30% | 41% | 63% | 35% | 27% | 43% | 41% |
| P504A | IRNGALLRVYVARSS SEQ ID NO: 209 | 91% | 125% | 49% | 122% | 117% | 206% | 60% | 35% | 26% | 18% | 74% |
| R505A | IRNGALLRVYVPASS SEQ ID NO: 210 | 95% | 83% | 87% | 127% | 133% | 147% | 131% | 36% | 23% | 30% | 87% |
| S506A | IRNGALLRVYVPRAS SEQ ID NO: 211 | 92% | 138% | 44% | 107% | 100% | 312% | 214% | 101% | 55% | 82% | 106% |
| S507A | IRNGALLRVYVPRSA SEQ ID NO: 212 | 99% | 96% | 51% | 69% | 106% | 235% | 137% | 71% | 83% | 84% | 94% |

TABLE 3

T cell response to alanine variant peptides and WT77.

| D/Pt | | HCL Pt 1 | HCL Pt 2 | HCL Pt 3 | HCL Pt 4 | Meso Pt 1 | D1 | D2 | D3 | Mean (n = 8) |
|---|---|---|---|---|---|---|---|---|---|---|
| No peptide | | 0% | 0% | 0% | 12% | 1% | 18% | 9% | 7% | 6% |
| wt 77 | GALLRVYVPRSSLPG SEQ ID NO: 213 | 100% | 100% | 100% | 100% | 100% | 100% | 100% | 100% | 100% |

TABLE 3-continued

T cell response to alanine variant peptides and WT77.

| D/Pt | | HCL Pt 1 | HCL Pt 2 | HCL Pt 3 | HCL Pt 4 | Meso Pt 1 | D1 | D2 | D3 | Mean (n = 8) |
|---|---|---|---|---|---|---|---|---|---|---|
| G496A | AALLRVYVPRSSLPG SEQ ID NO: 214 | 29% | 51% | 126% | 151% | 37% | 58% | 112% | 123% | 86% |
| A497G | GGLLRVYVPRSSLPG SEQ ID NO: 215 | 103% | 68% | 102% | 167% | 71% | 108% | 129% | 126% | 109% |
| L498A | GAALRVYVPRSSLPG SEQ ID NO: 216 | 61% | 38% | 7% | 166% | 43% | 20% | 13% | 140% | 61% |
| L499A | GALARVYVPRSSLPG SEQ ID NO: 217 | 46% | 24% | 33% | 162% | 1% | 26% | 73% | 61% | 53% |
| R500A | GALLAVYVPRSSLPG SEQ ID NO: 218 | 59% | 31% | 1% | 189% | 6% | 16% | 1% | 124% | 53% |
| V501A | GALLRAYVPRSSLPG SEQ ID NO: 219 | 7% | 18% | 18% | 84% | 15% | 26% | 49% | 28% | 31% |
| Y502A | GALLRVAVPRSSLPG SEQ ID NO: 220 | 14% | 1% | 4% | 10% | 0% | 25% | 8% | 9% | 9% |
| V503A | GALLRVYAPRSSLPG SEQ ID NO: 221 | 17% | 1% | 15% | 18% | 1% | 39% | 49% | 9% | 19% |
| P504A | GALLRVYVARSSLPG SEQ ID NO: 222 | 46% | 32% | 38% | 127% | 36% | 43% | 12% | 41% | 47% |
| R505A | GALLRVYVPASSLPG SEQ ID NO: 223 | 7% | 1% | 28% | 15% | 2% | 24% | 39% | 22% | 17% |
| S506A | GALLRVYVPRASLPG SEQ ID NO: 224 | 68% | 42% | 107% | 128% | 48% | 93% | 122% | 50% | 82% |
| S507A | GALLRVYVPRSALPG SEQ ID NO: 225 | 35% | 37% | 86% | 164% | 60% | 106% | 96% | 224% | 101% |
| L508A | GALLRVYVPRSSAPG SEQ ID NO: 226 | 8% | 0% | 73% | 12% | 46% | 99% | 88% | 15% | 43% |
| P509A | GALLRVYVPRSSLAG SEQ ID NO: 227 | 10% | 4% | 87% | 57% | 72% | 101% | 119% | 16% | 58% |

TABLE 4

T cell response to alanine variant peptides and WT 67

| | % from WT | HCL Pt 1 | HCL Pa 2 | HCL Pt 3 | Meso Pt 1 | Meso Pt 2 | D1 | D2 | D3 | D4 | D5 | Mean (n = 14) |
|---|---|---|---|---|---|---|---|---|---|---|---|---|
| No peptide | | 6% | 3% | 3% | 13% | 1% | 1% | 13% | 0% | 0% | 0% | 13% |
| WT 67 | WRGFYIAGDPALAYG SEQ ID NO: 228 | 100% | 100% | 100% | 100% | 100% | 100% | 100% | 100% | 100% | 100% | 100% |
| F469A | WRGAYIAGDPALAYG SEQ ID NO: 229 | 80% | 68% | 93% | 11% | 81% | 104% | 35% | 97% | 88% | 60% | 69% |
| Y470A | WRGFAIAGDPALAYG SEQ ID NO: 230 | 61% | 6% | 61% | 6% | 68% | 48% | 67% | 29% | 16% | 92% | 43% |
| I471A | WRGFYAAGDPALAYG SEQ ID NO: 231 | 17% | 36% | 22% | 7% | 35% | 20% | 20% | 22% | 12% | 55% | 24% |

TABLE 4-continued

T cell response to alanine variant peptides and WT 67

| | % from WT | HCL Pt 1 | HCL Pa 2 | HCL Pt 3 | Meso Pt 1 | Meso Pt 2 | D1 | D2 | D3 | D4 | D5 | Mean (n = 14) |
|---|---|---|---|---|---|---|---|---|---|---|---|---|
| A4720 | WRGFYIGGD PALAYG SEQ ID NO: 232 | 37% | 81% | 38% | 20% | 60% | 84% | 75% | 46% | 19% | 76% | 48% |
| P475A | WRGFYIAGD AALAYG SEQ ID NO: 233 | 72% | 18% | 46% | 73% | 38% | 34% | 57% | 15% | 16% | 70% | 43% |
| A476G | WRGFYIAGD PGLAYG SEQ ID NO: 234 | 75% | 49% | 40% | 110% | 32% | 207% | 26% | 67% | 35% | 115% | 70% |
| L477A | WRGFYIAGD PAAAYG SEQ ID NO: 235 | 54% | 32% | 54% | 92% | 52% | 25% | 42% | 26% | 16% | 71% | 44% |
| A478G | WRGFYIAGD PALGYG SEQ ID NO: 236 | 80% | 81% | 62% | 96% | 58% | 134% | 24% | 63% | 98% | 66% | 72% |
| Y479A | WRGFYIAGD PALAAG SEQ ID NO: 237 | 114% | 106% | 76% | 250% | 138% | 108% | 117% | 71% | 21% | 94% | 104% |

TABLE 5

Alanine scanning for peptides 93-94 GPEEEGGRLETILGWPLA (SEQ ID NO: 238)

| | | HCL Pt1 | D1 | D2 | HCL Pt 2 | Meso Pt 1 | Meso Pt 2 | Meso Pt 3 | D3 | D4 | D5 | Mean n = 10 |
|---|---|---|---|---|---|---|---|---|---|---|---|---|
| | Responder groups | 93 | 93 | 93 | 94 | 94 | 94 | 94 | 94 | 94 | 94 | |
| No peptide | | 3% | 9% | 2% | 7% | 4% | 3% | 15% | 35% | 25% | 12% | 11% |
| WT 93-94 | GPEEEGGRLETILGWPLA SEQ ID NO: 238 | 100% | 100% | 100% | 100% | 100% | 100% | 100% | 100% | 100% | 100% | 100% |
| E547A | GPEAEGGRLETILGWPLA SEQ ID NO: 239 | 73% | 18% | 254% | 85% | 120% | 122% | 136% | 73% | 106% | 90% | 108% |
| E548A | GPEEAGGRLETILGWPLA SEQ ID NO: 240 | 58% | 24% | 170% | 112% | 98% | 86% | 137% | 102% | 207% | 87% | 108% |
| R551A | GPEEGGALETILGWPLA SEQ ID NO:241 | 62% | 6% | 2% | 95% | 70% | 42% | 54% | 40% | 67% | 49% | 49% |
| L552A | GPEEEGGRAETILGWPLA SEQ ID NO: 242 | 54% | 44% | 10% | 91% | 35% | 11% | 14% | 85% | 51% | 46% | 44% |
| T554A | GPEEEGGRLEAILGWPLA SEQ ID NO: 243 | 77% | 9% | 5% | 94% | 133% | 130% | 129% | 110% | 95% | 112% | 89% |
| I555A | GPEEEGGRLETALGWPLA SEQ ID NO: 244 | 111% | 176% | 119% | 67% | 25% | 15% | 36% | 63% | 36% | 36% | 69% |
| L556A | GPEEEGGRLETIAGWPLA SEQ ID NO: 245 | 24% | 235% | 3% | 40% | 10% | 13% | 43% | 35% | 83% | 29% | 51% |
| W558A | GPEEEGGRLETILGAPLA SEQ ID NO: 246 | 20% | 200% | 13% | 13% | 26% | 7% | 26% | 46% | 54% | 31% | 44% |
| P559A | GPEEEGGRLETILGWALA SEQ ID NO: 247 | 24% | 197% | 208% | 95% | 69% | 37% | 74% | 65% | 121% | 46% | 94% |

TABLE 5-continued

Alanine scanning for peptides 93-94 GPEEEGGRLETILGWPLA (SEQ ID NO: 238)

| | | HCL Pt1 | D1 | D2 | HCL Pt 2 | Meso Pt 1 | Meso Pt 2 | Meso Pt 3 | D3 | D4 | D5 | Mean n = 10 |
|---|---|---|---|---|---|---|---|---|---|---|---|---|
| L560A | GPEEEGGRLETILGWPAA SEQ ID NO: 248 | 81% | 321% | 162% | 89% | 132% | 117% | 75% | 46% | 138% | 95% | 126% |

TABLE 6

Alanine scanning for peptide TVERLLQAHRQLEER (SEQ ID NO: 249)

| | | HCL Pt 1 | Meso Pt 1 | Meso Pt 2 | Meso Pt 3 | D1 | D2 | D3 | Mean n =7 |
|---|---|---|---|---|---|---|---|---|---|
| No peptide | | 0% | 1% | 0% | 1% | 13% | 14% | 7% | 5% |
| WT51 | TVERLLQAHRQLEER SEQ ID NO: 249 | 100% | 100% | 100% | 100% | 100% | 100% | 100% | 100% |
| R421A | TVEALLQAHRQLEER SEQ ID NO: 250 | 23% | 87% | 2% | 5% | 22% | 12% | 26% | 25% |
| L422A | TVERALQAHRQLEER SEQ ID NO: 251 | 29% | 18% | 0% | 1% | 31% | 10% | 16% | 17% |
| L423A | TVERLAQAHRQLEER SEQ ID NO:252 | 47% | 21% | 11% | 3% | 8% | 10% | 6% | 14% |
| A425G | TVERLLQGHRQLEER SEQ ID NO: 253 | 105% | 51% | 4% | 6% | 57% | 16% | 68% | 52% |
| R427A | TVERLLQAHAQLEER SEQ ID NO: 254 | 78% | 81% | 1% | 2% | 37% | 10% | 35% | 37% |
| L429A | TVERLLQAHRQAEER SEQ ID NO: 255 | 63% | 64% | 38% | 36% | 28% | 19% | 124% | 67% |
| E430A | TVERLLQAHRQLAER SEQ ID NO: 256 | 100% | 100% | 242% | 73% | 112% | 26% | 99% | 108% |
| R432A | TVERLLQAHRQLEEA SEQ ID NO: 257 | 105% | 92% | 87% | 69% | 65% | 57% | 142% | 106% |

TABLE 7

Alanine scanning for 18 mer peptide FVGYHGTFLEAAQSIVFG (57-58) (SEQ ID NO: 258)

| | | HCL Pt 1 | Meso Pt 1 | Meso Pt 2 | D1 | HCL Pt 2 | HCL Pt 3 | Meso Pt 3 | Meso Pt 4 | D2 | D3 | Avg |
|---|---|---|---|---|---|---|---|---|---|---|---|---|
| | Responder groups | 57 | 57 | 57 | 57 | 58 | 58 | 58 | 58 | 58 | 58 | |
| No peptide | | 0% | 0% | 0% | 4% | 0% | 1% | 1% | 0% | 10% | 9% | 4% |
| WT 57-58 | FVGYHGTFLEAAQSIVFG SEQ ID NO: 258 | 100% | 100% | 100% | 100% | 100% | 100% | 100% | 100% | 100% | 100% | 100% |
| F436A | AVGYHGTFLEAAQSIVFG SEQ ID NO: 259 | 57% | 98% | 159% | 7% | 103% | 103% | 89% | 45% | 41% | 123% | 83% |
| V437A | FAGYHGTFLEAAQSIVFG SEQ ID NO: 260 | 84% | 78% | 130% | 81% | 97% | 95% | 96% | 85% | 102% | 148% | 99% |
| G438A | FVAYHGTFLEAAQSIVFG SEQ ID NO: 261 | 67% | 52% | 78% | 79% | 71% | 88% | 118% | 91% | 98% | 68% | 83% |
| Y439A | FVGAHGTFLEAAQSIVFG SEQ ID NO: 262 | 22% | 96% | 21% | 17% | 79% | 97% | 125% | 147% | 110% | 154% | 91% |
| H440A | FVGYAGTFLEAAQSIVFG SEQ ID NO: 263 | 11% | 12% | 95% | 6% | 46% | 113% | 108% | 120% | 90% | 102% | 75% |

TABLE 7-continued

Alanine scanning for 18 mer peptide FVGYHGTFLEAAQSIVFG (57-58) (SEQ ID NO: 258)

| | | HCL Pt 1 | Meso Pt 1 | Meso Pt 2 | D1 | HCL Pt 2 | HCL Pt 3 | Meso Pt 3 | Meso Pt 4 | D2 | D3 | Avg |
|---|---|---|---|---|---|---|---|---|---|---|---|---|
| T442A | FVGYHGAFLEAAQSIVFG SEQ ID NO: 264 | 77% | 84% | 151% | 31% | 48% | 102% | 93% | 50% | 59% | 127% | 82% |
| F443A | FVGYHGTALEAAQSIVFG SEQ ID NO: 265 | 2% | 0% | 40% | 7% | 5% | 2% | 1% | 1% | 20% | 7% | 10% |
| L444A | FVGYHGTFAEAAQSIVFG SEQ ID NO: 266 | 69% | 54% | 74% | 140% | 9% | 4% | 55% | 8% | 14% | 0% | 37% |
| A446G | FVGYHGTFLEGAQSIVFG SEQ ID NO: 267 | 80% | 40% | 47% | 119% | 80% | 37% | 107% | 125% | 69% | 16% | 78% |
| A447G | FVGYHGTFLEAGQSIVFG SEQ ID NO: 268 | 65% | 104% | 57% | 103% | 19% | 28% | 118% | 87% | 43% | 7% | 67% |
| S449A | FVGYHGTFLEAAQAIVFG SEQ ID NO: 269 | 98% | 126% | 93% | 104% | 23% | 65% | 128% | 123% | 163% | 200% | 110% |
| I450A | FVGYHGTFLEAAQSAVFG SEQ ID NO: 270 | 138% | 159% | 130% | 124% | 2% | 66% | 108% | 104% | 31% | 11% | 78% |
| V451A | FVGYHGTFLEAAQSIAFG SEQ ID NO: 271 | 119% | 127% | 162% | 121% | 82% | 117% | 142% | 118% | 137% | 50% | 116% |
| F452A | FVGYHGTFLEAAQSIVAG SEQ ID NO: 272 | 119% | 126% | 154% | 156% | 99% | 104% | 103% | 151% | 104% | 123% | 127% |

Epitopes 2A and 2B were scanned separately to cover the 9 mer core of all five peptides that gave responses. Y502A diminished the responses of both epitopes (Tables 2 and 3). For epitopes 5 and 7, alanine mutants were compared to peptide 67 and 51, respectively, and I471A and L423A had the lowest T cell response (Tables 4 and 6). To cover all 9 mer cores in epitopes 6 and 8 that contained four positive peptides, 18 mer WT and alanine variants were synthesized. It was found that L552A was the most effective in lowering the response in epitope 6 (Table 5) and F443A was best for epitope 8 (Table 7).

Example 3

This example demonstrates the cytotoxic activity of point mutation proteins in HA22-LR.

Step 4 of Example 2 was carried out. The best variants identified in the alanine scan or using further in silico prediction are described in Table 1A.

Forty mutant RITs were constructed. The cytotoxic activity of point mutation proteins in HA22-LR was evaluated with respect to CA46, Raji, and Daudi cells. Yields of purified protein, calculated accessible surface areas (Lee et al., *J. Mol. Biol.,* 55:379-400 (1971); Roscoe et al., *Infect. Immunity,* 62:5055-5065 (1994)) of WT amino acids residues and cytotoxic activity of each RIT are shown in Table 8.

TABLE 8

| | | ASA | Protein yield | Protein activity Mean relative activity (%) ± SD | | |
|---|---|---|---|---|---|---|
| Peptide | Mutation | ($Å^2$)* | (mg) | CA46 | Raji | Daudi |
| 76 | R500A | 0 | A | | | |
| 76 | L498A | 4 | A | | | |
| 76 | L499A | 0.1 | A | | | |
| 76 | R494A | 35 | 2.0 | 21 ± 3 | 33 ± 10 | 36 ± 8 |
| 76 | R494D | 35 | 3.23 | | | 11 |
| 77 | R505A | 150 | 4 | 78 ± 13 | 185 ± 106 | |
| 76/77 | Y502A | 0 | A | | | |

TABLE 8-continued

| | | ASA | Protein yield | Protein activity Mean relative activity (%) ± SD | | |
|---|---|---|---|---|---|---|
| Peptide | Mutation | ($Å^2$)* | (mg) | CA46 | Raji | Daudi |
| 76/77 | Y502H | 0 | A | | | |
| 76/77 | Y502F | 0 | A | | | |
| 76/77 | Y502K | 0 | A | | | |
| 67 | I471A | 4 | 1.6 | | | 24 |
| 67 | I471V | 4 | 4 | 83 | | 108 |
| 67 | I471M | 4 | 3 | 3 | | |
| 67 | I471H | 4 | A | | | |
| 67 | I471G | 4 | A | | | |
| 67 | I471S | 4 | 1.3 | 2 | | |
| 67 | I471D | 4 | A | | | |
| 67 | Y470A | 98 | 2.3 | <1 | <1 | |
| 67 | L477A | 7 | 1.4 | 54 ± 21 | 47 ± 13 | |
| 67 | A476G | 38 | 5 | 67 ± 4 | 84 | |
| 67 | L477G | 7 | 4 | 14 ± 6 | 14 ± 6 | |
| 67 | L477T | 7 | 2.5 | <1 | <1 | |
| 67 | L477H | 7 | 3 | 101 ± 22 | 95 ± 13 | |
| 51 | L422A | 0 | 2 | <1 | | |
| 51 | L423A | 22 | 4 | 30 | | |
| 51 | L423N | 22 | 3 | 5 | | |
| 51 | L423T | 22 | 3.2 | 50 | | 76 |
| 51 | L423S | 22 | 5 | 65 | | |
| 51 | R421A | 16 | 1 | <10 | | |
| 51 | R427A | 142 | 0.71 | 185 ± 85 | 150 ± 61 | 150 ± 4 |
| 93 | R551A | 100 | 4 | 208 | | 188 ± 464 |
| 94 | W558A | 40 | 1 | <1 | | >2 |
| 94 | W558D | 40 | 1 | <1 | | |
| 94 | W558N | 40 | 0.7 | <1 | | |
| 94 | L556A | 0 | 1.2 | 2 | 0 | 2 ± 0.4 |
| 94 | L556V | 0 | 4.2 | 95 ± 32 | 77 | |
| 94 | L552N | 82 | 2.4 | 200 | | |
| 94 | L552E | 82 | 2.1 | 110 | | |
| 57/58 | F443A | 12 | 3.6 | 174 ± 110 | 113 ± 60 | |
| 57/58 | F443V | 12 | 2.26 | 95 | | |

A—aggregated

*Accessible Surface Areas (ASA) were calculated for the wild type residue.

Example 4

This example demonstrates that the substitutions in PE domain III diminish the epitope and do not create new epitopes due to the mutation.

The response of three donor samples and one patient sample to 22 peptide pools after stimulation with either HA22 (wt) or LR-R494A was measured. "LR" denotes the deletion of all of domain II except the furin cleavage sequence. The results are shown in FIGS. 2A-2D. As shown in FIGS. 2A-2D, the epitope in peptide 76 was diminished by the R494A mutation.

Figures 3A, 3B, 3C:
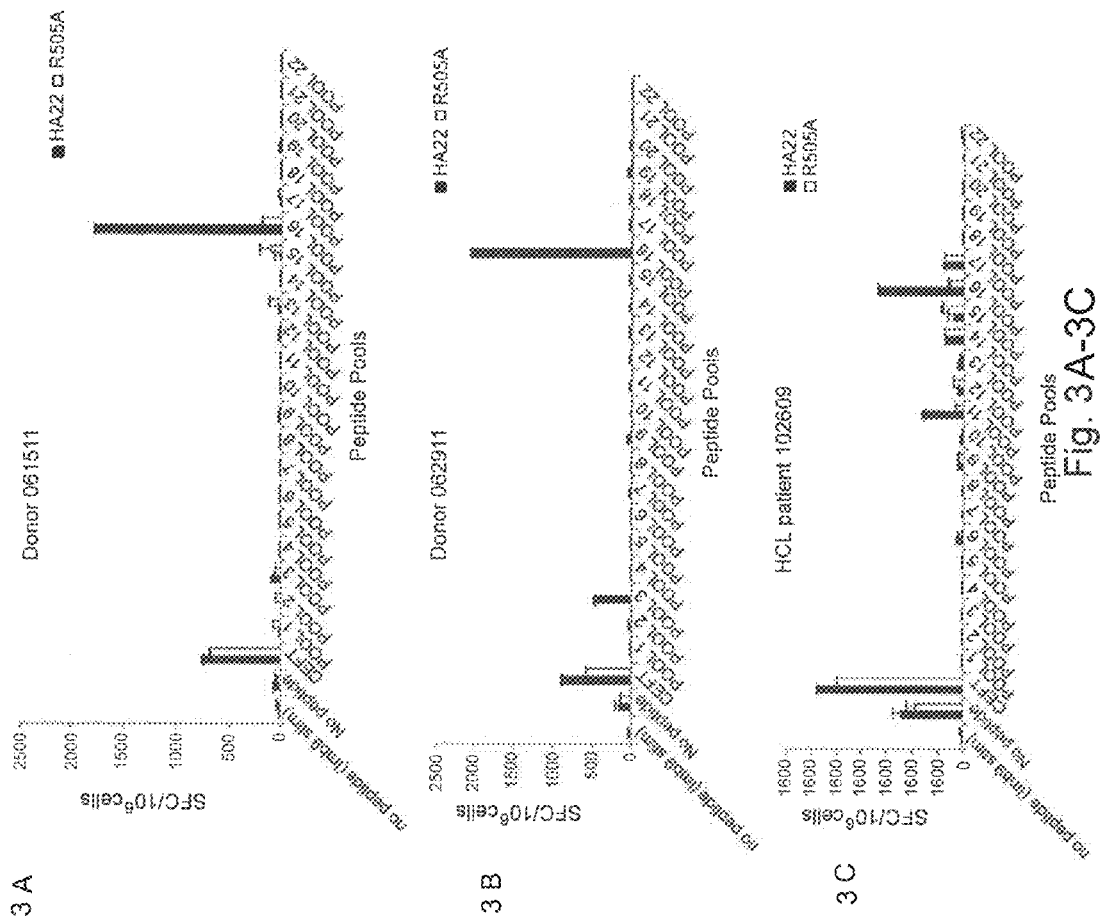
FIGS. 3A-3C are graphs showing the response of two donor samples (A-B) and one HCL patient sample (C) to one of 22 peptide pools, CEFT, or no peptide after stimulation with HA22 (shaded bars) or LR-R505A (unshaded bars) as measured in SFCs per $10 \times 10^6$ cells. * indicates statistical significance (p<0.01).

The response of two donor samples and one patient sample to 22 peptide pools after stimulation with either HA22 (wt) or LR-R505A was measured. The results are shown in FIGS. 3A-3C. As shown in FIGS. 3A-3C, the epitope in peptide 77 was diminished by the R505A mutation.

Figures 4A, 4B:
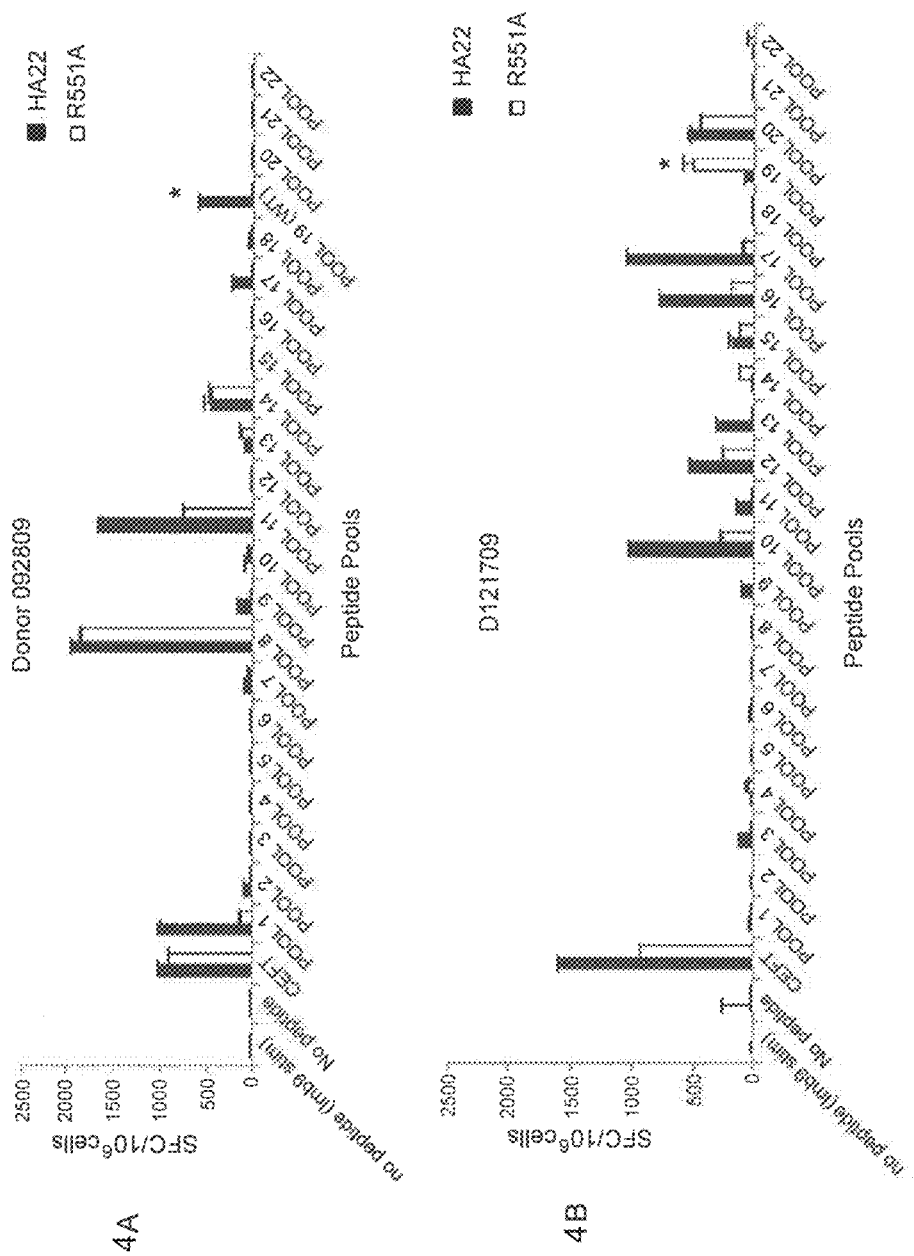
FIGS. 4A-4B are graphs showing the response of two donor samples (A-B) to one of 22 peptide pools, CEFT, or no peptide after stimulation with HA22 (shaded bars) or LR-R551A (unshaded bars) as measured in SFCs per $10 \times 10^6$ cells. * indicates statistical significance in student T test (p<0.01).
Figures 5A, 5B, 5C, 5D:
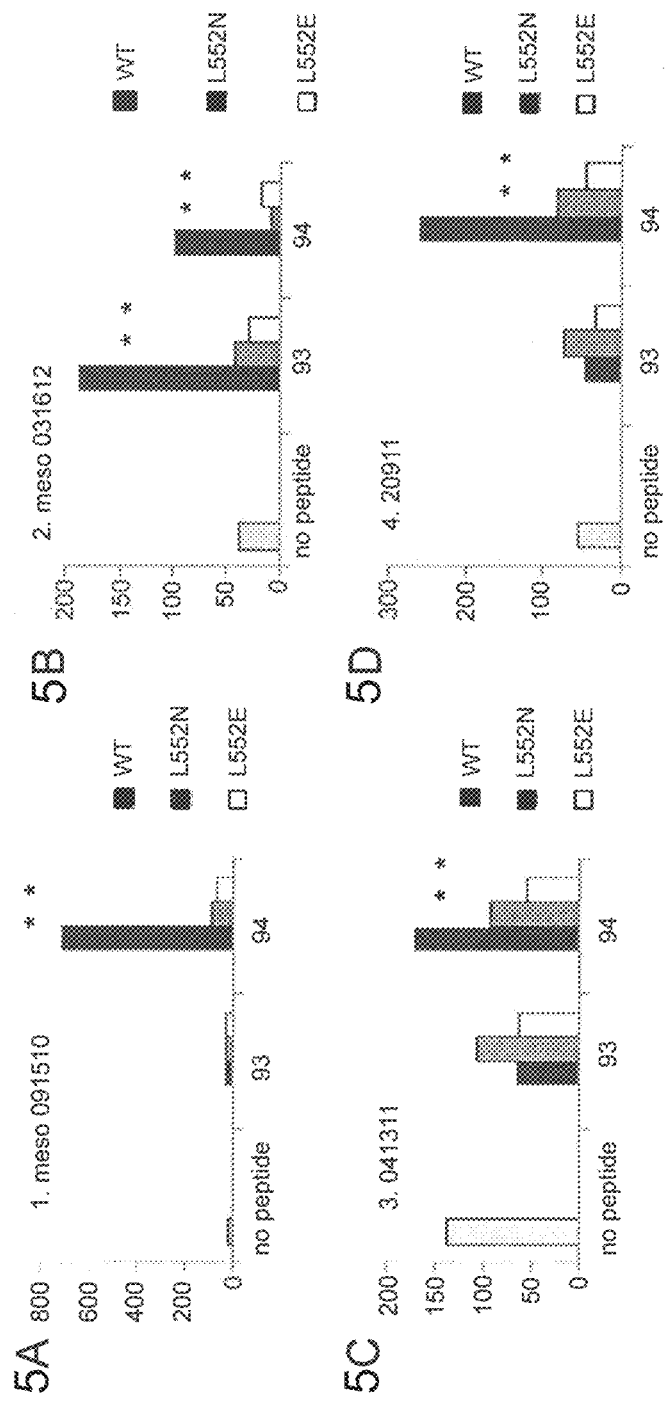
FIGS. 5A-5D are graphs showing the response of two donor samples (C-D) and two mesothelioma patient samples (A-B) after stimulation with recombinant immunotoxin (RIT) and restimulation with peptide 93 or 94 with either the wild-type (WT) amino acid sequence (black bars), L552N (dark grey bars), or L552E (unshaded bars), or treatment with no peptide (light grey bars). * indicates statistical significance in student T test (p<0.05).

The response of two donors to 22 peptide pools after stimulation with either HA22-LR (WT) or HA22-R551A and restimulation with the appropriate peptides was also measured. The results are shown in FIGS. 4A-4B. As shown in FIGS. 4A and 4B, the mutation R551A diminished the epitope in peptide 93.

The response of cells from two donors and two patients after stimulation with RIT and restimulation with peptides 93, 94 with either the WT amino acid sequence, L552E or L552N was measured. The results are shown in FIGS. 5A-5D. As shown in FIGS. 5A-5D, the epitope in peptides 93 and 94 was diminished by the L552N and L552E mutations.

Figures 6A, 6B, 6C:
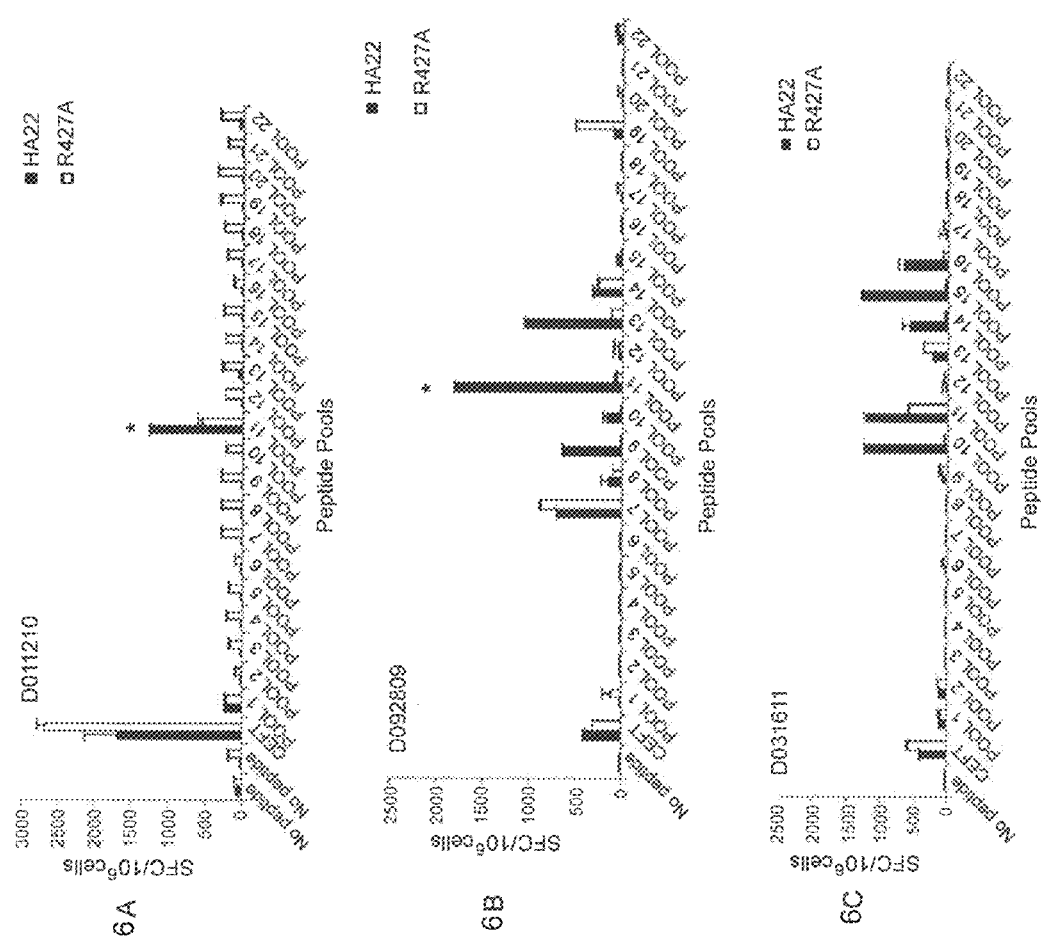
FIGS. 6A-6C are graphs showing the response of three donor samples to 22 peptide pools after stimulation with either HA22-LR (WT) (shaded bars) or LR-R427A (unshaded bars) and restimulation with the appropriate peptides as measured in SFCs per $10 \times 10^6$ cells. * indicates statistical significance (p<0.05).

The response of three donors to 22 peptide pools after stimulation with either HA22-LR (WT) or LR-R427A and restimulation with the appropriate peptides was also measured. The results are shown in FIGS. 6A-6C. As shown in FIGS. 6A-6C, the epitope in peptide 51 was diminished by the R427A mutation.

Figures 7A, 7B, 7C:
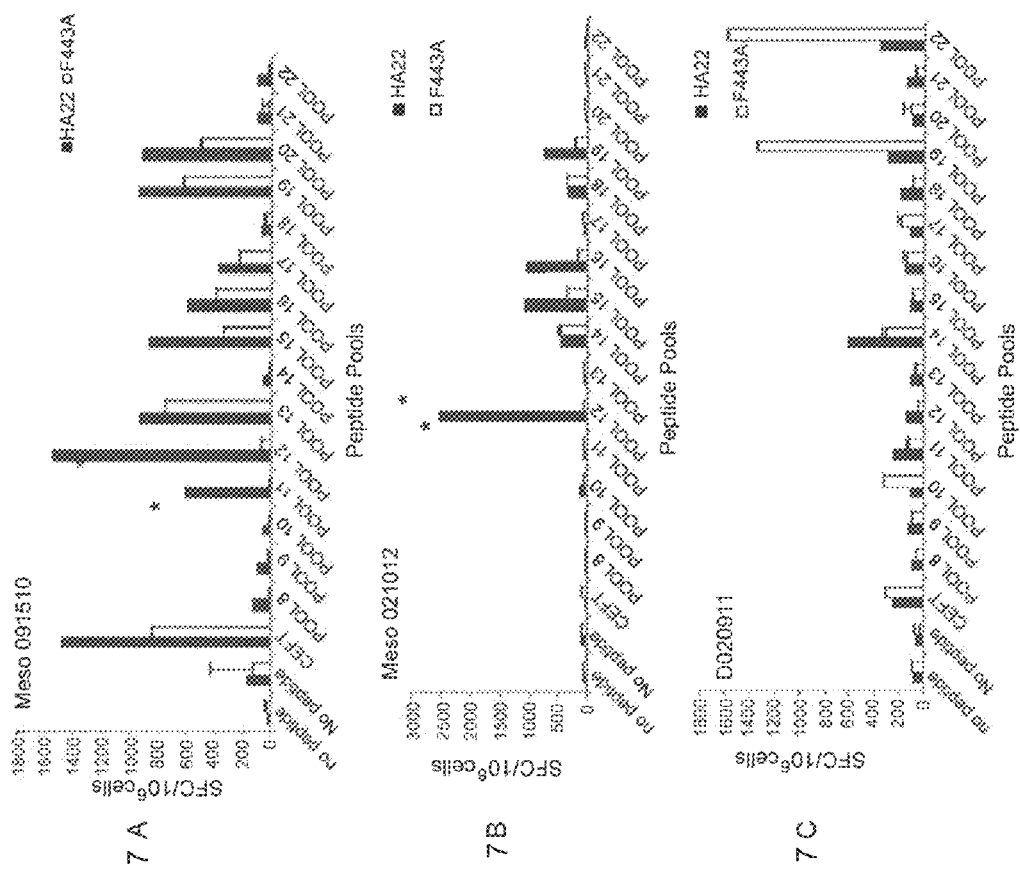
FIGS. 7A-7C are graphs showing the response of two patient samples (A-B) and one donor (C) to one of pools 8-22 after stimulation with either HA22-LR (WT) (shaded bars) or LR-F443A (unshaded bars) and restimulation with the appropriate peptides as measured in SFCs per $10 \times 10^6$ cells. * indicates statistical significance (p<0.05).
Figure 8:
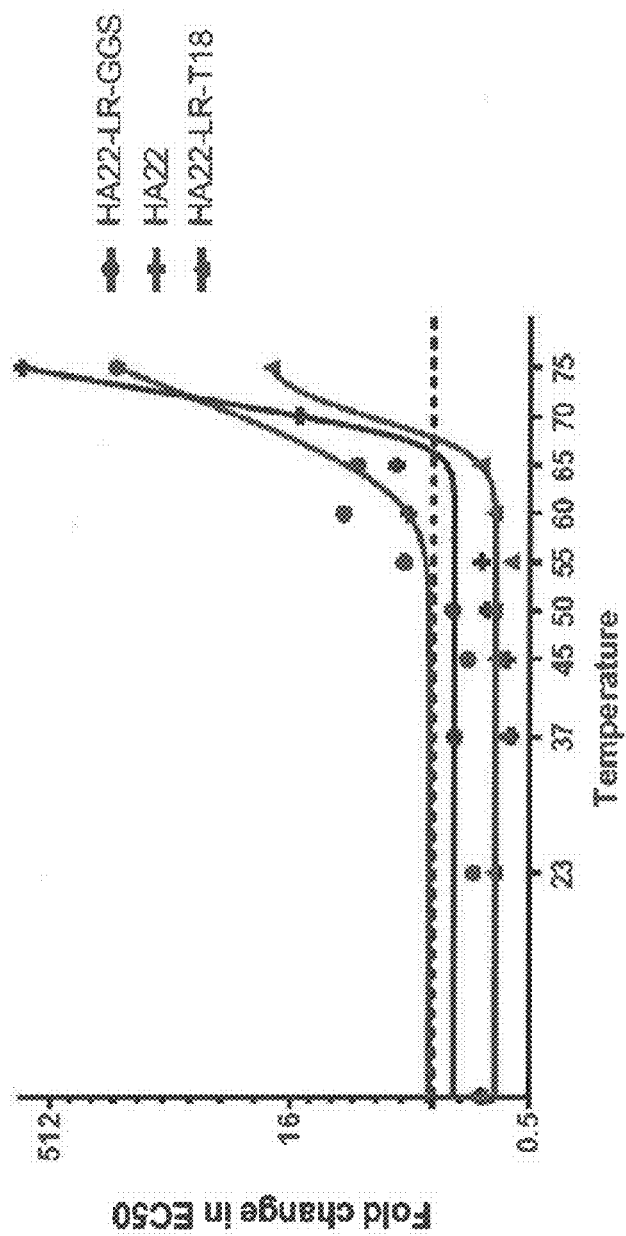
FIG. 8 is a graph showing the fold change in EC50 of HA22-LR-GGS (circles), HA22 (vertical dashes), or HA22-LR-T18 (triangles) at various temperatures.
Figures 9A, 9B, 9C, 9D:
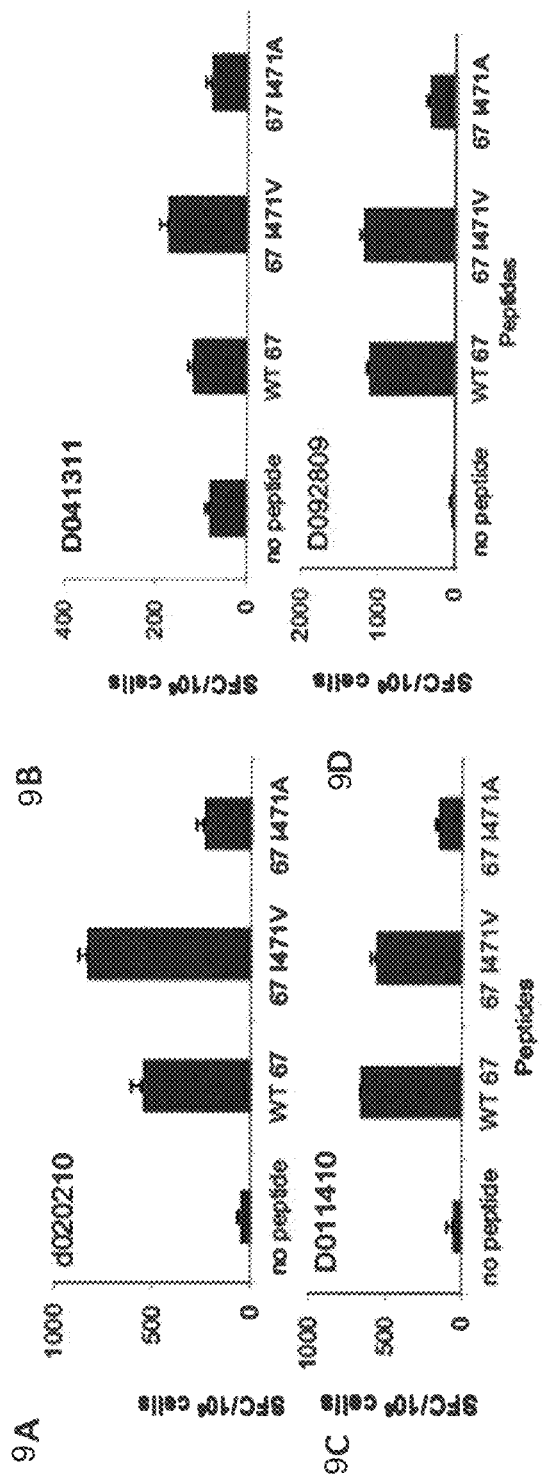
FIGS. 9A-9D are graphs showing the response of four donor samples after stimulation with RIT and restimulation with no peptide, WT peptide 67, or peptide 67 with either a valine or alanine substitution at position 471 as measured in SFCs per $10 \times 10^6$ cells.
Figures 10A, 10B, 10C, 10D, 10E:
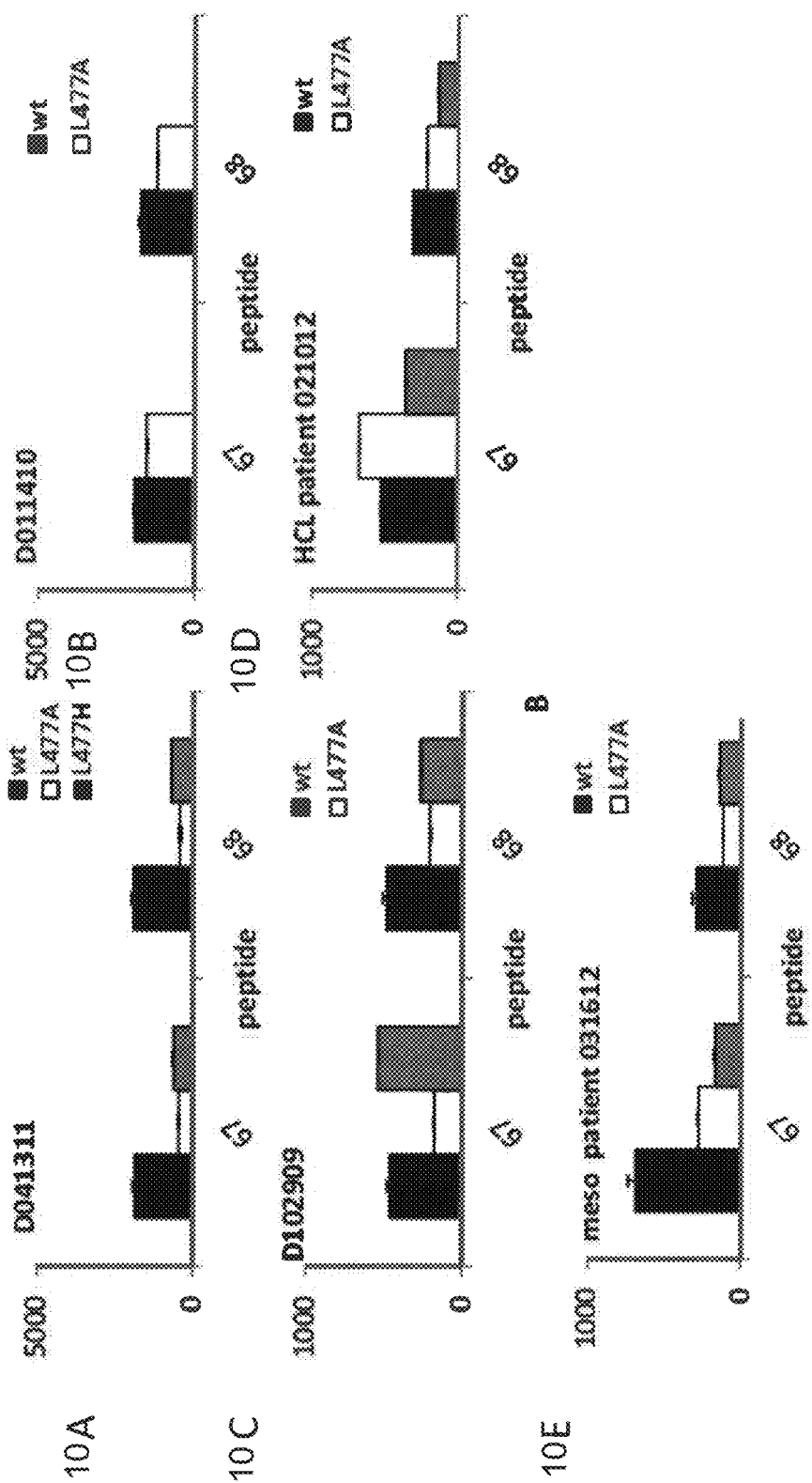
FIGS. 10A-10E are graphs showing the response of three donor samples (A-C), an HCL patient sample (D), and a mesothelioma patient sample (E) after stimulation with peptide 67 or 68 that contains an alanine mutation (white bars) or histidine mutation (grey bars) at position 477 or no mutation (WT) (black bars).

The response of two patients and one donor to pools 8-22 after stimulation with either HA22-LR (WT) or LR-F443A and restimulation with the appropriate peptides was measured. The results are shown in FIGS. 7A-7C. As shown in FIGS. 7A-7C, the epitope in pools 11 and 12 was diminished by the F443A mutation.

Four donor samples were stimulated with RIT and restimulated with peptide 67 containing a valine or alanine mutation at position I471. The response is shown in FIGS. 9A-9D in Spot Forming Cells (SFC)/$10^6$ cells. As shown in FIGS. 9A-9D, mutation I471V did not diminish the epitope in peptide 67.

T cell activation as a response to stimulation with peptide 67 or 68 that contained an alanine or histidine mutation at position L477 or no mutation (WT) was also measured. The results (SFC/$10^6$ cells) are shown in Table 9 and FIGS. 10A-10D. As shown in FIGS. 10A-10D and Table 9, the mutation L477H diminished the epitope in peptide 67 and 68.

TABLE 9

|  | 11410 | 41311 | 102909 | hcl 021012 | meso 031612 | Mean |
|---|---|---|---|---|---|---|
| WT 67 | 100 | 100 | 100 | 100 | 100 | 100 |
| 67 L477A | 81 | 21 | 24 | 133 | 39 | 60 |
| 67 L477H | 0 | 30 | 123 | 65 | 23 | 48 |
| WT 68 | 100 | 100 | 100 | 100 | 100 | 100 |

TABLE 9-continued

|  | 11410 | 41311 | 102909 | hcl 021012 | meso 031612 | Mean |
|---|---|---|---|---|---|---|
| 68 L477A | 69 | 19 | 31 | 62 | 38 | 44 |
| 68 L477H | 2 | 34 | 46 | 32 | 48 | 32 |

Figures 11A, 11B:
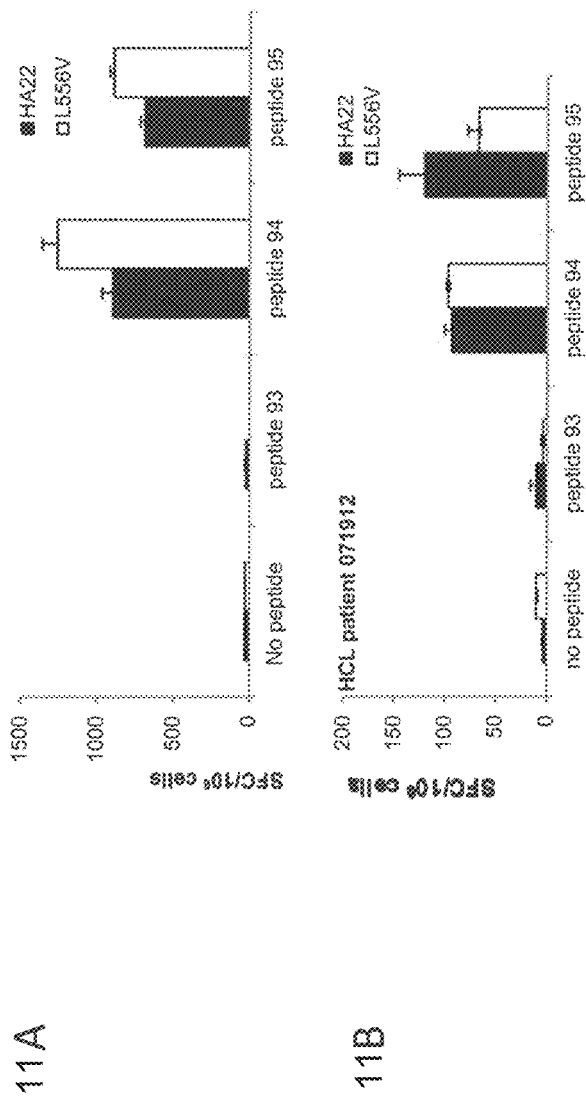
FIGS. 11A and 11B are graphs showing the response of samples from a meothelioma patient (A) and a hairy cell leukemia (HCL) patient (B) after stimulation with RIT and restimulation with no peptide, peptide 93, 94 or 95 with either the WT amino acid sequence (shaded bars) or L556V (unshaded bars).

Cells from two patients were stimulated with RIT and restimulated with peptide 93, 94 or 95 with either the WT amino acid sequence or L556V. The results are shown in FIGS. 11A and B. Mutation L477V did not diminish the epitope in peptide 94.

Example 5

This example demonstrates the activity of combinations of mutations in HA22-LR.

To combine the point mutations that were effective in diminishing the T cell epitopes and maintain good cytotoxic activity, genes were designed that contain different combinations of point mutations. The genes were cloned into the HA22-LR RIT plasmid. Table 10 shows the seven RITs that were constructed and also HA22-LR WT. Table 10 also shows the cytotoxic activity in two cell lines and the calculated remaining T cell response. The calculated remaining response is the sum of the responses shown in the epitope heat map for each of the epitopes, assuming that the mutation will eliminate the responses in the epitope completely. This calculation does not take into account the strength of the response.

As shown in Table 10, out of the 258 responses identified in the donor screen of PE38, 136 responses were in domain III and are present in HA22-LR. Elimination of the epitopes in peptide (77-78), (51-52) and (57-58) with mutations R505A, R427A and F443A (HA22-LR-T2) reduced the calculated responses to 82 responses and maintained a very active protein with 280% and 135% relative activity in CA46 and Raji cells, respectively, compared to WT. HA22-LR-T3 contains four mutations: R505A, R427A, F443A and R494A and had diminished activity of 55% and 50%. HA22-LR-T7 also has four mutations, (R505A, R427A, F443A and R551A) and had good cytotoxic activity with 113% and 100% relative activity in CA46 and Raji cells. For the construction of HA22-LR-T5, five mutations, R505A, R494A, L427A, R551A and F443A, were inserted which reduced the calculated remaining response to 39 responses. However, the protein's cytotoxic activity was severely reduced to 24% and 19% relative activity with $EC_{50}$>1 ng/ml. HA22-LR-T9 also had five point mutations (R505A, R427A, F443A, R494A and L477A). T9 had 46 calculated remaining responses; all 46 remaining responses were weak or medium). It maintained cytotoxic activity with $EC_{50}$<1 ng/ml with relative activity of 36% and 26% in CA46 and Raji cells, respectively. HA22-LR-T11 substitutes L477A in T9 with L477H which improved that activity to 0.2 ng/ml with 85% relative activity in CA46. Lastly, T18 (also referred to as "LMB-T18") was the first RIT that contains six mutations and diminished all the major epitopes that were identified. It had good relative activity with IC50<0.3 ng/ml and relative activity of 63% and 104% compared to HA22-LR in CA46 and Raji cells. To improve cytotoxic activity, a Gly-Gly-Ser peptide linker was inserted after the furin cleavage site.

TABLE 10

|  | HA22-LR | T2-HA | T3-HA | T5-HA | T7-HA | T9-HA | T11-HA | T18 |
|---|---|---|---|---|---|---|---|---|
| RIT backbone |  | HA22-LR | HA22-LR | HA22-LR | HA22-LR | HA22-LR | HA22-LR | HA22-LR |

TABLE 10-continued

|  |  | HA22-LR | T2-HA | T3-HA | T5-HA | T7-HA | T9-HA | T11-HA | T18 |
|---|---|---|---|---|---|---|---|---|---|
| R505A | 77-78 |  | + | + | + | + | + | + | + |
| R494A | 75-76 |  |  | + | + |  | + | + | + |
| L477A | 67-68 |  |  |  |  |  | + |  |  |
| L477H | 67-68 |  |  |  |  |  |  | + | + |
| R427A | 51-52 |  | + | + | + | + | + | + | + |
| R551A | 93-94 |  |  |  | + | + |  |  |  |
| L552E |  |  |  |  |  |  |  |  | + |
| F443A | 57-58 |  | + | + | + | + | + | + | + |
| Cytotoxic Activity |  |  |  |  |  |  |  |  |  |
| CA46 IC50* (ng/ml) |  | 0.17 | 0.06 | 0.31 | 0.71 | 0.15 | 0.48 | 0.2 | 0.27 |
| CA46 Relative activity |  | 100% | 280% | 55% | 24% | 113% | 36% | 85% | 63% |
| Raji IC50* (ng/ml) |  | 0.23 | 0.17 | 0.46 | 1.18 | 0.23 | 0.88 |  | 0.24 |
| Raji Relative activity |  | 100% | 135% | 50% | 19% | 100% | 26% |  | 104% |
| Calculated Responses |  | 136/258 | 82/258 | 62/258 | 39/258 | 59/258 | 46/258 | 46/258 | 19/258 |

*IC50 values are an average of 2-9 assays, depending on the protein.

To characterize the cytotoxic activity properties of T3 and T18, WST-8 assays were performed in four cell lines that express CD22: ca46, Raji, Daudi and HAL-01. Each assay was performed three times. Table 11A shows the average $EC_{50}$ values for each cell line. Both HA22-LR-T3 and HA22-LR-T18 were very cytotoxic, although somewhat less than the parent molecule HA22-LR-GGS. Compared with HA22-LR-GGS, HA22-LR-T18 showed relative activity that ranged between 28%-55% with $IC_{50}$<1 ng/ml in the four cell lines. HA22-LR-T3 was also very active, however, less active than T18.

TABLE 11A

Summary of $EC_{50}$ and relative activity of HA22-LR-T3 and HA22-LR-T18 RITs

| Cell Line |  | HA22-LR-GGS | HA22-LR-T3 | HA22-LR-T18 |
|---|---|---|---|---|
| CA46 | $EC_{50}$ ± (ng/mL) | 0.1 | 0.4 | 0.3 |
|  | SD | ±0.003 | ±0.08 | ±0.01 |
|  | Relative activity (%) | 100 | 18 | 28 |
| Raji | $EC_{50}$ ± (ng/mL) | 0.1 | 0.3 | 0.2 |
|  | SD | ±0.04 | 0.15 | ±0.07 |
|  | Relative activity (%) | 100 | 34 | 55 |
| Daudi | $EC_{50}$ ± (ng/mL) | 0.1 | 0.4 | 0.3 |
|  | SD | ±0.04 | 0.08 | ±0.17 |
|  | Relative activity (%) | 100 | 31 | 38 |
| HAL-01 | $EC_{50}$ ± (ng/mL) | 0.3 | 1.5 | 0.7 |
|  | SD | ±0.05 | ±0.47 | ±0.16 |
|  | Relative activity (%) | 100 | 20 | 42 |

Figures 27A, 27B, 27C, 27D, 27E, 27F:
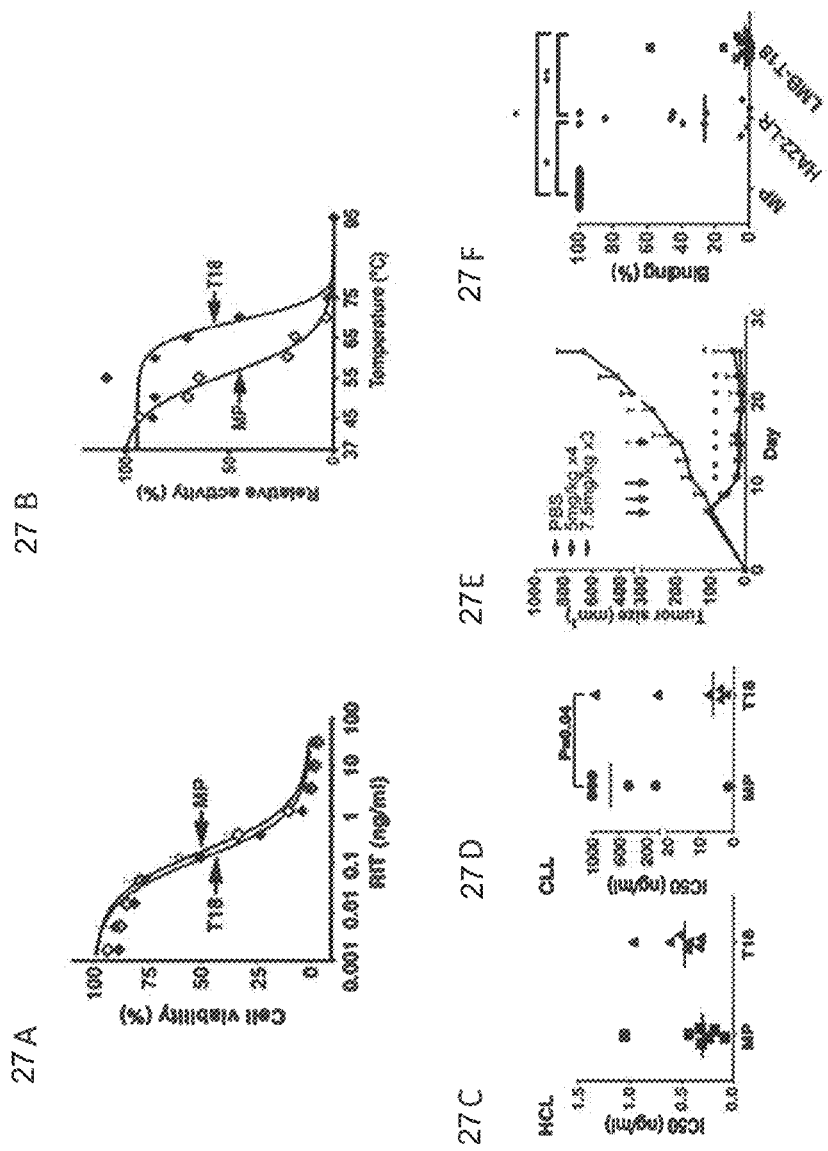
FIG. 27A is a graph showing cell viability (%) of CD22-expressing cell lines treated with various concentrations of T18 or MP RIT (ng/ml).
FIG. 27B is a graph showing the relative cytotoxic activity (%) of T18 or MP RIT that had been heated to one of various temperatures (° C.).
FIGS. 27C-D are graphs showing the cytotoxic activity (IC50 (ng/ml)) of MP or T18 RIT on cells from hairy cell leukemia (HCL) (C) or chronic lymphocytic leukemia (CLL) (D) patients.
FIG. 27E is a graph showing the effect of LMB-T18 on tumor size in a xenograft mouse model after four injections of 5 mg/kg (squares) of LMB-T18, three injections of 7.5 mg/kg (triangles) OF LMB-T18, or PBS-0.2% human serum albumin (circles). Arrows represent days of injection for all dose groups. Broken arrow indicates additional injection of 5 mg/ml group. (*) P>0.01 in one-way ANOVA. Error bars indicate SD.
FIG. 27F is a graph showing the % binding of MP, HA22-LR, and LMB-T18 to serum from patients with neutralizing antibodies to MP.

Cytotoxicity assays of LMB-T18 were performed on four CD22 expressing cell lines and compared with the cytotoxic activity of MP (FIG. 27A, Table 11B). LMB-T18 was very potent with an EC50<10 pM in all cell lines. Compared to MP, LMB-T18 had a small increase of 53% in activity in CA46 cells, 54% in Daudi cells and >200% in HAL-01 cells (p=0.2, 0.06 and 0.01 respectively in Student T test); however, in Raji cells LMB-T18 had a 52% activity decrease (p=0.3 in Student T test). Without being bound by a particular theory or mechanism, it is believed that the decrease in activity in Raji cells was probably due to the domain II deletion (Weldon et al., Blood, 113: 3792-3800 (2009)). The stability of LMB-T18 was compared with MP by heating samples for 15 minutes at various temperatures and, after cooling, measuring residual cytotoxic activities (FIG. 27B) on Raji cells. MP lost 50% of its activity after 15 minutes incubation at 56° C. Unexpectedly, LMB-T18 was more heat-resistant (p<0.05 in Student T test); it only lost 50% of its activity after a 15-minute incubation at 70° C. Cells from seven HCL and six chronic lymphocytic leukemia (CLL) patients were used to determine activity on patient cells. FIGS. 27C-D show that LMB-T18 is more active than MP on CLL cells though this difference is not seen with HCL cells.

TABLE 11B

|  | EC50 ± SD (pM) |  | Relative activity |  |
|---|---|---|---|---|
| Cell line | MP | LMB-T18 | (%) | P value |
| CA46 (n = 4) | 3.4 ± 1.7 | 2.2 ± 0.4 | 153 | 0.2 |
| Raji (n = 4) | 1.1 ± 0.3 | 2.3 ± 0.6 | 48 | 0.3 |
| Daudi (n = 4) | 3.7 ± 1.6 | 2.4 ± 0.8 | 154 | 0.06 |
| HAL-01 (n = 4) | 25.7 ± 3 | 8.1 ± 1 | 318 | 0.01 |

Example 6

This example demonstrates the relative activity of B and T cell epitope modified RIT.

B cell epitopes in PE38 were previously identified and the bulky surface residues were mutated with alanine or serine to reduce antigenicity (Liu et al., Protein Eng. Dec. Sel., (25)(1): 1-6 (2012)). The previously identified mutant RIT with low antigenicity was named SS1LO10R and it contained the following mutations: R505A, R427A, R490A, R463A, R467A, R538A.

To make a minimally immunogenic RIT targeting mesothelin, the LO10 modifications were incorporated into SS1P and then the T cell epitope-point mutations were incorporated one by one. Cytotoxic activity was tested for each one of the variants using mesothelin expressing cell lines (A9/431 and HAY). Two mutations R505A and R427A were found to be effective in diminishing both B and T cell epitopes.

Table 12 summarizes the cytotoxic activity of the mutated PE in two cell lines and the calculated remaining response of the combination RIT that were constructed. Combination of SS1-LO10 with a single point mutation F443A (SS1-LO10-T2) had high (100%-115%) relative activity that corresponded to the activity of these point mutations in HA22-LR. Combination of R494A and R551A in SS1-LO10-T1 gave a very low activity indicating that the combination of R551A and R494A diminished protein activity in both HA22 and SS1-LO10.

TABLE 12

Relative activity of B and T cell epitope modified RIT

| RIT | RIT Backbone | R505A 77-78 | R494A 75-76 | L477H 67-68 | R477H | R427A 51-52 | R551A 93-94 | L552E | L552N | F443A 57-58 | R456A |
|---|---|---|---|---|---|---|---|---|---|---|---|
| SS1 LO10R | | | | | | | | | | | |
| SS1 LO10R-T1 | SS1 LO10R | + | + | | | + | + | | | | |
| SS1 LO10R-T2 | SS1 LO10R | + | | | | + | | | | + | |
| SS1 LO10R-T3 | SS1 LO10R | + | + | | | + | | | | + | |
| SS1 LO10R-T4 | SS1 LO10R | + | + | | | + | | | | + | + |
| SS1 LO10R-T7 | SS1 LO10R | + | | | | + | + | | | + | |
| SS1 LO10R-T8 | SS1 LO10R | + | | | | + | + | | | + | + |
| SS1 LO10R-T9 | SS1 LO10R | + | + | + | | + | | | | + | |
| SS1 LO10R-T11 | SS1 LO10R | + | + | | + | + | | | | + | |
| SS1 LO10R-T14 | SS1 LO10R | + | + | | + | + | | + | | + | |
| SS1 LO10R-T15 | SS1 LO10R | + | + | | + | + | | | + | + | |

| RIT | Cytotoxic activity A431/H9 IC50* (ng/m) | Cytotoxic activity A431/H9 Relative activity | Cytotoxic activity HAY IC50* (ng/m) | Cytotoxic activity HAY Relative activity | Calculated responses |
|---|---|---|---|---|---|
| SS1 LO10R | 0.3 | | 0.5 | | 136/258 |
| SS1 LO10R-T1 | 1.6 | 19% | 50 | 10% | 52/258 |
| SS1 LO10R-T2 | 0.17 | 176% | 0.5 | 100% | 82/258 |
| SS1 LO10R-T3 | 0.29 | 103% | 0.6 | 83% | 62/258 |
| SS1 LO10R-T4 | 2 | 15% | nd | | 62/258 |
| SS1 LO10R-T7 | 0.6 | 50% | 2 | 50% | 59/258 |
| SS1 LO10R-T8 | 0.9 | 33% | 2.5 | 20% | 59/258 |
| SS1 LO10R-T9 | 1.1 | 27% | 6.9 | 7% | 46/258 |
| SS1 LO10R-T11 | 0.42 | 71% | 7 | 7% | 46/258 |
| SS1 LO10R-T | 0.23 | 130% | 1.5 | 33% | 19/258 |

TABLE 12-continued

| Relative activity of B and T cell epitope modified RIT | | | | | | |
|---|---|---|---|---|---|---|
| | T14<br>SS1<br>LO10R-<br>T15 | 0.27 | 111% | 1.9 | 26% | 19/258 |

*IC50 values are an average of 1-9 assays, depending on the protein;
nd—not done SS1 LO10R-T11, which contained R505A, R427A, R494A, F443A and L477H, had 71% activity in H9 cells but only 7% in HAY cells (assay in HAY was done once). T14 and T15, which contained R505A, R427A, R494A, F443A and L477H, with an additional mutation (L552E and L552N, respectively) had >100% relative activity in H9 cells and IC50>1 ng/ml. These two mutants represent the maximal T cell deimmunization done in this project thus far.

Mutant T14 was selected as the best candidate for clinical development because it includes the removal of B cell and many T cell epitopes, yet provides good cytotoxic activity on mesothelin expressing cell lines.

Example 7

This example demonstrates the anti-tumor activity of T14.

Anti-tumor experiments were carried out by injecting saline (control) or T14 into nude mice with A431/H9 xenografts. Tumor size was measured every other day and reported in mm. Animals were weighed at the same time and the weight was reported in grams. The results are shown in Table 13 below. In Table 13, the arrows show the day immunotoxin was injected. As shown in Table 13, doses up to 7 mg/kg×3 were well tolerated with no signs of toxicity in the mice. In addition, major tumor regressions were seen at all dose levels of T14.

TABLE 13

| | | Days | | | | | | | |
|---|---|---|---|---|---|---|---|---|---|
| Group | Mouse # | Day 5 ↓ | | 7 ↓ | | 9 ↓ | | 12 ↓ | 14 ↓ |
| A | 1 | 108 | 23 g | 114 | 22 g | 74 | 23 g | 46 | 36 |
| T14 | 2 | 100 | 22 g | 100 | 22 g | 56 | 22 g | 40 | 64 |
| 5 mg mg/kg × 5 | 3 | 97 | 20 g | 92 | 20 g | 31 | 20 g | 0 | 10 |
| iv QOD | 4 | 101 | 19 g | 94 | 19 g | 60 | 20 g | 52 | 74 |
| (100 ug/mouse) | 5 | 97 | 22 g | 83 | 22 g | 57 | 22 g | 41 | 70 |
| | 6 | 103 | 21 g | 95 | 21 g | 58 | 21 g | 37 | 58 |
| | Mean | 101 | | 96 | | 56 | | 36 | 52 |
| B | 1 | 100 | 22 g | 91 | 20 g | 81 | 20 g | 86 | 78 |
| T 14 | 2 | 96 | 23 g | 103 | 23 g | 50 | 23 g | 14 | 66 |
| 6 mg/kg × 3 | 3 | 100 | 21 g | 112 | 21 g | 91 | 22 g | 54 | 88 |
| iv QOD | 4 | 103 | 24 g | 117 | 24 g | 53 | 24 g | 55 | 98 |
| (120 ug/mouse) | 5 | 102 | 21 g | 121 | 20 g | 62 | 20 g | 82 | 125 |
| | Mean | 100 | | 109 | | 67 | | 58 | 91 |
| C | 1 | 100 | 21 g | 98 | 21 g | 36 | 22 g | 53 22 g | 69 |
| 7 mg/kg × 3 | 2 | 101 | 20 g | 126 | 19 g | 44 | 20 g | 65 21 g | 103 |
| iv GOD | Mean | 101 | | 112 | | 40 | | 59 | 86 |
| (140 ug/mouse) | | | | | | | | | |
| D | 1 | 100 | | 239 | | 440 | | 816 | |
| Control | 2 | 95 | | 133 | | 234 | | 612 | |
| saline | 3 | 104 | | 252 | | 463 | | 813 | |
| | 4 | 92 | | 138 | | 251 | | 543 | |
| | 5 | 100 | | 152 | | 231 | | 589 | |
| | Mean | 98 | | 183 | | 324 | | 675 | Over 800 |

Example 8

This example demonstrates the thermal stability of T18.

The stability of T18 was investigated by heating the RIT for 15 minutes at various temperatures. Cytotoxic assays were subsequently performed. EC50 of the different heated proteins were calculated. The results are shown in FIG. 8. The fold increase in EC50 is shown. As shown in FIG. 8, it was found that T18 maintained cytotoxic activity in 60° C. and lost 50% of its activity at 68° C. Leaver et al., *Methods in Enzymology,* 487: 545-74 (2011).

Example 9.1

This example demonstrates the construction, expression, and purification of anti-mesothelin deimmunized PE chimeric molecules with an elongated linker between the anti-mesothelin-Fab fragment heavy chain and the PE 24 domain and the removal of predicted T cell epitopes in the linker.

The linker sequence used in WO 2012/154530 and Weldon et al., *Mol. Cancer Ther.,* 12: 48-57 (2013) to fuse the dsFv fragment (via the C-terminus of VH domain) to the deimmunized PE was also used to fuse a Fab fragment (via the C-terminus of CH1 domain) to the deimmunized PE. The resulting peptide region, including parts of the CH1 domain, the linker, and part of the the deimmunized PE (SEQ ID NO: 273) was examined by TEPITOPE analysis (Bian et al., *Methods,* 34: 468-475 (2004)). Potential T cell epitopes relevant for European (EU) and United States populations were identified within the region between the CH1 domain and the linker and the region between the linker and the PE24 domain. Potential T cell epitopes were characterized by a confidence number of 3 or lower. The results are shown in Table 14. As shown in Table 14, the linker region without the specific elongations (SEQ ID NO: 273) showed seven potential T-cell epitopes. One potential T-cell epitope was located in the transition region WEQLGGSPT (SEQ ID NO: 274), and the other six T-cell epitopes were located in the transition region VEPKSCKAS (SEQ ID NO: 275). Both of these regions are relevant mainly for European (EU) and Asian populations.

The potential T cell epitopes were destroyed by inserting an amino acid sequence (insert) in each of the transition regions, thereby providing an insert on each of both sides of the furin cleavage site. The sequence DKTH (SEQ ID NO: 276) was inserted into the linker at a location not directly adjacent to the furin cleavage sequence (FCS), and the sequence GGG (SEQ ID NO: 277) was inserted into the linker at a location directly adjacent to the FCS without potential T-cell epitopes. The resulting elongated peptide region, including a) parts of the CH1 domain, b) the linker elongated at the Fab fusion area and elongated at the PE fusion area, and c) part of the of the the deimmunized PE comprised amino acid SEQ ID NO: 278. The elongated peptide region was studied using TEPITOPE analysis, and the results are shown in Table 15A. As shown in Table 15A, the elongated linker did not generate an alert in the TEPITOPE analysis (confidence numbers of 6 or higher) and, at the same time, provided improved stability (see Example 9.2 below).

TABLE 14

| Start Pos | Sequence | Score | Confidence | Profile | Anchor | Inhibitor | Allele | Pivot | Pept. | f (EU) | f (US) | f(NE Asia) | f(SE Asia) | f(SW Asia) | max f(all) |
|---|---|---|---|---|---|---|---|---|---|---|---|---|---|---|---|
| 26 | WEQLGGSPT (SEQ ID NO: 274) | 0.3 | 3 | ********* | 0 | 0 | HLA-DRB1*0101 | 1 | 0 | 8.0% | 0.6% | 5.7% | 0.1% | 4.1% | 8.0% |
| 8 | VEPKSCKAS (SEQ ID NO: 275) | 1.6 | 2 | *A*** | 1 | 0 | HLA-DRB1*0802 | 1 | 0 | 0.1% | 12.0% | 2.6% | 0.1% | 0.8% | 12.0% |
| 8 | VEPKSCKAS (SEQ ID NO: 275) | 2.6 | 2 | *A*** | 1 | 0 | HLA-DRB1*0804 | 1 | 0 | 0.1% | 0.1% | 0.6% | 0.0% | 0.0% | 0.6% |
| 8 | VEPKSCKAS (SEQ ID NO: 275) | 2.6 | 3 | *A*** | 1 | 0 | HLA-DRB1*0806 | 1 | 0 | 0.1% | 0.0% | 0.1% | 0.0% | 0.0% | 0.1% |
| 8 | VEPKSCKAS (SEQ ID NO: 275) | 1.9 | 3 | ********* | 0 | 0 | HLA-DRB1*1102 | 1 | 0 | 0.2% | 0.0% | 0.0% | 0.0% | 1.0% | 1.0% |
| 8 | VEPKSCKAS (SEQ ID NO: 275) | 1.9 | 3 | ********* | 0 | 0 | HLA-DRB1*1121 | 1 | 0 | N.A. | N.A. | N.A. | N.A. | N.A. | 0.0% |
| 8 | VEPKSCKAS (SEQ ID NO: 275) | 1.9 | 3 | ********* | 0 | 0 | HLA-DRB1*1322 | 1 | 0 | N.A. | N.A. | N.A. | N.A. | N.A. | 0.0% | all Alerts listed <= 3

TABLE 15A

| Start Pos | Sequence | Score | Confidence | Profile | Anchors | In hibitors | Allele | Pivot | Peptide | f (EU) | f (US) | f(NE Asia) | f(SE Asia) | f(SW Asia) |
|---|---|---|---|---|---|---|---|---|---|---|---|---|---|---|
| 30 | WEQLGGGGG (SEQ ID NO: 279) | -1.2 | 9 | ****I | 0 | 1 | HLA-DRB1*0101 | 1 | 0 | 8.0% | 0.6% | 5.7% | 0.1% | 4.1% |
| 33 | LGGGGGSPT (SEQ ID NO: 280) | -0.7 | 9 | ********* | 0 | 0 | HLA-DRB1*0102 | 1 | 0 | 0.6% | 0.1% | 0.0% | 0.0% | 0.7% |
| 30 | WEQLGGGGG (SEQ ID NO: 279) | -1 | 9 | *A**I | 1 | 1 | HLA-DRB1*1307 | 1 | 0 | 0.0% | 0.0% | 0.0% | 0.0% | 0.0% |
| 30 | WEQLGGGGG (SEQ ID NO: 279) | 1.4 | 6 | ********* | 0 | 0 | HLA-DRB5*0101 | 1 | 0 | N.A. | N.A. | N.A. | N.A. | N.A. |
| 30 | WEQLGGGGG (SEQ ID NO: 279) | 1.4 | 6 | ********* | 0 | 0 | HLA-DRB5*0105 | 1 | 0 | N.A. | N.A. | N.A. | N.A. | N.A. | no Alert <= 3

Example 9.2

This example demonstrates the stability of the deimmunized PE fusion proteins and conjugates having the elongated linker of SEQ ID NO: 36.

Six Fab-Linker-PE24 variants were produced and compared with respect to their thermal stability and propensity for aggregation. The six variants all contained the same humanized Fab variant H1/L1 of the SS1 antibody, but differed with respect to the linker and the PE24 mutant. For the linker, either the linker described in International Patent Application Publication WO 2012/154530 (kasggrhrqprgweqlggs (SEQ ID NO: 281)) or the elongated linker with the additional amino acids ("long linker"; SEQ ID NO: 36 ( dkthkasggrhrqprgweqlgggggs))) was used. As PE24 variants, LRO10R, LRO10R-456A (SEQ ID NO: 37) or LRO10R-456A-551A were employed in the constructs.

Figure 12:
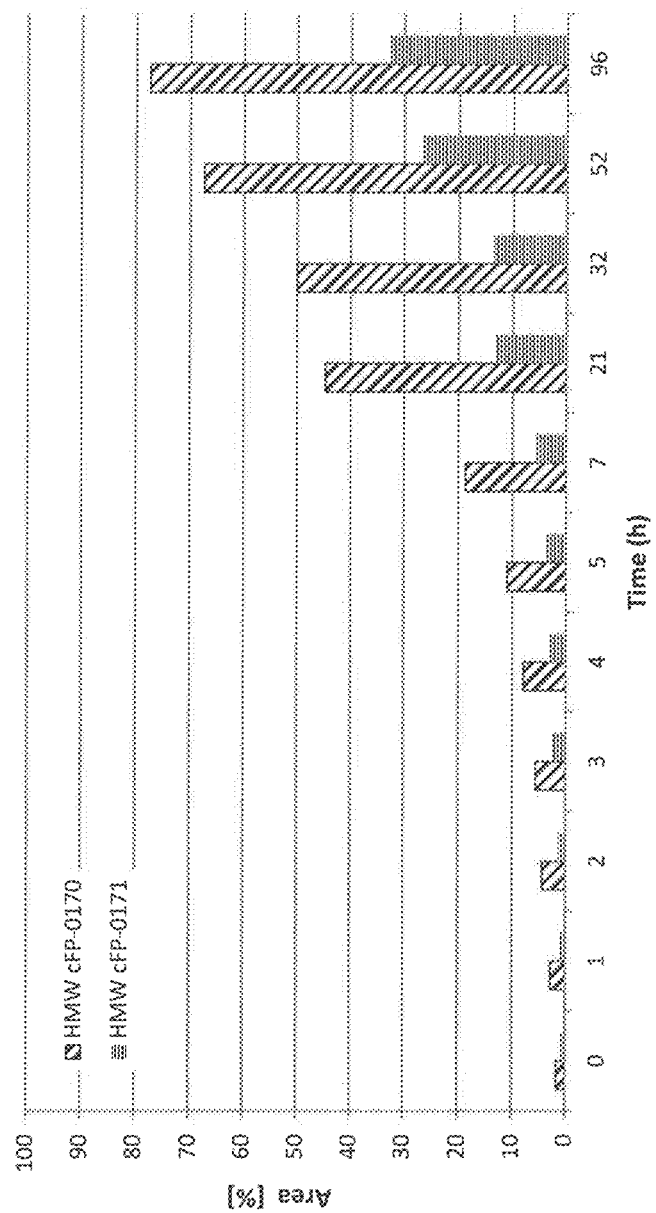
FIG. 12 is a graph showing the aggregation (% Area) of HMW cFP-0170 (Fab-LO10R-456A short linker; diagonally striped bars) or HMW cFP-0171 (Fab-LO10R-456A elongated liker; horizontally striped bars) as measured by size exclusion chromatograph (SEC) after incubation at 33° C.
Figure 13:
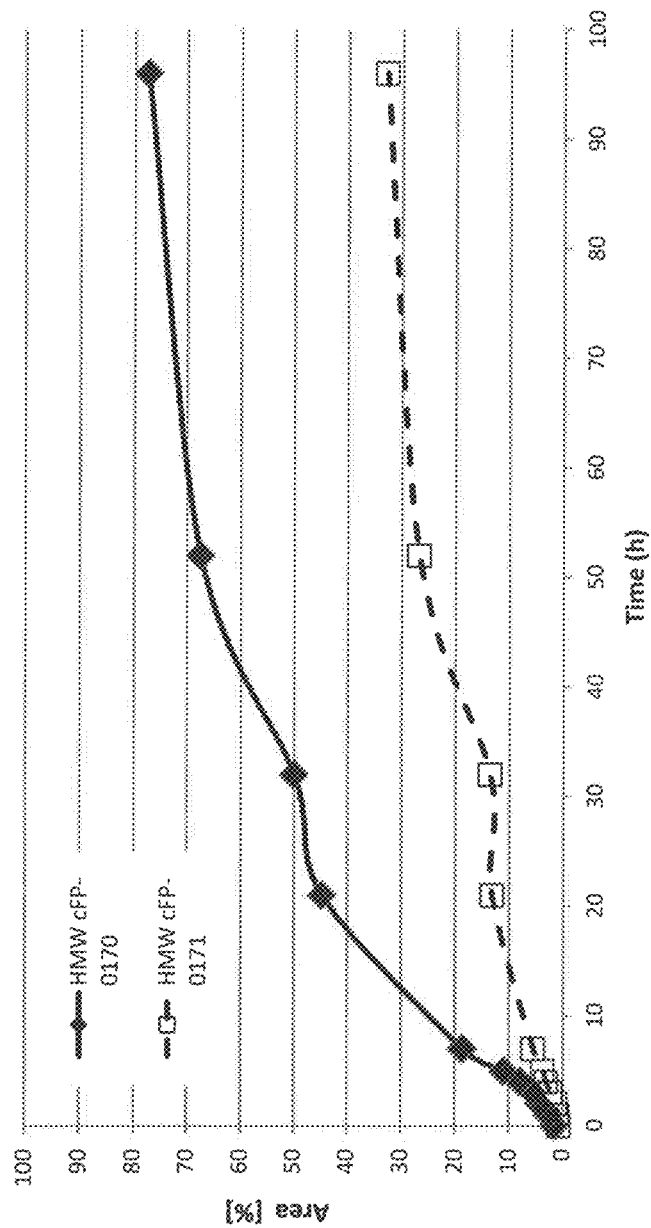
FIG. 13 is a graph showing the aggregation (% Area) of HMW cFP-0170 (Fab-LO10R-456A short linker; diamonds) or HMW cFP-0171 (Fab-LO10R-456A elongated liker; squares) as measured by size exclusion chromatograph (SEC) after incubation at 33° C.

FIGS. 12-13 show the level of aggregation of the two constructs with the PE24 variant LRO10R-456A that was measured in terms of the area under the aggregate peak by size exclusion chromatography (SEC) after incubation at 33° C. The two constructs in FIGS. 12-13 differed only with respect to the linker employed. The short linker SEQ ID NO: 281 was used in construct cFP-0170 and the elongated linker SEQ ID NO: 36 was used in construct cFP-0171.

Figure 14:
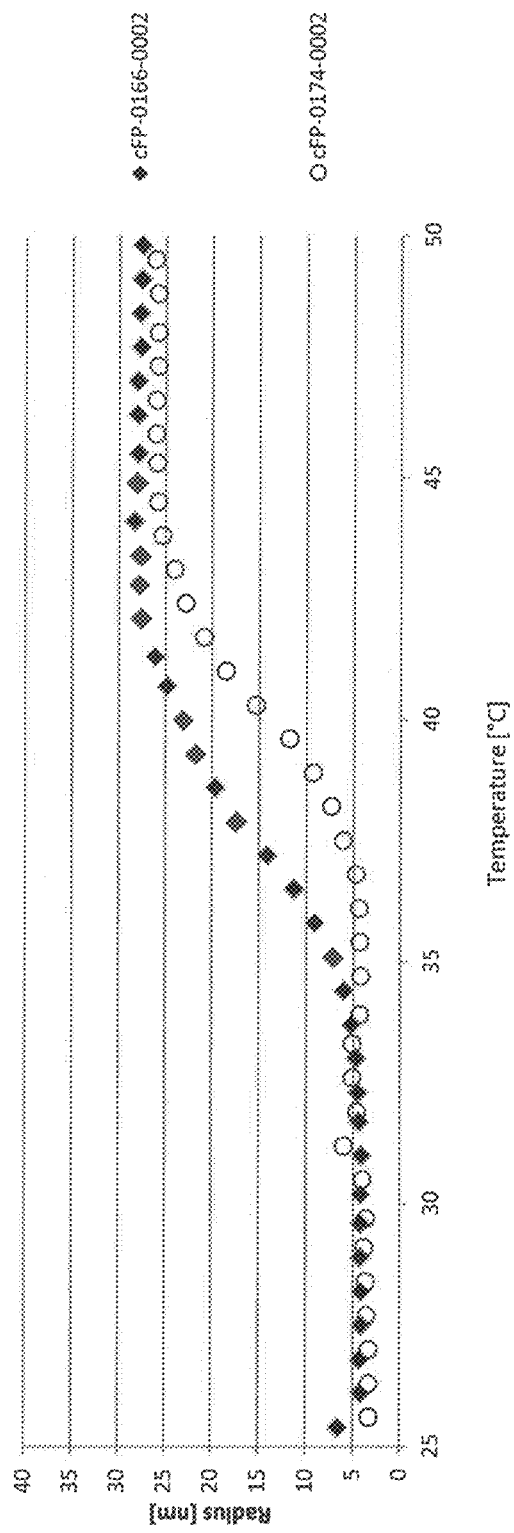
FIG. 14 is a graph showing the aggregation (radius in nm) of cFP-0166 (Fab-LO10R short linker; diamonds) or cFP- 0174 (Fab-LO10R elongated linker; circles) as measured by dynamic light scattering (DLS) at various temperatures in a range from 25° C. to 50° C.
Figure 15:
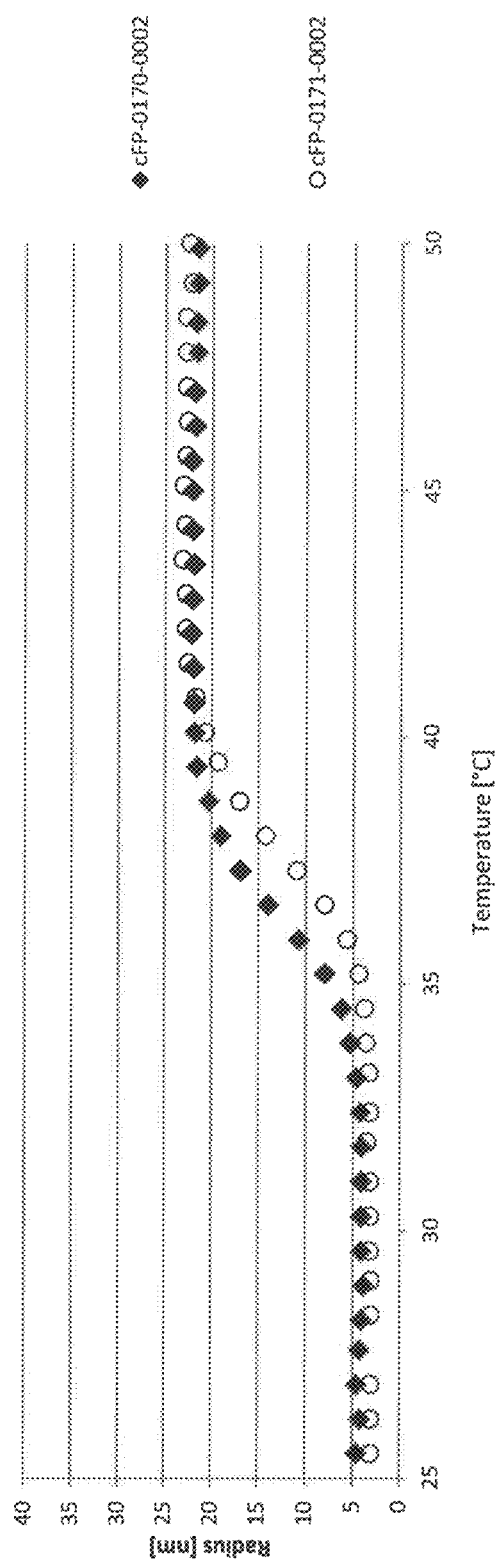
FIG. 15 is a graph showing the aggregation (radius in nm) of cFP-0170 (Fab-LO10R-456A short linker; diamonds) or cFP-0171 (Fab-LO10R-456A elongated linker; circles) as measured by DLS at various temperatures in a range from 25° C. to 50° C.
Figure 16:
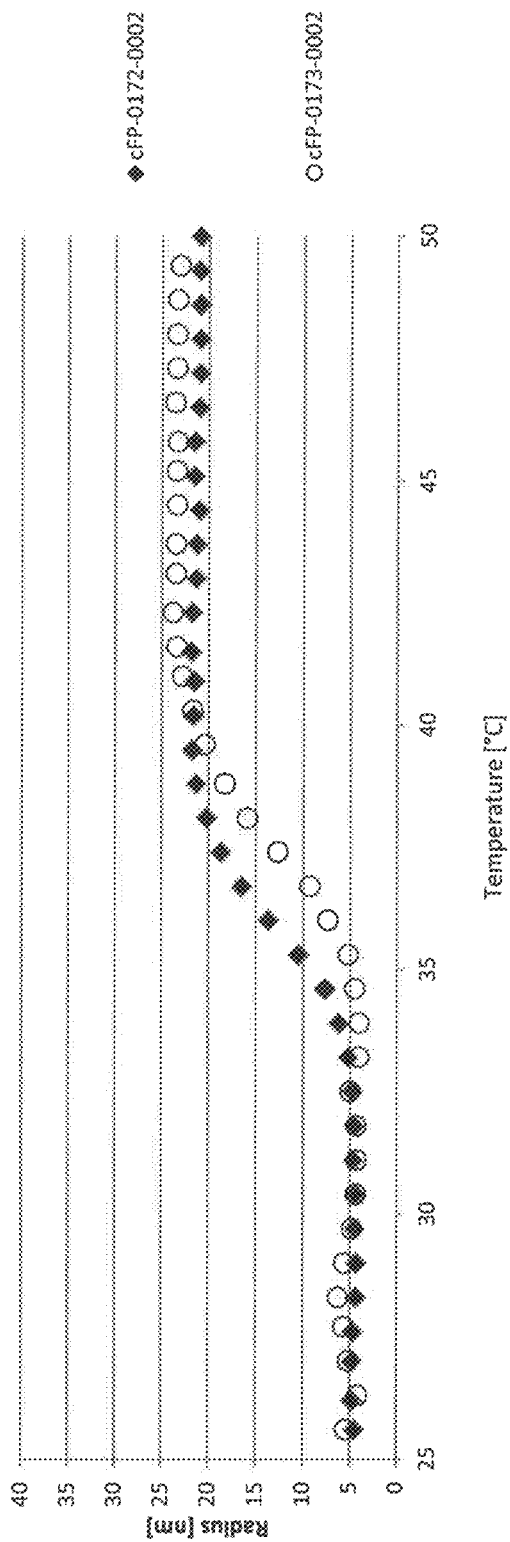
FIG. 16 is a graph showing the aggregation (radius in nm) of cFP-0172 (Fab-LO10R-456A-551A short linker; diamonds) or cFP-0173 (Fab-LO10R-456A-551A elongated linker; circles) as measured by DLS at various temperatures in a range from 25° C. to 50° C.
Figure 17:
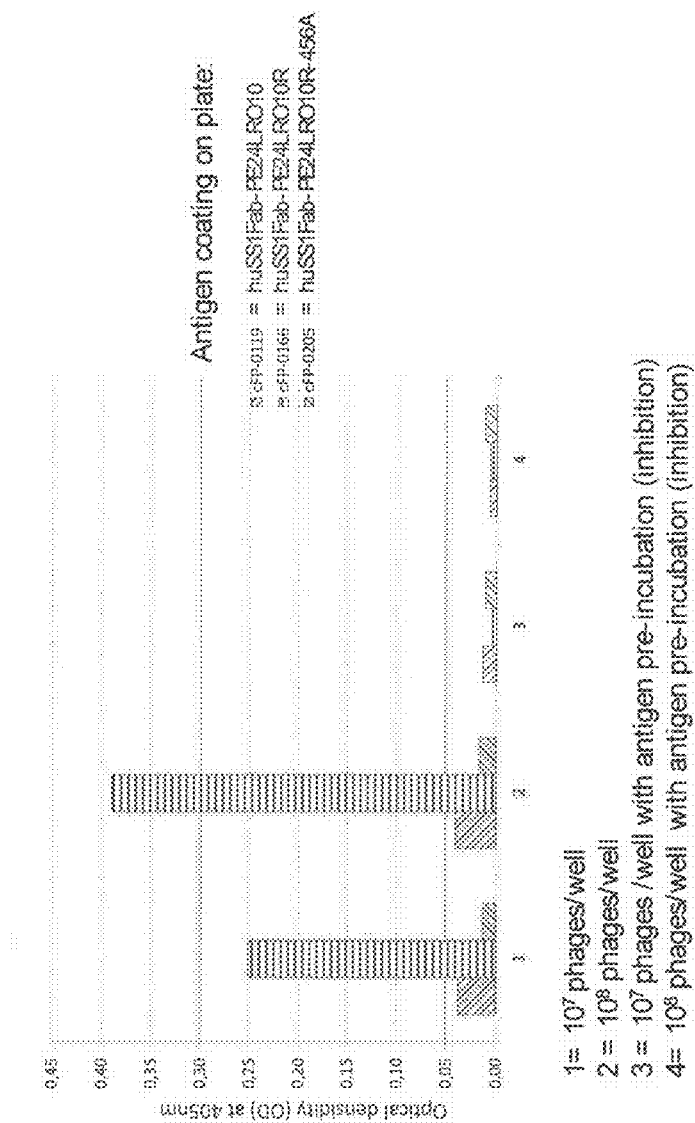
FIG. 17 is a graph showing the response of patient sera clone 9H3 to ($10^7$) or ($10^8$) phages/well or ($10^7$) or ($10^8$) phages/well with antigen pre-incubation incubated with huSS1Fab-PE24LRO10 (with 458A mutation) (left diagonally striped bars), huSS1Fab-PE24LRO10R (with 458R backmutation) (horizontally striped bars), or huSS1Fab-PE24LRO10R-456A (with 458R backmutation and 456A mutation) (right diagonally striped bars) as measured in optical density at 450 nm.
Figures 18A, 18B:
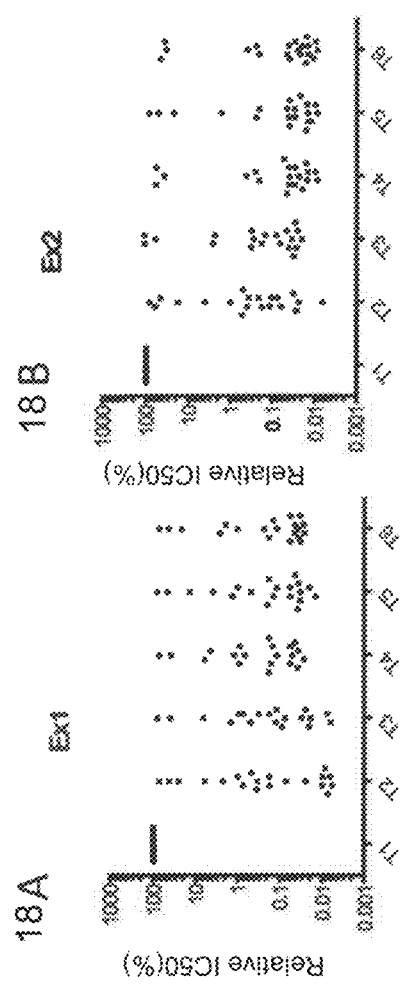
FIGS. 18A and 18B are graphs showing the antigenicity of the chimeric molecules SS1P (T1), SS1-dsFv-LR-LO10R (T2), SS1-dsFv-LR-LO10R456A (T3), SS1-FABLO10R (Roche 116, T4), SS1-FABLO10R456ALongLinker (Roche 171, T5), and SS1-FABLO10RLongLinker (Roche 174, T6) with respect to 20 patient sera. Two representative examples (A and B) are shown. The Y axis is relative IC50(%).

FIGS. 14-16 show the thermal stability of constructs as measured by dynamic light scattering (DLS). For dynamic light scattering, samples were prepared at a concentration of 1 mg/mL in 20 mM histidine/histidine chloride, 140 mM NaCl, pH 6.0, transferred into an optical 384-well plate by centrifugation through a 0.4 μm filter plate and covered with paraffin oil. The hydrodynamic radius was measured in a WYATT DYNAPRO Plate Reader II repeatedly by dynamic light scattering while the samples were heated at a rate of 0.05° C./min from 25° C. to 80° C. The aggregation onset temperature was defined as the temperature at which the hydrodynamic radius starts to increase. The results are shown in FIGS. 14-16. The DLS curves for the six constructs showed higher aggregation temperatures for the elongated linker compared to the short published linker, with a strong shift to a higher aggregation temperature for the LRO10R variant (FIGS. 14-16).

Table 15B shows the thermal stability of constructs cFP-0170 and cFP-0171 as measured by differential scanning calorimetry (DSC). Differential scanning calorimetry was performed using a MicroCal DSC system (GE Healthcare). The samples were adjusted to a protein concentration of approximately 1 mg/ml in 20 mM histidine/HCl, 140 mM sodium chloride, pH 6.0. The reference cell was filled with a buffer corresponding to the sample buffer. The samples were placed in the sample cell and heated from 4° C. to 110° C. at a heating rate of 60° C./hour. The pre-scan was 15 minutes, the filtering period was 10 seconds, and the feedback mode/gain was set to passive. The midpoint of a thermal transition temperature (Tm, or thermal transition temperature) was obtained by analyzing the data using MicroCal DSC analysis software.

TABLE 15B

| Construct | T-max of the Fab fragment part | T-max of the PE24 part |
|---|---|---|
| Humanized SS1 Fab long linker-LRO10R, LRO10R-456A | 73.6 | 41.2 |
| Humanized SS1 Fab long linker-LRO10R, LRO10R | 73.7 | 43.2 |

As shown in FIGS. 12-16 and Table 15B, all chimeric Fab-PE molecules with the elongated linker provided a decreased tendency toward aggregation and a higher aggregation temperature as compared to chimeric Fab-PE molecules with a short linker that was not elongated.

Example 10

This example demonstrates the ability of deimmunized PE fusion proteins with an extended linker to kill tumor cells and inhibit cellular protein synthesis. This example also demonstrates the antigenicity of the deimmunized PE fusion proteins with an extended linker.

The potency of different Fab-PE24 variants with respect to the ability to inhibit protein synthesis was compared. A clone of the pancreatic cancer cell line ASPC-1 (ASPC-1 Luc) that was stably transfected with luciferase was used. The luciferase protein in these cells undergoes a high turnover so that the measurable activity drops markedly within 24 hours of inhibition of its resynthesis. Briefly, cells were seeded on 96 well plates. After overnight culture, different concentrations of the cFP variants were added to the medium, and cells were incubated for another 72 hours. At the end of the incubation period, the cells were lysed, and luciferase activity was determined with the STEADY-GLOW assay according to the manufacturer's instructions. In a typical experiment, an 80-90% reduction of luciferase activity was observed in lysates from treated cells as compared to lysates from untreated control cells. EC50 values, i.e., the concentrations that achieve half maximal effects, were determined based on a free four parameter fit. Table 16 compares the relative potencies in a representative experiment by setting the IC50 of huFabLRO10R to 1.

Untargeted PE24 (variant LR8M) only inhibited at concentrations >3.5 μg/ml, while the previously described LRO10 variant fused to a humanized SS1 Fab fragment was ~500 fold more potent on a molar basis. The LRO10R backmutation increased potency 10 to 20 fold (EC50 values 1-2 ng/ml versus 18 ng/ml). The 456A mutation had no adverse effect on potency, while the 551A mutation did reduce activity to the level of LRO10 (EC50 10-23 ng/ml). The new extended linker also had no negative impact on the cellular potency of the molecules in a comparison of any of the three pairs of constructs with the extended linker versus those with the previously described shorter linker.

Using cell viability assessed by CELLTITERGLOW assays, the cytotoxic potency of different Fab-PE24 variants using the same humanized SS1 targeting variant on two different tumor cell lines (A431 H9 and H596) was compared. Briefly, cells were seeded on 96 well plates. After overnight culture, different concentrations of the cFPs were added to the medium, and cells were incubated for 72 hours. At the end of the incubation period, cell viability was determined using a CELLTITERGLOW assay. Table 16 compares the relative potencies by setting the IC50 of huFabLRO10R to 1.

TABLE 16

| Viability assay results Luciferase assay results cFP variant | A431 H9 | H596 | AsPC-1 Luc |
|---|---|---|---|
| | Fold potency reduction relative to huFabLRO10R | | |
| huFabLRO10 | 1.8 | 2.5 | 17.5 |
| LR8M | 400 | 450 | 9452 |
| huFabLRO10R | 1 | 1 | 1 |
| huFabLRO10R-long linker | 1.2 | 1 | 2.3 |

TABLE 16-continued

| | | | |
|---|---|---|---|
| huFabLRO10R-456A | 0.8 | 1 | 2.1 |
| huFabLRO10R-456A-longlinker | 0.9 | 1.2 | 3 |
| huFabLRO10R-456A-551A | 2.1 | 3.3 | 22.5 |
| huFabLRO10R-456A-551A-longlinker | 2.1 | 4.5 | 9.8 |

Results similar to those in Table 16 were also obtained using a cell viability assay with an 3-[4,5-dimethylthiazol-2-yl]-2,5 diphenyl tetrazolium bromide (MTT)-based read-out in different cell lines (Table 17).

TABLE 17

IC 50s in ng/ml (did not correct for MW differences)

| | Hu-1 | Hu2 | Hu3 | HAY | AGS | L55 |
|---|---|---|---|---|---|---|
| SS1P | 2 | 0.3 | 2.9 | 1.0 | 0.3 | 3.0 |
| SS1-LR-GGS | 0.25 | 0.01 | 0.7 | — | — | 1.0 |
| SS1-LR-GGS-010R | — | 0.01 | — | 0.3 | 1.0 | 2.0 |
| Fab-LR-GGS-010R Short | 0.25 | 0.08 | 0.4 | 2.5 | 0.6 | 3.5 |
| Fab-LR-GGS-010R 456A Short | 0.25 | 0.05 | 0.6 | 2.5 | 0.6 | 3.0 |
| Fab-LR-GGS-010R long | 0.35 | 0.04 | 1.8 | 2.5 | 0.9 | 5.0 |
| Fab-LR-GGS-010R 456A long | 0.25 | 0.04 | 2.0 | 1.4 | 1.1 | 5.0 |
| Fab-LR-GGS-010R 456A 551A Short | 0.7 | 0.18 | 4.2 | 4.0 | 6.0 | 20.0 |
| Fab-LR-GGS-010R 456A 551A long | Also low | Also low | Also low | Also low | Also low | Also low |

Example 11

This example demonstrates the removal of B-cell epitopes by 456A mutations in PE.

A phagemid containing the scFv 9H3 in the vector pCANTAB as described by Liu et al., *PNAS*, 109: 11782-11787 (2012) was prepared by standard methods as described in Sambrook, J. et al., *Molecular cloning: A laboratory manual*; Cold Spring Harbor Laboratory Press, Cold Spring Harbor, N.Y., 1989. The molecular biological reagents were used according to the manufacturer's instructions. The phagemid was transformed into electrocompetent TG1 cells. From single colonies, precultures were grown overnight and used to inoculate 4 ml cultures of 2×YT/1% glucose supplemented with the appropriate selective antibiotic ampicillin. At an $OD_{600}$ of 0.3-0.8, $10^{10}$ cfu VCSM 13 helper phage and IPTG was added to a final concentration of 1 mM. After incubation for 15 minutes at 37° C., the culture was grown at 37° C. overnight. Two hours after helper phage addition, kanamycin was added to final concentration of 30 μg/ml. The phage-containing supernatant was harvested from the overnight culture by centrifugation, and the scFv displaying phage were precipitated from the supernatant by addition of ⅕ v/v 20% PEG-6000/2.5 M NaCl and isolated by centrifugation. The phage pellet was dissolved in 0.5 ml PBS/1% BSA, and the phage solution was cleared by centrifugation and sterile filtration. The titer of the phage solution was determined by standard methods as described in Barbas, C. et al., *Phage Display—A laboratory manual*, Cold Spring Harbor Laboratory Press, Cold Spring Harbor, N.Y., 2001.

96 well MaxiSorp microtiter plates were coated with 100 μg/ml Fab-PE24 variants. After blocking with PBS buffer supplemented with 2% BSA, $10^7$ and $10^8$ scFv-displaying phage were captured on the plate for one hour. As specific negative controls, scFv-displaying phages were pre-incubated with 50 μg/m of the Fab-PE24 variants for 1 hour at room temperature (RT) before capturing them on the plate. Plates were washed with PBST buffer (PBS+0.5% Tween 20). Binding of scFv-displaying phage was detected with POD conjugated anti-m13 antibody (Progen). After a final wash, the plates were incubated with POD substrate. Absorbance was measured at 405 nm. Results are shown in FIG. 17, where it can be seen that the B-cell epitope contained in the phagemid containing the scFv 9H3 was not removed in LRO10R (with 458R backmutation) while it was eliminated by both mutations 458A and 456A with a slightly stronger effect for the 456A mutation.

Antigenicity testing was done as described in Weldon et al., *Mol. Cancer Ther.,* 12: 48-57 (2013). As shown in FIGS. 18A and 18B, compared to SS1P (T1), the de-immunized variant LRO10R (T2) had a 100-10,000 fold reduced reactivity with most sera from patients that have been previously exposed to a PE-based therapeutic fusion protein both with the murine dsFv fusion format and the humanized Fab fusion format. Also the introduction of the 456A mutation (T3 and T5) or the new extended linker (T5 and T6) showed a 100-10,000 fold reduced reactivity with most sera from patients that have been previously exposed to a PE-based therapeutic fusion protein.

Example 12

This example demonstrates the construction, expression and purification of deimmunized PE variants and Fab fusions thereof as well as dsFv fusions for comparison.

Example 12.1

Cloning of Anti-Mesothelin Deimmunized PE Chimeric Molecules cFP-0077 (SEQ ID NOs: 41 and 42) and cFP-0078 (SEQ ID NOs: 43 and 44)

For the expression of cFP-0077 and cFP-0078, the *E. coli* host/vector system, which enables an antibiotic-free plasmid selection by complementation of an *E. coli* auxotrophy (PyrF), was employed (European Patent Application Publication 0 972 838 and U.S. Pat. No. 6,291,245). Standard methods were used to manipulate DNA as described in Sambrook, J. et al., supra. The molecular biological reagents were used according to the manufacturer's instructions. Desired gene segments were made by commercial gene synthesis. The synthesized gene fragments were cloned into a specified expression vector. The DNA sequences of the subcloned gene fragments were confirmed by DNA sequencing.

The expression plasmids for the production of the light chain and the heavy chain, respectively, were prepared as follows: The light chain (LC) plasmids 15478 (based on the amino acid sequences of cFP-0077 and encoding SEQ ID NO: 41) and 15479 (based on the amino acid sequences of cFP-0078 and encoding SEQ ID NO: 43) are expression plasmids for the expression of an antibody light chain fragment in *E. coli*. They were generated by ligating the antibody VL domain fragment into the vector using the XhoI/BsiWI restriction sites for 15478, and XhoI/BlpI for 15479.

The light chain *E. coli* expression plasmids comprise the following elements:

- the origin of replication from the vector pBR322 for replication in *E. coli* (corresponding to positions 2517-3160 according to Sutcliffe et al., *Quant. Biol.,* 43: 77-90 (1979), the URA3 gene of *Saccharomyces cerevisiae* coding for orotidine 5'-phosphate decarboxylase (Rose et al., *Gene*, 29: 113-124 (1984) which allows plasmid selection by complementation of *E. coli* pyrF mutant strains (uracil auxotrophy), the antibody light chain expression cassette comprising:

the T5 hybrid promoter (T5-PN25/03/04 hybrid promoter according to Bujard et al., *Methods. Enzymol.*, 155: 416-433 (1987) and Stueber, et al., *Immunol. Methods IV*, 121-152 (1990) including a synthetic ribosomal binding site according to Stueber et al. (supra), the antibody light chain variable domain comprising the CDRs of SS1, and the human Ck domain for 15478 but not for 15479, two bacteriophage-derived transcription terminators, the λ-T0 terminator (Schwarz et al., *Nature*, 272: 410-414 (1978) and the fd-terminator (Beck et al., *Gene*, 1-3: 35-58 (1981), and the lad repressor gene from *E. coli* (Farabaugh, *Nature*, 274: 765-769 (1978).

The heavy chain (HC) plasmids 15476 (based on the amino acid sequences of cFP-0077 and encoding SEQ ID NO: 42) and 15477 (based on the amino acid sequences of cFP-0078 and encoding SEQ ID NO: 44) are expression plasmids for the expression of a fusion protein including an antibody heavy chain fragment, a linker containing a furin cleavage site, and a mutant of domain III of *Pseudomonas aeruginosa* Exotoxin A (PE), in *E. coli*. It was generated by ligation of the VH domain fragment into the vector using the XhoI/BsrGI restriction sites for 15476, and XhoI/HindIII restriction sites for 15477.

The cytolytic fusion protein heavy chain *E. coli* expression plasmids comprise the following elements:

the origin of replication from the vector pBR322 for replication in *E. coli* (corresponding to positions 2517-3160 according to Sutcliffe et al., *Quant. Biol.*, 43: 77-90 1979), the URA3 gene of *Saccharomyces cerevisiae* coding for orotidine 5'-phosphate decarboxylase (Rose et al., *Gene*, 29: 113-124 (1984) which allows plasmid selection by complementation of *E. coli* pyrF mutant strains (uracil auxotrophy), the heavy chain-PE domain III fusion protein expression cassette comprising the T5 hybrid promoter (T5-PN25/03/04 hybrid promoter according to Bujard et al., *Methods. Enzymol.*, 155: 416-433 (1987) and Stueber et al., *Immunol. Methods IV*, (1990) 121-152) including a synthetic ribosomal binding site according to Stueber et al. (supra), the antibody heavy chain variable domain comprising the CDRs of SS1, the human CH1 domain for 15476 but not for 15477, the linker comprising a furin cleavage site the mutant variant of *Pseudomonas aeruginosa* Exotoxin A domain III two bacteriophage-derived transcription terminators, the λ-T0 terminator (Schwarz et al., *Nature*, 272: 410-414 (1978) and the fd-terminator (Beck et al., *Gene*, 1-3: 35-58 (1981), and the lad repressor gene from *E. coli* (Farabaugh, *Nature*, 274: 765-769 (1978).

Example 12.2

Expression of Anti-Mesothelin Deimmunized PE Chimeric Molecules cFP-0077 and cFP-0078 in *E. coli*

All polypeptide chains were expressed separately in the *E. coli* strain CSPZ-6.

The *E. coli* K12 strain CSPZ-6 (thi-1, ΔpyrF) was transformed by electroporation with the expression plasmids 15476, 15477, 15478 and 15479, respectively, resulting in the 4 strains cFP-0019 (based on plasmid 15476), cFP-0020 (based on plasmid 15477), cFP-0040 (based on plasmid 15478) and cFP-0041 (based on plasmid 15479). For each of the four strains, the transformed *E. coli* cells were first grown at 37° C. on agar plates. A colony picked from this plate was transferred to a 3 mL roller culture and grown at 37° C. to an optical density of 1-2 (measured at 578 nm). Then 1000 μl of culture was mixed with 1000 μl sterile 86%-glycerol and immediately frozen at −80° C. for long time storage. The correct product expression of this clone was first verified in small scale shake flask experiments and analyzed with SDS-Page prior to the transfer to the 10 L fermenter.

Pre Cultivation:

For pre-fermentation, a chemically defined medium (CD-PCMv2.20) was used: $NH_4Cl$ 1.0 g/l, $K_2HPO_4*3H_2O$ 18.3 g/l, citrate 1.6 g/l, Glycine 0.78 g/l, L-Alanine 0.29 g/l, L-Arginine 0.41 g/l, L-Asparagine*$H_2O$ 0.37 g/l, L-Aspartate 0.05 g/l, L-Cysteine*HCl*$H_2O$ 0.05 g/l, L-Histidine 0.05 g/l, L-Isoleucine 0.31 g/l, L-Leucine 0.38 g/l, L-Lysine*HCl 0.40 g/l, L-Methionine 0.27 g/l, L-Phenylalanine 0.43 g/l, L-Proline 0.36 g/l, L-Serine 0.15 g/l, L-Threonine 0.40 g/l, L-Tryptophan 0.07 g/l, L-Valine 0.33 g/l, L-Tyrosine 0.51 g/l, L-Glutamine 0.12 g/l, Na-L-Glutamate*$H_2O$ 0.82 g/l, Glucose*$H_2O$ 6.0 g/l, trace elements solution 0.5 ml/l, $MgSO_4*7H_2O$ 0.86 g/l, and Thiamin*HCl 17.5 mg/l. The trace elements solution contained $FeSO_4*7H_2O$ 10.0 g/l, $ZnSO_4*7H_2O$ 2.25 g/l, $MnSO_4*H_2O$ 2.13 g/l, $H_3BO_3$ 0.50 g/l, $(NH_4)6Mo_7O_{24}*4H_2O$ 0.3 g/l, $CoCl_2*6H_2O$ 0.42 g/l, and $CuSO_4*5H_2O$ 1.0 g/l dissolved in 0.5M HCl.

For pre-fermentation, 220 ml of CD-PCMv2.20 medium in a 1000 ml Erlenmeyer-flask with four baffles was inoculated with 1.0 ml out of a research seed bank ampoule. The cultivation was performed on a rotary shaker for 8 hours at 32° C. and 170 rpm until an optical density (578 nm) of 2.9 was obtained. 100 ml of the pre cultivation was used to inoculate the batch medium of the 10 L bioreactor.

Fermentation of cFP-0019 and cFP-0020:

For fermentation in a 10 l Biostat C, DCU3 fermenter (Sartorius, Melsungen, Germany) the following chemically defined batch medium was used: $KH_2PO_4$ 1.59 g/l, $(NH_4)_2HPO_4$ 7.45 g/l, $K_2HPO_4*3H_2O$ 13.32 g/l, citrate 2.07 g/l, L-methionine 1.22 g/l, $NaHCO_3$ 0.82 g/l, trace elements solution 7.3 ml/l, $MgSO_4*7 H_2O$ 0.99 g/l, thiamine*HCl 20.9 mg/l, glucose*$H_2O$ 29.3 g/l, biotin 0.2 mg/l, and 1.2 ml/l Synperonic 10% anti foam agent. The trace elements solution contained $FeSO_4*7H_2O$ 10 g/l, $ZnSO_4*7H_2O$ 2.25 g/l, $MnSO_4*H_2O$ 2.13 g/l, $CuSO_4*5H_2O$ 1.0 g/l, $CoCl_2*6H_2O$ 0.42 g/l, $(NH_4)6Mo_7O_{24}*4H_2O$ 0.3 g/l, and $H_3BO_3$ 0.50 g/l solubilized in 0.5M HCl solution.

The feed 1 solution contained 700 g/l glucose*$H_2O$, 7.4 g/l $MgSO_4*7 H_2O$ and 0.1 g/l $FeSO_4*7H_2O$. Feed 2 comprises $KH_2PO_4$ 52.7 g/l, $K_2HPO_4*3H_2O$ 139.9 g/l and $(NH_4)_2HPO_4$ 66 g/l. All components were dissolved in deionized water. The alkaline solution for pH regulation was an aqueous 12.5% (w/v) $NH_3$ solution supplemented with 11.25 g/l L-methionine.

Starting with 4.2 l sterile batch medium plus 100 ml inoculum from the pre-cultivation, the batch fermentation was performed at 31° C., pH 6.9±0.2, 800 mbar back pressure and an initial aeration rate of 10 l/min. The relative value of dissolved oxygen ($pO^2$) was kept at 50% throughout the fermentation by increasing the stirrer speed up to 1500 rpm. After the initially supplemented glucose was depleted, indicated by a steep increase in dissolved oxygen values, the temperature was shifted to 25° C., and 15 minutes later the fermentation entered the fed-batch mode with the start of both feeds (60 and 14 g/h respectively). The rate of feed of 2 was kept constant, while the rate of feed 1 was increased stepwise with a predefined feeding profile from 60 to finally 160 g/h within 7 hours. When carbon dioxide off gas concentration leveled above 2%, the aeration rate was constantly increased from 10 to 20 l/min within 5 hours. The expression of recombinant protein was induced by the addition of 2.4 g IPTG at an optical density of approx. 120. The target protein was expressed as inclusion bodies within the cytoplasm.

After 24 hours of cultivation, an optical density of 209 was achieved, and the whole broth was cooled down to 4-8° C. The bacteria were harvested via centrifugation with a flow-through centrifuge (13,000 rpm, 13 l/h) and the obtained biomass was stored at −20° C. until further processing (cell disruption).

Fermentation of cFP-0040 and cFP-0041:

For fermentation in a 10 l Biostat C, DCU3 fermenter (Sartorius, Melsungen, Germany) the following complex batch medium was used: Bacto-Trypton 20 g/l, yeast extract 15 g/l, $KH_2PO_4$ 1.5 g/l, $K2HPO4*3H2O$ 6.6 g/l, NaCl 1.0 g/l, $MgSO_4*7 H_2O$ 0.74 g/l, glucose*$H_2O$ 3.0 g/l, and 0.2 ml/l Synperonic 10% anti foam agent.

The feed 1 solution contained Bacto-Trypton 250 g/l and yeast extract 175 g/l. pH was controlled using a 75% glucose*$H_2O$. All components were dissolved in deionized water.

Starting with 7.6 l sterile batch medium plus 100 ml inoculum from the pre cultivation, the batch fermentation was performed at 37° C., pH 7.0±0.3, 500 mbar back pressure and an initial aeration rate of 10 l/min. The relative value of dissolved oxygen ($pO^2$) was kept at 50% throughout the fermentation by increasing the stirrer speed up to 1500 rpm. The feeding of feed 1 was started after the culture reached an optical density of 15. When carbon dioxide off gas concentration leveled above 2%, the aeration rate was constantly increased from 10 to 20 l/min within 5 hours. The expression of recombinant protein was induced by the addition of 2.4 g IPTG at an optical density of approx. 20. The target protein was expressed insoluble to inclusion bodies within the cytoplasm.

After 13 hours of cultivation, an optical density of 100-115 was achieved and the whole broth was cooled down to 4-8° C. The bacteria were harvested via centrifugation with a flow-through centrifuge (13,000 rpm, 13 l/h) and the obtained biomass was stored at −20° C. until further processing (cell disruption and inclusion body preparation).

Analysis of Product Formation (for cFP-0019, -0020-0040 and -0041):

Samples were drawn from the fermenter, one prior to induction and the others at dedicated time points after induction of protein expression, were analyzed with SDS-polyacrylamide gel electrophoresis. From every sample, the same amount of cells ($OD_{Target}$=10) were suspended in 5 mL PBS buffer and disrupted via sonication on ice. Then 100 μL of each suspension were centrifuged (15,000 rpm, 5 minutes), and each supernatant was withdrawn and transferred to a separate vial. This was to discriminate between soluble and insoluble expressed target protein. To each supernatant (=soluble protein fraction) 100 μL and to each pellet (=insoluble protein fraction) 200 μL of SDS sample buffer (Laemmli, *Nature,* 227: 680-685 (1970)) were added. Samples were heated for 15 minutes at 95° C. under intense mixing to solubilize and reduce all proteins in the samples. After cooling to room temperature, 5 μL of each sample were transferred to a 4-20% TGX Criterion Stain Free polyacrylamide gel (Bio-Rad). Additionally, 5 μl molecular weight standard (Precision Plus Protein Standard, Bio-Rad) were applied.

The electrophoresis was run for 60 minutes at 200 V and thereafter the gel was transferred the GELDOC EZ Imager (Bio-Rad) and processed for 5 minutes with UV radiation. Gel images were analyzed using IMAGE LAB analysis software (Bio-Rad). Relative quantification of protein expression was done by comparing the volume of the product bands to the volume of the 25 kDa band of the molecular weight standard.

Inclusion Body Preparation:

The inclusion body preparations (IBP) of the 10 L fermentations were started directly after the harvest of the bacteria with the re-suspension of the harvested bacteria cells in buffer 1 (12.1 g/l Tris, 0.246 g/l MgSO4*7H2O, 12 ml/l 25%-HCl). The buffer volume was calculated in dependence of the dry matter content of the biomass. Lysozyme (100 kU/mg, 0.12 mg/g DCW) and a small amount of benzonase (5 U/g DCW) were added. Then the suspension was homogenized at 900 bar (APV Rannie 5, 1 pass) to disrupt the bacteria cells followed by the addition of further benzonase (30 U/g DCW) and an incubation for 30 minutes at 30-37° C. Then the first wash buffer (60 g/l Brij, 87.6 g/l NaCl, 22.5 g/l EDTA, 6 ml/l 10N NaOH) was added, and again the suspension was incubated for 30 minutes. The following centrifugation step (BP 12, Sorvall) led to the inclusion body slurry, which was re-suspended in the second wash buffer (12.1 g/l Tris, 7.4 g/l EDTA, 11 ml/l 25%-HCl) and incubated for 20 minutes. A further separation step harvested the inclusion bodies, which were stored frozen at −20° C. or immediately solubilized for refolding and purification.

Example 12.3

Refolding and Purification of Anti-Mesothelin Deimmunized PE Chimeric Molecules cFP-0077 and cFP-0078 cFP-0077 and cFP-0078 were both obtained by refolding and purification.

Renaturation and Purification of Fab-PE24 (cFP-0077):

Inclusion bodies of HC-PE24 and LC were solubilized separately in 8 M Guanidinium-Hydrochloride, 100 mM Tris/HCl, 1 mM EDTA, pH 8.0+100 mM Dithiothreitol (DTT) overnight at RT (1 g IB in 5 mL). Solubilizates were adjusted to pH 3 and centrifuged, and the pellet was discarded. After extensive dialysis against 8 M Guanidinium-HCl, 10 mM EDTA, pH 3.0 to remove DTT, the total protein concentration was determined using the Biuret method. The purity of HC and LC content was estimated via SDS-PAGE.

Solubilizates were diluted at a 1:1 molar ratio in renaturation buffer containing 0.5 M arginine, 2 mM EDTA, pH 10+0.9 mM GSH/GSSG, respectively, at 2-10° C. The target protein concentration was increased in two steps to 0.22 g/L, with an incubation time of 4 h between the two doses. Afterwards, the renaturation solution was kept at 2-10° C. overnight.

The renaturate was diluted with $H_2O$ to <3 mS/cm and pumped onto an anion exchange column (AIEX) equilibrated in 20 mM Tris/HCl, pH 7.4. After washing the column with equilibration buffer, the protein was eluted with a gradient up to 20 mM Tris/HCl, 400 mM NaCl, pH 7.4. Peak fractions containing Fab-PE24 were pooled, concentrated and applied onto a preparative Size Exclusion Column (SEC) in 20 mM Tris, 150 mM NaCl, pH 7.4 to remove aggregates, fragments and *E. coli* proteins. The final protein pool was adjusted to the required protein concentration and analyzed via SDS-PAGE, analytical SEC and $UV_{280}$, and identity was confirmed by mass spectrometry.

Renaturation and Purification of dsFv-PE24 (cFP-0078):

Inclusion bodies of HC-PE24 and LC were solubilized separately 8 M Guanidinium-Hydrochloride, 100 mM Tris/HCl, 1 mM EDTA, pH 8.5+100 mM DTT overnight at RT (1 g IB in 5 mL). Solubilisates were adjusted to pH 3 and centrifuged, and the pellet was discarded. After extensive dialysis against 7.2 M Guanidinium-HCl, 10 mM EDTA, pH 3.0 to remove DTT, the total protein concentration was determined using the Biuret method, and the purity of HC and LC content was estimated via SDS-PAGE.

Solubilizates were diluted 1:100 in renaturation buffer containing 0.5 M arginine, 2 mM EDTA, pH 10+0.9 mM GSH/GSSG, respectively, at a 1:1 molar ratio and kept overnight at 2-10° C.

The renaturate was diluted with $H_2O$ to <3 mS/cm and pumped onto an anion exchange column (AIEX) equilibrated in 20 mM Tris/HCl, 1 mM EDTA, pH 7.4. After washing the column with equilibration buffer, the protein was eluted with a gradient up to 20 mM Tris/HCl, 1 mM EDTA, 400 mM NaCl, pH 7.4. Peak fractions containing dsFv-PE24 were pooled, concentrated and applied onto a preparative Size Exclusion Column (SEC) in 20 mM Tris/HCl, 150 mM NaCl, pH 7.4 to remove aggregates, fragments and *E. coli* proteins. The final protein pool was adjusted to the required protein concentration and analyzed via CE-SDS, analytical SEC and $UV_{280}$. Identity was confirmed by mass spectrometry.

Example 12.4

Protein Analysis of cFP-0077 and cFP-0078

Samples were analyzed by OD 280 nm using a UV spectrophotometer to determine the protein concentration in solution. The extinction coefficient required for this was calculated from the amino acid sequence according to Pace et al., *Protein Science*, 4: 2411-2423 (1995). Size-exclusion chromatography (SE-HPLC) was performed on TSK-Gel300SWXL or Superdex 200 columns with a 0.2 M potassium phosphate buffer, comprising 0.25 M KCl, pH 7.0 as mobile phase in order to determine the content of monomeric, aggregated and degraded species in the samples. Sodium dodecyl sulfate (SDS) polyacrylamide gel electrophoresis (reducing and non-reducing) was performed to analyze the purity of the complex preparations with regard to product-related degradation products and unrelated impurities (for details, see below). Electrospray ionisation mass spectrometry (ESI-MS) was performed with reduced (TCEP) samples to confirm the correct mass/identity of each chain and detect chemical modifications. ESI-MS of the non-reduced samples was carried out to analyze the nature and quality of the fully assembled protein and detect potential product-related side products.

Method for SDS-PAGE and Coomassie Staining
Device: Invitrogen XCELL SURE LOCK Mini-Cell
Gel: 4-20% Tris-Glycine Gel, Invitrogen EC6025BOX
Buffer: Tris-Glycine SDS Running Buffer (10×), Invitrogen LC2675-5
Sample buffer: Tris-Glycine SDS Sample Buffer (2×), Invitrogen LC2676
Reducing buffer: NuPAGE Sample Reducing Agent (10×), Invitrogen NP0004
Molecular Weight Marker: Mark 12, MW Standard, Invitrogen LC5677

The sample was adjusted to a protein concentration of 1 mg/ml with buffer. For sample reduction, the following procedure was carried out: A reduction buffer including 4 ml Sample buffer (2×) and 1 ml reducing buffer (10×) was prepared. The sample was diluted 1:1 with reduction buffer and incubated for 5 minutes at 70° C.

The gel electrophoresis was carried out at 125 V for 90 minutes. The gels were stained with SIMPLY BLUE Safe Stain (Invitrogen, Cat. No. LC6065).

Example 12.5

Comparison of Fab vs dsFv Fusion Protein-Cytotoxic Properties

The cytotoxic potency of a dsFv-PE24 fusion protein format and a Fab-PE24 format was compared using the same humanized SS1 targeting moiety on three different tumor cell lines (MKN45, H596, and A431H9). Briefly, cells were seeded, on 96 well plates. After overnight culture, different concentrations of the cFPs were added to the medium and cells were incubated for 72 h. At the end of incubation period, cell viability was determined using a CELLTITERGLOW assay.

In each case, the dose-response curves and IC50 values for inhibition of cell viability were similar for the dsFv-PE24 and the Fab-PE24 format. The molar ratio of the IC50 values is listed in Table 18. Depending on the cell line tested, the targeted PE24 fusion proteins were several hundred to one thousand fold more potent than untargeted PE24.

TABLE 18

| Cell line | Ratio of the molar IC50 values dsFv-PE24/Fab-PE24 |
|---|---|
| A431H9 | 0.37 |
| MKN45 | 2.3 |
| H596 | 0.38 |

Example 12.6

Comparison of Fab Versus dsFv Fusion Protein-Serum Kinetics

The serum kinetics of the following three *Pseudomonas* exotoxin A (PE)-based anti-mesothelin immunotoxins in SCID beige mice was compared: SS1dsFv-PE38 (MW: 62.5 kDa), SS1dsFv-PE24 (MW: 49.9 kDa) and SS1Fab-PE24 (MW: 72.2 kDa). The murine SS1 antibody moiety was used for all constructs. The kinetics were compared at doses equimolar to 0.2 mg/kg (3.2 nmol/kg) SS1P) corresponding to 0.231 mg/kg SS1Fab-PE24, and 0.160 mg/kg for SS1dsFv-PE24.

The constructs were administered as a single intravenous dose, and their serum levels were analyzed at 0.08, 0.5, 1, 1.5, 2, 3, 4, 5, and 7 hours after dosing. Nine mice per group were administered the study medication, and blood was collected in a staggered manner at three times per animal by retro-orbital puncture, resulting in nine time points with n=3 samples. Serum samples were analyzed by an ELISA that detects only intact test compounds having the antibody fragment plus the PE part. In this assay format, the cFP is captured on a MSLN-coated surface and the PE moiety is detected with a rabbit polyclonal anti-PE antibody and biotinylated anti-rabbit secondary antibody.

Figure 19:
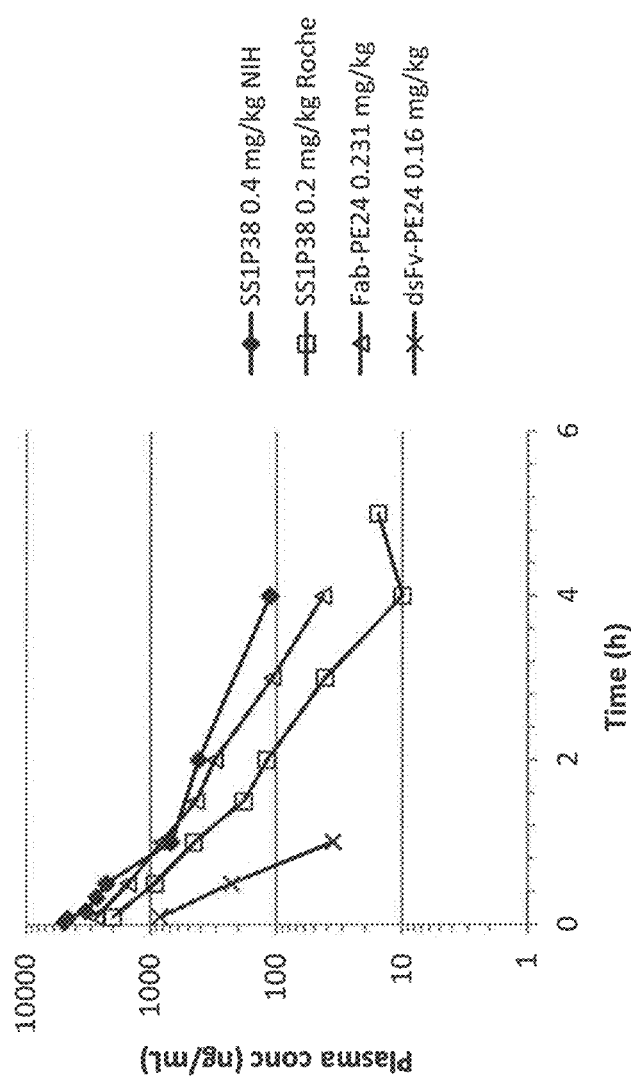
FIG. 19 is a graph showing plasma concentration (ng/ml) of chimeric molecules SS1P38 (0.4 mg/kg (diamonds)), SS1P38 (0.2 mg/kg (squares)), Fab-PE24 (0.231 mg/kg (triangles)), (dsFv-PE24 (0.16 mg/kg (x)) administered to mice over a period of time (hours (h)).

For each time point, average serum values from three animals were plotted for the treatment groups together with historical data from CD2F1 mice. The SS1dsFv-PE24 construct was very rapidly cleared with a serum half-life of only ~12 minutes. In agreement with the historical data, clearance of SS1P was much slower, resulting in a serum half life of between 35 and 44 minutes (values derived from measured and historical data, respectively). The pharmacokinetic properties of the SS1Fab-PE24 construct were very similar to SS1dsFv-PE38 with a serum half life of 43 minutes and similar values were also obtained for clearance rate, volume of distribution, $c_{max}$ and area under the curve (Table 19 and FIG. 19).

TABLE 19

Comparison Fab versus dsFv fusion protein- Serum kinetics

| Parameter | Unit | SS1P | SS1-Fab-PE24 | SS1-dsFv-PE24 |
|---|---|---|---|---|
| $C_L$ | mL/(min · kg) | 2.24 | 1.53 | 7.06 |
| $V_C$ | mL/kg | 84.3 | 75.4 | 146 |
| $V_{SS}$ | mL/kg | 92 | 80.5 | 103 |
| $T_{1/2}$ | h | 0.574 | 0.716 | 0.201 |
| $C_{max}$ | ng/mL | 1990 | 2730 | 837 |
| AUC (0-inf) | ng · h/mL | 1490 | 2520 | 378 |

Example 13

This example demonstrates the humanization of the anti-mesothelin antibody SS1.

Example 13.1

Design of Humanized Heavy and Light Chain Variable Regions

The structures of the VH and the VL domain of the SS1 antibody were modeled in silico, and the model was compared to a structural database of human VH and VL domains. A panel of the most structurally similar V domains were chosen for grafting the CDRs of SS1 onto the human VH and VL domains. In addition, similarities in the primary sequence were taken into account to narrow down the choice of the human V domains by aligning the primary sequence of the VH and VL domain of SS1 to the human V domain repertoire. Backmutations within the human framework regions to mouse parent residues were introduced in some humanization variants. Similarly, mutations in the CDRs were introduced in some variants, where appropriate, to potentially increase the affinity to the antigen or to maintain the CDR tertiary structure.

The designed V domain variants were cloned into heavy chain and light chain vectors 6318 and 6319 via unique cloning sites to generate human IgG light and heavy chains. The heavy and light chain vectors were co-transfected into HEK293 suspension cells in microtiter culture plates in a matrix manner to obtain cell cultures expressing full size IgG having all possible light/heavy chain combinations. After 5 days, cultivation at 37° C., the supernatants were harvested and purified by Protein A affinity chromatography in the microtiter scale.

Example 13.2

Cloning of Humanized Heavy and Light Chain Variable Regions

Standard methods were used to manipulate DNA as described in Sambrook, J. et al., supra. The molecular biological reagents were used according to the manufacturer's instructions. Desired gene segments were prepared by commercial gene synthesis. The synthesized gene fragments were cloned into a specified expression vector. The DNA sequence of the subcloned gene fragments were confirmed by DNA sequencing.

Expression Vector for the Antibody Heavy Chains:

The gene segments of the designed humanized antibody heavy chain variable domains were cloned into the specified expression vector via the unique restriction sites HindIII and XhoI. The expression vector was designed to express the antibody heavy chain variable domain in fusion with the human antibody domains CH1, hinge, CH2 and CH3 in HEK293 cells, resulting in a conventional antibody heavy chain. All domains were separated by introns. Besides the expression cassette for the antibody heavy chain, the vector contained:
  an origin of replication from the vector pUC18 which allows replication of this plasmid in E. coli,
  a β-lactamase gene which confers ampicillin resistance in E. coli,
  an SV40 promotor and origin for expression of the DHFR selection marker,
  Murine dihydrofolate reductase (DHFR) as selection marker for antibody expression, and
  SV40' early polyadenylation ("early poly A") signal sequence.

The transcription unit of the antibody heavy chain is composed of the following elements:
  the immediate early enhancer and promoter from the human cytomegalovirus,
  a 5'-untranslated region of a human antibody germline gene,
  a murine immunoglobulin heavy chain signal sequence including a signal sequence intron (signal sequence 1, intron, signal sequence 2 [L1-intron-L2]),
  the VH sequence followed by an intron,
  human CH1, hinge, CH2, CH3 domains separated by introns,
  the bovine growth hormone (bGH) polyadenylation ("poly A") signal sequence, and
  the human gastrin transcription terminator (HGT).

Expression Vector for the Antibody Light Chains:

The gene segments of the designed humanized antibody light chain variable domains were cloned into a specified expression vector via the unique restriction sites BsmI and CelI. The expression vector was designed to place the antibody light chain variable domain in fusion with the human antibody domain Ck in HEK293 cells. Both domains were separated by an intron. Besides the expression cassette for the antibody light chain, the vector contains:
  an origin of replication from the vector pUC18 which allows replication of this plasmid in E. coli, and
  a β-lactamase gene which confers ampicillin resistance in E. coli.

The transcription unit of the antibody light chain is composed of the following elements:
  the immediate early enhancer and promoter from the human cytomegalovirus,
  a 5'-untranslated region of the human cytomegalovirus, an Intron A sequence of the human cytomegalovirus,
a 5'-untranslated region of a human antibody germline gene,
a murine immunoglobulin heavy chain signal sequence including a signal sequence intron (signal sequence 1, intron, signal sequence 2 [L1-intron-L2]) and the unique restriction site BsmI at the 3' end of L2,
a VL domain followed by an intron,
human Ck domain,
the bovine growth hormone (bGH) polyadenylation ("poly A") signal sequence, and
Human gastrin transcription termination factor (HGT).

Example 13.3

Expression of Humanized Antibodies

Transient Transfection of Humanized Antibody Light and Heavy Chains:
Recombinant humanized antibody variants were generated by transient transfection of HEK293-Freestyle cells (human embryonic kidney cell line 293, Invitrogen) grown in suspension. The transfected cells were cultivated in F17 medium (Gibco) or Freestyle 293 medium (Invitrogen), either one supplemented with 6 mM glutamine, either ultra-glutamine (Biowhittake/Lonza) or L-glutamine (Sigma), with 8% $CO_2$ at 37° C. in shake flasks in the scale of 2 ml medium in 48-deep-well plates to 1 L medium in shake flasks. 293-Free transfection reagent (Novagen/Merck) was used in a ratio of reagent (µl) to DNA (µg) of 4:3. Light and heavy chains were expressed from two different plasmids using a molar ratio of light chain to heavy chain encoding plasmid ranging from 1:2 to 2:1, respectively. Humanized antibody containing cell culture supernatants were harvested at day 6 to 8 after transfection. General information regarding the recombinant expression of human immunoglobulins in, e.g., HEK293 cells, is given in: Meissner et al., *Biotechnol. Bioeng.*, 75: 197-203 (2001). The supernatants were purified by affinity chromatography on MabSelect Sure (GE, Protein A) equilibrated in PBS. After application of the filtrated supernatants, the antibodies were eluted with 50 mM sodium acetate, pH 3.2. The pH of the eluates was adjusted immediately to pH >6 with 2 M Tris/HCl, pH 9.0 followed by dialysis into 20 mM histidine, 140 mM NaCl, pH 6.0. Antibodies were analyzed by $UV_{280}$, SDS-PAGE and analytical SEC. The sequence was confirmed by mass spectrometry.

Example 13.4

Characterization of Humanized SS1 Variants

ELISA Screening of Humanized SS1 Variants:
All SS1 humanization variants in the IgG format were screened for affinity by ELISA. 384 well MaxiSorp microtiter plates were coated with 0.5 µg/ml anti-His antibody (Novagen). After blocking with PBS buffer supplemented with 2% BSA, 0.1% Tween 20, and 0.2 µg/ml human/cynomolgus/murine mesothelin (in house/R&D Systems), all proteins with a His-tag were captured on the plate for one hour. The plates were washed with PBST Buffer (PBS+0.1% Tween 20) and dilutions of humanized anti-mesothelin antibodies in PBS were incubated for 1 hour at room temperature. Binding of antibodies was detected with HRP conjugated anti human Fc antibody (GE Healthcare). After a final wash, the plates were incubated with HRP substrate. Absorbance was measured at 370 nm on an ENVISION plate reader. EC50 curve fit analysis was performed using XLfit4 analysis plug-in for EXCEL software (model 205).

To normalize the obtained values to the IgG titer, quantitation of human IgG was performed by sandwich ELISA using streptavidin coated plates. Streptavidin-coated 384 well microtiter plates (Microcoat) were incubated with a mixture of 0.25 µg/ml biotinylated anti-human IgG antibody (Jackson Imm. Res.), 0.05 µg/ml anti-human IgG-HRP conjugate (Jackson Imm. Res.), and dilutions of the humanized anti-mesothelin antibodies. After 1.5 hours incubation at room temperature (RT), plates were washed with PBS buffer supplemented with 0.1% Tween 20. HRP substrate was added, and the absorbance was measured at 370 nm on an ENVISION plate reader. The calculation of data was performed using a human IgG reference as a standard (in house) for calibration and XLfit4 analysis plug-in for EXCEL software (model 205) for curve fit analysis.

In Tables 20-21 below, the ELISA data of all humanization variants are shown. ELISA/BIACORE binding to huMesothelin (EC50 ng/ml) was measured, and the results are shown in Table 20 (in house) and Table 21 (R&D). Normalized to IgG titer, this primary screen identified the variant VL001/VH001 as one of the combinations with the best EC50 value.

BiaCore Screening of Humanized SS1 Variants:
The best variants containing CDRs most similar to SS1 were chosen for kinetics analysis by surface plasmon resonance (SPR). An SPR based assay has been used to determine the kinetic parameters of the binding between several MSLN PE cFP humanization variants and human mesothelin. Therefore, Protein A was immobilized by amine coupling to the surface of the CM5 biosensor chip. The samples were then captured, and human mesothelin was injected. The sensor chip surface was regenerated between each analysis cycle. The equilibrium constant $K_D$ as well as the rate constants $k_d$ and $k_a$ were finally gained by fitting the data to a 1:1 langmuir interaction model. About 175 response units (RU) of Protein A (10 µg/ml) were coupled onto the CM5 sensor chip at pH 4.0 by using an amine coupling kit supplied by GE Healthcare (10 minutes activation). The sample and system buffer was HBS-P+ (0.01 M HEPES, 0.15 M NaCl, 0.005% surfactant P20 sterile-filtered, pH 7.4). The flow cell temperature was set to 25° C., and the sample compartment temperature was set to 12° C. The system was primed with running buffer. The protein A binding sites were saturated with IgGs (about 0.03 µg/mL) to generate similar capture levels for each sample, by injecting them for 40 seconds at a flow rate of 10 µl/min. Afterwards, a single 50 nM human mesothelin solution was injected for 120 seconds at a flow rate of 30 µl/min, followed by a 180 second dissociation phase. Thereby a relative KD determination allowed a ranking of different MSLN binders. Each cycle was regenerated with two injections of glycine-HCl pH 1.5 (30 seconds, 30 µl/min).

Table 22 below lists the BiaCore data of 12 selected humanization variants. The final humanization variant VL01/VH01 shows one of the lowest Kd values among all humanization variants. Table 22 shows the Biacore results for cFP.15438-15457 and cFP.15438-15459, all comprising humanized VH1. cFP.15438, which comprises the amino acid sequence of SEQ ID NO: 45, displays the highest affinity of the humanized variants of SS1 antibody. Thus, the VH of cFP.15438 provides advantageous binding properties.

The five best variants were cloned into the Fab-Linker-PE format containing the published linker and LRO10 as the PE24 variant, expressed, refolded and purified. Cloning, expression, refolding and purification were carried out as described below for cFP-0205. The five humanization variants in the cytolytic fusion format were analyzed for stability at 37° C. for 7 days by the method of dynamic light scattering described in Example 9.2, size exclusion chromatography, SDS-PAGE, and mass spectrometry at distinct time points.

Size-exclusion chromatography (SE-HPLC) was performed on TSK-Gel300SWXL or Superdex 200 columns with a 0.2 M potassium phosphate buffer comprising 0.25 M KCl (pH 7.0) as the mobile phase in order to determine the content of monomeric, aggregated, and degraded species in the samples. Sodium dodecyl sulfate (SDS) polyacrylamide gel electrophoresis (reducing and non-reducing) was performed to analyze the purity of the complex preparations with regard to product-related degradation products and unrelated impurities (for details, see below). Electrospray ionisation mass spectrometry (ESI-MS) was performed with reduced (TCEP) samples to confirm the correct mass/identity of each chain and to detect chemical modifications. ESI-MS of the non-reduced samples was carried out to analyze the nature and quality of the fully assembled protein and to detect potential product-related side products.

The active concentration of the Fab fragments within the cytolytic fusion format after temperature stress at 37° C. for 7 days was monitored by surface plasmon resonance (SPR). Mesothelin was immobilized onto the surface of a SPR biosensor. By injecting the sample into the flow cells of the SPR spectrometer, it formed a complex with the immobilized mesothelin, resulting in an increased mass on the sensor chip surface and, therefore, a higher response (as 1 RU is defined as 1 pg/mm$^2$). Afterwards, the sensor chip is regenerated by dissolving the sample-mesothelin-complex. The gained responses are then evaluated relative to the response displayed by the reference standard (which is assumed to be 100% active). First, around 50 resonance units (RU) of human MSLN (0.75 µg/ml) were coupled on a C1 chip (GE Healthcare) at pH 4.5 by using the amine coupling kit of GE Healthcare. The sample and system buffer was HBS-P+ (0.01 M HEPES, 0.15 M NaCl, 0.005% surfactant P20 sterile-filtered, pH 7.4). The flow cell temperature was set to 25° C., and the sample compartment temperature was set to 12° C. The system was primed with running buffer. Then, a 5 nM solution of the MSLN PE cFP construct was injected for 60 seconds at a flow rate of 30 µl/min, followed by a 60 second dissociation phase. Then, the sensor chip surface was regenerated by two 20 second long injections of the regeneration solution (0.31 M KSCN, 1.22M MgCl$_2$, 0.61M urea, 1.22M Gua-HCl, 6.7 mM EDTA) at a flow rate of 30 µl/min, followed by an extra wash step with buffer and a 5 second stabilization period.

Stability data were obtained by incubating the 5 best humanized variants in the Fab-linker-PE24LRO10 format at 37° C. for 7 days. The results are shown in Table 23. As shown in Table 23, the variant VH01/VL01 was the only variant that showed no fragmentation after temperature stress. The VL01 promoted recovery as all VL01 combinations formed only aggregates after temperature stress but did not precipitate. Negative results of affinity measurements after temperature stress were due to these aggregates. Accordingly, the humanization variant VH1/VL1 (SEQ ID NO: 45)/(SEQ ID NO: 46) was chosen for further development. VH1 (SEQ ID NO: 45) provided favorable functionality and binding properties. The combination of VH1 (SEQ ID NO: 45)/VL1 (SEQ ID NO: 46) provided favorable developability.

TABLE 20

|  |  |  | z | a | b | c | d |
|---|---|---|---|---|---|---|---|
|  |  |  |  |  | VL |  |  |
|  |  |  | 000/15456 mouse mVL | 001/15457 (SEQ ID NO: 46) | 002/15458 | 003/15459 | 004/15460 |
|  |  |  |  |  | humanized |  |  |
|  |  | VH | Past (C99Q) | IMGT_hVK_1_39 | IMGT_hVK_3_11 | IMGT_hVK_1_39 | Hercept. |
| Mouse | 0 | 000/15437 mVH Past (C44Q) | 20.10 | 17.80 | 13.36 | 20.80 | 32.72 |
| Humanized | 1 | 001/15438 (SEQ ID NO: 45) IMGT_hVH_1_46 | 32.04 | 20.27 | 15.57 | 22.44 | 28.95 |
|  | 2 | 002/15439 VBase_VH1_1 | 88.85 | 204.74 | 32.01 | 48.39 | 38.63 |
|  | 3 | 003/15440 VBase_VH1_1 | 37.76 | 100.18 | 31.58 | 39.86 | 63.66 |
|  | 4 | 004/15441 VBase_VH1_1 | 39.46 | 46.18 | 20.21 | 52.31 | 112.42 |
|  | 5 | 005/15442 Herceptin | 71.84 | 432.87 | 39.39 | 70.55 | 94.99 |
|  | 6 | 006/15443 IMGT_hVH_5_51 | 196.59 | 287.08 | 41.11 | 144.51 | 466.56 |
|  | 7 | 007/15444 IMGT_hVH_5_51 | 155.21 | 67.47 | 137.39 | 71.03 | >500.0 |
|  | 8 | 008/15445 IMGT_hVH_5_51 | 431.47 | 44.39 | 42.37 | 17.40 | 143.88 |
|  | 9 | 009/15446 IMGT_hVH_1_8 | 118.32 | 62.23 | 71.58 | 31.00 | 230.84 |
|  | 10 | 010/15447 IGHV4-34-05 | 41.35 | 93.85 | 35.06 | 33.49 | 135.83 |
|  | 11 | 011/15448 IMGT_hVH_3_21 | 44.04 | 52.11 | 24.52 | 41.68 | 54.65 |
|  | 12 | 012/15449 VBase_VH1_1 | 30.19 | 37.51 | 7.86 | 47.87 | 36.40 |
|  | 13 | 013/15450 VBase_VH1_1 | 70.85 | >500.0 | 58.84 | 129.80 | 111.42 |
|  | 14 | 014/15451 VBase_VH1_1 | #N/A | #N/A | #N/A | #N/A | #N/A |
|  | M1 | MSAb-1/15452 Morphotek | 25.65 | 19.12 | 13.24 | 18.82 | 33.79 |
|  | M2 | MSAb-2/15453 Morphotek | 23.42 | 15.51 | 33.37 | 18.46 | 30.84 |
|  | M3 | MSAb-3/15454 Morphotek | 34.70 | 62.58 | 17.71 | 15.82 | 64.02 |
|  | SS1 | HC_SS1/15436 Pastan | 47.15 | 38.16 | 26.40 | 28.85 | 60.38 |

TABLE 20-continued

| | | | e | m1 | m2 VL | m3 | ss1 |
|---|---|---|---|---|---|---|---|
| | | | 005/ 15461 | MSAb-1/ 15462 | MSAb-2/ 15463 humanized | MSAb-3/ 15464 | LC_SS1/ 15455 |
| | | | IMGT_ hVK_1_39 | Morphotek PAT | Morphotek PAT | Morphotek PAT | Pastan PAT |
| Mouse | | 0 | 20.15 | 16.89 | 26.38 | 13.89 | 17.42 |
| Humanized | | 1 | 30.31 | 33.50 | 21.78 | 21.23 | 27.22 |
| | | 2 | 103.46 | 181.39 | 81.92 | 47.73 | 271.77 |
| | | 3 | 70.03 | 26.60 | 108.18 | 39.95 | 230.87 |
| | | 4 | 68.93 | 73.53 | 71.82 | 89.99 | 270.06 |
| | | 5 | 119.52 | 26.06 | 326.88 | 60.33 | >500.0 |
| | | 6 | 163.55 | >500.0 | 83.61 | 78.58 | 52.29 |
| | | 7 | 69.42 | 210.52 | 89.05 | 182.10 | 181.13 |
| | | 8 | 25.90 | 20.03 | 16.34 | 37.09 | 87.91 |
| | | 9 | 68.65 | 103.29 | 97.08 | 80.73 | 44.37 |
| | | 10 | 95.84 | 66.42 | 65.63 | 26.84 | 235.42 |
| | | 11 | 62.08 | 15.60 | 124.88 | 35.08 | 47.05 |
| | | 12 | 61.27 | 30.13 | 35.53 | 20.68 | 86.50 |
| | | 13 | 132.05 | 16.51 | 204.88 | 33.20 | >500.0 |
| | | 14 | #N/A | #N/A | #N/A | #N/A | #N/A |
| | | M1 | 21.71 | 26.82 | 13.24 | 17.05 | 7.37 |
| | | M2 | 30.16 | 39.31 | 23.75 | 35.77 | 30.54 |
| | | M3 | 53.63 | 117.75 | 19.86 | 42.60 | 45.23 |
| | | SS1 | 37.42 | 29.65 | 29.79 | 14.77 | 41.13 |

TABLE 21

| | | | | z | a | b VL | c | d |
|---|---|---|---|---|---|---|---|---|
| | | | | 000/ 15456 mouse mVL | 001/ 15457 (SEQ ID NO: 46) | 002/ 15458 humanized | 003/ 15459 | 004/ 15460 |
| | | | VH | Past (C99Q) | IMGT_ hVK_1_39 | IMGT_ hVK_3_11 | IMGT_ hVK_1_39 | Hercept |
| Mouse | 0 | 000/15437 | mVH Past (C44Q) | 24.93 | 18.25 | 14.91 | 16.97 | 28.24 |
| Humanized | 1 | 001/15438 (SEQ ID NO: 45) | IMGT_hVH_1_46 | 22.81 | 15.55 | 16.22 | 21.03 | 14.77 |
| | 2 | 002/15439 | VBase_VH1_1 | 20.80 | 30.71 | 9.67 | 22.61 | 18.10 |
| | 3 | 003/15440 | VBase_VH1_1 | 11.17 | 64.84 | 21.95 | 24.52 | 27.66 |
| | 4 | 004/15441 | VBase_VH1_1 | 13.30 | 18.79 | 11.38 | 20.34 | 20.71 |
| | 5 | 005/15442 | Herceptin | 57.64 | 75.30 | 21.79 | 26.38 | 22.71 |
| | 6 | 006/15443 | IMGT_hVH_5_51 | 37.98 | 68.72 | 17.00 | 31.68 | 96.41 |
| | 7 | 007/15444 | IMGT_hVH_5_51 | 30.92 | 32.33 | 50.56 | 47.93 | 97.81 |
| | 8 | 008/15445 | IMGT_hVH_5_51 | 27.84 | 32.16 | 13.63 | 17.70 | 36.39 |
| | 9 | 009/15446 | IMGT_hVH_1_8 | 37.15 | 20.48 | 23.00 | 9.24 | 99.49 |
| | 10 | 010/15447 | IGHV4-34-05 | 17.19 | 36.94 | 18.55 | 3.79 | 33.67 |
| | 11 | 011/15448 | IMGT_hVH_3_21 | 17.85 | 19.31 | 12.09 | 26.23 | 19.38 |
| | 12 | 012/15449 | VBase_VH1_1 | 26.50 | 18.36 | 4.84 | 25.45 | 32.87 |
| | 13 | 013/15450 | VBase_VH1_1 | 17.11 | 48.46 | 26.21 | 32.81 | 17.97 |
| | 14 | 014/15451 | VBase_VH1_1 | #N/A | #N/A | #N/A | #N/A | #N/A |
| | M1 | MSAb-1/ 15452 | Morphotek | 16.76 | 26.05 | 10.85 | 15.40 | 27.67 |
| | M2 | MSAb-2/ 15453 | Morphotek | 18.94 | 13.24 | 25.61 | 18.06 | 18.24 |
| | M3 | MSAb-3/ 15454 | Morphotek | 43.79 | 80.00 | 24.10 | 20.13 | 57.15 |
| | SS1 | HC_SS1/ 15436 | Pastan | 34.77 | 37.48 | 30.64 | 28.76 | 50.76 |

TABLE 21-continued

| | | e | m1 | m2 | m3 | ss1 |
|---|---|---|---|---|---|---|
| | | | | VL | | |
| | | 005/ 15461 | MSAb-1/ 15462 | MSAb-2/ 15463 humanized | MSAb-3/ 15464 | LC_SS1/ 15455 |
| | | IMGT_ hVK_1_39 | Morph PAT | Morph PAT | Morph PAT | Pastan PAT |
| Mouse | 0 | 19.65 | 13.30 | 20.08 | 16.62 | 21.59 |
| Humanized | 1 | 21.75 | 33.91 | 21.69 | 18.48 | 20.27 |
| | 2 | 23.88 | 26.61 | 30.97 | 26.83 | 23.16 |
| | 3 | 46.86 | 11.40 | 33.78 | 23.40 | 43.11 |
| | 4 | 23.06 | 18.22 | 20.33 | 19.35 | 35.09 |
| | 5 | 32.75 | 7.46 | 78.60 | 41.55 | 51.40 |
| | 6 | 77.48 | 59.94 | 13.32 | 37.23 | 9.70 |
| | 7 | 21.06 | 35.60 | 49.19 | 35.21 | 26.52 |
| | 8 | 14.14 | 8.96 | 12.58 | 15.26 | 14.19 |
| | 9 | 45.65 | 13.29 | 16.81 | 20.11 | 11.92 |
| | 10 | 29.20 | 15.63 | 19.91 | 14.16 | 58.47 |
| | 11 | 25.78 | 6.71 | 42.47 | 25.88 | 26.04 |
| | 12 | 32.83 | 22.30 | 16.38 | 21.03 | 30.01 |
| | 13 | 55.13 | 18.76 | 40.91 | 16.60 | 70.42 |
| | 14 | #N/A | #N/A | #N/A | #N/A | #N/A |
| | M1 | 15.26 | 18.45 | 10.07 | 14.15 | 10.22 |
| | M2 | 32.68 | 49.52 | 33.94 | 33.72 | 31.20 |
| | M3 | 51.29 | 76.89 | 21.74 | 57.13 | 43.21 |
| | SS1 | 48.23 | 24.34 | 31.68 | 17.66 | 46.14 |

TABLE 22

| Antibody | Antigen | Curve | Temp (° C.) | Fit | ka | kd | KD | KD [nM] |
|---|---|---|---|---|---|---|---|---|
| cFP-0004-0002 | Mesothelin | Fc = 4-3 | 25 | 1:1 Binding | 7.88E+05 | 2.39E−04 | 3.04E−10 | 0.30 |
| cFP-0006-0002 | Mesothelin | Fc = 4-3 | 25 | 1:1 Binding | 9.29E+05 | 2.62E−04 | 2.83E−10 | 0.28 |
| cFP.15438-15457 | Mesothelin | Fc = 4-3 | 25 | 1:1 Binding | 8.39E+05 | 2.20E−04 | 2.63E−10 | 0.26 |
| cFP.15438-15459 | Mesothelin | Fc = 4-3 | 25 | 1:1 Binding | 7.13E+05 | 1.97E−04 | 2.77E−10 | 0.28 |
| cFP.15438-15460 | Mesothelin | Fc = 4-3 | 25 | 1:1 Binding | 4.92E+05 | 1.63E−04 | 3.31E−10 | 0.33 |
| cFP.15442-15457 | Mesothelin | Fc = 4-3 | 25 | 1:1 Binding | 2.15E+05 | 0.001387 | 6.45E−09 | 6.45 |
| cFP.15442-15459 | Mesothelin | Fc = 4-3 | 25 | 1:1 Binding | 2.25E+05 | 0.002445 | 1.09E−08 | 10.89 |
| cFP.15442-15460 | Mesothelin | Fc = 4-3 | 25 | 1:1 Binding | 1.42E+05 | 0.002221 | 1.57E−08 | 15.70 |
| cFP.15447-15457 | Mesothelin | Fc = 4-3 | 25 | 1:1 Binding | 6.31E+05 | 9.76E−04 | 1.55E−09 | 1.55 |
| cFP.15447-15459 | Mesothelin | Fc = 4-3 | 25 | 1:1 Binding | 5.14E+05 | 0.001916 | 3.73E−09 | 3.73 |
| cFP.15447-15460 | Mesothelin | Fc = 4-3 | 25 | 1:1 Binding | 3.55E+05 | 0.002069 | 5.82E−09 | 5.82 |
| cFP.15448-15457 | Mesothelin | Fc = 4-3 | 25 | 1:1 Binding | 1.77E+05 | 0.001729 | 9.79E−09 | 9.79 |
| cFP.15448-15459 | Mesothelin | Fc = 4-3 | 25 | 1:1 Binding | 1.73E+05 | 0.001909 | 1.11E−08 | 11.05 |
| cFP.15448-15460 | Mesothelin | Fc = 4-3 | 25 | 1:1 Binding | 1.12E+05 | 0.00216 | 1.93E−08 | 19.32 |

TABLE 23

| VL | VH | $T_{agggreagetion}$ [° C.] | Recovery | SEC | SDS-PAGE | ESI-MS d | ESI-MS d&r | Target binding | Stress effect on binding |
|---|---|---|---|---|---|---|---|---|---|
| VL01 | VH10 | 40 | + | HMW | Fragmentation | Fragmentation. | Fragmentation. | +/− | HMW |
| VL03 | VH01 | ~35 | − | LMW | Fragmentation. | Fragmentation. | Fragmentation. | + | +/− |
| VL01 | VH01 | 37 | + | HMWs | No fragmentation | No fragmentation | No fragmentation | + | HMW |
| VL03 | VH10 | 37 | − | HMW | +/− | Fragmentation. | Fragmentation. | +/− | +/− |
| VL04 | VH01 | 34 | − | LMW | +/− | No fragmentation | No fragmentation | + | + |

Example 14

This example demonstrates the cloning, expression, refolding, and purification of chimeric deimmunized PE LOR10-456A as a Fab fusion with humanized anti-mesothelin SS1 (cFP-0205).

The chimeric PE anti-mesothelin molecule cFP-0205 was obtained after cloning, expression, refolding, and purification. cFP-0205 (also referred to as R205 or RG7787) comprises amino acid sequences SEQ ID NO: 39 and 40.

Cloning of cFP-0205:

For the expression of cFP-0205, the *E. coli* host/vector system which enables an antibiotic-free plasmid selection by complementation of an *E. coli* auxotrophy (PyrF) was employed (EP 0 972 838 and U.S. Pat. No. 6,291,245). Standard methods were used to manipulate DNA as described in Sambrook, J. et al., supra. The molecular biological reagents were used according to the manufacturer's instructions. Desired gene segments were made by commercial gene synthesis. The synthesized gene fragments were cloned into a specified expression vector. The DNA sequences of the subcloned gene fragments were confirmed by DNA sequencing.

The expression plasmids for the production of the light chain (LC) and the heavy chain (HC), respectively, were prepared as follows: The LC Plasmid 15496 is an expression plasmid for the expression of an antibody light chain in *E. coli*. It was generated by ligating the antibody VL domain fragment into the vector using the NdeI/BsiWI restriction sites.

The light chain *E. coli* expression plasmid comprises the following elements:
- the origin of replication from the vector pBR322 for replication in *E. coli* (corresponding to positions 2517-3160 according to Sutcliffe et al., *Quant. Biol.*, 43: 77-90 (1979),
- the URA3 gene of *Saccharomyces cerevisiae* coding for orotidine 5'-phosphate decarboxylase (Rose et al., *Gene*, 29: 113-124 (1984), which allows plasmid selection by complementation of *E. coli* pyrF mutant strains (uracil auxotrophy),
- the antibody light chain expression cassette, comprising
- the T5 hybrid promoter (T5-PN25/03/04 hybrid promoter according to Bujard et al., *Methods. Enzymol.*, 155: 416-433 (1987) and Stueber et al., *Immunol. Methods IV*, 121-152 (1990) including a synthetic ribosomal binding site according to Stueber et al. (supra),
- the antibody light chain variable domain comprising the CDRs of SS1,
- the human Ck domain,
- two bacteriophage-derived transcription terminators, the λ-T0 terminator (Schwarz et al., *Nature*, 272: 410-414 (1978) and the fd-terminator (Beck et al., *Gene*, 1-3: 35-58 (1981), and
- the lad repressor gene from *E. coli* (Farabaugh, P. J., *Nature*, 274 (1978) 765-769).

The HC Plasmid 18023 is an expression plasmid for the expression of a fusion protein including an antibody heavy chain, a linker containing a furin cleavage site, and a mutant of domain III of *Pseudomonas* Exotoxin A, in *E. coli*. It was generated by ligation of the VH domain fragment into the vector using the NdeI/BsrGI restriction sites. The specific PE variant fragment was exchanged using the BsrGI/BsiWI restriction sites.

The cytolytic fusion protein heavy chain *E. coli* expression plasmid comprises the following elements:

- the origin of replication from the vector pBR322 for replication in *E. coli* (corresponding to positions 2517-3160 according to Sutcliffe et al., *Quant. Biol.,* 43: 77-90 (1979),
- the URA3 gene of *Saccharomyces cerevisiae* coding for orotidine 5'-phosphate decarboxylase (Rose et al., *Gene,* 29: 113-124 (1984), which allows plasmid selection by complementation of *E. coli* pyrF mutant strains (uracil auxotrophy),
- the heavy chain-PE domain III fusion protein expression cassette, comprising:
- the T5 hybrid promoter (T5-PN25/03/04 hybrid promoter according to Bujard et al., *Methods. Enzymol.,* 155: 416-433 (1987) and Stueber et al., *Immunol. Methods IV,* 121-152 (1990), including a synthetic ribosomal binding site according to Stueber et al. (supra),
- the antibody heavy chain variable domain comprising the CDRs of SS1,
- the human CH1 domain,
- the linker comprising a furin cleavage site,
- the mutant variant of *Pseudomonas* Exotoxin A domain III,
- two bacteriophage-derived transcription terminators, the λ-T0 terminator (Schwarz et al., Nature, 272: 410-414 (1978) and the fd-terminator (Beck et al., *Gene,* 1-3: 35-58 (1981), and
- the lad repressor gene from *E. coli* (Farabaugh, *Nature,* 274: 765-769 (1978).

Expression of cFP-0205 in *E. coli:*

The *E. coli* K12 strains CSPZ-6 (thi-1, ΔpyrF) and CSPZ-13 (thi-1, ΔompT, ΔpyrF) were transformed by electroporation with the expression plasmid nos. 15496 and 18023, respectively. The transformed *E. coli* cells were first grown at 37° C. on agar plates. For each transformation, a colony picked from this plate was transferred to a 3 mL roller culture and grown at 37° C. to an optical density of 1-2 (measured at 578 nm). Then 1000 μl of culture were mixed with 1000 μl sterile 86%-glycerol and immediately frozen at −80° C. for long term storage. The correct product expression of these clones was first verified by small scale shake flask experiments and analyzed with SDS-Page prior to the transfer to the 10 L fermenter.

Pre Cultivation:

For pre-fermentation, a chemically defined medium (CD-PCMv2.60) was used: $NH_4Cl$ 1.25 g/l, $K_2HPO_4*3H_2O$ 18.3 g/l, citrate 1.6 g/l, L-Methionine 0.20 g/l, Glucose*$H_2O$ 8.0 g/l, trace elements solution 0.5 ml/l, $MgSO_4*7H_2O$ 0.86 g/l, and Thiamin*HCl 17.5 mg/l. The trace elements solution contained $FeSO_4*7H_2O$ 10.0 g/l, $ZnSO_4*7H_2O$ 2.25 g/l, $MnSO_4*H_2O$ 2.13 g/l, $H_3BO_3$ 0.50 g/l, $(NH_4)_6Mo_7O_{24}*4H_2O$ 0.3 g/l, $CoCl_2*6H_2O$ 0.42 g/l, $CuSO_4*5H_2O$ 1.0 g/l dissolved in 0.5M HCl.

For pre-fermentation, five 1000 mL shake-flasks with four baffles filled with 220 mL of medium were inoculated with 1.0 mL each out of a primary seed bank ampoule. The cultivation was performed on a rotary shaker for 11-12 hours at 37° C. and 170 rpm until an optical density (578 nm) of 7 to 9 was obtained. The shake flasks were pooled, and the optical density was determined. The inoculum volume was calculated with Vinoc.=1000 mL*5/ODPC and is dependent on the optical density of the pre cultivation to inoculate the batch medium of each 100 L bioreactor run with an equal amount of cells.

100 L Scale Fermentation:

For fermentation in a 100 L fermenter (Sartorius, Melsungen, Germany), the following chemically defined batch medium was used: $KH_2PO_4$ 1.59 g/l, $(NH_4)_2HPO_4$ 7.45 g/l, $K_2HPO_4*3H_2O$ 13.32 g/l, citrate 2.07 g/l, L-methionine 1.22 g/l, $NaHCO_3$ 0.82 g/l, trace elements solution 7.3 ml/l, $MgSO_4*7\ H_2O$ 0.99 g/l, thiamine*HCl 20.9 mg/l, glucose*$H_2O$ 29.3 g/l, biotin 0.2 mg/1, 1.2 ml/l Synperonic 10% anti foam agent. The trace elements solution contained $FeSO_4*7H_2O$ 10 g/l, $ZnSO_4*7H_2O$ 2.25 g/l, $MnSO_4*H_2O$ 2.13 g/l, $CuSO_4*5H_2O$ 1.0 g/l, $CoCl_2*6H_2O$ 0.42 g/l, $(NH_4)_6Mo_7O_{24}*4H_2O$ 0.3 g/l, $H_3BO_3$ 0.50 g/l solubilized in a 0.5M HCl solution.

The feed 1 solution contained 700 g/l glucose*$H_2O$, 7.4 g/l $MgSO_4*7\ H_2O$ and 0.1 g/l $FeSO_4*7H_2O$. Feed 2 comprised $KH_2PO_4$ 52.7 g/l, $K_2HPO_4*3H_2O$ 139.9 g/l and $(NH_4)_2HPO_4$ 66.0 g/l. All components were dissolved in deionized water. The alkaline solution for pH regulation was an aqueous 12.5% (w/v) $NH_3$ solution supplemented with 11.25 g/l L-methionine.

Starting with 42 L of sterile batch medium plus the calculated inoculum of the pre cultivation the batch, fermentation was performed at 31° C., pH 6.9±0.2, 800 mbar back pressure and an initial aeration rate of 50 l/min. The relative value of dissolved oxygen ($pO^2$) was kept at 50% throughout the fermentation by increasing the stirrer speed up to 1000 rpm.

After the initially supplemented glucose was depleted, indicated by a steep increase in dissolved oxygen values, the temperature was shifted to 37° C. when producing the light chain or kept constant when producing the heavy chain construct and 15 minutes later, the fermentation entered the fed-batch mode with the start of both feeds (600 and 140 g/h respectively). The rate of feed 2 was kept constant, while the rate of feed 1 was increased stepwise with a predefined feeding profile from 600 to finally 1400 g/h when producing the light chain or 1600 g/h when producing the heavy chain construct within 6-7 hours. When carbon dioxide off gas concentration leveled above 2%, the aeration rate was stepwise increased by 10 L/min from 50 to 100 l/min within 5 hours. The expression of recombinant target proteins as insoluble inclusion bodies located in the cytoplasm was induced by the addition of 24 g IPTG at an optical density of approx. 40 for the variable light Fab-chain and 120 for the variable heavy Fab-chain.

After 24 hours of cultivation, the whole broth was cooled down to 4-8° C. and stored overnight in the fermenter vessel. The bacteria were harvested via centrifugation with a flow-through centrifuge (13,000 rpm, 13 l/h) or a separator and the obtained biomass was stored at −20° C. until further processing (cell disruption) or immediately processed for inclusion body isolation.

Analysis of Product Formation:

Samples were drawn from the fermenter, one prior to induction and the others at dedicated time points after induction of protein expression. The samples were analyzed by SDS-Polyacrylamide gel electrophoresis. For every sample, the same amount of cells ($OD_{Target}$=10) was suspended in 5 mL PBS buffer and disrupted via sonication on ice. Then, 100 µL of each suspension were centrifuged (15,000 rpm, 5 minutes) and each supernatant was withdrawn and transferred to a separate vial. This was to discriminate between soluble and insoluble expressed target protein. To each supernatant (=soluble protein fraction) 100 µL and to each pellet (=insoluble protein fraction) 200 µL of SDS sample buffer (Laemmli, *Nature,* 227: 680-685 (1970)) were added. Samples were heated for 15 minutes at 95° C. under intense mixing to solubilize and reduce all proteins in the samples. After cooling to room temperature, 5 µL of each sample were transferred to a 4-20% TGX Criterion Stain Free polyacrylamide gel (Bio-Rad). Additionally, 5 µl molecular weight standard (Precision Plus Protein Standard, Bio-Rad) and 3 amounts (0.3 µl, 0.6 µl and 0.9 µl) quantification standard with known target protein concentration (0.1 µg/µl) were applied.

The electrophoresis was run for 60 Minutes at 200 V and, thereafter, the gel was transferred the GELDOC EZ Imager (Bio-Rad) and processed for 5 minutes with UV radiation. Gel images were analyzed using Image Lab analysis software (Bio-Rad). With the three standards, a linear regression curve was calculated with a coefficient of >0.99 and the concentrations of target protein in the original sample were calculated. The yield was up to 3-4 g/L of the Fab-light chain and 10-12 g/L for the Fab-heavy chain PE fusion.

Inclusion Body Preparation:

The inclusion body preparations (IBP) of the 100 L fermentations were started directly after the harvest of the bacteria with the re-suspension of the harvested bacteria cells in buffer 1 (12.1 g/L Tris, 0.246 g/L $MgSO_4*7H_2O$, 12 mL/L 25%-HCl). The buffer volume was calculated in dependence of the dry matter content of the biomass. Lysozyme (100 kU/mg, 0.12 mg/g DCW) and a small amount of benzonase (5 U/g DCW) were added. Then, the suspension was homogenized at 900 bar (APV Rannie 5, 1 pass) to disrupt the bacteria cells followed by the addition further benzonase (30 U/g DCW) and an incubation for 30 minutes at 30-37° C. Then, the first wash buffer (60 g/L Brij, 87.6 g/L NaCl, 22.5 g/L EDTA, 6 mL/L 10N NaOH) was added and again the suspension was incubated for 30 minutes. The following separation step (CSCE, Westfalia) led to an inclusion body slurry which was re-suspended in the second wash buffer (12.1 g/L Tris, 7.4 g/L EDTA, 11 mL/L 25%-HCl) and incubated for 20 minutes. A further separation step harvested the inclusion bodies to a single use, sterile, plastic bag, which was immediately transferred to the DSP department.

Results:

The fermentations of the light chain yielded an optical density measured at 578 nm of 170-190 and a final product yield of 10-12 g/L. The fermentations of the heavy chain toxin fusion yielded an optical density measured at 578 nm of 210-230 and a final product yield of 3-4.5 g/L.

Refolding and Purification of cFP-0205:

Inclusion bodies of HC-PE24 and LC were solubilized separately in 8 M guanidinium-hydrochloride, 100 mM Tris/HCl, 1 mM EDTA, pH 8.0+100 mM dithiothreitol (DTT) overnight at RT (1 g IB in 5 mL). Solubilizates were adjusted to pH 3 and centrifuged, and the pellet was discarded. After extensive dialysis against 8 M guanidinium-HCl, 10 mM EDTA, pH 3.0 to remove DTT, the total protein concentration was determined using the Biuret method. The purity of the HC and LC content was estimated via SDS-PAGE.

Solubilizates were diluted at a 1:1 molar ratio in renaturation buffer containing 0.5 M arginine, 2 mM EDTA, pH 10+1 mM GSH/GSSG, respectively, at 2-10° C. The target protein concentration was increased stepwise from 0.1 g/L up to 0.5 g/L, with an incubation time of 2 hours between each dose. After up to 5 pulses, the renaturation solution was kept at 2-10° C. overnight.

The renaturate was diluted with $H_2O$ to <3 mS/cm and pumped onto an anion exchange column (AIEX) equilibrated in 20 mM Tris/HCl, pH 7.4. After washing the column with equilibration buffer, the protein was eluted with a gradient up to 20 mM Tris/HCl, 400 mM NaCl, pH 7.4. Peak fractions containing Fab-PE24 were pooled, concentrated and applied onto a preparative Size Exclusion Column (SEC) in 20 mM His, 140 mM NaCl, pH 5.5 or 6.0 to remove aggregates, fragments, and *E. coli* proteins. The final protein pool was adjusted to the required protein concentration and analyzed via SDS-PAGE or CE-SDS, analytical SEC and $UV_{280}$. Identity was confirmed by mass spectrometry.

Protein Analysis of cFP-0205:

Sample analysis was carried out as described above. Characterization of Final Deimmunized PE Variant as Fab Fusion with Humanized Anti-Mesothelin SS1 (cFP0205).

Cytotoxicity and In Vitro Tumor Cell Killing:

The cytotoxic potency of cFP0205 was compared to that of SS1P in cell viability assays with different cancer cell lines and primary mesothelioma cells. The results are shown in Table 24. As shown in Table 24, for many cancer cell lines, SS1P and cFP0205 had comparable potencies (difference in $IC_{50}$ values ≤3). However, some cell lines (e.g., Hu-1 and Hu-2) and also the primary mesothelioma cells (RH19, RH21) were significantly more sensitive to cFP0205 than to SS1P (6-10 fold lower $IC_{50}$ values).

TABLE 24

| Cell line | SS1P (IC50 in ng/ml) | cFP0205 (IC50 in ng/ml) |
|---|---|---|
| Hu-1 | 2 | 0.25 |
| Hu-2 | 0.3 | 0.04 |

TABLE 24-continued

| Cell line | SS1P (IC50 in ng/ml) | cFP0205 (IC50 in ng/ml) |
|---|---|---|
| Hu-3 | 2.9 | 2 |
| HAY | 1 | 1.4 |
| AG5 | 0.3 | 1.1 |
| L55 | 3 | 5 |
| MKN-28 | 0.5 | 2 |
| ASPC-1-luc | 1.3 | 2.4 |
| H596 | 4.6 | 15.7 |
| RH19 | 3.7 | 1.2 |
| RH21 | 2.3 | 0.35 |

Characterization of Final Deimmunized PE Variant as Fab Fusion with Humanized Anti-Mesothelin SS1 (cFP0205).

Figure 20:
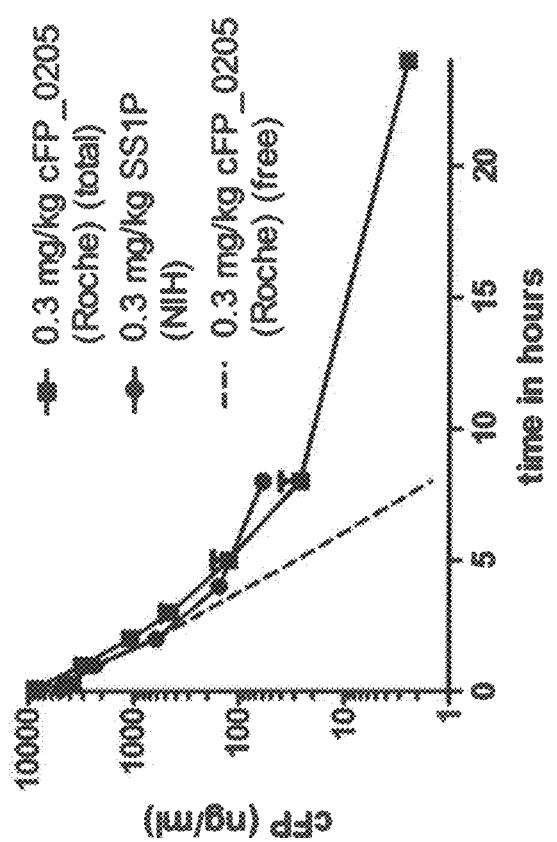
FIG. 20 is a graph showing the serum half life cFP (ng/ml) of 0.3 mg/kg cFP_0205 (squares), 0.3 mg/kg SS1P (circles), or 0.3 mg/kg cFP_0205 (dashed lines) over time (hours) in cyno monkeys.

Serum Half Life:

A pilot study was performed in cynomolgus monkeys (1 male and 1 female) with cFP0205 in order to assess the pharmacokinetics of single doses. The animals were intravenously dosed with 0.3 mg/kg of cFP0205. For pharmacokinetics, blood samples were taken predose, 0.083 (5 minutes, end of infusion), 1, 2, 3, 5, 8, 24, 48 and 168 hours postdose. Levels of free drug (dashed line) as well as total drug (black squares and solid line) were determined by different ELISA formats (FIG. 20). For determining total drug levels, a one-step acid dissociation was performed before the capturing step on mesothelin coated plates. The free and total drug levels were plotted over time. For comparison, historical data with SS1P were also inserted into FIG. 20 (black circles and solid line). These historical data were generated with a cytotoxic activity assay as a read-out for serum levels of SS1P. The cytotoxicity assay detects free drug, but also detects, at least in part, drug bound to soluble mesothelin which might contribute to the observed activity. The measured free drug levels for cFP0205 were similar to the first phase of the historical data with SS1P. The measured total drug levels for cFP0205 were comparable to the second phase of the kinetic observed for SS1P. In summary, not only in mice, but also in cynomolgus monkey, the serum level kinetics of SS1P and cFP0205 were very comparable.

Characterization of Final Deimmunized PE Variant as Fab Fusion with Humanized Anti Mesothelin SS1 (cFP0205)

Reduced Off-Target Toxicity:

SCID beige mice with small subcutaneous tumors of H596 lung cancer cells (average tumor volume 100 mm³) were dosed with 0.5, 1, 2, and 3 mg/kg cFP0205 3x/w qod and body weight loss was monitored over one month. The results are shown in FIG. 21.

Figure 21:
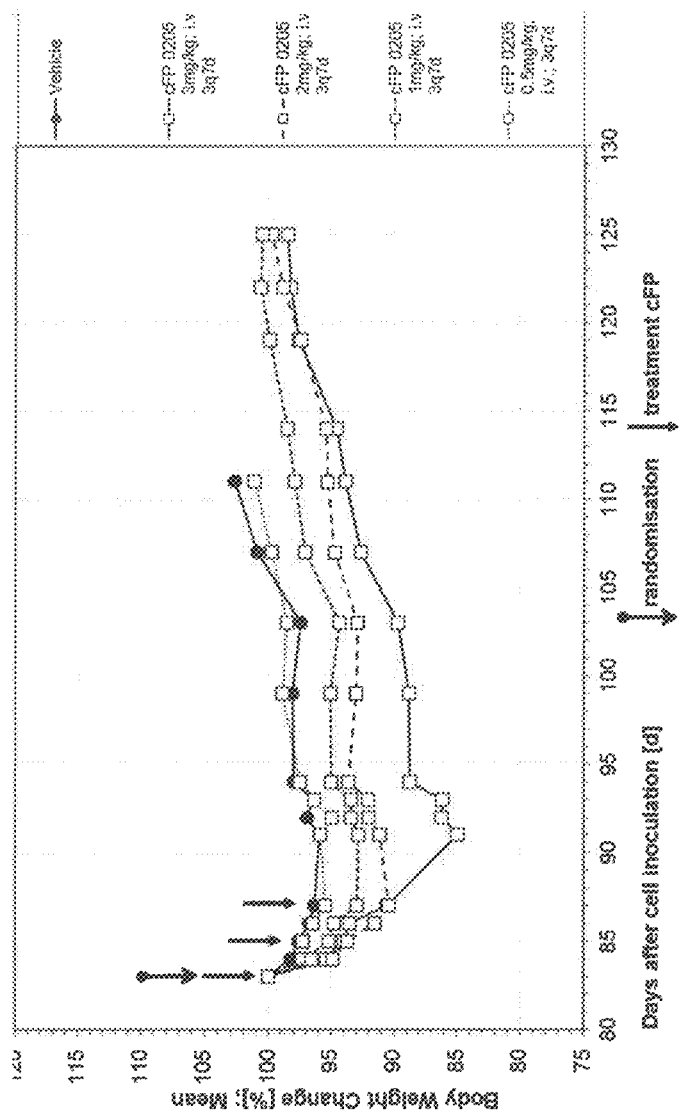
FIG. 21 is a graph showing the body weight change of of mice treated with control (vehicle; circles); cFP 0205 3 mg/kg i.v. 3q7d (squares on solid line); cFP 0205 2 mg/kg i.v. 3q7d (squares on larger dashed line); cFP 0205 1 mg/kg i.v. 3q7d (squares on short dashed line); cFP 0205 0.5 mg/kg i.v. 3q7d (squares on dotted line) over time (days after cell inoculation).
Figures 22A, 22B, 22C, 22D, 22E, 22F, 22G, 22H, 22I, 22J, 22K, 22L:
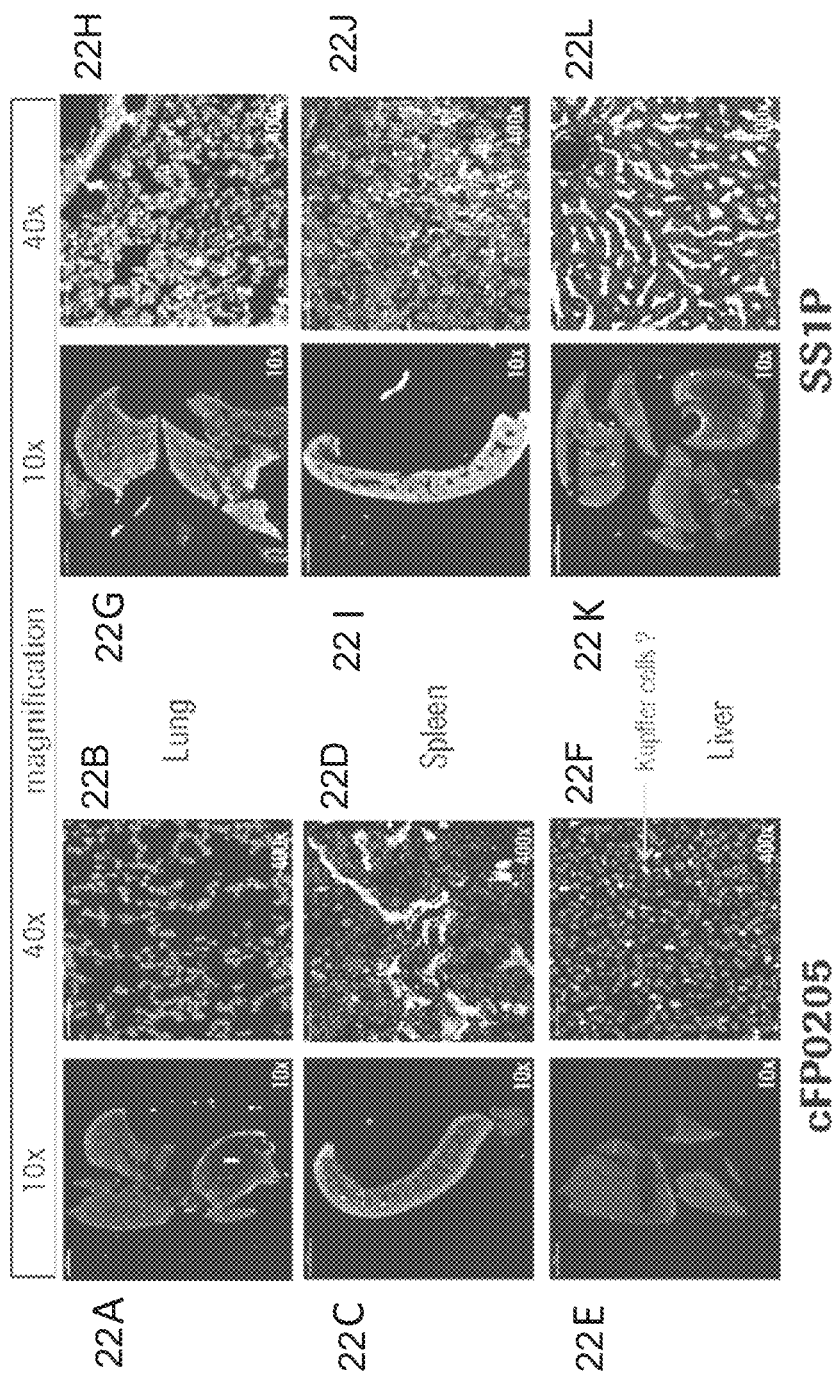
FIGS. 22A-F are fluorescence images of sections of lung (A-B), spleen (C-D) or liver (E-F) of mice treated with labeled cFP0205 at 10× (A, C, E) or 40× (B, D, F) magnification.
FIGS. 22G-L are fluorescence images of sections of lung (G-H), spleen (I-J) or liver (K-L) of mice treated with labeled SS1P at 10× (G, I, K) or 40× (H, J, L) magnification.

As shown in FIG. 21, the maximally tolerated dose of SS1P in mice given intravenously 3x/w qod was 0.4 mg/kg. cFP0205 given with this same regimen was tolerated in SCID beige mice at doses up to 3 mg/kg. Some body weight loss was observed in all treatment groups. However, the effect of the 0.5 mg/kg dose of cFP0205 was indiscriminable from the vehicle control. Dose-dependently, an increasing loss of body weight occurred with 1, 2, and 3 mg/kg. In the 3 mg/kg group, the maximum weight loss was 15% and this was observed 4 days after the last application of cFP0205. In the 2 and 3 mg/kg treatment groups, no further decline in body weight was observed after the last application. All animals started to recover body weight from day 5 after the last treatment onwards. Initial body weight recovery was most pronounced in the 3 mg/kg group. In summary, despite similar pharmacokinetic properties of both molecules in mice, cFP0205 was tolerated at an almost 10 fold higher dose compared to SS1P.

A single intravenous dose (short infusion) toxicology study was done in 8 week old female Wistar Furth rats (150-175 g body weight) in order to evaluate and compare the off-target toxicity of SS1P and cFP0205. In particular, the risk of inducing vascular leak (edema) in the lung caused by the test item was investigated. Three animals per group received the active substance or vehicle by an intravenous short infusion at an infusion rate of 0.3 ml/min. Animals were necropsied 24 hours after dosing. Lung with mainstem bronchi and liver were macroscopically evaluated, fluid collection in the lung was assessed, and clinical chemistry assays were performed on blood samples. The results are shown in Table 25.

TABLE 25

| | SS1P | cFP0205 |
|---|---|---|
| Dose (i.v.), n = 3 | 2 mg/kg | 10 mg/kg |
| In-life (clinical signs, bw) | rales (lung), rolling gait, hunched posture, piloerection and slight bw loss | none |
| Necropsy | tan-stained thoracic fluid in 2 rats; brown discoloration of liver in all 3 rats | none |
| Fluid Smear Evaluation | mesothelial cells and eosinophils | none |
| Clinical Chemistry | Liver: ↑↑↑ in ALT (30×), AST (40×), γGT, GLDH, SDH; VLS: ↓ Protein, ↓ albumin (serum protein loss) Hemolysis ?: ↑ bilirubin (but no hematology indication) ↑ BUN: poor physical condition (↑ protein catabolism) | Liver: marginal SDH ↑ |

The serum half life of SS1P and cFP0205 is expected to be very similar in rats as shown for mice.

As shown in Table 25, two out of three rats that were dosed intravenously with 2 mg/kg of SS1P showed fluid accumulation in the lungs. All animals in this group showed clear clinical signs of toxicity and, for all animals, clinical chemistry values were indicative of severe liver damage. In contrast to this, all three animals treated with 10 mg/kg of cFP0205 showed no signs of toxicity. Only in one animal was the value for one of the liver enzymes slightly elevated. These findings demonstrate that the cFP0205 molecule causes much less hepatotoxicity and vascular leak syndrome than the SS1P classical immunotoxin format.

A pilot toxicology study was performed in cynomolgus monkeys (1 male and 1 female) with cFP0205 in order to determine the tolerability of repeated daily doses of the test item following intravenous administration and to check for potential late onset toxicity (up to 72 hrs after last repeat-dose). Postdosing observations of the animals were performed immediately, 0.25, 0.5, 1, 2, and 4 hours after end of dosing. During the dosing phase, the general behavior and appearance of the animals was observed twice daily, while body weight, food consumption and feces were analysed daily.

Dosing cFP0205 at 1 mg/kg daily for 5 consecutive days was well tolerated by both animals. No hemorrhaging, acute inflammation, or ulceration at the injection site were observed. That the animals showed no clinical signs of toxicity or non-tolerability firmly established 1 mg/kg/d 5× as the non-severely toxic dose, while the classical immunotoxin format represented by SS1P had previously been shown to be non-tolerated at a dose of 0.3 mg/kg/d 5× with animals showing persistent clinical signs of toxicity like hunched posture with tremors, hypoactivity, and poor appetite. In summary, cFP0205 is much better tolerated than SS1P not only in mice, but also in cynomolgus monkeys, a fully cross-reactive species for the targeting moieties of these immunoconjugates.

Characterization of Final Deimmunized PE Variant as Fab Fusion with Humanized SS1 (cFP0205)

cFP0205 and SS1P were labeled with Cy5 on free amino groups. Outstaged SCID beige mice with subcutaneous H596 tumors were intravenously injected (4 mice/group) at a dose of 2 mg/kg with the 2 fluorescent-labeled molecules. After 6 hours, the animals were sacricifed. The lung, liver, and spleen were formalin-fixed, embedded and sectioned. Fluorescence images of representative sections of these organs were taken at different magnification. The results are shown in FIGS. 22A-22L.

As shown in FIGS. 22A-22L, SS1P treatment led to pronounced fluorescence staining of lung and spleen tissue and massively stained what appeared to be the reticuloendothelial system in the liver. In contrast to this, there was no staining of lung tissue observed upon cFP0205 application. Also, staining of the spleen was much less pronounced and the staining pattern was different from that of SS1P treated animals. Also in the liver, the staining with cFP0205 was drastically reduced compared to SS1P. Only isolated single cells that appear to be Kupffer cells were fluorescently stained. This suggests that the lower off-target toxicity of a Fab-PE24 compared to a dsFv-PE38 is due to differences in normal tissue distribution.

Example 15

This example demonstrates the production of anti-glypican 3-PE variant chimeric molecules.

An anti-glypican 3-PE variant chimeric molecule comprising a linker comprising the amino acid sequence of SEQ ID NO: 36, a PE comprising SEQ ID NO: 37 (L010R-456A), the variable heavy chain domain VH of SEQ ID NO: 61, and the variable light chain domain of SEQ ID NO: 62 (GPC3-PE24-LR-LO10R-456A-long-linker) was prepared by a method analogous to the method of preparing the anti-mesothelin PE variant chimeric molecule cFP-077 described in Example 12 (from cloning to purification).

An anti-glypican 3-PE variant chimeric molecule comprising a linker comprising the amino acid sequence of SEQ ID NO: 36, a PE comprising SEQ ID NO: 37 (L010R-456A), the variable heavy chain domain VH of SEQ ID NO: 77, and the variable light chain domain of SEQ ID NO: 78 was also prepared by a method analogous to the method of preparing the anti-mesothelin PE variant chimeric molecule cFP-077 described in Example 12 (from cloning to purification).

Example 16

This example demonstrates the cytotoxic properties of the anti-glypican 3-PE variant chimeric molecule GPC3-PE24-LR-LO10R-456A-long-linker as compared to GPC3-PE24-LR-LO10R.

The cytotoxic potency of GPC3-PE24-LR-LO1 OR was compared to that of GPC3-PE24-LR-LO10R-456A-long-linker on the glypican 3-positive liver cancer cell line HepG2. Briefly, HepG2 cells were seeded at a density of 6000 cells/well on 96 well plates. After overnight culture, different concentrations of the cFPs were added to the medium, and the cells were incubated for 72 hours. At the end of incubation period, cell viability was determined using a CELLTITER-GLOW assay. The results are shown in Table 26.

As shown in Table 26, comparable dose-response curves for the inhibition of cell viability were observed on HepG2 cells for both molecules. The $IC_{50}$ value of the more completely de-immunized PE variant with the 456A mutation and the longer linker was even slightly lower than that of the LR-LO10R variant with the short linker. Non-targeted ("free PE24") or mistargeted PE24 ("CD33-Fab-PE"; HepG2 cells do not express CD33) did not show any significant reduction of cell viability at concentrations <30 µM. In summary, the more completely de-immunized GPC3-targeted LR-LO10R-456A-long-linker variant had the same or even slightly better cytotoxic potency as compared to the GPC3-targeted LR-LO1 OR variant with the shorter linker. Due to the additional 456A mutation within the PE, all B-cell epitopes were removed.

TABLE 26

| Fusion protein | IC50 in CELLTITERGLOW assay with HepG2 (expressing glypican-3) |
|---|---|
| GPC3-PE24-LR-LO10R-short-linker | 0.68 nM |
| GPC3-PE24-LR-LO10R-456A-long-linker | 0.54 nM |
| Non-targeted PE24 | >>30 µM |
| CD33-PE24-LR-LO10R-short-linker | no effect up to 30 µM |

Example 17

This example demonstrates the cytotoxicity of deimmunized PE fusion proteins having a A458R mutation.

The cytotoxicity of SS1P, SS1-LR-GGS, SS1-LR-GGS-LO10, SS1-LR-GGS-LO10-A458R, and SS1-LR-GGS-LO10-A458-456A was measured using the WST method. The results are shown in Table 27.

TABLE 27

| | A431/H9 | HAY | M30 | Hu-Meso | AGS |
|---|---|---|---|---|---|
| SS1P | 0.05 (N = 14) | 1.49 (N = 6) | 0.28 (N = 5) | 0.48 (N = 5) | 0.36 (N = 5) |
| SS1-LR-GGS | 0.16 (N = 2) | ND | ND | ND | 0.3 |
| SS1-LR-GGS-LO10 | 0.17 (N = 5) | 0.68 | 3.99 | 0.11 | 11 (N = 2) |
| SS1-LR-GGS-LO10-A458R | 0.13 (N = 18) | 0.39 (N = 11) | 0.57 (N = 3) | 0.03 (N = 4) | 1.05 (N = 9) |
| SS1-LR-GGS-LO10-A458R-456A | 0.07 (N = 4) | 0.1 (N = 2) | 0.58 (N = 3) | ND | 0.5 |

As shown in Table 27, the A458R mutation increased the activity of SS1-LR-GGS-L010 on several cell lines. The addition of the 456A mutation further increased activity on several cell lines. A431/H9 is an epidermoid carcinoma expressing mesothelin, and Hay is a mesothelioma line. M30 is also a mesothelioma cell line, and AGS is a stomach cancer cell line. Hu-Meso are cells from a mesothelioma patient that were placed in culture for a few months.

Example 18

This example demonstrates the treatment of HCC70 tumors using RG7787.

Female nude mice were innoculated into the intramammary fat pad with HCC70 cells at time 0. HCC70 is a breast cancer cell line. Intravenous treatment with RG7787 (2.5 mg/kg IV) or vehicle was begun on day 6 and continued every other day for a total of 5 doses (arrows). The size of the tumor was measured. The results are shown in FIG. 24.

Figure 24:
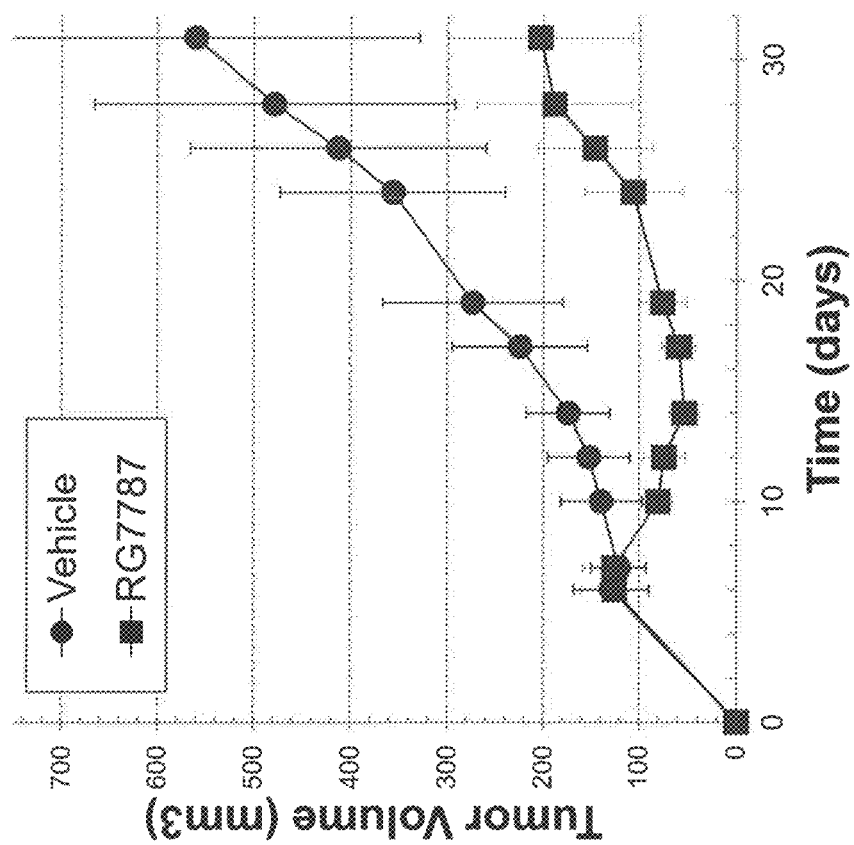
FIG. 24 is a graph showing the tumor size of mice that were untreated (vehicle) (circles) or treated with RG7787 (squares) over time measured in days. Each data point represents the average of mean tumor volume for n=9 animals treated with RG7787 and n 8 control animals. Error bars show standard deviations.

As shown in FIG. 24, the tumor size of mice treated with RG7787 was decreased as compared to that of control mice (vehicle). There is a statistically significant difference between the 2 groups beginning at day 10, with p<0.00001 by day 14.

Example 19

This example demonstrates the treatment of KLM1 tumors in mice using a combination of paclitaxel and RG7787.

Four week, four day old mice were injected with $4 \times 10^6$ KLM1 cells. KLM1 is a pancreatic cancer cell line that expresses mesothelin. Thirteen days later, mice were untreated or treated with paclitaxel (50 mg/kg), RG7787 (2.5 mg/kg), or a combination of RG7787 (2.5 mg/kg) and paclitaxel (50 mg/kg). Tumor size was measured for up to 89 days after treatment. The results are shown in FIG. 23.

Figure 23:
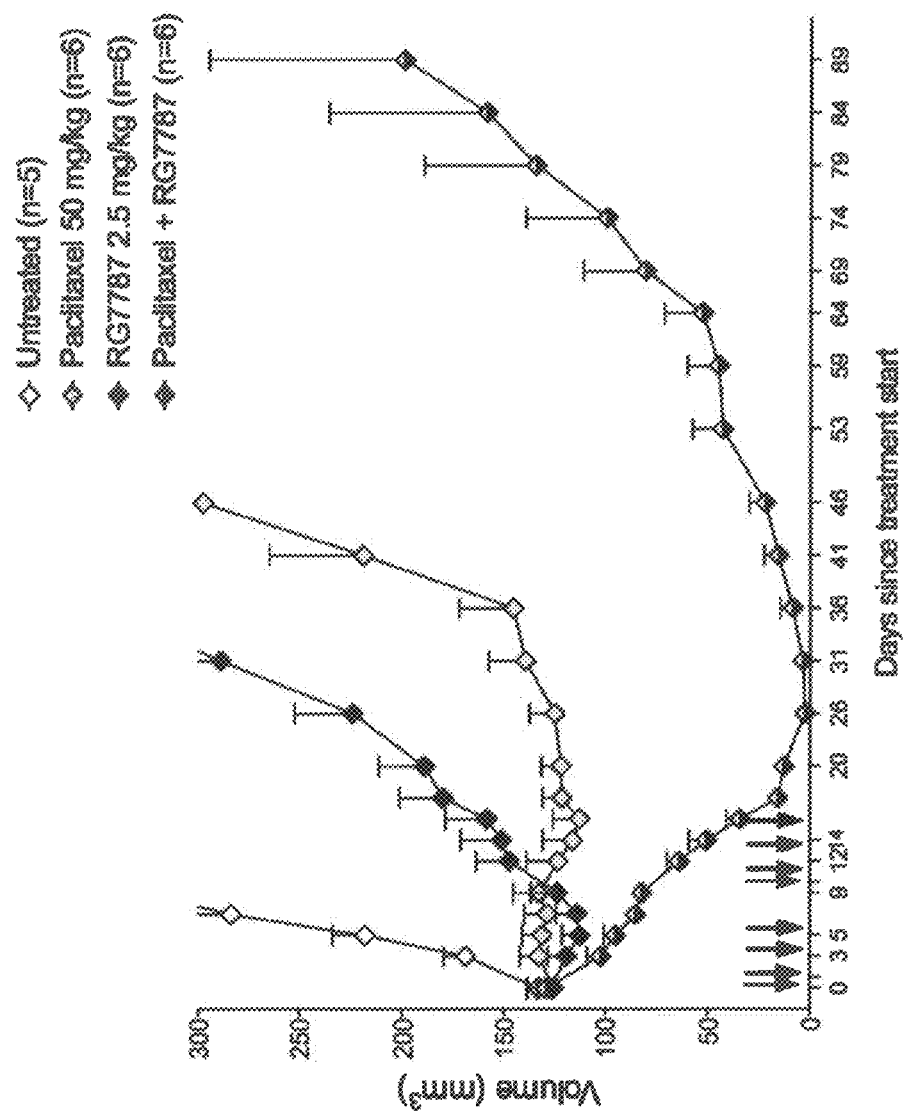
FIG. 23 is a graph showing the tumor size of mice that were untreated (open diamonds) or treated with paclitaxel alone, (grey diamonds) RG7787 (also referred to as R205 or cFP 0205) alone (black diamonds), or a combination of RG7787 and paclitaxel (black and white diamonds) over time measured in days.

As shown in FIG. 23, the tumor size of mice treated with the combination of paclitaxel and RG7787 was decreased as compared to that of control mice (untreated) or that of the mice treated with paclitaxel alone or RG7787 alone.

Example 20

This example demonstrates the treatment of HCC70 tumors in mice using a combination of paclitaxel and RG7787.

Female athymic nude mice were inoculated with HCC70 cells at time 0. Animals were treated with vehicle, RG7787 with IP vehicle injection, paclitaxel with IV vehicle injection, or paclitaxel and RG7787 combination. Paclitaxel (50 mg/kg) was administered by IP injection on days marked with long arrows. RG7787 (2.5 mg/kg) was administered IV on days indicated by short arrows. Mean tumor volumes for n=5 vehicle and n=6 mice treated with RG7787, paclitaxel or the combination are indicated by the markers. The results are shown in FIG. 25.

Figure 25:
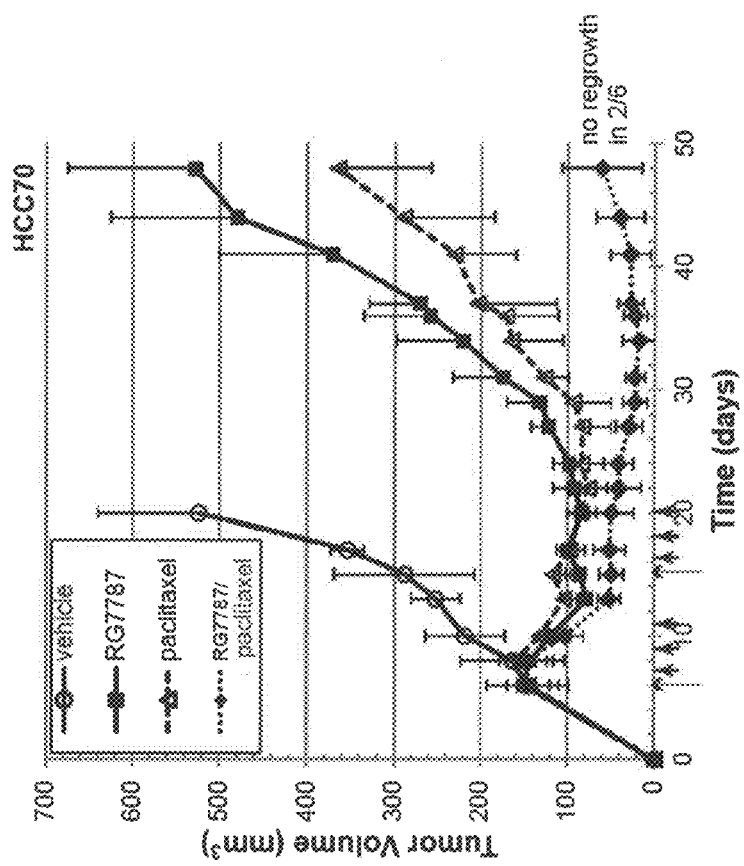
FIG. 25 is a graph showing the tumor size of mice that were treated with vehicle (control) (circles), RG7787 alone (squares), paclitaxel alone (triangles), or a combination of RG7787 and paclitaxel (diamonds) over time measured in days. Error bars show standard deviations.

As shown in FIG. 25, the tumor size of mice treated with the combination of paclitaxel and RG7787 was decreased as compared to that of control mice (vehicle) or that of the mice treated with paclitaxel alone or RG7787 alone.

Example 21

This example demonstrates the treatment of MKN-28 tumors in mice using a combination of paclitaxel and R205.

Athymic nude mice were inoculated with MKN-28 cells at time 0. MKN-28 is a gastric cancer cell line which expresses mesothelin. Animals were untreated (UT) or treated with Roche 205 (R205 or 205) alone, paclitaxel (taxol) alone, or a combination of R205 and paclitaxel. Tumor size was measured. The results are shown in FIG. 26.

Figure 26:
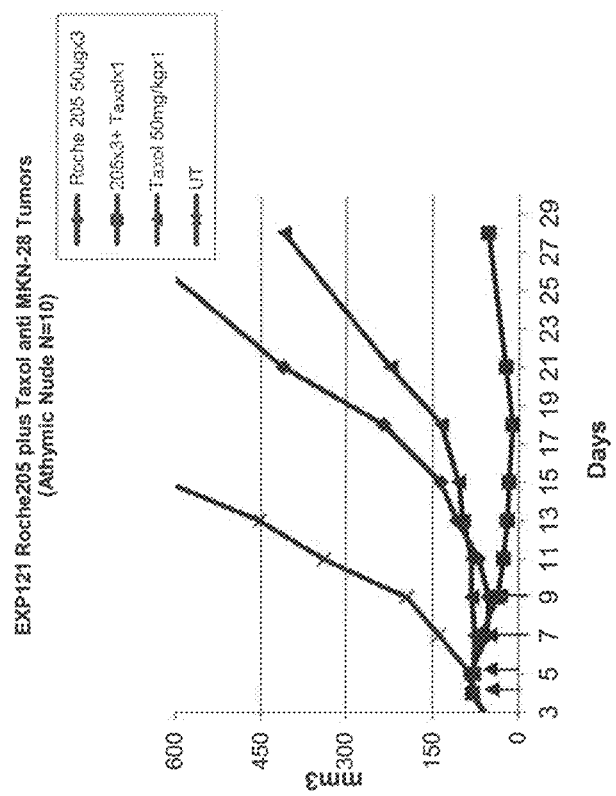
FIG. 26 is a graph showing the tumor size of untreated (UT) (x) mice or mice treated with R205 alone (diamonds), a combination of R205 and taxol (squares), or taxol alone (triangles) over time measured in days.

As shown in FIG. 26, the tumor size of mice treated with the combination of paclitaxel and R205 was decreased as compared to that of control mice (untreated) or that of the mice treated with paclitaxel alone or R205 alone.

Example 22

This example demonstrates the in vivo antitumor activity of LMB-T18. Severe combined immunodeficient (SCID) mice were implanted with CA46 cells. Seven days later, when tumors reached over 100 mm³ in size, the mice were treated with PBS (control) or LMB-T18 (5 mg/kg×4 or 7.5 mg/kg×3) intravenously. Mice receiving 5.0 mg/kg were treated four times, on days 7, 9, 11 and 16, and the higher dose group was treated with 7.5 mg/kg three times on days 7, 9 and 11. Marked tumor regressions were observed in all mice (FIG. 27E) with only minor weight loss (average of 6%). 5/7 mice treated with 5.0 mg/kg maintained complete tumor regression on day 33, and 3/7 maintained complete tumor regression in the 7.5 mg/kg group. To assess the nonspecific toxicity of LMB-T18, six tumor bearing mice were treated intravenously with two doses of 10 mg/kg QOD. One mouse showed severe weight loss and was euthanized.

Example 23

This example demonstrates that LMB-T18 has greatly diminished T cell activation.

To determine if LMB-T18 had a decrease in T cell stimulation or if new T cell epitopes were created by the mutations, PBMCs were stimulated from the highest responder donors (n=13) and HCL and mesothelioma patients (n=7) with MP or LMB-T18. Cells were re-stimulated with the 39 novel peptides representing the differences between MP and LMB-T18. A decrease of 90% in donor T cell activation (p<0.0001 in Student T test) was observed. Even in patients with activated T cells, there was an 83% decrease. (p<0.0001 in Student T test). Furthermore, no new epitopes were created by the mutations.

Example 24

This example demonstrates that LMB-T18 has reduced binding to anti-sera from patients.

The antigenicity of LMB-T18 was evaluated by comparing the reactivity of MP, HA22-LR and LMB-T18 with serum from patients with neutralizing antibodies to MP. Binding was measured using ICC-ELISA with serum from 13 MP treated patients and is shown in FIG. 27F. It was found that like HA22-LR, LMB-T18 had a significantly reduced binding to serum compared to MP ($p<0.001$ one-way ANOVA). It was also found that LMB-T18 had significantly lower binding compared to HA22-LR ($p<0.001$ one-way ANOVA), indicating that the mutations in LMB-T18 reduced the binding to anti-sera.

Example 25

This example demonstrates the production of anti-FAP-PE variant chimeric molecules.

Three anti-FAP-PE variant chimeric molecules comprising:

(a) a linker comprising the amino acid sequence of SEQ ID NO: 36, a PE comprising SEQ ID NO: 37 (L010R-456A)), the variable heavy chain domain VH of SEQ ID NO: 93, and the variable light chain domain of SEQ ID NO: 94 (iFAP-PE24-LR-LO10R-456A-long-linker)

(b) a linker comprising the amino acid sequence of SEQ ID NO: 36, a PE comprising SEQ ID NO: 37 ((L010R-456A)), the variable heavy chain domain VH of SEQ ID NO: 93, and the variable light chain domain of SEQ ID NO: 294 (LCL4-PE24-LR-LO10R-456A-long-linker) (including the VL variant of SEQ ID NO: 290), and (c) a linker comprising the amino acid sequence of SEQ ID NO: 36, a PE comprising SEQ ID NO: 37 (T-20), the variable heavy chain domain VH of SEQ ID NO: 93, and the variable light chain domain of SEQ ID NO: 290 (LCL4-T20);

were prepared by a method analogous to the method of preparing the anti-mesothelin PE variant chimeric molecule cFP-077 described in Example 12 (from cloning to purification), except as described below.

The anti-FAP-PE variant chimeric molecules (b) and (c) included a modified variable light chain domain (VL) in which the methionine at position 4 of the original VL sequence of SEQ ID NO: 94 was substituted with leucine to provide a modified VL sequence of SEQ ID NO: 290 ("LCL4"). The modified variable light chain domain SEQ ID NO: 290 was found to reduce the production of impurities related to N-terminal modifications. These N-terminal modifications provided a mixture of variants with different light chain lengths due to the initiation of expression of the unmodified sequence at either the N-terminal methionine or the methionine at position 4 of of SEQ ID NO: 94.

Pre-Cultivation:

For pre-fermentation, the same chemically defined medium (CD-PCMv2.20) was used as described in Example 12.

The cultivation was performed on a rotary shaker for 8 hours at 37° C. and 170 rpm until an optical density (578 nm) of 13.3 or 14.4 was obtained. 150 ml of the pre-cultivation was used to inoculate the batch medium of the 10 L bioreactor.

Fermentation:

For fermentation in a 10l Biostat C, DCU3 fermenter (Sartorius, Melsungen, Germany), the same chemically-defined batch medium as described in Example 12 was used.

One feed solution that was used contained 700 g/l glucose*$H_2O$, 7.4 g/l $MgSO_4$*7 $H_2O$ and 0.1 g/l $FeSO_4$*7$H_2O$. All components were dissolved in deionized water. The alkaline solution for pH regulation was an aqueous 12.5% (w/v) $NH_3$ solution supplemented with 11.25 g/l L-methionine and 10 g/L Leucine and 10 g/L Threonine.

Starting with 6.24 L sterile batch medium plus 150 mL inoculum from the pre-cultivation, the batch fermentation was performed at 32° C., pH 6.9±0.2, 800 mbar back pressure and an initial aeration rate of 10 l/min. The relative value of dissolved oxygen ($pO_2$) was kept at 50% throughout the fermentation by increasing the stirrer speed up to 1500 rpm. After the initially supplemented glucose was depleted, indicated by a steep increase in dissolved oxygen values, the temperature was shifted to 32° C. or 37° C., and 15 minutes later, the fermentation entered the fed-batch mode with the start of both the feeds (60 and 14 g/h respectively). The rate of the feed was increased stepwise with a predefined feeding profile from 90 to finally 210 or 240 g/h within 5.5 or 6.5 hours. When carbon dioxide off gas concentration leveled above 2%, the aeration rate was constantly increased from 10 to 20 l/min within 5 hours. The expression of recombinant protein was induced by the addition of 3.6 g IPTG at an optical density of approx. 40 or 120. The target protein was expressed as inclusion bodies within the cytoplasm.

After 24 hours of cultivation, an optical density of 179 or 171 was achieved, and the whole broth was cooled down to 4-8° C. The bacteria were harvested via centrifugation with lab centrifuge (4500 rpm, cooling at 4° C., for 1 h) and the obtained biomass was stored at −20° C. until further processing (cell disruption).

Analysis of Product Formation:

The specific differences in comparison to the method of Example 12 are described below:

The same amount of cells ($OD_{Target}$=10) from every sample were suspended in 5 mL PBS buffer and disrupted via sonication on ice. Then 100 µL of each suspension were centrifuged (8,000 rpm, 5 minutes) and each supernatant was withdrawn and transferred to a separate vial.

After adding Laemmli buffer, the samples were heated for 45 minutes 40° C. under intense mixing to solubilize and reduce all proteins in the samples.

Inclusion Body Preparation:

The inclusion body preparations (IBP) of the 10 L fermentations were processed in a manner analogous to the method described in Example 12, with the exception that after disruption of the bacteria cells, further benzoase (30 U/g DCW) was added and incubated for 60 minutes at 25° C.

Solubilization, renaturation and purification were performed in a manner similar to that described in Example 12. The following sequences were used:

Sequence of iFAP-PE24-LR-LO10R-456A-long-linker and LCL4-PE24-LR-LO10R-456A-long-linker chimeric full length heavy chain comprising the variable domain VH of SEQ ID NO: 93, a linker comprising the amino acid sequence of SEQ ID NO: 36, and a PE comprising SEQ ID NO: 37 (SEQ ID NO: 291);

Sequence LCL4-T20 chimeric heavy chain construct comprising the full length heavy chain comprising the variable domain VH of SEQ ID NO: 93, a linker comprising the amino acid sequence of SEQ ID NO: 36 and a PE comprising SEQ ID NO: 289 (T18/T20) (SEQ ID NO: 292);

Sequence of full length iFAP light chain (SEQ ID NO: 293) comprising the variable light chain domain of SEQ ID NO: 94 and constant region;

Sequence of full length LCL4 light chain (SEQ ID NO: 294) comprising the variable light chain domain of SEQ ID NO: 290 and constant region; and Sequence of the variable light chain domain of SEQ ID NO: 290 (with mutation M4L at position 4 (compared to SEQ ID NO: 94).

Example 26

This example demonstrates the cytotoxicity of the anti-FAP-PE variant chimeric molecules iFAP-PE24-LR-LO10R-456A-long-linker, LCL4-PE24-LR-LO10R-456A-long-linker, and LCL4-T20.

The cytotoxicity of iFAP-PE24-LR-LO10R-456A-long-linker was compared to that of LCL4-PE24-LR-LO10R-456A-long-linker and LCL4-T20 ("cFPs") with respect to the FAP-positive fibroblast cell line MRC-5, the FAP-positive desmoplastic melanoma cell line LOX-IMVI, and the FAP-positive sarcoma cell line OsA-CL. Briefly, cells were seeded at a density of 10,000 cells/well on 96-well plates. After overnight culture, different concentrations of the cFPs were added to the medium, and the cells were incubated for 72 hours. At the end of incubation period, cell viability was determined using a CELLTITER GLO assay. The results are shown in Table 28 and Table 29.

As shown in Table 28, comparable IC50 values for the inhibition of cell viability were observed on all 3 tested cell lines for iFAP-PE24-LR-LO10R-456A-long-linker (3 different batches) and for LCL4-PE24-LR-LO10R-456A-long-linker. As shown in Table 29, LCL4-T20 also showed potent inhibition of cell viability. In summary, iFAP-PE24-LR-LO10R-456A-long-linker, LCL4-PE24-LR-LO10R-456A-long-linker, and LCL4-T20 showed potent cytotoxic effects on FAP-positive tumor cell lines and fibroblasts.

TABLE 28

| Fusion protein | IC50 in CELLTITER GLO assay with cell lines expressing FAP(ng/ml) | | | |
|---|---|---|---|---|
| | MRC-5 (experiment 1) | MRC-5 (experiment 2) | LOX-IMVI | OsA-CL |
| iFAP- PE24-LR-LO10R-456A-long-linker (Batch 1) | 14.3 | 8.5 | 6.6 | 98.3 |
| iFAP- PE24-LR-LO10R-456A-long-linker (Batch 2) | 14.4 | 9.3 | 9.1 | 46.3 |
| iFAP- PE24-LR-LO10R-456A-long-linker (Batch 3) | 10.0 | 5.5 | 5.7 | 55.3 |
| LCL4- PE24-LR-LO10R-456A-long-linker | 13.9 | 9.8 | 9.7 | 103.1 |

TABLE 29

| Fusion protein | IC50 in CELLTITER GLO assay with cell lines expressing FAP(nM) | | |
|---|---|---|---|
| | MRC-5 | LOX-IMVI | OsA-CL |
| LCL4- PE24-LR-LO10R-456A-long-linker | 0.15 nM | 0.33 nM | 0.23 nM |
| LCL4-T20 | 0.98 nM | 8.99 nM | 0.50 nM |

Example 27

This example demonstrates the production of anti-CAIX-PE variant chimeric molecules.

Two anti-CAIX-PE variant chimeric molecules comprising:
(a) a linker comprising the amino acid sequence of SEQ ID NO: 36, a PE comprising SEQ ID NO: 37 (L010R-456A), the variable heavy chain domain VH of SEQ ID NO: 125, and the variable light chain domain of SEQ ID NO: 126; or
(b) a linker comprising the amino acid sequence of SEQ ID NO: 36, a PE comprising SEQ ID NO: 289 (T-20), the variable heavy chain domain VH of SEQ ID NO: 125, and the variable light chain domain of SEQ ID NO: 126;
were prepared by a method analogous to that described for the anti-mesothelin PE variant chimeric molecule cFP-077 of Example 12 (from cloning to purification), except as described below.

Samples were analyzed by OD 280 nm using a UV spectrophotometer to determine the protein concentration in solution. The materials for the SDS-PAGE and Coomassie Staining Device are set forth in Table 30 below.

TABLE 30

| | |
|---|---|
| Invitrogen XCell Sure Lock Mini-Cell | |
| Gel: | 4-12% Bis-Tris Gel, Invitrogen NP0321 |
| Buffer: | MES SDS Running Buffer (10×), Invitrogen NP0002 |
| Sample buffer: | Tris-Glycine SDS Sample Buffer (2×), Invitrogen LC2676 |
| Reducing buffer: | NUPAGE Sample Reducing Agent (10×), Invitrogen NP0004 |
| Molecular Weight Marker: | Precision Plus KALEIDOSCOPE Standard 161-0375 |

After adding Laemmli buffer, the samples were heated for 45 minutes at 40° C. under intense mixing to solubilize and reduce all proteins in the samples.

The sample was adjusted to a protein concentration of 1 mg/ml with buffer. Sample reduction used a reduction buffer comprising 4 ml of sample buffer (2×) and 1 ml of reducing buffer (10×). The samples were reduced by diluting the sample 1:1 with reduction buffer and incubating the sample for 10 minutes at 70° C.

The gel electrophoresis was carried out at 200 V for 40 minutes. The gels were stained with SIMPLY BLUE Safe Stain (Invitrogen, Cat. No. LC6065).

Inclusion Body Preparation:

The inclusion body preparations (IBP) of the 10 L fermentations were processed in a manner analogous to that described in Example 12, with the exception that after disruption of the bacteria cells, further benzoase (30 U/g DCW) was added and incubated for 60 minutes at 25° C.

Solubilization, renaturation and purification were performed in a manner similar to that described in Example 12.

The following sequences were used:

Sequence of CAIX-PE24-LR-LO10R-456A-long-linker chimeric heavy chain construct (SEQ ID NO: 295): comprising the variable heavy chain domain VH of SEQ ID NO: 125, a linker comprising the amino acid sequence of SEQ ID NO: 36, and a PE comprising SEQ ID NO: 37;

Sequence of CAIX-T20 chimeric heavy chain construct (SEQ ID NO: 296) comprising the variable heavy chain domain VH of SEQ ID NO: 125, a linker comprising the amino acid sequence of SEQ ID NO: 36 and a PE comprising SEQ ID NO: 289 (T18/T20); and Sequence of full length light chain (SEQ ID NO: 297) comprising the variable light chain domain of SEQ ID NO: 126) and constant region.

Example 28

This example demonstrates the cytotoxicity (in vitro tumor cell killing) of the anti-CAIX-PE variant chimeric molecules CAIX-PE24-LR-LO10R-456A-long-linker and CAIX-T20.

The cytotoxicity of CAIX-PE24-LR-LO10R-456A-long-linker and CAIX-T20 ("cFPs") was compared in cell viability assays using CAIX-expressing RCC-MF cells. Briefly, cells were seeded at a density of 7,500 cells/well on 96 well plates. After overnight culture, different concentrations of the cFPs were added to the medium, and the cells were incubated for 72 hours. At the end of incubation period, cell viability was determined using a CELLTITER GLO assay. The results are shown in Table 31.

In summary, CAIX-PE24-LR-LO10R-456A-long-linker and CAIX-T20 showed potent cytotoxic effects on CAIX-positive tumor cell lines.

TABLE 31

| Fusion protein | IC50 in CELLTITER GLO assay with cell lines expressing CAIX (nM) RCC-MF cells |
|---|---|
| CAIX-PE24-LR-LO10R-456A-long-linker | 0.02 nM |
| CAIX-T20 | 0.048 nM |

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A *Pseudomonas* exotoxin A (PE) comprising a PE amino acid sequence wherein one or more of amino acid residues F443, R456, L477, R494, and L552 as defined by reference to SEQ ID NO: 1 are, independently, substituted, wherein the PE optionally has:

(i) a further substitution of one or more amino acid residues within one or more B cell epitopes, and the further substitution for an amino acid within one or more B-cell epitopes is a substitution of, independently, one or more of amino acid residues D403, D406, R412, R427, E431, R432, D461, R463, R467, R490, R505, R513, E522, R538, E548, R551, R576, Q592, and L597 as defined by reference to SEQ ID NO: 1, (ii) a further substitution of one or more amino acid residues within one or more T-cell epitopes, (iii) a deletion of one or more continuous amino acid residues of residues 1-273 and 285-394 as defined by SEQ ID NO: 1, or (iv) a combination of any one, two, or three of (i)-(iii).

2. An isolated, mutated *Pseudomonas* exotoxin A (PE), comprising a sequence of the following formula:

$R^1_n$-FCS-$R^2_n$-$R^3_n$-PE functional domain III wherein:

n=0 or 1 independently for each of $R^1$, $R^2$ and $R^3$, $R^1$=1 to 10 amino acid residues FCS=a furin cleavage sequence of amino acid residues, which sequence is cleavable by furin and has an amino end and a carboxyl end, $R^2$=1 to 10 amino acid residues;

$R^3$=1 or more contiguous residues of residues 365-394 of SEQ ID NO: 1; and,

PE functional domain III=residues 395-613 of SEQ ID NO:1, wherein one or more of amino acid residues F443, R456, L477, R494, and L552 as defined by reference to SEQ ID NO: 1 are, independently, substituted, wherein the PE optionally has:

(i) a further substitution of one or more amino acid residues within one or more B cell epitopes, and the further substitution for an amino acid within one or more B-cell epitopes is a substitution of, independently, one or more of amino acid residues D403, D406, R412, R427, E431, R432, D461, R463, R467, R490, R505, R513, E522, R538, E548, R551, R576, Q592, and L597 as defined by reference to SEQ ID NO: 1, (ii) a further substitution of one or more amino acid residues within one or more T-cell epitopes, or (iii) both (i) and (ii).

3. The mutated PE of claim 2, further wherein the FCS is represented by the formula P4-P3-P2-P1, wherein P4 is an amino acid residue at the amino end, P1 is an amino acid residue at the carboxyl end, P1 is an arginine or a lysine residue, and the sequence is cleavable at the carboxyl end of P1 by furin.

4. The mutated PE of claim 3, further wherein the FCS (i) further comprises amino acid residues represented by P6-P5 at the amino end, (ii) further comprises amino acid residues represented by P1'-P2' at the carboxyl end, (iii) wherein if P1 is an arginine or a lysine residue, P2' is tryptophan, and P4 is arginine, valine or lysine, provided that if P4 is not arginine, then P6 and P2 are basic residues, and (iv) the sequence is cleavable at the carboxyl end of P1 by furin.

5. The mutated PE of claim 2, further wherein the PE functional domain III consists of the sequence of residues 395 to 613 of SEQ ID NO: 1.

6. The mutated PE of claim 2, wherein the mutated PE comprises one or more contiguous residues of residues 365-394 of SEQ ID NO: 1 between the FCS and the PE domain III.

7. The mutated PE of claim 2, wherein n is 1 for $R^1$ and R2.

8. The mutated PE of claim 2, wherein the FCS is SEQ ID NO: 8.

9. The mutated PE of claim 2, wherein $R^1$=a linker of the amino acid sequence of SEQ ID NO: 282, $R^2$=a linker of the amino acid sequence SEQ ID NO: 284, and the FCS=SEQ ID NO: 8.

10. The mutated PE of claim 2, wherein n is 0 for $R^3$.

11. The mutated PE of claim 2, wherein PE functional domain III comprises the amino acid sequence of SEQ ID NO: 37.

12. The mutated PE of claim 2, wherein $R^1_n$-FCS-$R^2_n$=SEQ ID NO: 36.

13. The PE of claim 1, wherein the substitution of one or more of amino acid residues F443, R456, L477, R494, and L552 is a substitution of, independently, alanine, glutamic acid, histidine, or asparagine in place of one or more of amino acid residues F443, R456, L477, R494, and L552.

14. The PE of claim 1, wherein the substitution of L552 is a substitution of glutamic acid or asparagine in place of L552 and the substitution of L477 is a substitution of histidine in place of L477.

15. The PE of claim 1, wherein the further substitution of an amino acid within one or more B-cell epitopes is a substitution of, independently, alanine, glycine, serine, or glutamine in place of one or more of amino acid residues E282, E285, P290, R313, N314, P319, D324, E327, E331, Q332, D403, D406, R412, R427, E431, R432, D461, R463, 8467, R490, R505, R513, E522, R538, E548, R551, R576, K590, Q592, and L597, as defined by reference to SEQ ID NO: 1.

16. The PE of claim 1, wherein the PE has the further substitution of an amino acid within one or more T-cell epitopes, and the further substitution of an amino acid within one or more T-cell epitopes is a substitution of, independently, alanine, glycine, serine, or glutamine in place of one or more of amino acid residues R421, L422, L423, A425, R427, L429, Y439, H440, F443, L444, A446, A447, I450, 463-519, R551, L552, T554, I555, L556, and W558 as defined by reference to SEQ ID NO: 1.

17. The PE of claim 1, wherein the substitution of one or more of amino acid residues F443, R456, L477, R494, and L552 is a substitution of alanine in place of amino acid residue F443; a substitution of alanine in place of amino acid residue R456; a substitution of histidine in place of amino acid residue L477; a substitution of alanine in place of amino acid residue R494; and a substitution of glutamic acid in place of amino acid residue L552, the PE has an arginine residue at position 458, and the further substitution of an amino acid within one or more B-cell epitopes is:
(a) a substitution of alanine for amino acid residue R427;
(b) a substitution of alanine for amino acid residue R463;
(c) a substitution of alanine for amino acid residue R467;
(d) a substitution of alanine for amino acid residue R490;
(e) a substitution of alanine for amino acid residue R505; and
(f) a substitution of alanine for amino acid residue R538; as defined by reference to SEQ ID NO: 1.

18. The PE of claim 1, wherein the substitution of one or more of amino acid residues F443, R456, L477, R494, and L552 is a substitution of alanine in place of amino acid residue R456, the PE has an arginine residue at position 458, and the further substitution of an amino acid within one or more B-cell epitopes is:
(a) a substitution of alanine for amino acid residue R427;
(b) a substitution of alanine for amino acid residue R463;
(c) a substitution of alanine for amino acid residue R467;
(d) a substitution of alanine for amino acid residue R490;
(e) a substitution of alanine for amino acid residue R505; and
(f) a substitution of alanine for amino acid residue R538; as defined by reference to SEQ ID NO: 1.

19. The PE of claim 1, wherein the substitution of one or more of amino acid residues F443, R456, L477, R494, and L552 is a substitution of alanine in place of amino acid residue F443; a substitution of alanine in place of amino acid residue R456; a substitution of histidine in place of amino acid residue L477; a substitution of alanine in place of amino acid residue R494; and a substitution of asparagine in place of amino acid residue L552, the PE has an arginine residue at position 458, and the further substitution of an amino acid within one or more B-cell epitopes is:
(a) a substitution of alanine for amino acid residue R427;
(b) a substitution of alanine for amino acid residue R463;
(c) a substitution of alanine for amino acid residue R467;
(d) a substitution of alanine for amino acid residue R490;
(e) a substitution of alanine for amino acid residue R505; and
(f) a substitution of alanine for amino acid residue R538; as defined by reference to SEQ ID NO: 1.

20. The mutated PE of claim 2, wherein one or more of amino acid residues F443, L477, R494, and L552 as defined by reference to SEQ ID NO: 1 are, independently, substituted.

21. The mutated PE of claim 20, wherein the substitution of one or more of amino acid residues F443, L477, R494, and L552 is a substitution of alanine in place of amino acid residue F443, a substitution of histidine in place of amino acid residue L477, a substitution of alanine in place of amino acid residue R494, and a substitution of glutamic acid or asparagine in place of amino acid residue L552.

22. An isolated, mutated *Pseudomonas* exotoxin A (PE), comprising a sequence of the following formula:

$$R^1_n\text{-FCS-}R^2_n\text{-}R^3_n\text{-PE functional domain III}$$

wherein:
n=0 or 1 independently for each of $R^1$, $R^2$ and $R^3$,
$R^1$=1 to 10 amino acid residues
FCS=a furin cleavage sequence of amino acid residues, which sequence is cleavable by furin and has an amino end and a carboxyl end,
$R^2$=1 to 10 amino acid residues;
$R^3$=1 or more contiguous residues of residues 365-394 of SEQ ID NO:1; and,
PE functional domain III=residues 395-613 of SEQ ID NO:1, wherein the PE includes an arginine at position 458, as defined by reference to SEQ ID NO: 1, and wherein the PE has:
(a) a substitution of alanine for amino acid residue R427;
(b) a substitution of alanine for amino acid residue R463;
(c) a substitution of alanine for amino acid residue R467;
(d) a substitution of alanine for amino acid residue R490;
(e) a substitution of alanine for amino acid residue R505; and
(f) a substitution of alanine for amino acid residue R538.

23. A chimeric molecule comprising (a) a targeting moiety conjugated or fused to (b) the PE of claim 1.

24. The chimeric molecule of claim 23, wherein the targeting moiety is a monoclonal antibody or an antigen binding portion of the monoclonal antibody.

25. The chimeric molecule of claim 24, wherein the monoclonal antibody or antigen binding portion of the monoclonal antibody specifically binds to a cell surface marker selected from the group consisting of CD19, CD21, CD22, CD25, CD30, CD79b, transferrin receptor, epidermal growth factor (EGF) receptor, mesothelin, cadherin, Lewis Y, glypican-3, FAP (fibroblast activation protein alpha), PSMA (prostate specific membrane antigen), CA9=CAIX (carbonic anhydrase IX), L1CAM (neural cell adhesion molecule L1), endosialin, HER3 (activated conformation of epidermal growth factor receptor family member 3), Alk1/BMP9 complex (anaplastic lymphoma kinase 1/bone morphogenetic protein 9), TPBG=5T4 (trophoblast glycoprotein), CD33 (sialic acid binding Ig-like lectin 3, myeloid cell surface antigen), CD123 (interleukin 3 receptor alpha), MUC1 (tumor-associated epithelial mucin), ROR1 (receptor tyrosine kinase-like surface antigen), HER1 (activated conformation of epidermal growth factor receptor), and CLL1 (C-type lectin domain family 12, member A).

26. The chimeric molecule of claim 23, wherein the targeting moiety is selected from the group consisting of B3, RFB4, SS, SS1, MN, MB, HN1, HN2, HB21, MORAb-009, antigen binding portions thereof, and the antigen binding portion of HA22.

27. The chimeric molecule of claim 23, wherein the targeting moiety is a humanized SS1 or an antigen binding portion of the humanized SS1.

28. The chimeric molecule of claim 23, wherein the targeting moiety comprises:
   (a) SEQ ID NOs: 31 and 34;
   (b) SEQ ID NOs: 45 and 46;
   (c) SEQ ID NOs: 61 and 62;
   (d) SEQ ID NOs: 77 and 78;
   (e) SEQ ID NOs: 93 and 94;
   (f) SEQ ID NOs: 109 and 110;
   (g) SEQ ID NOs: 125 and 126;
   (h) SEQ ID NOs: 141 and 142;
   (i) SEQ ID NOs: 157 and 158;
   (j) SEQ ID NOs: 173 and 174;
   (k) SEQ ID NOs: 49, 50, 53, 54, 57, and 58;
   (l) SEQ ID NOs: 65, 66, 69, 70, 73, and 74;
   (m) SEQ ID NOs: 81, 82, 85, 86, 89, and 90;
   (n) SEQ ID NOs: 97, 98, 101, 102, 105, and 106;
   (o) SEQ ID NOs: 113, 114, 117, 118, 121, and 122;
   (p) SEQ ID NOs: 129, 130, 133, 134, 137, and 138;
   (q) SEQ ID NOs: 145, 146, 149, 150, 153, and 154;
   (r) SEQ ID NOs: 161, 162, 165, 166, 169, and 170;
   (s) SEQ ID NOs: 177, 178, 181, 182, 185, and 186;
   (t) SEQ ID NOs: 31-32 and 34-36;
   (u) SEQ ID NOs: 33 and 38; or
   (v) SEQ ID NOs: 93 and 290.

29. The chimeric molecule of claim 23, wherein the chimeric molecule comprises a linker comprising SEQ ID NO: 36.

30. The chimeric molecule of claim 23, comprising
   (a) SEQ ID NOs: 39 and 40;
   (b) SEQ ID NOs: 41 and 42;
   (c) SEQ ID NOs: 43 and 44;
   (d) SEQ ID NOs: 291 and 293;
   (e) SEQ ID NOs: 291 and 294;
   (f) SEQ ID NOs: 292 and 294;
   (g) SEQ ID NOs: 295 and 297; or
   (h) SEQ ID NOs:296 and 297.

31. A nucleic acid comprising a nucleotide sequence encoding the PE of claim 1.

32. A recombinant expression vector comprising the nucleic acid of claim 31.

33. A host cell comprising the recombinant expression vector of claim 32.

34. A population of cells comprising at least one host cell of claim 33.

35. A pharmaceutical composition comprising (a) the PE of claim 1 and (b) a pharmaceutically acceptable carrier.

36. A method of treating or preventing cancer in a mammal, the method comprising administering to the mammal the PE of claim 1 in an amount effective to treat or prevent cancer in the mammal.

37. A method of inhibiting growth of a target cell, the method comprising contacting the cell with the PE of claim 1 in an amount effective to inhibit growth of the target cell.

38. The method of claim 37, wherein the target cell is a cancer cell.

39. The method of claim 37, wherein the target cell expresses a cell surface marker selected from the group consisting of CD19, CD21, CD22, CD25, CD30, CD79b, transferrin receptor, EGF receptor, mesothelin, cadherin, Lewis Y, glypican-3, FAP (fibroblast activation protein alpha), PSMA (prostate specific membrane antigen), CA9=CAIX (carbonic anhydrase IX), L1CAM (neural cell adhesion molecule L1), Endosialin, HER3 (activated conformation of epidermal growth factor receptor family member 3), Alk1/BMP9 complex (anaplastic lymphoma kinase 1/bone morphogenetic protein 9), TPBG=5T4 (trophoblast glycoprotein), CD33 (sialic acid binding Ig-like lectin 3, myeloid cell surface antigen), CD123 (interleukin 3 receptor alpha), MUC1 (tumor-associated epithelial mucin), ROR1 (receptor tyrosine kinase-like surface antigen), HER1 (activated conformation of epidermal growth factor receptor), and CLL1 (C-type lectin domain family 12, member A).

40. A method of producing the PE of claim 1 comprising (a) recombinantly expressing the PE and (b) purifying the PE.

41. A method of producing the chimeric molecule of claim 23 comprising (a) recombinantly expressing the chimeric molecule and (b) purifying the chimeric molecule.

42. A method of producing the chimeric molecule of claim 23 comprising (a) recombinantly expressing the PE of any one of claims 1-22, (b) purifying the PE, and (c) covalently linking a targeting moiety to the purified PE.

* * * * *

SEQUENCE LISTING

<160> NUMBER OF SEQ ID NOS: 297

<210> SEQ ID NO 1
<211> LENGTH: 613
<212> TYPE: PRT
<213> ORGANISM: Pseudomonas aeruginosa

<400> SEQUENCE: 1

Ala Glu Glu Ala Phe Asp Leu Trp Asn Glu Cys Ala Lys Ala Cys Val
1               5                   10                  15

Leu Asp Leu Lys Asp Gly Val Arg Ser Ser Arg Met Ser Val Asp Pro
            20                  25                  30

Ala Ile Ala Asp Thr Asn Gly Gln Gly Val Leu His Tyr Ser Met Val
        35                  40                  45

Leu Glu Gly Gly Asn Asp Ala Leu Lys Leu Ala Ile Asp Asn Ala Leu
    50                  55                  60

Ser Ile Thr Ser Asp Gly Leu Thr Ile Arg Leu Glu Gly Gly Val Glu
65                  70                  75                  80

Pro Asn Lys Pro Val Arg Tyr Ser Tyr Thr Arg Gln Ala Arg Gly Ser
                85                  90                  95

Trp Ser Leu Asn Trp Leu Val Pro Ile Gly His Glu Lys Pro Ser Asn
            100                 105                 110

Ile Lys Val Phe Ile His Glu Leu Asn Ala Gly Asn Gln Leu Ser His
        115                 120                 125

Met Ser Pro Ile Tyr Thr Ile Glu Met Gly Asp Glu Leu Leu Ala Lys
    130                 135                 140

Leu Ala Arg Asp Ala Thr Phe Phe Val Arg Ala His Glu Ser Asn Glu
145                 150                 155                 160

Met Gln Pro Thr Leu Ala Ile Ser His Ala Gly Val Ser Val Val Met
                165                 170                 175

```
Ala Gln Thr Gln Pro Arg Arg Glu Lys Arg Trp Ser Glu Trp Ala Ser
                180                 185                 190
Gly Lys Val Leu Cys Leu Leu Asp Pro Leu Asp Gly Val Tyr Asn Tyr
            195                 200                 205
Leu Ala Gln Gln Arg Cys Asn Leu Asp Asp Thr Trp Glu Gly Lys Ile
        210                 215                 220
Tyr Arg Val Leu Ala Gly Asn Pro Ala Lys His Asp Leu Asp Ile Lys
225                 230                 235                 240
Pro Thr Val Ile Ser His Arg Leu His Phe Pro Glu Gly Gly Ser Leu
                245                 250                 255
Ala Ala Leu Thr Ala His Gln Ala Cys His Leu Pro Leu Glu Thr Phe
            260                 265                 270
Thr Arg His Arg Gln Pro Arg Gly Trp Glu Gln Leu Glu Gln Cys Gly
        275                 280                 285
Tyr Pro Val Gln Arg Leu Val Ala Leu Tyr Leu Ala Ala Arg Leu Ser
        290                 295                 300
Trp Asn Gln Val Asp Gln Val Ile Arg Asn Ala Leu Ala Ser Pro Gly
305                 310                 315                 320
Ser Gly Gly Asp Leu Gly Glu Ala Ile Arg Glu Gln Pro Glu Gln Ala
                325                 330                 335
Arg Leu Ala Leu Thr Leu Ala Ala Ala Glu Ser Glu Arg Phe Val Arg
            340                 345                 350
Gln Gly Thr Gly Asn Asp Glu Ala Gly Ala Ala Asn Ala Asp Val Val
        355                 360                 365
Ser Leu Thr Cys Pro Val Ala Gly Glu Cys Ala Gly Pro Ala Asp
370                 375                 380
Ser Gly Asp Ala Leu Leu Glu Arg Asn Tyr Pro Thr Gly Ala Glu Phe
385                 390                 395                 400
Leu Gly Asp Gly Gly Asp Val Ser Phe Ser Thr Arg Gly Thr Gln Asn
                405                 410                 415
Trp Thr Val Glu Arg Leu Leu Gln Ala His Arg Gln Leu Glu Glu Arg
            420                 425                 430
Gly Tyr Val Phe Val Gly Tyr His Gly Thr Phe Leu Glu Ala Ala Gln
        435                 440                 445
Ser Ile Val Phe Gly Gly Val Arg Ala Arg Ser Gln Asp Leu Asp Ala
450                 455                 460
Ile Trp Arg Gly Phe Tyr Ile Ala Gly Asp Pro Ala Leu Ala Tyr Gly
465                 470                 475                 480
Tyr Ala Gln Asp Gln Glu Pro Asp Ala Arg Gly Arg Ile Arg Asn Gly
                485                 490                 495
Ala Leu Leu Arg Val Tyr Val Pro Arg Ser Ser Leu Pro Gly Phe Tyr
            500                 505                 510
Arg Thr Ser Leu Thr Leu Ala Ala Pro Glu Ala Ala Gly Glu Val Glu
        515                 520                 525
Arg Leu Ile Gly His Pro Leu Pro Leu Arg Leu Asp Ala Ile Thr Gly
        530                 535                 540
Pro Glu Glu Glu Gly Gly Arg Leu Glu Thr Ile Leu Gly Trp Pro Leu
545                 550                 555                 560
Ala Glu Arg Thr Val Val Ile Pro Ser Ala Ile Pro Thr Asp Pro Arg
                565                 570                 575
Asn Val Gly Gly Asp Leu Asp Pro Ser Ser Ile Pro Asp Lys Glu Gln
            580                 585                 590
Ala Ile Ser Ala Leu Pro Asp Tyr Ala Ser Gln Pro Gly Lys Pro Pro
```

-continued

```
                595                 600                 605

Arg Glu Asp Leu Lys
    610

<210> SEQ ID NO 2
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa at position 1 is Leu or Ala
<220> FEATURE:
<221> NAME/KEY: MISC_FEATURE
<222> LOCATION: (4)..(4)
<223> OTHER INFORMATION: Xaa at position 4 is Leu or Ala
<220> FEATURE:
<221> NAME/KEY: MISC_FEATURE
<222> LOCATION: (5)..(5)
<223> OTHER INFORMATION: Xaa at position 5 is Tyr or Ala
<220> FEATURE:
<221> NAME/KEY: MISC_FEATURE
<222> LOCATION: (6)..(6)
<223> OTHER INFORMATION: Xaa at position 6 is Leu or Ala
<220> FEATURE:
<221> NAME/KEY: MISC_FEATURE
<222> LOCATION: (9)..(9)
<223> OTHER INFORMATION: Xaa at position 9 is Arg or Ala

<400> SEQUENCE: 2

Xaa Val Ala Xaa Xaa Xaa Ala Ala Xaa Leu Ser Trp
1               5                   10

<210> SEQ ID NO 3
<211> LENGTH: 12
<212> TYPE: PRT
<213> ORGANISM: Pseudomonas aeruginosa

<400> SEQUENCE: 3

Leu Val Ala Leu Tyr Leu Ala Ala Arg Leu Ser Trp
1               5                   10

<210> SEQ ID NO 4
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa at position 2 is any amino acid
<220> FEATURE:
<221> NAME/KEY: MISC_FEATURE
<222> LOCATION: (3)..(3)
<223> OTHER INFORMATION: Xaa at position 3 is Arg or Lys

<400> SEQUENCE: 4

Arg Xaa Xaa Arg
1

<210> SEQ ID NO 5
<211> LENGTH: 4
<212> TYPE: PRT
<213> ORGANISM: Artificial Sequence
<220> FEATURE:
<223> OTHER INFORMATION: Synthetic

<400> SEQUENCE: 5
```

```
Lys Asp Glu Leu
1

<210> SEQ ID NO 6
<211> LENGTH: 5
<212> TYPE: PRT
<213> ORGANISM: Pseudomonas aeruginosa

<400> SEQUENCE: 6

Arg Glu Asp Leu Lys
1               5

<210> SEQ ID NO 7
<211> LENGTH: 4
<212> TYPE: PRT
<213> ORGANISM: Pseudomonas aeruginosa

<400> SEQUENCE: 7

Arg Glu Asp Leu
1

<210> SEQ ID NO 8
<211> LENGTH: 11
<212> TYPE: PRT
<213> ORGANISM: Pseudomonas aeruginosa

<400> SEQUENCE: 8

Arg His Arg Gln Pro Arg Gly Trp Glu Gln Leu
1               5                   10

<210> SEQ ID NO 9
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(3)
<223> OTHER INFORMATION: Xaa can be any naturally occurring amino acid

<400> SEQUENCE: 9

Arg Xaa Xaa Arg
1

<210> SEQ ID NO 10
<211> LENGTH: 4
<212> TYPE: PRT
<213> ORGANISM: Artificial Sequence
<220> FEATURE:
<223> OTHER INFORMATION: Synthetic

<400> SEQUENCE: 10

Arg Lys Lys Arg
1

<210> SEQ ID NO 11
<211> LENGTH: 4
<212> TYPE: PRT
<213> ORGANISM: Artificial Sequence
<220> FEATURE:
<223> OTHER INFORMATION: Synthetic

<400> SEQUENCE: 11

Arg Arg Arg Arg
1
```

<210> SEQ ID NO 12
<211> LENGTH: 4
<212> TYPE: PRT
<213> ORGANISM: Artificial Sequence
<220> FEATURE:
<223> OTHER INFORMATION: Synthetic

<400> SEQUENCE: 12

Arg Lys Ala Arg
1

<210> SEQ ID NO 13
<211> LENGTH: 6
<212> TYPE: PRT
<213> ORGANISM: Artificial Sequence
<220> FEATURE:
<223> OTHER INFORMATION: Synthetic

<400> SEQUENCE: 13

Ser Arg Val Ala Arg Ser
1               5

<210> SEQ ID NO 14
<211> LENGTH: 9
<212> TYPE: PRT
<213> ORGANISM: Artificial Sequence
<220> FEATURE:
<223> OTHER INFORMATION: Synthetic

<400> SEQUENCE: 14

Thr Ser Ser Arg Lys Arg Arg Phe Trp
1               5

<210> SEQ ID NO 15
<211> LENGTH: 9
<212> TYPE: PRT
<213> ORGANISM: Artificial Sequence
<220> FEATURE:
<223> OTHER INFORMATION: Synthetic

<400> SEQUENCE: 15

Ala Ser Arg Arg Lys Ala Arg Ser Trp
1               5

<210> SEQ ID NO 16
<211> LENGTH: 8
<212> TYPE: PRT
<213> ORGANISM: Artificial Sequence
<220> FEATURE:
<223> OTHER INFORMATION: Synthetic

<400> SEQUENCE: 16

Arg Arg Val Lys Lys Arg Phe Trp
1               5

<210> SEQ ID NO 17
<211> LENGTH: 8
<212> TYPE: PRT
<213> ORGANISM: Artificial Sequence
<220> FEATURE:
<223> OTHER INFORMATION: Synthetic

<400> SEQUENCE: 17

Arg Asn Val Val Arg Arg Asp Trp
1               5

<210> SEQ ID NO 18
<211> LENGTH: 9
<212> TYPE: PRT
<213> ORGANISM: Artificial Sequence
<220> FEATURE:
<223> OTHER INFORMATION: Synthetic

<400> SEQUENCE: 18

Thr Arg Ala Val Arg Arg Arg Ser Trp
1               5

<210> SEQ ID NO 19
<211> LENGTH: 4
<212> TYPE: PRT
<213> ORGANISM: Artificial Sequence
<220> FEATURE:
<223> OTHER INFORMATION: Synthetic

<400> SEQUENCE: 19

Arg Gln Pro Arg
1

<210> SEQ ID NO 20
<211> LENGTH: 8
<212> TYPE: PRT
<213> ORGANISM: Artificial Sequence
<220> FEATURE:
<223> OTHER INFORMATION: Synthetic

<400> SEQUENCE: 20

Arg His Arg Gln Pro Arg Gly Trp
1               5

<210> SEQ ID NO 21
<211> LENGTH: 9
<212> TYPE: PRT
<213> ORGANISM: Artificial Sequence
<220> FEATURE:
<223> OTHER INFORMATION: Synthetic

<400> SEQUENCE: 21

Arg His Arg Gln Pro Arg Gly Trp Glu
1               5

<210> SEQ ID NO 22
<211> LENGTH: 9
<212> TYPE: PRT
<213> ORGANISM: Artificial Sequence
<220> FEATURE:
<223> OTHER INFORMATION: Synthetic

<400> SEQUENCE: 22

His Arg Gln Pro Arg Gly Trp Glu Gln
1               5

<210> SEQ ID NO 23
<211> LENGTH: 7
<212> TYPE: PRT
<213> ORGANISM: Artificial Sequence
<220> FEATURE:
<223> OTHER INFORMATION: Synthetic

<400> SEQUENCE: 23

Arg Gln Pro Arg Gly Trp Glu
1               5

```
<210> SEQ ID NO 24
<211> LENGTH: 11
<212> TYPE: PRT
<213> ORGANISM: Artificial Sequence
<220> FEATURE:
<223> OTHER INFORMATION: Synthetic

<400> SEQUENCE: 24

Arg His Arg Ser Lys Arg Gly Trp Glu Gln Leu
1               5                   10

<210> SEQ ID NO 25
<211> LENGTH: 4
<212> TYPE: PRT
<213> ORGANISM: Artificial Sequence
<220> FEATURE:
<223> OTHER INFORMATION: Synthetic

<400> SEQUENCE: 25

Arg Ser Lys Arg
1

<210> SEQ ID NO 26
<211> LENGTH: 8
<212> TYPE: PRT
<213> ORGANISM: Artificial Sequence
<220> FEATURE:
<223> OTHER INFORMATION: Synthetic

<400> SEQUENCE: 26

Arg His Arg Ser Lys Arg Gly Trp
1               5

<210> SEQ ID NO 27
<211> LENGTH: 8
<212> TYPE: PRT
<213> ORGANISM: Artificial Sequence
<220> FEATURE:
<223> OTHER INFORMATION: Synthetic

<400> SEQUENCE: 27

His Arg Ser Lys Arg Gly Trp Glu
1               5

<210> SEQ ID NO 28
<211> LENGTH: 9
<212> TYPE: PRT
<213> ORGANISM: Artificial Sequence
<220> FEATURE:
<223> OTHER INFORMATION: Synthetic

<400> SEQUENCE: 28

Arg Ser Lys Arg Gly Trp Glu Gln Leu
1               5

<210> SEQ ID NO 29
<211> LENGTH: 10
<212> TYPE: PRT
<213> ORGANISM: Artificial Sequence
<220> FEATURE:
<223> OTHER INFORMATION: Synthetic

<400> SEQUENCE: 29

His Arg Ser Lys Arg Gly Trp Glu Gln Leu
1               5                   10

<210> SEQ ID NO 30
```

```
<211> LENGTH: 6
<212> TYPE: PRT
<213> ORGANISM: Artificial Sequence
<220> FEATURE:
<223> OTHER INFORMATION: Synthetic

<400> SEQUENCE: 30

Arg His Arg Ser Lys Arg
1               5

<210> SEQ ID NO 31
<211> LENGTH: 106
<212> TYPE: PRT
<213> ORGANISM: Artificial Sequence
<220> FEATURE:
<223> OTHER INFORMATION: Synthetic

<400> SEQUENCE: 31

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Val Ser Tyr Met
            20                  25                  30

His Trp Tyr Gln Gln Lys Ser Gly Lys Ala Pro Lys Leu Leu Ile Tyr
            35                  40                  45

Asp Thr Ser Lys Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ser Lys His Pro Leu Thr
                85                  90                  95

Phe Gly Gln Gly Thr Lys Leu Glu Ile Lys
            100                 105

<210> SEQ ID NO 32
<211> LENGTH: 107
<212> TYPE: PRT
<213> ORGANISM: Artificial Sequence
<220> FEATURE:
<223> OTHER INFORMATION: Synthetic

<400> SEQUENCE: 32

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
            35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 33
<211> LENGTH: 214
<212> TYPE: PRT
<213> ORGANISM: Artificial Sequence
<220> FEATURE:
```

<223> OTHER INFORMATION: Synthetic

<400> SEQUENCE: 33

```
Met Asp Ile Gln Met Thr Gln Ser Pro Ser Ser Leu Ser Ala Ser Val
1               5                   10                  15
Gly Asp Arg Val Thr Ile Thr Cys Ser Ala Ser Ser Val Ser Tyr
            20                  25                  30
Met His Trp Tyr Gln Gln Lys Ser Gly Lys Ala Pro Lys Leu Leu Ile
        35                  40                  45
Tyr Asp Thr Ser Lys Leu Ala Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Trp Ser Lys His Pro Leu
                85                  90                  95
Thr Phe Gly Gln Gly Thr Lys Leu Glu Ile Lys Arg Thr Val Ala Ala
            100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210
```

<210> SEQ ID NO 34
<211> LENGTH: 119
<212> TYPE: PRT
<213> ORGANISM: Artificial Sequence
<220> FEATURE:
<223> OTHER INFORMATION: Synthetic

<400> SEQUENCE: 34

```
Gln Val Gln Leu Val Gln Ser Gly Ala Glu Val Lys Lys Pro Gly Ala
1               5                   10                  15
Ser Val Lys Val Ser Cys Lys Ala Ser Gly Tyr Ser Phe Thr Gly Tyr
            20                  25                  30
Thr Met Asn Trp Val Arg Gln Ala Pro Gly Gln Gly Leu Glu Trp Met
        35                  40                  45
Gly Leu Ile Thr Pro Tyr Asn Gly Ala Ser Ser Tyr Asn Gln Lys Phe
    50                  55                  60
Arg Gly Lys Ala Thr Met Thr Val Asp Thr Ser Thr Ser Thr Val Tyr
65                  70                  75                  80
Met Glu Leu Ser Ser Leu Arg Ser Glu Asp Thr Ala Val Tyr Tyr Cys
                85                  90                  95
Ala Arg Gly Gly Tyr Asp Gly Arg Gly Phe Asp Tyr Trp Gly Gln Gly
            100                 105                 110
Thr Leu Val Thr Val Ser Ser
            115
```

```
<210> SEQ ID NO 35
<211> LENGTH: 103
<212> TYPE: PRT
<213> ORGANISM: Artificial Sequence
<220> FEATURE:
<223> OTHER INFORMATION: Synthetic

<400> SEQUENCE: 35

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys
            100

<210> SEQ ID NO 36
<211> LENGTH: 26
<212> TYPE: PRT
<213> ORGANISM: Artificial Sequence
<220> FEATURE:
<223> OTHER INFORMATION: Synthetic

<400> SEQUENCE: 36

Asp Lys Thr His Lys Ala Ser Gly Gly Arg His Arg Gln Pro Arg Gly
1               5                   10                  15

Trp Glu Gln Leu Gly Gly Gly Gly Gly Ser
            20                  25

<210> SEQ ID NO 37
<211> LENGTH: 219
<212> TYPE: PRT
<213> ORGANISM: Artificial Sequence
<220> FEATURE:
<223> OTHER INFORMATION: Synthetic

<400> SEQUENCE: 37

Pro Thr Gly Ala Glu Phe Leu Gly Asp Gly Gly Asp Val Ser Phe Ser
1               5                   10                  15

Thr Arg Gly Thr Gln Asn Trp Thr Val Glu Arg Leu Leu Gln Ala His
            20                  25                  30

Ala Gln Leu Glu Glu Arg Gly Tyr Val Phe Val Gly Tyr His Gly Thr
        35                  40                  45

Phe Leu Glu Ala Ala Gln Ser Ile Val Phe Gly Gly Val Ala Ala Arg
    50                  55                  60

Ser Gln Asp Leu Ala Ala Ile Trp Ala Gly Phe Tyr Ile Ala Gly Asp
65                  70                  75                  80

Pro Ala Leu Ala Tyr Gly Tyr Ala Gln Asp Gln Glu Pro Asp Ala Ala
                85                  90                  95

Gly Arg Ile Arg Asn Gly Ala Leu Leu Arg Val Tyr Val Pro Ala Ser
            100                 105                 110
```

```
Ser Leu Pro Gly Phe Tyr Arg Thr Ser Leu Thr Leu Ala Ala Pro Glu
            115                 120                 125

Ala Ala Gly Glu Val Glu Arg Leu Ile Gly His Pro Leu Pro Leu Ala
        130                 135                 140

Leu Asp Ala Ile Thr Gly Pro Glu Glu Gly Gly Arg Leu Glu Thr
145                 150                 155                 160

Ile Leu Gly Trp Pro Leu Ala Glu Arg Thr Val Val Ile Pro Ser Ala
                165                 170                 175

Ile Pro Thr Asp Pro Arg Asn Val Gly Gly Asp Leu Asp Pro Ser Ser
            180                 185                 190

Ile Pro Asp Lys Glu Gln Ala Ile Ser Ala Leu Pro Asp Tyr Ala Ser
        195                 200                 205

Gln Pro Gly Lys Pro Pro Arg Glu Asp Leu Lys
    210                 215

<210> SEQ ID NO 38
<211> LENGTH: 223
<212> TYPE: PRT
<213> ORGANISM: Artificial Sequence
<220> FEATURE:
<223> OTHER INFORMATION: Synthetic

<400> SEQUENCE: 38

Met Gln Val Gln Leu Val Gln Ser Gly Ala Glu Val Lys Lys Pro Gly
1               5                   10                  15

Ala Ser Val Lys Val Ser Cys Lys Ala Ser Gly Tyr Ser Phe Thr Gly
            20                  25                  30

Tyr Thr Met Asn Trp Val Arg Gln Ala Pro Gly Gln Gly Leu Glu Trp
        35                  40                  45

Met Gly Leu Ile Thr Pro Tyr Asn Gly Ala Ser Ser Tyr Asn Gln Lys
    50                  55                  60

Phe Arg Gly Lys Ala Thr Met Thr Val Asp Thr Ser Thr Ser Thr Val
65                  70                  75                  80

Tyr Met Glu Leu Ser Ser Leu Arg Ser Glu Asp Thr Ala Val Tyr Tyr
                85                  90                  95

Cys Ala Arg Gly Gly Tyr Asp Gly Arg Gly Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys
    210                 215                 220

<210> SEQ ID NO 39
<211> LENGTH: 214
<212> TYPE: PRT
<213> ORGANISM: Artificial Sequence
<220> FEATURE:
```

<223> OTHER INFORMATION: Synthetic

<400> SEQUENCE: 39

```
Met Asp Ile Gln Met Thr Gln Ser Pro Ser Ser Leu Ser Ala Ser Val
1               5                   10                  15

Gly Asp Arg Val Thr Ile Thr Cys Ser Ala Ser Ser Val Ser Tyr
            20                  25                  30

Met His Trp Tyr Gln Gln Lys Ser Gly Lys Ala Pro Lys Leu Leu Ile
            35                  40                  45

Tyr Asp Thr Ser Lys Leu Ala Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Trp Ser Lys His Pro Leu
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 40
<211> LENGTH: 468
<212> TYPE: PRT
<213> ORGANISM: Artificial Sequence
<220> FEATURE:
<223> OTHER INFORMATION: Synthetic

<400> SEQUENCE: 40

```
Met Gln Val Gln Leu Val Gln Ser Gly Ala Glu Val Lys Lys Pro Gly
1               5                   10                  15

Ala Ser Val Lys Val Ser Cys Lys Ala Ser Gly Tyr Ser Phe Thr Gly
            20                  25                  30

Tyr Thr Met Asn Trp Val Arg Gln Ala Pro Gly Gln Gly Leu Glu Trp
            35                  40                  45

Met Gly Leu Ile Thr Pro Tyr Asn Gly Ala Ser Tyr Asn Gln Lys
        50                  55                  60

Phe Arg Gly Lys Ala Thr Met Thr Val Asp Thr Ser Thr Ser Thr Val
65                  70                  75                  80

Tyr Met Glu Leu Ser Ser Leu Arg Ser Glu Asp Thr Ala Val Tyr Tyr
                85                  90                  95

Cys Ala Arg Gly Gly Tyr Asp Gly Arg Gly Phe Asp Tyr Trp Gly Gln
            100                 105                 110

Gly Thr Leu Val Thr Val Ser Ser Ala Ser Thr Lys Gly Pro Ser Val
            115                 120                 125
```

Phe Pro Leu Ala Pro Ser Ser Lys Ser Thr Ser Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Lys Ala Ser Gly Arg His Arg Gln Pro Arg Gly Trp
225                 230                 235                 240

Glu Gln Leu Gly Gly Gly Gly Ser Pro Thr Gly Ala Glu Phe Leu
                245                 250                 255

Gly Asp Gly Gly Asp Val Ser Phe Ser Thr Arg Gly Thr Gln Asn Trp
                260                 265                 270

Thr Val Glu Arg Leu Leu Gln Ala His Ala Gln Leu Glu Glu Arg Gly
            275                 280                 285

Tyr Val Phe Val Gly Tyr His Gly Thr Phe Leu Glu Ala Ala Gln Ser
290                 295                 300

Ile Val Phe Gly Gly Val Ala Ala Arg Ser Gln Asp Leu Ala Ala Ile
305                 310                 315                 320

Trp Ala Gly Phe Tyr Ile Ala Gly Asp Pro Ala Leu Ala Tyr Gly Tyr
                325                 330                 335

Ala Gln Asp Gln Glu Pro Asp Ala Ala Gly Arg Ile Arg Asn Gly Ala
            340                 345                 350

Leu Leu Arg Val Tyr Val Pro Ala Ser Ser Leu Pro Gly Phe Tyr Arg
        355                 360                 365

Thr Ser Leu Thr Leu Ala Ala Pro Glu Ala Ala Gly Glu Val Glu Arg
    370                 375                 380

Leu Ile Gly His Pro Leu Pro Leu Ala Leu Asp Ala Ile Thr Gly Pro
385                 390                 395                 400

Glu Glu Glu Gly Gly Arg Leu Glu Thr Ile Leu Gly Trp Pro Leu Ala
                405                 410                 415

Glu Arg Thr Val Val Ile Pro Ser Ala Ile Pro Thr Asp Pro Arg Asn
            420                 425                 430

Val Gly Gly Asp Leu Asp Pro Ser Ser Ile Pro Asp Lys Glu Gln Ala
        435                 440                 445

Ile Ser Ala Leu Pro Asp Tyr Ala Ser Gln Pro Gly Lys Pro Pro Arg
    450                 455                 460

Glu Asp Leu Lys
465

<210> SEQ ID NO 41
<211> LENGTH: 214
<212> TYPE: PRT
<213> ORGANISM: Artificial Sequence
<220> FEATURE:
<223> OTHER INFORMATION: Synthetic

<400> SEQUENCE: 41

Met Asp Ile Glu Leu Thr Gln Ser Pro Ala Ile Met Ser Ala Ser Pro
1               5                   10                  15

```
Gly Glu Lys Val Thr Met Thr Cys Ser Ala Ser Ser Val Ser Tyr
            20                  25                  30

Met His Trp Tyr Gln Gln Lys Ser Gly Thr Ser Pro Lys Arg Trp Ile
        35                  40                  45

Tyr Asp Thr Ser Lys Leu Ala Ser Gly Val Pro Gly Arg Phe Ser Gly
    50                  55                  60

Ser Gly Ser Gly Asn Ser Tyr Ser Leu Thr Ile Ser Ser Val Glu Ala
65                  70                  75                  80

Glu Asp Asp Ala Thr Tyr Tyr Cys Gln Gln Trp Ser Lys His Pro Leu
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 42
<211> LENGTH: 461
<212> TYPE: PRT
<213> ORGANISM: Artificial Sequence
<220> FEATURE:
<223> OTHER INFORMATION: Synthetic

<400> SEQUENCE: 42

Met Gln Val Gln Leu Gln Gln Ser Gly Pro Glu Leu Glu Lys Pro Gly
1               5                   10                  15

Ala Ser Val Lys Ile Ser Cys Lys Ala Ser Gly Tyr Ser Phe Thr Gly
            20                  25                  30

Tyr Thr Met Asn Trp Val Lys Gln Ser His Gly Lys Gly Leu Glu Trp
        35                  40                  45

Ile Gly Leu Ile Thr Pro Tyr Asn Gly Ala Ser Ser Tyr Asn Gln Lys
    50                  55                  60

Phe Arg Gly Lys Ala Thr Leu Thr Val Asp Lys Ser Ser Ser Thr Ala
65                  70                  75                  80

Tyr Met Asp Leu Leu Ser Leu Thr Ser Glu Asp Ser Ala Val Tyr Phe
                85                  90                  95

Cys Ala Arg Gly Gly Tyr Asp Gly Arg Gly Phe Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160
```

```
Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Lys
    210                 215                 220

Ala Ser Gly Gly Arg His Arg Gln Pro Arg Gly Trp Glu Gln Leu Gly
225                 230                 235                 240

Gly Ser Pro Thr Gly Ala Glu Phe Leu Gly Asp Gly Asp Val Ser
                245                 250                 255

Phe Ser Thr Arg Gly Thr Gln Asn Trp Thr Val Glu Arg Leu Leu Gln
                260                 265                 270

Ala His Ala Gln Leu Glu Glu Arg Gly Tyr Val Phe Val Gly Tyr His
            275                 280                 285

Gly Thr Phe Leu Glu Ala Ala Gln Ser Ile Val Phe Gly Gly Val Arg
        290                 295                 300

Ala Ala Ser Gln Asp Leu Ala Ala Ile Trp Ala Gly Phe Tyr Ile Ala
305                 310                 315                 320

Gly Asp Pro Ala Leu Ala Tyr Gly Tyr Ala Gln Asp Gln Glu Pro Asp
                325                 330                 335

Ala Ala Gly Arg Ile Arg Asn Gly Ala Leu Leu Arg Val Tyr Val Pro
                340                 345                 350

Ala Ser Ser Leu Pro Gly Phe Tyr Arg Thr Ser Leu Thr Leu Ala Ala
            355                 360                 365

Pro Glu Ala Ala Gly Glu Val Glu Arg Leu Ile Gly His Pro Leu Pro
        370                 375                 380

Leu Ala Leu Asp Ala Ile Thr Gly Pro Glu Glu Gly Gly Arg Leu
385                 390                 395                 400

Glu Thr Ile Leu Gly Trp Pro Leu Ala Glu Arg Thr Val Val Ile Pro
                405                 410                 415

Ser Ala Ile Pro Thr Asp Pro Arg Asn Val Gly Gly Asp Leu Asp Pro
                420                 425                 430

Ser Ser Ile Pro Asp Lys Glu Gln Ala Ile Ser Ala Leu Pro Asp Tyr
            435                 440                 445

Ala Ser Gln Pro Gly Lys Pro Pro Arg Glu Asp Leu Lys
450                 455                 460

<210> SEQ ID NO 43
<211> LENGTH: 107
<212> TYPE: PRT
<213> ORGANISM: Artificial Sequence
<220> FEATURE:
<223> OTHER INFORMATION: Synthetic

<400> SEQUENCE: 43

Met Asp Ile Glu Leu Thr Gln Ser Pro Ala Ile Met Ser Ala Ser Pro
1               5                   10                  15

Gly Glu Lys Val Thr Met Thr Cys Ser Ala Ser Ser Ser Val Ser Tyr
                20                  25                  30

Met His Trp Tyr Gln Gln Lys Ser Gly Thr Ser Pro Lys Arg Trp Ile
            35                  40                  45

Tyr Asp Thr Ser Lys Leu Ala Ser Gly Val Pro Gly Arg Phe Ser Gly
        50                  55                  60
```

Ser Gly Ser Gly Asn Ser Tyr Ser Leu Thr Ile Ser Ser Val Glu Ala
65                  70                  75                  80

Glu Asp Asp Ala Thr Tyr Tyr Cys Gln Gln Trp Ser Lys His Pro Leu
                85                  90                  95

Thr Phe Gly Cys Gly Thr Lys Leu Glu Ile Lys
            100                 105

<210> SEQ ID NO 44
<211> LENGTH: 358
<212> TYPE: PRT
<213> ORGANISM: Artificial Sequence
<220> FEATURE:
<223> OTHER INFORMATION: Synthetic

<400> SEQUENCE: 44

Met Gln Val Gln Leu Gln Gln Ser Gly Pro Glu Leu Glu Lys Pro Gly
1               5                   10                  15

Ala Ser Val Lys Ile Ser Cys Lys Ala Ser Gly Tyr Ser Phe Thr Gly
                20                  25                  30

Tyr Thr Met Asn Trp Val Lys Gln Ser His Gly Lys Cys Leu Glu Trp
            35                  40                  45

Ile Gly Leu Ile Thr Pro Tyr Asn Gly Ala Ser Ser Tyr Asn Gln Lys
50              55                  60

Phe Arg Gly Lys Ala Thr Leu Thr Val Asp Lys Ser Ser Ser Thr Ala
65                  70                  75                  80

Tyr Met Asp Leu Leu Ser Leu Thr Ser Glu Asp Ser Ala Val Tyr Phe
                85                  90                  95

Cys Ala Arg Gly Gly Tyr Asp Gly Arg Gly Phe Asp Tyr Trp Gly Gln
            100                 105                 110

Gly Thr Thr Val Thr Val Ser Ser Lys Ala Ser Gly Arg His Arg
        115                 120                 125

Gln Pro Arg Gly Trp Glu Gln Leu Gly Gly Ser Pro Thr Gly Ala Glu
130                 135                 140

Phe Leu Gly Asp Gly Gly Asp Val Ser Phe Ser Thr Arg Gly Thr Gln
145                 150                 155                 160

Asn Trp Thr Val Glu Arg Leu Leu Gln Ala His Ala Gln Leu Glu Glu
                165                 170                 175

Arg Gly Tyr Val Phe Val Gly Tyr His Gly Thr Phe Leu Glu Ala Ala
            180                 185                 190

Gln Ser Ile Val Phe Gly Gly Val Arg Ala Ala Ser Gln Asp Leu Ala
        195                 200                 205

Ala Ile Trp Ala Gly Phe Tyr Ile Ala Gly Asp Pro Ala Leu Ala Tyr
210                 215                 220

Gly Tyr Ala Gln Asp Gln Glu Pro Asp Ala Ala Gly Arg Ile Arg Asn
225                 230                 235                 240

Gly Ala Leu Leu Arg Val Tyr Val Pro Ala Ser Ser Leu Pro Gly Phe
                245                 250                 255

Tyr Arg Thr Ser Leu Thr Leu Ala Ala Pro Glu Ala Ala Gly Glu Val
            260                 265                 270

Glu Arg Leu Ile Gly His Pro Leu Pro Leu Ala Leu Asp Ala Ile Thr
        275                 280                 285

Gly Pro Glu Glu Glu Gly Gly Arg Leu Glu Thr Ile Leu Gly Trp Pro
290                 295                 300

Leu Ala Glu Arg Thr Val Val Ile Pro Ser Ala Ile Pro Thr Asp Pro
305                 310                 315                 320

Arg Asn Val Gly Gly Asp Leu Asp Pro Ser Ser Ile Pro Asp Lys Glu
                325                 330                 335

Gln Ala Ile Ser Ala Leu Pro Asp Tyr Ala Ser Gln Pro Gly Lys Pro
            340                 345                 350

Pro Arg Glu Asp Leu Lys
        355

<210> SEQ ID NO 45
<211> LENGTH: 119
<212> TYPE: PRT
<213> ORGANISM: Artificial Sequence
<220> FEATURE:
<223> OTHER INFORMATION: Synthetic

<400> SEQUENCE: 45

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
            20                  25                  30

Thr Met Asn Trp Val Arg Gln Ala Pro Gly Gln Gly Leu Glu Trp Met
        35                  40                  45

Gly Leu Ile Thr Pro Tyr Asn Gly Ala Ser Ser Tyr Asn Gln Lys Phe
    50                  55                  60

Arg Gly Lys Ala Thr Met Thr Val Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Gly Tyr Asp Gly Arg Gly Phe Asp Tyr Trp Gly Gln Gly
            100                 105                 110

Thr Leu Val Thr Val Ser Ser
        115

<210> SEQ ID NO 46
<211> LENGTH: 106
<212> TYPE: PRT
<213> ORGANISM: Artificial Sequence
<220> FEATURE:
<223> OTHER INFORMATION: Synthetic

<400> SEQUENCE: 46

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Val Ser Tyr Met
            20                  25                  30

His Trp Tyr Gln Gln Lys Ser Gly Lys Ala Pro Lys Leu Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ser Lys His Pro Leu Thr
                85                  90                  95

Phe Gly Gln Gly Thr Lys Leu Glu Ile Lys
            100                 105

<210> SEQ ID NO 47
<211> LENGTH: 30
<212> TYPE: PRT

```
<213> ORGANISM: Artificial Sequence
<220> FEATURE:
<223> OTHER INFORMATION: Synthetic

<400> SEQUENCE: 47

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Ser Phe Thr
            20                  25                  30

<210> SEQ ID NO 48
<211> LENGTH: 23
<212> TYPE: PRT
<213> ORGANISM: Artificial Sequence
<220> FEATURE:
<223> OTHER INFORMATION: Synthetic

<400> SEQUENCE: 48

Asp Ile Gln Met Thr Gln Ser Pro Ser Ser Leu Ser Ala Ser Val Gly
1               5                   10                  15
Asp Arg Val Thr Ile Thr Cys
            20

<210> SEQ ID NO 49
<211> LENGTH: 5
<212> TYPE: PRT
<213> ORGANISM: Artificial Sequence
<220> FEATURE:
<223> OTHER INFORMATION: Synthetic

<400> SEQUENCE: 49

Gly Tyr Thr Met Asn
1               5

<210> SEQ ID NO 50
<211> LENGTH: 10
<212> TYPE: PRT
<213> ORGANISM: Artificial Sequence
<220> FEATURE:
<223> OTHER INFORMATION: Synthetic

<400> SEQUENCE: 50

Ser Ala Ser Ser Ser Val Ser Tyr Met His
1               5                   10

<210> SEQ ID NO 51
<211> LENGTH: 14
<212> TYPE: PRT
<213> ORGANISM: Artificial Sequence
<220> FEATURE:
<223> OTHER INFORMATION: Synthetic

<400> SEQUENCE: 51

Trp Val Arg Gln Ala Pro Gly Gln Gly Leu Glu Trp Met Gly
1               5                   10

<210> SEQ ID NO 52
<211> LENGTH: 15
<212> TYPE: PRT
<213> ORGANISM: Artificial Sequence
<220> FEATURE:
<223> OTHER INFORMATION: Synthetic

<400> SEQUENCE: 52

Trp Tyr Gln Gln Lys Ser Gly Lys Ala Pro Lys Leu Leu Ile Tyr
1               5                   10                  15
```

```
<210> SEQ ID NO 53
<211> LENGTH: 17
<212> TYPE: PRT
<213> ORGANISM: Artificial Sequence
<220> FEATURE:
<223> OTHER INFORMATION: Synthetic

<400> SEQUENCE: 53

Leu Ile Thr Pro Tyr Asn Gly Ala Ser Ser Tyr Asn Gln Lys Phe Arg
1               5                   10                  15

Gly

<210> SEQ ID NO 54
<211> LENGTH: 7
<212> TYPE: PRT
<213> ORGANISM: Artificial Sequence
<220> FEATURE:
<223> OTHER INFORMATION: Synthetic

<400> SEQUENCE: 54

Asp Thr Ser Lys Leu Ala Ser
1               5

<210> SEQ ID NO 55
<211> LENGTH: 32
<212> TYPE: PRT
<213> ORGANISM: Artificial Sequence
<220> FEATURE:
<223> OTHER INFORMATION: Synthetic

<400> SEQUENCE: 55

Lys Ala Thr Met Thr Val Asp Thr Ser Thr Ser Thr Val Tyr Met Glu
1               5                   10                  15

Leu Ser Ser Leu Arg Ser Glu Asp Thr Ala Val Tyr Tyr Cys Ala Arg
                20                  25                  30

<210> SEQ ID NO 56
<211> LENGTH: 32
<212> TYPE: PRT
<213> ORGANISM: Artificial Sequence
<220> FEATURE:
<223> OTHER INFORMATION: Synthetic

<400> SEQUENCE: 56

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
                20                  25                  30

<210> SEQ ID NO 57
<211> LENGTH: 10
<212> TYPE: PRT
<213> ORGANISM: Artificial Sequence
<220> FEATURE:
<223> OTHER INFORMATION: Synthetic

<400> SEQUENCE: 57

Gly Gly Tyr Asp Gly Arg Gly Phe Asp Tyr
1               5                   10

<210> SEQ ID NO 58
<211> LENGTH: 9
<212> TYPE: PRT
<213> ORGANISM: Artificial Sequence
```

```
<220> FEATURE:
<223> OTHER INFORMATION: Synthetic

<400> SEQUENCE: 58

Gln Gln Trp Ser Lys His Pro Leu Thr
1               5

<210> SEQ ID NO 59
<211> LENGTH: 11
<212> TYPE: PRT
<213> ORGANISM: Artificial Sequence
<220> FEATURE:
<223> OTHER INFORMATION: Synthetic

<400> SEQUENCE: 59

Trp Gly Gln Gly Thr Leu Val Thr Val Ser Ser
1               5                   10

<210> SEQ ID NO 60
<211> LENGTH: 10
<212> TYPE: PRT
<213> ORGANISM: Artificial Sequence
<220> FEATURE:
<223> OTHER INFORMATION: Synthetic

<400> SEQUENCE: 60

Phe Gly Gln Gly Thr Lys Leu Glu Ile Lys
1               5                   10

<210> SEQ ID NO 61
<211> LENGTH: 115
<212> TYPE: PRT
<213> ORGANISM: Artificial Sequence
<220> FEATURE:
<223> OTHER INFORMATION: Synthetic

<400> SEQUENCE: 61

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Glu Met His Trp Val Arg Gln Ala Pro Gly Gln Gly Leu Glu Trp Met
        35                  40                  45

Gly Ala Leu Asp Pro Lys Thr Gly Asp Thr Ala Tyr Ser Gln Lys Phe
    50                  55                  60

Lys Gly Arg Val Thr Leu Thr Ala Asp Lys Ser Thr Ser Thr Ala Tyr
65                  70                  75                  80

Met Glu Leu Ser Ser Leu Thr Ser Glu Asp Thr Ala Val Tyr Tyr Cys
                85                  90                  95

Thr Arg Phe Tyr Ser Tyr Thr Tyr Trp Gly Gln Gly Thr Leu Val Thr
            100                 105                 110

Val Ser Ser
        115

<210> SEQ ID NO 62
<211> LENGTH: 112
<212> TYPE: PRT
<213> ORGANISM: Artificial Sequence
<220> FEATURE:
<223> OTHER INFORMATION: Synthetic

<400> SEQUENCE: 62

Asp Val Val Met Thr Gln Ser Pro Leu Ser Leu Pro Val Thr Pro Gly
```

```
            1               5                  10                  15
          Glu Pro Ala Ser Ile Ser Cys Arg Ser Ser Gln Ser Leu Val His Ser
                        20                  25                  30

Asn Arg Asn Thr Tyr Leu His Trp Tyr Leu Gln Lys Pro Gly Gln Ser
                        35                  40                  45

Pro Gln Leu Leu Ile Tyr Lys Val Ser Asn Arg Phe Ser Gly Val Pro
                        50                  55                  60

Asp Arg Phe Ser Gly Ser Gly Ser Gly Thr Asp Phe Thr Leu Lys Ile
           65                  70                  75                  80

Ser Arg Val Glu Ala Glu Asp Val Gly Val Tyr Tyr Cys Ser Gln Asn
                              85                  90                  95

Thr His Val Pro Pro Thr Phe Gly Gln Gly Thr Lys Leu Glu Ile Lys
                       100                 105                 110
```

<210> SEQ ID NO 63
<211> LENGTH: 30
<212> TYPE: PRT
<213> ORGANISM: Artificial Sequence
<220> FEATURE:
<223> OTHER INFORMATION: Synthetic

<400> SEQUENCE: 63

```
Gln Val Gln Leu Val Gln Ser Gly Ala Glu Val Lys Lys Pro Gly Ala
1               5                  10                  15

Ser Val Lys Val Ser Cys Lys Ala Ser Gly Tyr Thr Phe Thr
             20                  25                  30
```

<210> SEQ ID NO 64
<211> LENGTH: 23
<212> TYPE: PRT
<213> ORGANISM: Artificial Sequence
<220> FEATURE:
<223> OTHER INFORMATION: Synthetic

<400> SEQUENCE: 64

```
Asp Val Val Met Thr Gln Ser Pro Leu Ser Leu Pro Val Thr Pro Gly
1               5                  10                  15

Glu Pro Ala Ser Ile Ser Cys
             20
```

<210> SEQ ID NO 65
<211> LENGTH: 5
<212> TYPE: PRT
<213> ORGANISM: Artificial Sequence
<220> FEATURE:
<223> OTHER INFORMATION: Synthetic

<400> SEQUENCE: 65

```
Asp Tyr Glu Met His
1               5
```

<210> SEQ ID NO 66
<211> LENGTH: 16
<212> TYPE: PRT
<213> ORGANISM: Artificial Sequence
<220> FEATURE:
<223> OTHER INFORMATION: Synthetic

<400> SEQUENCE: 66

```
Arg Ser Ser Gln Ser Leu Val His Ser Asn Arg Asn Thr Tyr Leu His
1               5                  10                  15
```

-continued

```
<210> SEQ ID NO 67
<211> LENGTH: 14
<212> TYPE: PRT
<213> ORGANISM: Artificial Sequence
<220> FEATURE:
<223> OTHER INFORMATION: Synthetic

<400> SEQUENCE: 67

Trp Val Arg Gln Ala Pro Gly Gln Gly Leu Glu Trp Met Gly
1               5                   10

<210> SEQ ID NO 68
<211> LENGTH: 15
<212> TYPE: PRT
<213> ORGANISM: Artificial Sequence
<220> FEATURE:
<223> OTHER INFORMATION: Synthetic

<400> SEQUENCE: 68

Trp Tyr Leu Gln Lys Pro Gly Gln Ser Pro Gln Leu Leu Ile Tyr
1               5                   10                  15

<210> SEQ ID NO 69
<211> LENGTH: 17
<212> TYPE: PRT
<213> ORGANISM: Artificial Sequence
<220> FEATURE:
<223> OTHER INFORMATION: Synthetic

<400> SEQUENCE: 69

Ala Leu Asp Pro Lys Thr Gly Asp Thr Ala Tyr Ser Gln Lys Phe Lys
1               5                   10                  15

Gly

<210> SEQ ID NO 70
<211> LENGTH: 7
<212> TYPE: PRT
<213> ORGANISM: Artificial Sequence
<220> FEATURE:
<223> OTHER INFORMATION: Synthetic

<400> SEQUENCE: 70

Lys Val Ser Asn Arg Phe Ser
1               5

<210> SEQ ID NO 71
<211> LENGTH: 32
<212> TYPE: PRT
<213> ORGANISM: Artificial Sequence
<220> FEATURE:
<223> OTHER INFORMATION: Synthetic

<400> SEQUENCE: 71

Arg Val Thr Leu Thr Ala Asp Lys Ser Thr Ser Thr Ala Tyr Met Glu
1               5                   10                  15

Leu Ser Ser Leu Thr Ser Glu Asp Thr Ala Val Tyr Tyr Cys Thr Arg
                20                  25                  30

<210> SEQ ID NO 72
<211> LENGTH: 32
<212> TYPE: PRT
<213> ORGANISM: Artificial Sequence
<220> FEATURE:
<223> OTHER INFORMATION: Synthetic

<400> SEQUENCE: 72
```

Gly Val Pro Asp Arg Phe Ser Gly Ser Gly Ser Gly Thr Asp Phe Thr
1               5                   10                  15

Leu Lys Ile Ser Arg Val Glu Ala Glu Asp Val Gly Val Tyr Tyr Cys
            20                  25                  30

<210> SEQ ID NO 73
<211> LENGTH: 6
<212> TYPE: PRT
<213> ORGANISM: Artificial Sequence
<220> FEATURE:
<223> OTHER INFORMATION: Synthetic

<400> SEQUENCE: 73

Phe Tyr Ser Tyr Thr Tyr
1               5

<210> SEQ ID NO 74
<211> LENGTH: 9
<212> TYPE: PRT
<213> ORGANISM: Artificial Sequence
<220> FEATURE:
<223> OTHER INFORMATION: Synthetic

<400> SEQUENCE: 74

Ser Gln Asn Thr His Val Pro Pro Thr
1               5

<210> SEQ ID NO 75
<211> LENGTH: 11
<212> TYPE: PRT
<213> ORGANISM: Artificial Sequence
<220> FEATURE:
<223> OTHER INFORMATION: Synthetic

<400> SEQUENCE: 75

Trp Gly Gln Gly Thr Leu Val Thr Val Ser Ser
1               5                   10

<210> SEQ ID NO 76
<211> LENGTH: 10
<212> TYPE: PRT
<213> ORGANISM: Artificial Sequence
<220> FEATURE:
<223> OTHER INFORMATION: Synthetic

<400> SEQUENCE: 76

Phe Gly Gln Gly Thr Lys Leu Glu Ile Lys
1               5                   10

<210> SEQ ID NO 77
<211> LENGTH: 115
<212> TYPE: PRT
<213> ORGANISM: Artificial Sequence
<220> FEATURE:
<223> OTHER INFORMATION: Synthetic

<400> SEQUENCE: 77

Gln Val Gln Leu Val Gln Ser Gly Ala Glu Val Lys Lys Pro Gly Ala
1               5                   10                  15

Ser Val Thr Val Ser Cys Lys Ala Ser Gly Tyr Thr Phe Thr Asp Tyr
            20                  25                  30

Glu Met His Trp Ile Arg Gln Pro Pro Gly Glu Gly Leu Glu Trp Ile
        35                  40                  45

Gly Ala Ile Asp Pro Lys Thr Gly Asp Thr Ala Tyr Ser Glu Ser Phe
    50                  55                  60

```
Gln Asp Arg Val Thr Leu Thr Ala Asp Lys Ser Thr Ser Thr Ala Tyr
 65                  70                  75                  80

Met Glu Leu Ser Ser Leu Thr Ser Glu Asp Thr Ala Val Tyr Tyr Cys
                 85                  90                  95

Thr Arg Phe Tyr Ser Tyr Thr Tyr Trp Gly Gln Gly Thr Leu Val Thr
            100                 105                 110

Val Ser Ser
        115

<210> SEQ ID NO 78
<211> LENGTH: 112
<212> TYPE: PRT
<213> ORGANISM: Artificial Sequence
<220> FEATURE:
<223> OTHER INFORMATION: Synthetic

<400> SEQUENCE: 78

Asp Ile Val Met Thr Gln Ser Pro Leu Ser Leu Pro Val Thr Pro Gly
 1               5                  10                  15

Glu Pro Ala Ser Ile Ser Cys Gln Ala Ser Glu Ser Leu Val His Ser
                20                  25                  30

Asn Arg Asn Thr Tyr Leu His Trp Tyr Leu Gln Lys Pro Gly Gln Ser
             35                  40                  45

Pro Gln Leu Leu Ile Tyr Lys Val Ser Asn Arg Phe Ser Gly Val Pro
         50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ser Gln Asn
                 85                  90                  95

Thr His Val Pro Pro Thr Phe Gly Gln Gly Thr Lys Val Glu Ile Glu
            100                 105                 110

<210> SEQ ID NO 79
<211> LENGTH: 30
<212> TYPE: PRT
<213> ORGANISM: Artificial Sequence
<220> FEATURE:
<223> OTHER INFORMATION: Synthetic

<400> SEQUENCE: 79

Gln Val Gln Leu Val Gln Ser Gly Ala Glu Val Lys Lys Pro Gly Ala
 1               5                  10                  15

Ser Val Thr Val Ser Cys Lys Ala Ser Gly Tyr Thr Phe Thr
                20                  25                  30

<210> SEQ ID NO 80
<211> LENGTH: 23
<212> TYPE: PRT
<213> ORGANISM: Artificial Sequence
<220> FEATURE:
<223> OTHER INFORMATION: Synthetic

<400> SEQUENCE: 80

Asp Ile Val Met Thr Gln Ser Pro Leu Ser Leu Pro Val Thr Pro Gly
 1               5                  10                  15

Glu Pro Ala Ser Ile Ser Cys
                20

<210> SEQ ID NO 81
<211> LENGTH: 5
```

```
<212> TYPE: PRT
<213> ORGANISM: Artificial Sequence
<220> FEATURE:
<223> OTHER INFORMATION: Synthetic

<400> SEQUENCE: 81

Asp Tyr Glu Met His
1               5

<210> SEQ ID NO 82
<211> LENGTH: 16
<212> TYPE: PRT
<213> ORGANISM: Artificial Sequence
<220> FEATURE:
<223> OTHER INFORMATION: Synthetic

<400> SEQUENCE: 82

Gln Ala Ser Glu Ser Leu Val His Ser Asn Arg Asn Thr Tyr Leu His
1               5                   10                  15

<210> SEQ ID NO 83
<211> LENGTH: 14
<212> TYPE: PRT
<213> ORGANISM: Artificial Sequence
<220> FEATURE:
<223> OTHER INFORMATION: Synthetic

<400> SEQUENCE: 83

Trp Ile Arg Gln Pro Pro Gly Glu Gly Leu Glu Trp Ile Gly
1               5                   10

<210> SEQ ID NO 84
<211> LENGTH: 15
<212> TYPE: PRT
<213> ORGANISM: Artificial Sequence
<220> FEATURE:
<223> OTHER INFORMATION: Synthetic

<400> SEQUENCE: 84

Trp Tyr Leu Gln Lys Pro Gly Gln Ser Pro Gln Leu Leu Ile Tyr
1               5                   10                  15

<210> SEQ ID NO 85
<211> LENGTH: 17
<212> TYPE: PRT
<213> ORGANISM: Artificial Sequence
<220> FEATURE:
<223> OTHER INFORMATION: Synthetic

<400> SEQUENCE: 85

Ala Ile Asp Pro Lys Thr Gly Asp Thr Ala Tyr Ser Glu Ser Phe Gln
1               5                   10                  15

Asp

<210> SEQ ID NO 86
<211> LENGTH: 7
<212> TYPE: PRT
<213> ORGANISM: Artificial Sequence
<220> FEATURE:
<223> OTHER INFORMATION: Synthetic

<400> SEQUENCE: 86

Lys Val Ser Asn Arg Phe Ser
1               5

<210> SEQ ID NO 87
```

```
<211> LENGTH: 32
<212> TYPE: PRT
<213> ORGANISM: Artificial Sequence
<220> FEATURE:
<223> OTHER INFORMATION: Synthetic

<400> SEQUENCE: 87

Arg Val Thr Leu Thr Ala Asp Lys Ser Thr Ser Thr Ala Tyr Met Glu
1               5                   10                  15

Leu Ser Ser Leu Thr Ser Glu Asp Thr Ala Val Tyr Tyr Cys Thr Arg
            20                  25                  30

<210> SEQ ID NO 88
<211> LENGTH: 32
<212> TYPE: PRT
<213> ORGANISM: Artificial Sequence
<220> FEATURE:
<223> OTHER INFORMATION: Synthetic

<400> SEQUENCE: 88

Gly Val Pro Asp Arg Phe Ser Gly Ser Gly Ser Gly Thr Asp Phe Thr
1               5                   10                  15

Leu Lys Ile Ser Arg Val Glu Ala Glu Asp Val Gly Val Tyr Tyr Cys
            20                  25                  30

<210> SEQ ID NO 89
<211> LENGTH: 6
<212> TYPE: PRT
<213> ORGANISM: Artificial Sequence
<220> FEATURE:
<223> OTHER INFORMATION: Synthetic

<400> SEQUENCE: 89

Phe Tyr Ser Tyr Thr Tyr
1               5

<210> SEQ ID NO 90
<211> LENGTH: 9
<212> TYPE: PRT
<213> ORGANISM: Artificial Sequence
<220> FEATURE:
<223> OTHER INFORMATION: Synthetic

<400> SEQUENCE: 90

Ser Gln Asn Thr His Val Pro Pro Thr
1               5

<210> SEQ ID NO 91
<211> LENGTH: 11
<212> TYPE: PRT
<213> ORGANISM: Artificial Sequence
<220> FEATURE:
<223> OTHER INFORMATION: Synthetic

<400> SEQUENCE: 91

Trp Gly Gln Gly Thr Leu Val Thr Val Ser Ser
1               5                   10

<210> SEQ ID NO 92
<211> LENGTH: 10
<212> TYPE: PRT
<213> ORGANISM: Artificial Sequence
<220> FEATURE:
<223> OTHER INFORMATION: Synthetic

<400> SEQUENCE: 92
```

Phe Gly Gln Gly Thr Lys Val Glu Ile Glu
1               5                  10

<210> SEQ ID NO 93
<211> LENGTH: 124
<212> TYPE: PRT
<213> ORGANISM: Artificial Sequence
<220> FEATURE:
<223> OTHER INFORMATION: Synthetic

<400> SEQUENCE: 93

Gln Val Gln Leu Val Gln Ser Gly Ala Glu Val Lys Pro Gly Ala
1               5                   10                  15

Ser Val Lys Val Ser Cys Lys Thr Ser Arg Tyr Thr Phe Thr Glu Tyr
                20                  25                  30

Thr Ile His Trp Val Arg Gln Ala Pro Gly Gln Arg Leu Glu Trp Ile
            35                  40                  45

Gly Gly Ile Asn Pro Asn Asn Gly Ile Pro Asn Tyr Asn Gln Lys Phe
        50                  55                  60

Lys Gly Arg Val Thr Ile Thr Val Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Ile Ala Tyr Gly Tyr Asp Glu Gly His Ala Met Asp
            100                 105                 110

Tyr Trp Gly Gln Gly Thr Leu Val Thr Val Ser Ser
            115                 120

<210> SEQ ID NO 94
<211> LENGTH: 113
<212> TYPE: PRT
<213> ORGANISM: Artificial Sequence
<220> FEATURE:
<223> OTHER INFORMATION: Synthetic

<400> SEQUENCE: 94

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Tyr Ser
                20                  25                  30

Arg Asn Gln Lys Asn Tyr Leu Ala Trp Tyr Gln Gln Lys Pro Gly Gln
            35                  40                  45

Pro Pro Lys Leu Leu Ile Phe Trp Ala Ser Thr Arg Glu Ser Gly Val
        50                  55                  60

Pro Asp Arg Phe Ser Gly Ser Gly Phe Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Phe Ser Tyr Pro Leu Thr Phe Gly Gln Gly Thr Lys Val Glu Ile
            100                 105                 110

Lys

<210> SEQ ID NO 95
<211> LENGTH: 30
<212> TYPE: PRT
<213> ORGANISM: Artificial Sequence
<220> FEATURE:
<223> OTHER INFORMATION: Synthetic

<400> SEQUENCE: 95

```
Gln Val Gln Leu Val Gln Ser Gly Ala Glu Val Lys Lys Pro Gly Ala
1               5                   10                  15

Ser Val Lys Val Ser Cys Lys Thr Ser Arg Tyr Thr Phe Thr
            20                  25                  30

<210> SEQ ID NO 96
<211> LENGTH: 23
<212> TYPE: PRT
<213> ORGANISM: Artificial Sequence
<220> FEATURE:
<223> OTHER INFORMATION: Synthetic

<400> SEQUENCE: 96

Asp Ile Val Met Thr Gln Ser Pro Asp Ser Leu Ala Val Ser Leu Gly
1               5                   10                  15

Glu Arg Ala Thr Ile Asn Cys
            20

<210> SEQ ID NO 97
<211> LENGTH: 5
<212> TYPE: PRT
<213> ORGANISM: Artificial Sequence
<220> FEATURE:
<223> OTHER INFORMATION: Synthetic

<400> SEQUENCE: 97

Glu Tyr Thr Ile His
1               5

<210> SEQ ID NO 98
<211> LENGTH: 17
<212> TYPE: PRT
<213> ORGANISM: Artificial Sequence
<220> FEATURE:
<223> OTHER INFORMATION: Synthetic

<400> SEQUENCE: 98

Lys Ser Ser Gln Ser Leu Leu Tyr Ser Arg Asn Gln Lys Asn Tyr Leu
1               5                   10                  15

Ala

<210> SEQ ID NO 99
<211> LENGTH: 14
<212> TYPE: PRT
<213> ORGANISM: Artificial Sequence
<220> FEATURE:
<223> OTHER INFORMATION: Synthetic

<400> SEQUENCE: 99

Trp Val Arg Gln Ala Pro Gly Gln Arg Leu Glu Trp Ile Gly
1               5                   10

<210> SEQ ID NO 100
<211> LENGTH: 15
<212> TYPE: PRT
<213> ORGANISM: Artificial Sequence
<220> FEATURE:
<223> OTHER INFORMATION: Synthetic

<400> SEQUENCE: 100

Trp Tyr Gln Gln Lys Pro Gly Gln Pro Pro Lys Leu Leu Ile Phe
1               5                   10                  15

<210> SEQ ID NO 101
```

<211> LENGTH: 17
<212> TYPE: PRT
<213> ORGANISM: Artificial Sequence
<220> FEATURE:
<223> OTHER INFORMATION: Synthetic

<400> SEQUENCE: 101

Gly Ile Asn Pro Asn Asn Gly Ile Pro Asn Tyr Asn Gln Lys Phe Lys
1               5                   10                  15
Gly

<210> SEQ ID NO 102
<211> LENGTH: 7
<212> TYPE: PRT
<213> ORGANISM: Artificial Sequence
<220> FEATURE:
<223> OTHER INFORMATION: Synthetic

<400> SEQUENCE: 102

Trp Ala Ser Thr Arg Glu Ser
1               5

<210> SEQ ID NO 103
<211> LENGTH: 32
<212> TYPE: PRT
<213> ORGANISM: Artificial Sequence
<220> FEATURE:
<223> OTHER INFORMATION: Synthetic

<400> SEQUENCE: 103

Arg Val Thr Ile Thr Val Asp Thr Ser Ala Ser Thr Ala Tyr Met Glu
1               5                   10                  15
Leu Ser Ser Leu Arg Ser Glu Asp Thr Ala Val Tyr Tyr Cys Ala Arg
            20                  25                  30

<210> SEQ ID NO 104
<211> LENGTH: 32
<212> TYPE: PRT
<213> ORGANISM: Artificial Sequence
<220> FEATURE:
<223> OTHER INFORMATION: Synthetic

<400> SEQUENCE: 104

Gly Val Pro Asp Arg Phe Ser Gly Ser Gly Phe Gly Thr Asp Phe Thr
1               5                   10                  15
Leu Thr Ile Ser Ser Leu Gln Ala Glu Asp Val Ala Val Tyr Tyr Cys
            20                  25                  30

<210> SEQ ID NO 105
<211> LENGTH: 15
<212> TYPE: PRT
<213> ORGANISM: Artificial Sequence
<220> FEATURE:
<223> OTHER INFORMATION: Synthetic

<400> SEQUENCE: 105

Arg Arg Ile Ala Tyr Gly Tyr Asp Glu Gly His Ala Met Asp Tyr
1               5                   10                  15

<210> SEQ ID NO 106
<211> LENGTH: 9
<212> TYPE: PRT
<213> ORGANISM: Artificial Sequence
<220> FEATURE:
<223> OTHER INFORMATION: Synthetic

```
<400> SEQUENCE: 106

Gln Gln Tyr Phe Ser Tyr Pro Leu Thr
1               5

<210> SEQ ID NO 107
<211> LENGTH: 11
<212> TYPE: PRT
<213> ORGANISM: Artificial Sequence
<220> FEATURE:
<223> OTHER INFORMATION: Synthetic

<400> SEQUENCE: 107

Trp Gly Gln Gly Thr Leu Val Thr Val Ser Ser
1               5                   10

<210> SEQ ID NO 108
<211> LENGTH: 10
<212> TYPE: PRT
<213> ORGANISM: Artificial Sequence
<220> FEATURE:
<223> OTHER INFORMATION: Synthetic

<400> SEQUENCE: 108

Phe Gly Gln Gly Thr Lys Val Glu Ile Lys
1               5                   10

<210> SEQ ID NO 109
<211> LENGTH: 115
<212> TYPE: PRT
<213> ORGANISM: Artificial Sequence
<220> FEATURE:
<223> OTHER INFORMATION: Synthetic

<400> SEQUENCE: 109

Glu Val Gln Leu Gln Gln Ser Gly Pro Glu Leu Val Lys Pro Gly Thr
1               5                   10                  15

Ser Val Arg Ile Ser Cys Lys Thr Ser Gly Tyr Thr Phe Thr Glu Tyr
            20                  25                  30

Thr Ile His Trp Val Lys Gln Ser His Gly Lys Ser Leu Glu Trp Ile
        35                  40                  45

Gly Asn Ile Asn Pro Asn Asn Gly Gly Thr Thr Tyr Asn Gln Lys Phe
    50                  55                  60

Glu Asp Lys Ala Thr Leu Thr Val Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Ala Gly Trp Asn Phe Asp Tyr Trp Gly Gln Gly Thr Thr Leu Thr
            100                 105                 110

Val Ser Ser
        115

<210> SEQ ID NO 110
<211> LENGTH: 107
<212> TYPE: PRT
<213> ORGANISM: Artificial Sequence
<220> FEATURE:
<223> OTHER INFORMATION: Synthetic

<400> SEQUENCE: 110

Asp Ile Val Met Thr Gln Ser His Lys Phe Met Ser Thr Ser Val Gly
1               5                   10                  15

Asp Arg Val Ser Ile Ile Cys Lys Ala Ser Gln Asp Val Gly Thr Ala
```

```
                    20                  25                  30
Val Asp Trp Tyr Gln Gln Lys Pro Gly Gln Ser Pro Lys Leu Leu Ile
            35                  40                  45

Tyr Trp Ala Ser Thr Arg His Thr Gly Val Pro Asp Arg Phe Thr Gly
        50                  55                  60

Ser Gly Ser Gly Thr Asp Phe Thr Leu Thr Ile Thr Asn Val Gln Ser
65                  70                  75                  80

Glu Asp Leu Ala Asp Tyr Phe Cys Gln Gln Tyr Asn Ser Tyr Pro Leu
                85                  90                  95

Thr Phe Gly Ala Gly Thr Met Leu Asp Leu Lys
            100                 105

<210> SEQ ID NO 111
<211> LENGTH: 30
<212> TYPE: PRT
<213> ORGANISM: Artificial Sequence
<220> FEATURE:
<223> OTHER INFORMATION: Synthetic

<400> SEQUENCE: 111

Glu Val Gln Leu Gln Gln Ser Gly Pro Glu Leu Val Lys Pro Gly Thr
1               5                   10                  15

Ser Val Arg Ile Ser Cys Lys Thr Ser Gly Tyr Thr Phe Thr
            20                  25                  30

<210> SEQ ID NO 112
<211> LENGTH: 23
<212> TYPE: PRT
<213> ORGANISM: Artificial Sequence
<220> FEATURE:
<223> OTHER INFORMATION: Synthetic

<400> SEQUENCE: 112

Asp Ile Val Met Thr Gln Ser His Lys Phe Met Ser Thr Ser Val Gly
1               5                   10                  15

Asp Arg Val Ser Ile Ile Cys
            20

<210> SEQ ID NO 113
<211> LENGTH: 5
<212> TYPE: PRT
<213> ORGANISM: Artificial Sequence
<220> FEATURE:
<223> OTHER INFORMATION: Synthetic

<400> SEQUENCE: 113

Glu Tyr Thr Ile His
1               5

<210> SEQ ID NO 114
<211> LENGTH: 11
<212> TYPE: PRT
<213> ORGANISM: Artificial Sequence
<220> FEATURE:
<223> OTHER INFORMATION: Synthetic

<400> SEQUENCE: 114

Lys Ala Ser Gln Asp Val Gly Thr Ala Val Asp
1               5                   10

<210> SEQ ID NO 115
<211> LENGTH: 14
<212> TYPE: PRT
```

```
<213> ORGANISM: Artificial Sequence
<220> FEATURE:
<223> OTHER INFORMATION: Synthetic

<400> SEQUENCE: 115

Trp Val Lys Gln Ser His Gly Lys Ser Leu Glu Trp Ile Gly
1               5                   10

<210> SEQ ID NO 116
<211> LENGTH: 15
<212> TYPE: PRT
<213> ORGANISM: Artificial Sequence
<220> FEATURE:
<223> OTHER INFORMATION: Synthetic

<400> SEQUENCE: 116

Trp Tyr Gln Gln Lys Pro Gly Gln Ser Pro Lys Leu Leu Ile Tyr
1               5                   10                  15

<210> SEQ ID NO 117
<211> LENGTH: 17
<212> TYPE: PRT
<213> ORGANISM: Artificial Sequence
<220> FEATURE:
<223> OTHER INFORMATION: Synthetic

<400> SEQUENCE: 117

Asn Ile Asn Pro Asn Asn Gly Gly Thr Thr Tyr Asn Gln Lys Phe Glu
1               5                   10                  15

Asp

<210> SEQ ID NO 118
<211> LENGTH: 7
<212> TYPE: PRT
<213> ORGANISM: Artificial Sequence
<220> FEATURE:
<223> OTHER INFORMATION: Synthetic

<400> SEQUENCE: 118

Trp Ala Ser Thr Arg His Thr
1               5

<210> SEQ ID NO 119
<211> LENGTH: 32
<212> TYPE: PRT
<213> ORGANISM: Artificial Sequence
<220> FEATURE:
<223> OTHER INFORMATION: Synthetic

<400> SEQUENCE: 119

Lys Ala Thr Leu Thr Val Asp Lys Ser Ser Thr Ala Tyr Met Glu
1               5                   10                  15

Leu Arg Ser Leu Thr Ser Glu Asp Ser Ala Val Tyr Tyr Cys Ala Ala
                20                  25                  30

<210> SEQ ID NO 120
<211> LENGTH: 32
<212> TYPE: PRT
<213> ORGANISM: Artificial Sequence
<220> FEATURE:
<223> OTHER INFORMATION: Synthetic

<400> SEQUENCE: 120

Gly Val Pro Asp Arg Phe Thr Gly Ser Gly Ser Gly Thr Asp Phe Thr
1               5                   10                  15
```

```
Leu Thr Ile Thr Asn Val Gln Ser Glu Asp Leu Ala Asp Tyr Phe Cys
            20                  25                  30

<210> SEQ ID NO 121
<211> LENGTH: 6
<212> TYPE: PRT
<213> ORGANISM: Artificial Sequence
<220> FEATURE:
<223> OTHER INFORMATION: Synthetic

<400> SEQUENCE: 121

Gly Trp Asn Phe Asp Tyr
1               5

<210> SEQ ID NO 122
<211> LENGTH: 9
<212> TYPE: PRT
<213> ORGANISM: Artificial Sequence
<220> FEATURE:
<223> OTHER INFORMATION: Synthetic

<400> SEQUENCE: 122

Gln Gln Tyr Asn Ser Tyr Pro Leu Thr
1               5

<210> SEQ ID NO 123
<211> LENGTH: 11
<212> TYPE: PRT
<213> ORGANISM: Artificial Sequence
<220> FEATURE:
<223> OTHER INFORMATION: Synthetic

<400> SEQUENCE: 123

Trp Gly Gln Gly Thr Thr Leu Thr Val Ser Ser
1               5                   10

<210> SEQ ID NO 124
<211> LENGTH: 10
<212> TYPE: PRT
<213> ORGANISM: Artificial Sequence
<220> FEATURE:
<223> OTHER INFORMATION: Synthetic

<400> SEQUENCE: 124

Phe Gly Ala Gly Thr Met Leu Asp Leu Lys
1               5                   10

<210> SEQ ID NO 125
<211> LENGTH: 119
<212> TYPE: PRT
<213> ORGANISM: Artificial Sequence
<220> FEATURE:
<223> OTHER INFORMATION: Synthetic

<400> SEQUENCE: 125

Asp Val Lys Leu Val Glu Ser Gly Gly Leu Val Lys Leu Gly Gly
1               5                   10                  15

Ser Leu Lys Leu Ser Cys Ala Ala Ser Gly Phe Thr Phe Ser Asn Tyr
            20                  25                  30

Tyr Met Ser Trp Val Arg Gln Thr Pro Glu Lys Arg Leu Glu Leu Val
        35                  40                  45

Ala Ala Ile Asn Ser Asp Gly Gly Ile Thr Tyr Tyr Leu Asp Thr Val
    50                  55                  60

Lys Gly Arg Phe Thr Ile Ser Arg Asp Asn Ala Lys Asn Thr Leu Tyr
65                  70                  75                  80
```

```
Leu Gln Met Ser Ser Leu Lys Ser Glu Asp Thr Ala Leu Phe Tyr Cys
                85                  90                  95

Ala Arg His Arg Ser Gly Tyr Phe Ser Met Asp Tyr Trp Gly Gln Gly
            100                 105                 110

Thr Ser Val Thr Val Ser Ser
        115

<210> SEQ ID NO 126
<211> LENGTH: 107
<212> TYPE: PRT
<213> ORGANISM: Artificial Sequence
<220> FEATURE:
<223> OTHER INFORMATION: Synthetic

<400> SEQUENCE: 126

Asp Ile Val Met Thr Gln Ser Gln Arg Phe Met Ser Thr Thr Val Gly
1               5                   10                  15

Asp Arg Val Ser Ile Thr Cys Lys Ala Ser Gln Asn Val Val Ser Ala
            20                  25                  30

Val Ala Trp Tyr Gln Gln Lys Pro Gly Gln Ser Pro Lys Leu Leu Ile
        35                  40                  45

Tyr Ser Ala Ser Asn Arg Tyr Thr Gly Val Pro Asp Arg Phe Thr Gly
    50                  55                  60

Ser Gly Ser Gly Thr Asp Phe Thr Leu Thr Ile Ser Asn Met Gln Ser
65                  70                  75                  80

Glu Asp Leu Ala Asp Phe Phe Cys Gln Gln Tyr Ser Asn Tyr Pro Trp
                85                  90                  95

Thr Phe Gly Gly Gly Thr Lys Leu Glu Ile Lys
            100                 105

<210> SEQ ID NO 127
<211> LENGTH: 30
<212> TYPE: PRT
<213> ORGANISM: Artificial Sequence
<220> FEATURE:
<223> OTHER INFORMATION: Synthetic

<400> SEQUENCE: 127

Asp Val Lys Leu Val Glu Ser Gly Gly Gly Leu Val Lys Leu Gly Gly
1               5                   10                  15

Ser Leu Lys Leu Ser Cys Ala Ala Ser Gly Phe Thr Phe Ser
            20                  25                  30

<210> SEQ ID NO 128
<211> LENGTH: 23
<212> TYPE: PRT
<213> ORGANISM: Artificial Sequence
<220> FEATURE:
<223> OTHER INFORMATION: Synthetic

<400> SEQUENCE: 128

Asp Ile Val Met Thr Gln Ser Gln Arg Phe Met Ser Thr Thr Val Gly
1               5                   10                  15

Asp Arg Val Ser Ile Thr Cys
            20

<210> SEQ ID NO 129
<211> LENGTH: 5
<212> TYPE: PRT
<213> ORGANISM: Artificial Sequence
<220> FEATURE:
```

```
<223> OTHER INFORMATION: Synthetic

<400> SEQUENCE: 129

Asn Tyr Tyr Met Ser
1               5

<210> SEQ ID NO 130
<211> LENGTH: 11
<212> TYPE: PRT
<213> ORGANISM: Artificial Sequence
<220> FEATURE:
<223> OTHER INFORMATION: Synthetic

<400> SEQUENCE: 130

Lys Ala Ser Gln Asn Val Val Ser Ala Val Ala
1               5                  10

<210> SEQ ID NO 131
<211> LENGTH: 14
<212> TYPE: PRT
<213> ORGANISM: Artificial Sequence
<220> FEATURE:
<223> OTHER INFORMATION: Synthetic

<400> SEQUENCE: 131

Trp Val Arg Gln Thr Pro Glu Lys Arg Leu Glu Leu Val Ala
1               5                   10

<210> SEQ ID NO 132
<211> LENGTH: 15
<212> TYPE: PRT
<213> ORGANISM: Artificial Sequence
<220> FEATURE:
<223> OTHER INFORMATION: Synthetic

<400> SEQUENCE: 132

Trp Tyr Gln Gln Lys Pro Gly Gln Ser Pro Lys Leu Leu Ile Tyr
1               5                   10                  15

<210> SEQ ID NO 133
<211> LENGTH: 17
<212> TYPE: PRT
<213> ORGANISM: Artificial Sequence
<220> FEATURE:
<223> OTHER INFORMATION: Synthetic

<400> SEQUENCE: 133

Ala Ile Asn Ser Asp Gly Gly Ile Thr Tyr Tyr Leu Asp Thr Val Lys
1               5                   10                  15

Gly

<210> SEQ ID NO 134
<211> LENGTH: 7
<212> TYPE: PRT
<213> ORGANISM: Artificial Sequence
<220> FEATURE:
<223> OTHER INFORMATION: Synthetic

<400> SEQUENCE: 134

Ser Ala Ser Asn Arg Tyr Thr
1               5

<210> SEQ ID NO 135
<211> LENGTH: 32
<212> TYPE: PRT
<213> ORGANISM: Artificial Sequence
```

```
<220> FEATURE:
<223> OTHER INFORMATION: Synthetic

<400> SEQUENCE: 135

Arg Phe Thr Ile Ser Arg Asp Asn Ala Lys Asn Thr Leu Tyr Leu Gln
1               5                   10                  15

Met Ser Ser Leu Lys Ser Glu Asp Thr Ala Leu Phe Tyr Cys Ala Arg
            20                  25                  30

<210> SEQ ID NO 136
<211> LENGTH: 32
<212> TYPE: PRT
<213> ORGANISM: Artificial Sequence
<220> FEATURE:
<223> OTHER INFORMATION: Synthetic

<400> SEQUENCE: 136

Gly Val Pro Asp Arg Phe Thr Gly Ser Gly Ser Gly Thr Asp Phe Thr
1               5                   10                  15

Leu Thr Ile Ser Asn Met Gln Ser Glu Asp Leu Ala Asp Phe Phe Cys
            20                  25                  30

<210> SEQ ID NO 137
<211> LENGTH: 10
<212> TYPE: PRT
<213> ORGANISM: Artificial Sequence
<220> FEATURE:
<223> OTHER INFORMATION: Synthetic

<400> SEQUENCE: 137

His Arg Ser Gly Tyr Phe Ser Met Asp Tyr
1               5                   10

<210> SEQ ID NO 138
<211> LENGTH: 9
<212> TYPE: PRT
<213> ORGANISM: Artificial Sequence
<220> FEATURE:
<223> OTHER INFORMATION: Synthetic

<400> SEQUENCE: 138

Gln Gln Tyr Ser Asn Tyr Pro Trp Thr
1               5

<210> SEQ ID NO 139
<211> LENGTH: 11
<212> TYPE: PRT
<213> ORGANISM: Artificial Sequence
<220> FEATURE:
<223> OTHER INFORMATION: Synthetic

<400> SEQUENCE: 139

Trp Gly Gln Gly Thr Ser Val Thr Val Ser Ser
1               5                   10

<210> SEQ ID NO 140
<211> LENGTH: 10
<212> TYPE: PRT
<213> ORGANISM: Artificial Sequence
<220> FEATURE:
<223> OTHER INFORMATION: Synthetic

<400> SEQUENCE: 140

Phe Gly Gly Gly Thr Lys Leu Glu Ile Lys
1               5                   10
```

```
<210> SEQ ID NO 141
<211> LENGTH: 117
<212> TYPE: PRT
<213> ORGANISM: Artificial Sequence
<220> FEATURE:
<223> OTHER INFORMATION: Synthetic

<400> SEQUENCE: 141

Gln Val Gln Leu Gln Gln Pro Gly Ala Glu Leu Val Lys Ser Gly Ala
1               5                   10                  15

Ser Val Asn Leu Ser Cys Arg Ala Ser Gly Tyr Thr Phe Thr Arg Tyr
            20                  25                  30

Trp Met Leu Trp Val Arg Gln Arg Pro Gly His Gly Leu Glu Trp Val
        35                  40                  45

Gly Glu Ile Asn Pro Arg Asn Asp Arg Thr Asn Tyr Asn Glu Lys Phe
    50                  55                  60

Lys Thr Lys Ala Thr Leu Thr Val Asp Arg Ser Ser Thr Ala Tyr
65                  70                  75                  80

Met Gln Leu Thr Ser Leu Thr Ser Glu Asp Ser Ala Val Tyr Phe Cys
                85                  90                  95

Ala Leu Gly Gly Gly Tyr Ala Met Asp Tyr Trp Gly Gln Gly Thr Ser
            100                 105                 110

Val Thr Val Ser Ser
        115

<210> SEQ ID NO 142
<211> LENGTH: 107
<212> TYPE: PRT
<213> ORGANISM: Artificial Sequence
<220> FEATURE:
<223> OTHER INFORMATION: Synthetic

<400> SEQUENCE: 142

Asp Ile Gln Met Thr Gln Thr Thr Ser Ser Leu Ser Ala Phe Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Phe Ala Thr Tyr Phe Cys Gln Gln Gly Asn Thr Leu Pro Trp
                85                  90                  95

Thr Phe Gly Gly Gly Thr Lys Leu Glu Ile Lys
            100                 105

<210> SEQ ID NO 143
<211> LENGTH: 30
<212> TYPE: PRT
<213> ORGANISM: Artificial Sequence
<220> FEATURE:
<223> OTHER INFORMATION: Synthetic

<400> SEQUENCE: 143

Gln Val Gln Leu Gln Gln Pro Gly Ala Glu Leu Val Lys Ser Gly Ala
1               5                   10                  15

Ser Val Asn Leu Ser Cys Arg Ala Ser Gly Tyr Thr Phe Thr
```

<210> SEQ ID NO 144
<211> LENGTH: 23
<212> TYPE: PRT
<213> ORGANISM: Artificial Sequence
<220> FEATURE:
<223> OTHER INFORMATION: Synthetic

<400> SEQUENCE: 144

Asp Ile Gln Met Thr Gln Thr Thr Ser Ser Leu Ser Ala Phe Leu Gly
1               5                   10                  15

Asp Arg Val Thr Ile Ser Cys
            20

<210> SEQ ID NO 145
<211> LENGTH: 5
<212> TYPE: PRT
<213> ORGANISM: Artificial Sequence
<220> FEATURE:
<223> OTHER INFORMATION: Synthetic

<400> SEQUENCE: 145

Arg Tyr Trp Met Leu
1               5

<210> SEQ ID NO 146
<211> LENGTH: 11
<212> TYPE: PRT
<213> ORGANISM: Artificial Sequence
<220> FEATURE:
<223> OTHER INFORMATION: Synthetic

<400> SEQUENCE: 146

Arg Ala Ser Gln Asp Ile Ser Asn Tyr Leu Asn
1               5                   10

<210> SEQ ID NO 147
<211> LENGTH: 14
<212> TYPE: PRT
<213> ORGANISM: Artificial Sequence
<220> FEATURE:
<223> OTHER INFORMATION: Synthetic

<400> SEQUENCE: 147

Trp Val Arg Gln Arg Pro Gly His Gly Leu Glu Trp Val Gly
1               5                   10

<210> SEQ ID NO 148
<211> LENGTH: 15
<212> TYPE: PRT
<213> ORGANISM: Artificial Sequence
<220> FEATURE:
<223> OTHER INFORMATION: Synthetic

<400> SEQUENCE: 148

Trp Tyr Gln Gln Lys Pro Asp Gly Thr Val Lys Leu Leu Ile Tyr
1               5                   10                  15

<210> SEQ ID NO 149
<211> LENGTH: 17
<212> TYPE: PRT
<213> ORGANISM: Artificial Sequence
<220> FEATURE:
<223> OTHER INFORMATION: Synthetic

<400> SEQUENCE: 149

```
Glu Ile Asn Pro Arg Asn Asp Arg Thr Asn Tyr Asn Glu Lys Phe Lys
1               5                   10                  15

Thr

<210> SEQ ID NO 150
<211> LENGTH: 7
<212> TYPE: PRT
<213> ORGANISM: Artificial Sequence
<220> FEATURE:
<223> OTHER INFORMATION: Synthetic

<400> SEQUENCE: 150

Tyr Thr Ser Arg Leu His Ser
1               5

<210> SEQ ID NO 151
<211> LENGTH: 32
<212> TYPE: PRT
<213> ORGANISM: Artificial Sequence
<220> FEATURE:
<223> OTHER INFORMATION: Synthetic

<400> SEQUENCE: 151

Lys Ala Thr Leu Thr Val Asp Arg Ser Ser Thr Ala Tyr Met Gln
1               5                   10                  15

Leu Thr Ser Leu Thr Ser Glu Asp Ser Ala Val Tyr Phe Cys Ala Leu
                20                  25                  30

<210> SEQ ID NO 152
<211> LENGTH: 32
<212> TYPE: PRT
<213> ORGANISM: Artificial Sequence
<220> FEATURE:
<223> OTHER INFORMATION: Synthetic

<400> SEQUENCE: 152

Gly Val Pro Ser Arg Phe Ser Gly Ser Gly Ser Gly Thr Asp Tyr Ser
1               5                   10                  15

Leu Thr Ile Ser Asn Leu Glu Gln Glu Asp Phe Ala Thr Tyr Phe Cys
                20                  25                  30

<210> SEQ ID NO 153
<211> LENGTH: 8
<212> TYPE: PRT
<213> ORGANISM: Artificial Sequence
<220> FEATURE:
<223> OTHER INFORMATION: Synthetic

<400> SEQUENCE: 153

Gly Gly Gly Tyr Ala Met Asp Tyr
1               5

<210> SEQ ID NO 154
<211> LENGTH: 9
<212> TYPE: PRT
<213> ORGANISM: Artificial Sequence
<220> FEATURE:
<223> OTHER INFORMATION: Synthetic

<400> SEQUENCE: 154

Gln Gln Gly Asn Thr Leu Pro Trp Thr
1               5

<210> SEQ ID NO 155
```

```
<211> LENGTH: 11
<212> TYPE: PRT
<213> ORGANISM: Artificial Sequence
<220> FEATURE:
<223> OTHER INFORMATION: Synthetic

<400> SEQUENCE: 155

Trp Gly Gln Gly Thr Ser Val Thr Val Ser Ser
1               5                   10

<210> SEQ ID NO 156
<211> LENGTH: 10
<212> TYPE: PRT
<213> ORGANISM: Artificial Sequence
<220> FEATURE:
<223> OTHER INFORMATION: Synthetic

<400> SEQUENCE: 156

Phe Gly Gly Gly Thr Lys Leu Glu Ile Lys
1               5                   10

<210> SEQ ID NO 157
<211> LENGTH: 117
<212> TYPE: PRT
<213> ORGANISM: Artificial Sequence
<220> FEATURE:
<223> OTHER INFORMATION: Synthetic

<400> SEQUENCE: 157

Glu Val Gln Leu Val Gln Ser Gly Gly Gly Leu Val Gln Ser Gly Gly
1               5                   10                  15

Ser Leu Arg Leu Ser Cys Arg Ala Ser Gly Tyr Thr Phe Thr Arg Tyr
            20                  25                  30

Trp Met Leu Trp Val Arg Gln Arg Pro Gly His Gly Leu Glu Trp Val
        35                  40                  45

Gly Glu Ile Asn Pro Arg Asn Asp Arg Thr Asn Tyr Asn Glu Lys Phe
    50                  55                  60

Lys Thr Arg Phe Thr Ile Ser Val Asp Arg Ser Lys Ser Thr Ala Tyr
65                  70                  75                  80

Leu Gln Met Asp Ser Leu Arg Ala Glu Asp Thr Ala Val Tyr Phe Cys
                85                  90                  95

Ala Leu Gly Gly Gly Tyr Ala Met Asp Tyr Trp Gly Gln Gly Thr Leu
            100                 105                 110

Val Thr Val Ser Ser
        115

<210> SEQ ID NO 158
<211> LENGTH: 107
<212> TYPE: PRT
<213> ORGANISM: Artificial Sequence
<220> FEATURE:
<223> OTHER INFORMATION: Synthetic

<400> SEQUENCE: 158

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60
```

```
Ser Gly Ser Gly Thr Asp Tyr Thr Leu Thr Ile Ser Ser Leu Gln Pro
 65                  70                  75                  80

Glu Asp Phe Ala Thr Tyr Phe Cys Gln Gln Gly Asn Thr Leu Pro Trp
                 85                  90                  95

Thr Phe Gly Gly Gly Thr Lys Leu Glu Ile Lys
            100                 105
```

<210> SEQ ID NO 159
<211> LENGTH: 30
<212> TYPE: PRT
<213> ORGANISM: Artificial Sequence
<220> FEATURE:
<223> OTHER INFORMATION: Syntheti

<400> SEQUENCE: 159

```
Glu Val Gln Leu Val Gln Ser Gly Gly Gly Leu Val Gln Ser Gly Gly
 1               5                   10                  15

Ser Leu Arg Leu Ser Cys Arg Ala Ser Gly Tyr Thr Phe Thr
            20                  25                  30
```

<210> SEQ ID NO 160
<211> LENGTH: 23
<212> TYPE: PRT
<213> ORGANISM: Artificial Sequence
<220> FEATURE:
<223> OTHER INFORMATION: Syntheti

<400> SEQUENCE: 160

```
Asp Ile Gln Met Thr Gln Ser Pro Ser Ser Leu Ser Ala Ser Val Gly
 1               5                   10                  15

Asp Arg Val Thr Ile Thr Cys
            20
```

<210> SEQ ID NO 161
<211> LENGTH: 5
<212> TYPE: PRT
<213> ORGANISM: Artificial Sequence
<220> FEATURE:
<223> OTHER INFORMATION: Synthetic

<400> SEQUENCE: 161

```
Arg Tyr Trp Met Leu
 1               5
```

<210> SEQ ID NO 162
<211> LENGTH: 11
<212> TYPE: PRT
<213> ORGANISM: Artificial Sequence
<220> FEATURE:
<223> OTHER INFORMATION: Synthetic

<400> SEQUENCE: 162

```
Arg Ala Ser Gln Asp Ile Ser Asn Tyr Leu Asn
 1               5                   10
```

<210> SEQ ID NO 163
<211> LENGTH: 14
<212> TYPE: PRT
<213> ORGANISM: Artificial Sequence
<220> FEATURE:
<223> OTHER INFORMATION: Synthetic

<400> SEQUENCE: 163

Trp Val Arg Gln Arg Pro Gly His Gly Leu Glu Trp Val Gly

```
<210> SEQ ID NO 164
<211> LENGTH: 15
<212> TYPE: PRT
<213> ORGANISM: Artificial Sequence
<220> FEATURE:
<223> OTHER INFORMATION: Synthetic

<400> SEQUENCE: 164

Trp Tyr Gln Gln Lys Pro Gly Lys Ala Pro Lys Leu Leu Ile Tyr
1               5                   10                  15

<210> SEQ ID NO 165
<211> LENGTH: 17
<212> TYPE: PRT
<213> ORGANISM: Artificial Sequence
<220> FEATURE:
<223> OTHER INFORMATION: Synthetic

<400> SEQUENCE: 165

Glu Ile Asn Pro Arg Asn Asp Arg Thr Asn Tyr Asn Glu Lys Phe Lys
1               5                   10                  15

Thr

<210> SEQ ID NO 166
<211> LENGTH: 7
<212> TYPE: PRT
<213> ORGANISM: Artificial Sequence
<220> FEATURE:
<223> OTHER INFORMATION: Synthetic

<400> SEQUENCE: 166

Tyr Thr Ser Arg Leu His Ser
1               5

<210> SEQ ID NO 167
<211> LENGTH: 32
<212> TYPE: PRT
<213> ORGANISM: Artificial Sequence
<220> FEATURE:
<223> OTHER INFORMATION: Synthetic

<400> SEQUENCE: 167

Arg Phe Thr Ile Ser Val Asp Arg Ser Lys Ser Thr Ala Tyr Leu Gln
1               5                   10                  15

Met Asp Ser Leu Arg Ala Glu Asp Thr Ala Val Tyr Phe Cys Ala Leu
                20                  25                  30

<210> SEQ ID NO 168
<211> LENGTH: 32
<212> TYPE: PRT
<213> ORGANISM: Artificial Sequence
<220> FEATURE:
<223> OTHER INFORMATION: Synthetic

<400> SEQUENCE: 168

Gly Val Pro Ser Arg Phe Ser Gly Ser Gly Ser Gly Thr Asp Tyr Thr
1               5                   10                  15

Leu Thr Ile Ser Ser Leu Gln Pro Glu Asp Phe Ala Thr Tyr Phe Cys
                20                  25                  30

<210> SEQ ID NO 169
<211> LENGTH: 8
<212> TYPE: PRT
```

<213> ORGANISM: Artificial Sequence
<220> FEATURE:
<223> OTHER INFORMATION: Synthetic

<400> SEQUENCE: 169

Gly Gly Gly Tyr Ala Met Asp Tyr
1               5

<210> SEQ ID NO 170
<211> LENGTH: 9
<212> TYPE: PRT
<213> ORGANISM: Artificial Sequence
<220> FEATURE:
<223> OTHER INFORMATION: Synthetic

<400> SEQUENCE: 170

Gln Gln Gly Asn Thr Leu Pro Trp Thr
1               5

<210> SEQ ID NO 171
<211> LENGTH: 11
<212> TYPE: PRT
<213> ORGANISM: Artificial Sequence
<220> FEATURE:
<223> OTHER INFORMATION: Synthetic

<400> SEQUENCE: 171

Trp Gly Gln Gly Thr Leu Val Thr Val Ser Ser
1               5                   10

<210> SEQ ID NO 172
<211> LENGTH: 10
<212> TYPE: PRT
<213> ORGANISM: Artificial Sequence
<220> FEATURE:
<223> OTHER INFORMATION: Synthetic

<400> SEQUENCE: 172

Phe Gly Gly Gly Thr Lys Leu Glu Ile Lys
1               5                   10

<210> SEQ ID NO 173
<211> LENGTH: 117
<212> TYPE: PRT
<213> ORGANISM: Artificial Sequence
<220> FEATURE:
<223> OTHER INFORMATION: Synthetic

<400> SEQUENCE: 173

Glu Val Gln Leu Val Gln Ser Gly Gly Gly Leu Val Gln Ser Gly Gly
1               5                   10                  15

Ser Leu Arg Leu Ser Cys Arg Ala Ser Gly Tyr Thr Phe Thr Arg Tyr
            20                  25                  30

Trp Met Leu Trp Val Arg Gln Arg Pro Gly Lys Gly Leu Glu Trp Val
        35                  40                  45

Ala Glu Ile Asn Pro Arg Asn Asp Arg Thr Asn Tyr Asn Glu Lys Phe
    50                  55                  60

Lys Thr Arg Phe Thr Ile Ser Val Asp Arg Ser Lys Asn Thr Leu Tyr
65                  70                  75                  80

Leu Gln Met Asp Ser Leu Arg Ala Glu Asp Thr Ala Val Tyr Phe Cys
                85                  90                  95

Ala Leu Gly Gly Gly Tyr Ala Met Asp Tyr Trp Gly Gln Gly Thr Leu
            100                 105                 110

Val Thr Val Ser Ser
        115

<210> SEQ ID NO 174
<211> LENGTH: 107
<212> TYPE: PRT
<213> ORGANISM: Artificial Sequence
<220> FEATURE:
<223> OTHER INFORMATION: Synthetic

<400> SEQUENCE: 174

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Phe Ala Thr Tyr Phe Cys Gln Gln Gly Asn Thr Leu Pro Trp
                85                  90                  95

Thr Phe Gly Gly Gly Thr Lys Leu Glu Ile Lys
            100                 105

<210> SEQ ID NO 175
<211> LENGTH: 30
<212> TYPE: PRT
<213> ORGANISM: Artificial Sequence
<220> FEATURE:
<223> OTHER INFORMATION: Synthetic

<400> SEQUENCE: 175

Glu Val Gln Leu Val Gln Ser Gly Gly Gly Leu Val Gln Ser Gly Gly
1               5                   10                  15

Ser Leu Arg Leu Ser Cys Arg Ala Ser Gly Tyr Thr Phe Thr
            20                  25                  30

<210> SEQ ID NO 176
<211> LENGTH: 23
<212> TYPE: PRT
<213> ORGANISM: Artificial Sequence
<220> FEATURE:
<223> OTHER INFORMATION: Synthetic

<400> SEQUENCE: 176

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 177
<211> LENGTH: 5
<212> TYPE: PRT
<213> ORGANISM: Artificial Sequence
<220> FEATURE:
<223> OTHER INFORMATION: Synthetic

<400> SEQUENCE: 177

Arg Tyr Trp Met Leu
1               5

<210> SEQ ID NO 178
<211> LENGTH: 11
<212> TYPE: PRT
<213> ORGANISM: Artificial Sequence
<220> FEATURE:
<223> OTHER INFORMATION: Synthetic

<400> SEQUENCE: 178

Arg Ala Ser Gln Asp Ile Ser Asn Tyr Leu Asn
1               5                   10

<210> SEQ ID NO 179
<211> LENGTH: 14
<212> TYPE: PRT
<213> ORGANISM: Artificial Sequence
<220> FEATURE:
<223> OTHER INFORMATION: Synthetic

<400> SEQUENCE: 179

Trp Val Arg Gln Arg Pro Gly Lys Gly Leu Glu Trp Val Ala
1               5                   10

<210> SEQ ID NO 180
<211> LENGTH: 15
<212> TYPE: PRT
<213> ORGANISM: Artificial Sequence
<220> FEATURE:
<223> OTHER INFORMATION: Synthetic

<400> SEQUENCE: 180

Trp Tyr Gln Gln Lys Pro Gly Lys Ala Pro Lys Leu Leu Ile Tyr
1               5                   10                  15

<210> SEQ ID NO 181
<211> LENGTH: 17
<212> TYPE: PRT
<213> ORGANISM: Artificial Sequence
<220> FEATURE:
<223> OTHER INFORMATION: Synthetic

<400> SEQUENCE: 181

Glu Ile Asn Pro Arg Asn Asp Arg Thr Asn Tyr Asn Glu Lys Phe Lys
1               5                   10                  15
Thr

<210> SEQ ID NO 182
<211> LENGTH: 7
<212> TYPE: PRT
<213> ORGANISM: Artificial Sequence
<220> FEATURE:
<223> OTHER INFORMATION: Synthetic

<400> SEQUENCE: 182

Tyr Thr Ser Arg Leu His Ser
1               5

<210> SEQ ID NO 183
<211> LENGTH: 32
<212> TYPE: PRT
<213> ORGANISM: Artificial Sequence
<220> FEATURE:
<223> OTHER INFORMATION: Synthetic

<400> SEQUENCE: 183

Arg Phe Thr Ile Ser Val Asp Arg Ser Lys Asn Thr Leu Tyr Leu Gln
1               5                   10                  15

```
Met Asp Ser Leu Arg Ala Glu Asp Thr Ala Val Tyr Phe Cys Ala Leu
            20                  25                  30

<210> SEQ ID NO 184
<211> LENGTH: 32
<212> TYPE: PRT
<213> ORGANISM: Artificial Sequence
<220> FEATURE:
<223> OTHER INFORMATION: Synthetic

<400> SEQUENCE: 184

Gly Val Pro Ser Arg Phe Ser Gly Ser Gly Ser Gly Thr Asp Tyr Thr
1               5                   10                  15

Leu Thr Ile Ser Ser Leu Gln Pro Glu Asp Phe Ala Thr Tyr Phe Cys
            20                  25                  30

<210> SEQ ID NO 185
<211> LENGTH: 8
<212> TYPE: PRT
<213> ORGANISM: Artificial Sequence
<220> FEATURE:
<223> OTHER INFORMATION: Synthetic

<400> SEQUENCE: 185

Gly Gly Gly Tyr Ala Met Asp Tyr
1               5

<210> SEQ ID NO 186
<211> LENGTH: 9
<212> TYPE: PRT
<213> ORGANISM: Artificial Sequence
<220> FEATURE:
<223> OTHER INFORMATION: Synthetic

<400> SEQUENCE: 186

Gln Gln Gly Asn Thr Leu Pro Trp Thr
1               5

<210> SEQ ID NO 187
<211> LENGTH: 11
<212> TYPE: PRT
<213> ORGANISM: Artificial Sequence
<220> FEATURE:
<223> OTHER INFORMATION: Synthetic

<400> SEQUENCE: 187

Trp Gly Gln Gly Thr Leu Val Thr Val Ser Ser
1               5                   10

<210> SEQ ID NO 188
<211> LENGTH: 10
<212> TYPE: PRT
<213> ORGANISM: Artificial Sequence
<220> FEATURE:
<223> OTHER INFORMATION: Synthetic

<400> SEQUENCE: 188

Phe Gly Gly Gly Thr Lys Leu Glu Ile Lys
1               5                   10

<210> SEQ ID NO 189
<211> LENGTH: 15
<212> TYPE: PRT
<213> ORGANISM: Artificial Sequence
<220> FEATURE:
<223> OTHER INFORMATION: Synthetic
```

```
<400> SEQUENCE: 189

Leu Val Ala Leu Tyr Leu Ala Ala Arg Leu Ser Trp Asn Gln Val
1               5                   10                  15

<210> SEQ ID NO 190
<211> LENGTH: 15
<212> TYPE: PRT
<213> ORGANISM: Artificial Sequence
<220> FEATURE:
<223> OTHER INFORMATION: Synthetic

<400> SEQUENCE: 190

Gly Ala Leu Leu Arg Val Tyr Val Pro Arg Ser Ser Leu Pro Gly
1               5                   10                  15

<210> SEQ ID NO 191
<211> LENGTH: 15
<212> TYPE: PRT
<213> ORGANISM: Artificial Sequence
<220> FEATURE:
<223> OTHER INFORMATION: Synthetic

<400> SEQUENCE: 191

Ile Arg Asn Gly Ala Leu Leu Arg Val Tyr Val Pro Arg Ser Ser
1               5                   10                  15

<210> SEQ ID NO 192
<211> LENGTH: 15
<212> TYPE: PRT
<213> ORGANISM: Artificial Sequence
<220> FEATURE:
<223> OTHER INFORMATION: Synthetic

<400> SEQUENCE: 192

Arg Gln Pro Arg Gly Trp Glu Gln Leu Glu Gln Cys Gly Tyr Pro
1               5                   10                  15

<210> SEQ ID NO 193
<211> LENGTH: 15
<212> TYPE: PRT
<213> ORGANISM: Artificial Sequence
<220> FEATURE:
<223> OTHER INFORMATION: Synthetic

<400> SEQUENCE: 193

Leu Pro Leu Glu Thr Phe Thr Arg His Arg Gln Pro Arg Gly Trp
1               5                   10                  15

<210> SEQ ID NO 194
<211> LENGTH: 15
<212> TYPE: PRT
<213> ORGANISM: Artificial Sequence
<220> FEATURE:
<223> OTHER INFORMATION: Synthetic

<400> SEQUENCE: 194

Trp Arg Gly Phe Tyr Ile Ala Gly Asp Pro Ala Leu Ala Tyr Gly
1               5                   10                  15

<210> SEQ ID NO 195
<211> LENGTH: 18
<212> TYPE: PRT
<213> ORGANISM: Artificial Sequence
<220> FEATURE:
<223> OTHER INFORMATION: Synthetic
```

<400> SEQUENCE: 195

Gly Pro Glu Glu Glu Gly Gly Arg Leu Glu Thr Ile Leu Gly Trp Pro
1               5                   10                  15
Leu Ala

<210> SEQ ID NO 196
<211> LENGTH: 15
<212> TYPE: PRT
<213> ORGANISM: Artificial Sequence
<220> FEATURE:
<223> OTHER INFORMATION: Synthetic

<400> SEQUENCE: 196

Thr Val Glu Arg Leu Leu Gln Ala His Arg Gln Leu Glu Glu Arg
1               5                   10                  15

<210> SEQ ID NO 197
<211> LENGTH: 18
<212> TYPE: PRT
<213> ORGANISM: Artificial Sequence
<220> FEATURE:
<223> OTHER INFORMATION: Synthetic

<400> SEQUENCE: 197

Phe Val Gly Tyr His Gly Thr Phe Leu Glu Ala Ala Gln Ser Ile Val
1               5                   10                  15
Phe Gly

<210> SEQ ID NO 198
<211> LENGTH: 15
<212> TYPE: PRT
<213> ORGANISM: Artificial Sequence
<220> FEATURE:
<223> OTHER INFORMATION: Synthetic

<400> SEQUENCE: 198

Ile Arg Asn Gly Ala Leu Leu Arg Val Tyr Val Pro Arg Ser Ser
1               5                   10                  15

<210> SEQ ID NO 199
<211> LENGTH: 15
<212> TYPE: PRT
<213> ORGANISM: Artificial Sequence
<220> FEATURE:
<223> OTHER INFORMATION: Synthetic

<400> SEQUENCE: 199

Ala Arg Asn Gly Ala Leu Leu Arg Val Tyr Val Pro Arg Ser Ser
1               5                   10                  15

<210> SEQ ID NO 200
<211> LENGTH: 15
<212> TYPE: PRT
<213> ORGANISM: Artificial Sequence
<220> FEATURE:
<223> OTHER INFORMATION: Synthetic

<400> SEQUENCE: 200

Ile Ala Asn Gly Ala Leu Leu Arg Val Tyr Val Pro Arg Ser Ser
1               5                   10                  15

<210> SEQ ID NO 201
<211> LENGTH: 15
<212> TYPE: PRT
<213> ORGANISM: Artificial Sequence

```
<220> FEATURE:
<223> OTHER INFORMATION: Synthetic

<400> SEQUENCE: 201

Ile Arg Ala Gly Ala Leu Leu Arg Val Tyr Val Pro Arg Ser Ser
1               5                   10                  15

<210> SEQ ID NO 202
<211> LENGTH: 15
<212> TYPE: PRT
<213> ORGANISM: Artificial Sequence
<220> FEATURE:
<223> OTHER INFORMATION: Synthetic

<400> SEQUENCE: 202

Ile Arg Asn Ala Ala Leu Leu Arg Val Tyr Val Pro Arg Ser Ser
1               5                   10                  15

<210> SEQ ID NO 203
<211> LENGTH: 15
<212> TYPE: PRT
<213> ORGANISM: Artificial Sequence
<220> FEATURE:
<223> OTHER INFORMATION: Synthetic

<400> SEQUENCE: 203

Ile Arg Asn Gly Ala Ala Leu Arg Val Tyr Val Pro Arg Ser Ser
1               5                   10                  15

<210> SEQ ID NO 204
<211> LENGTH: 15
<212> TYPE: PRT
<213> ORGANISM: Artificial Sequence
<220> FEATURE:
<223> OTHER INFORMATION: Synthetic

<400> SEQUENCE: 204

Ile Arg Asn Gly Ala Leu Ala Arg Val Tyr Val Pro Arg Ser Ser
1               5                   10                  15

<210> SEQ ID NO 205
<211> LENGTH: 15
<212> TYPE: PRT
<213> ORGANISM: Artificial Sequence
<220> FEATURE:
<223> OTHER INFORMATION: Synthetic

<400> SEQUENCE: 205

Ile Arg Asn Gly Ala Leu Leu Ala Val Tyr Val Pro Arg Ser Ser
1               5                   10                  15

<210> SEQ ID NO 206
<211> LENGTH: 15
<212> TYPE: PRT
<213> ORGANISM: Artificial Sequence
<220> FEATURE:
<223> OTHER INFORMATION: Synthetic

<400> SEQUENCE: 206

Ile Arg Asn Gly Ala Leu Leu Arg Ala Tyr Val Pro Arg Ser Ser
1               5                   10                  15

<210> SEQ ID NO 207
<211> LENGTH: 15
<212> TYPE: PRT
<213> ORGANISM: Artificial Sequence
<220> FEATURE:
```

```
<223> OTHER INFORMATION: Synthetic

<400> SEQUENCE: 207

Ile Arg Asn Gly Ala Leu Leu Arg Val Ala Val Pro Arg Ser Ser
1               5                   10                  15

<210> SEQ ID NO 208
<211> LENGTH: 15
<212> TYPE: PRT
<213> ORGANISM: Artificial Sequence
<220> FEATURE:
<223> OTHER INFORMATION: Synthetic

<400> SEQUENCE: 208

Ile Arg Asn Gly Ala Leu Leu Arg Val Tyr Ala Pro Arg Ser Ser
1               5                   10                  15

<210> SEQ ID NO 209
<211> LENGTH: 15
<212> TYPE: PRT
<213> ORGANISM: Artificial Sequence
<220> FEATURE:
<223> OTHER INFORMATION: Synthetic

<400> SEQUENCE: 209

Ile Arg Asn Gly Ala Leu Leu Arg Val Tyr Val Ala Arg Ser Ser
1               5                   10                  15

<210> SEQ ID NO 210
<211> LENGTH: 15
<212> TYPE: PRT
<213> ORGANISM: Artificial Sequence
<220> FEATURE:
<223> OTHER INFORMATION: Synthetic

<400> SEQUENCE: 210

Ile Arg Asn Gly Ala Leu Leu Arg Val Tyr Val Pro Ala Ser Ser
1               5                   10                  15

<210> SEQ ID NO 211
<211> LENGTH: 15
<212> TYPE: PRT
<213> ORGANISM: Artificial Sequence
<220> FEATURE:
<223> OTHER INFORMATION: Synthetic

<400> SEQUENCE: 211

Ile Arg Asn Gly Ala Leu Leu Arg Val Tyr Val Pro Arg Ala Ser
1               5                   10                  15

<210> SEQ ID NO 212
<211> LENGTH: 15
<212> TYPE: PRT
<213> ORGANISM: Artificial Sequence
<220> FEATURE:
<223> OTHER INFORMATION: Synthetic

<400> SEQUENCE: 212

Ile Arg Asn Gly Ala Leu Leu Arg Val Tyr Val Pro Arg Ser Ala
1               5                   10                  15

<210> SEQ ID NO 213
<211> LENGTH: 15
<212> TYPE: PRT
<213> ORGANISM: Artificial Sequence
<220> FEATURE:
<223> OTHER INFORMATION: Synthetic
```

<400> SEQUENCE: 213

Gly Ala Leu Leu Arg Val Tyr Val Pro Arg Ser Ser Leu Pro Gly
1               5                   10                  15

<210> SEQ ID NO 214
<211> LENGTH: 15
<212> TYPE: PRT
<213> ORGANISM: Artificial Sequence
<220> FEATURE:
<223> OTHER INFORMATION: Synthetic

<400> SEQUENCE: 214

Ala Ala Leu Leu Arg Val Tyr Val Pro Arg Ser Ser Leu Pro Gly
1               5                   10                  15

<210> SEQ ID NO 215
<211> LENGTH: 15
<212> TYPE: PRT
<213> ORGANISM: Artificial Sequence
<220> FEATURE:
<223> OTHER INFORMATION: Synthetic

<400> SEQUENCE: 215

Gly Gly Leu Leu Arg Val Tyr Val Pro Arg Ser Ser Leu Pro Gly
1               5                   10                  15

<210> SEQ ID NO 216
<211> LENGTH: 15
<212> TYPE: PRT
<213> ORGANISM: Artificial Sequence
<220> FEATURE:
<223> OTHER INFORMATION: Synthetic

<400> SEQUENCE: 216

Gly Ala Ala Leu Arg Val Tyr Val Pro Arg Ser Ser Leu Pro Gly
1               5                   10                  15

<210> SEQ ID NO 217
<211> LENGTH: 15
<212> TYPE: PRT
<213> ORGANISM: Artificial Sequence
<220> FEATURE:
<223> OTHER INFORMATION: Synthetic

<400> SEQUENCE: 217

Gly Ala Leu Ala Arg Val Tyr Val Pro Arg Ser Ser Leu Pro Gly
1               5                   10                  15

<210> SEQ ID NO 218
<211> LENGTH: 15
<212> TYPE: PRT
<213> ORGANISM: Artificial Sequence
<220> FEATURE:
<223> OTHER INFORMATION: Synthetic

<400> SEQUENCE: 218

Gly Ala Leu Leu Ala Val Tyr Val Pro Arg Ser Ser Leu Pro Gly
1               5                   10                  15

<210> SEQ ID NO 219
<211> LENGTH: 15
<212> TYPE: PRT
<213> ORGANISM: Artificial Sequence
<220> FEATURE:
<223> OTHER INFORMATION: Synthetic

```
<400> SEQUENCE: 219

Gly Ala Leu Leu Arg Ala Tyr Val Pro Arg Ser Ser Leu Pro Gly
1               5                   10                  15

<210> SEQ ID NO 220
<211> LENGTH: 15
<212> TYPE: PRT
<213> ORGANISM: Artificial Sequence
<220> FEATURE:
<223> OTHER INFORMATION: Synthetic

<400> SEQUENCE: 220

Gly Ala Leu Leu Arg Val Ala Val Pro Arg Ser Ser Leu Pro Gly
1               5                   10                  15

<210> SEQ ID NO 221
<211> LENGTH: 15
<212> TYPE: PRT
<213> ORGANISM: Artificial Sequence
<220> FEATURE:
<223> OTHER INFORMATION: Synthetic

<400> SEQUENCE: 221

Gly Ala Leu Leu Arg Val Tyr Ala Pro Arg Ser Ser Leu Pro Gly
1               5                   10                  15

<210> SEQ ID NO 222
<211> LENGTH: 15
<212> TYPE: PRT
<213> ORGANISM: Artificial Sequence
<220> FEATURE:
<223> OTHER INFORMATION: Synthetic

<400> SEQUENCE: 222

Gly Ala Leu Leu Arg Val Tyr Val Ala Arg Ser Ser Leu Pro Gly
1               5                   10                  15

<210> SEQ ID NO 223
<211> LENGTH: 15
<212> TYPE: PRT
<213> ORGANISM: Artificial Sequence
<220> FEATURE:
<223> OTHER INFORMATION: Synthetic

<400> SEQUENCE: 223

Gly Ala Leu Leu Arg Val Tyr Val Pro Ala Ser Ser Leu Pro Gly
1               5                   10                  15

<210> SEQ ID NO 224
<211> LENGTH: 15
<212> TYPE: PRT
<213> ORGANISM: Artificial Sequence
<220> FEATURE:
<223> OTHER INFORMATION: Synthetic

<400> SEQUENCE: 224

Gly Ala Leu Leu Arg Val Tyr Val Pro Arg Ala Ser Leu Pro Gly
1               5                   10                  15

<210> SEQ ID NO 225
<211> LENGTH: 12
<212> TYPE: PRT
<213> ORGANISM: Artificial Sequence
<220> FEATURE:
<223> OTHER INFORMATION: Synthetic

<400> SEQUENCE: 225
```

```
Gly Ala Leu Leu Arg Val Tyr Val Pro Arg Ser Ala
1               5                   10
```

<210> SEQ ID NO 226
<211> LENGTH: 15
<212> TYPE: PRT
<213> ORGANISM: Artificial Sequence
<220> FEATURE:
<223> OTHER INFORMATION: Synthetic

<400> SEQUENCE: 226

```
Gly Ala Leu Leu Arg Val Tyr Val Pro Arg Ser Ser Ala Pro Gly
1               5                   10                  15
```

<210> SEQ ID NO 227
<211> LENGTH: 15
<212> TYPE: PRT
<213> ORGANISM: Artificial Sequence
<220> FEATURE:
<223> OTHER INFORMATION: Synthetic

<400> SEQUENCE: 227

```
Gly Ala Leu Leu Arg Val Tyr Val Pro Arg Ser Ser Leu Ala Gly
1               5                   10                  15
```

<210> SEQ ID NO 228
<211> LENGTH: 15
<212> TYPE: PRT
<213> ORGANISM: Artificial Sequence
<220> FEATURE:
<223> OTHER INFORMATION: Synthetic

<400> SEQUENCE: 228

```
Trp Arg Gly Phe Tyr Ile Ala Gly Asp Pro Ala Leu Ala Tyr Gly
1               5                   10                  15
```

<210> SEQ ID NO 229
<211> LENGTH: 15
<212> TYPE: PRT
<213> ORGANISM: Artificial Sequence
<220> FEATURE:
<223> OTHER INFORMATION: Synthetic

<400> SEQUENCE: 229

```
Trp Arg Gly Ala Tyr Ile Ala Gly Asp Pro Ala Leu Ala Tyr Gly
1               5                   10                  15
```

<210> SEQ ID NO 230
<211> LENGTH: 15
<212> TYPE: PRT
<213> ORGANISM: Artificial Sequence
<220> FEATURE:
<223> OTHER INFORMATION: Synthetic

<400> SEQUENCE: 230

```
Trp Arg Gly Phe Ala Ile Ala Gly Asp Pro Ala Leu Ala Tyr Gly
1               5                   10                  15
```

<210> SEQ ID NO 231
<211> LENGTH: 15
<212> TYPE: PRT
<213> ORGANISM: Artificial Sequence
<220> FEATURE:
<223> OTHER INFORMATION: Synthetic

<400> SEQUENCE: 231

```
Trp Arg Gly Phe Tyr Ala Ala Gly Asp Pro Ala Leu Ala Tyr Gly
1               5                   10                  15

<210> SEQ ID NO 232
<211> LENGTH: 15
<212> TYPE: PRT
<213> ORGANISM: Artificial Sequence
<220> FEATURE:
<223> OTHER INFORMATION: Synthetic

<400> SEQUENCE: 232

Trp Arg Gly Phe Tyr Ile Gly Gly Asp Pro Ala Leu Ala Tyr Gly
1               5                   10                  15

<210> SEQ ID NO 233
<211> LENGTH: 15
<212> TYPE: PRT
<213> ORGANISM: Artificial Sequence
<220> FEATURE:
<223> OTHER INFORMATION: Synthetic

<400> SEQUENCE: 233

Trp Arg Gly Phe Tyr Ile Ala Gly Asp Ala Ala Leu Ala Tyr Gly
1               5                   10                  15

<210> SEQ ID NO 234
<211> LENGTH: 15
<212> TYPE: PRT
<213> ORGANISM: Artificial Sequence
<220> FEATURE:
<223> OTHER INFORMATION: Synthetic

<400> SEQUENCE: 234

Trp Arg Gly Phe Tyr Ile Ala Gly Asp Pro Gly Leu Ala Tyr Gly
1               5                   10                  15

<210> SEQ ID NO 235
<211> LENGTH: 15
<212> TYPE: PRT
<213> ORGANISM: Artificial Sequence
<220> FEATURE:
<223> OTHER INFORMATION: Synthetic

<400> SEQUENCE: 235

Trp Arg Gly Phe Tyr Ile Ala Gly Asp Pro Ala Ala Ala Tyr Gly
1               5                   10                  15

<210> SEQ ID NO 236
<211> LENGTH: 15
<212> TYPE: PRT
<213> ORGANISM: Artificial Sequence
<220> FEATURE:
<223> OTHER INFORMATION: Synthetic

<400> SEQUENCE: 236

Trp Arg Gly Phe Tyr Ile Ala Gly Asp Pro Ala Leu Gly Tyr Gly
1               5                   10                  15

<210> SEQ ID NO 237
<211> LENGTH: 15
<212> TYPE: PRT
<213> ORGANISM: Artificial Sequence
<220> FEATURE:
<223> OTHER INFORMATION: Synthetic

<400> SEQUENCE: 237

Trp Arg Gly Phe Tyr Ile Ala Gly Asp Pro Ala Leu Ala Ala Gly
```

<210> SEQ ID NO 238
<211> LENGTH: 18
<212> TYPE: PRT
<213> ORGANISM: Artificial Sequence
<220> FEATURE:
<223> OTHER INFORMATION: Synthetic

<400> SEQUENCE: 238

Gly Pro Glu Glu Glu Gly Gly Arg Leu Glu Thr Ile Leu Gly Trp Pro
1               5                   10                  15

Leu Ala

<210> SEQ ID NO 239
<211> LENGTH: 18
<212> TYPE: PRT
<213> ORGANISM: Artificial Sequence
<220> FEATURE:
<223> OTHER INFORMATION: Synthetic

<400> SEQUENCE: 239

Gly Pro Glu Ala Glu Gly Gly Arg Leu Glu Thr Ile Leu Gly Trp Pro
1               5                   10                  15

Leu Ala

<210> SEQ ID NO 240
<211> LENGTH: 18
<212> TYPE: PRT
<213> ORGANISM: Artificial Sequence
<220> FEATURE:
<223> OTHER INFORMATION: Synthetic

<400> SEQUENCE: 240

Gly Pro Glu Glu Ala Gly Gly Arg Leu Glu Thr Ile Leu Gly Trp Pro
1               5                   10                  15

Leu Ala

<210> SEQ ID NO 241
<211> LENGTH: 18
<212> TYPE: PRT
<213> ORGANISM: Artificial Sequence
<220> FEATURE:
<223> OTHER INFORMATION: Synthetic

<400> SEQUENCE: 241

Gly Pro Glu Glu Glu Gly Gly Ala Leu Glu Thr Ile Leu Gly Trp Pro
1               5                   10                  15

Leu Ala

<210> SEQ ID NO 242
<211> LENGTH: 18
<212> TYPE: PRT
<213> ORGANISM: Artificial Sequence
<220> FEATURE:
<223> OTHER INFORMATION: Synthetic

<400> SEQUENCE: 242

Gly Pro Glu Glu Glu Gly Gly Arg Ala Glu Thr Ile Leu Gly Trp Pro
1               5                   10                  15

Leu Ala

<210> SEQ ID NO 243

<211> LENGTH: 18
<212> TYPE: PRT
<213> ORGANISM: Artificial Sequence
<220> FEATURE:
<223> OTHER INFORMATION: Synthetic

<400> SEQUENCE: 243

Gly Pro Glu Glu Glu Gly Gly Arg Leu Glu Ala Ile Leu Gly Trp Pro
1               5                   10                  15

Leu Ala

<210> SEQ ID NO 244
<211> LENGTH: 18
<212> TYPE: PRT
<213> ORGANISM: Artificial Sequence
<220> FEATURE:
<223> OTHER INFORMATION: Synthetic

<400> SEQUENCE: 244

Gly Pro Glu Glu Glu Gly Gly Arg Leu Glu Thr Ala Leu Gly Trp Pro
1               5                   10                  15

Leu Ala

<210> SEQ ID NO 245
<211> LENGTH: 18
<212> TYPE: PRT
<213> ORGANISM: Artificial Sequence
<220> FEATURE:
<223> OTHER INFORMATION: Synthetic

<400> SEQUENCE: 245

Gly Pro Glu Glu Glu Gly Gly Arg Leu Glu Thr Ile Ala Gly Trp Pro
1               5                   10                  15

Leu Ala

<210> SEQ ID NO 246
<211> LENGTH: 18
<212> TYPE: PRT
<213> ORGANISM: Artificial Sequence
<220> FEATURE:
<223> OTHER INFORMATION: Synthetic

<400> SEQUENCE: 246

Gly Pro Glu Glu Glu Gly Gly Arg Leu Glu Thr Ile Leu Gly Ala Pro
1               5                   10                  15

Leu Ala

<210> SEQ ID NO 247
<211> LENGTH: 18
<212> TYPE: PRT
<213> ORGANISM: Artificial Sequence
<220> FEATURE:
<223> OTHER INFORMATION: Synthetic

<400> SEQUENCE: 247

Gly Pro Glu Glu Glu Gly Gly Arg Leu Glu Thr Ile Leu Gly Trp Ala
1               5                   10                  15

Leu Ala

<210> SEQ ID NO 248
<211> LENGTH: 18
<212> TYPE: PRT
<213> ORGANISM: Artificial Sequence
<220> FEATURE:

<223> OTHER INFORMATION: Synthetic

<400> SEQUENCE: 248

Gly Pro Glu Glu Glu Gly Gly Arg Leu Glu Thr Ile Leu Gly Trp Pro
1               5                   10                  15
Ala Ala

<210> SEQ ID NO 249
<211> LENGTH: 15
<212> TYPE: PRT
<213> ORGANISM: Artificial Sequence
<220> FEATURE:
<223> OTHER INFORMATION: Synthetic

<400> SEQUENCE: 249

Thr Val Glu Arg Leu Leu Gln Ala His Arg Gln Leu Glu Glu Arg
1               5                   10                  15

<210> SEQ ID NO 250
<211> LENGTH: 15
<212> TYPE: PRT
<213> ORGANISM: Artificial Sequence
<220> FEATURE:
<223> OTHER INFORMATION: Synthetic

<400> SEQUENCE: 250

Thr Val Glu Ala Leu Leu Gln Ala His Arg Gln Leu Glu Glu Arg
1               5                   10                  15

<210> SEQ ID NO 251
<211> LENGTH: 15
<212> TYPE: PRT
<213> ORGANISM: Artificial Sequence
<220> FEATURE:
<223> OTHER INFORMATION: Synthetic

<400> SEQUENCE: 251

Thr Val Glu Arg Ala Leu Gln Ala His Arg Gln Leu Glu Glu Arg
1               5                   10                  15

<210> SEQ ID NO 252
<211> LENGTH: 15
<212> TYPE: PRT
<213> ORGANISM: Artificial Sequence
<220> FEATURE:
<223> OTHER INFORMATION: Synthetic

<400> SEQUENCE: 252

Thr Val Glu Arg Leu Ala Gln Ala His Arg Gln Leu Glu Glu Arg
1               5                   10                  15

<210> SEQ ID NO 253
<211> LENGTH: 15
<212> TYPE: PRT
<213> ORGANISM: Artificial Sequence
<220> FEATURE:
<223> OTHER INFORMATION: Synthetic

<400> SEQUENCE: 253

Thr Val Glu Arg Leu Leu Gln Gly His Arg Gln Leu Glu Glu Arg
1               5                   10                  15

<210> SEQ ID NO 254
<211> LENGTH: 15
<212> TYPE: PRT
<213> ORGANISM: Artificial Sequence

```
<220> FEATURE:
<223> OTHER INFORMATION: Synthetic

<400> SEQUENCE: 254

Thr Val Glu Arg Leu Leu Gln Ala His Ala Gln Leu Glu Glu Arg
1               5                   10                  15

<210> SEQ ID NO 255
<211> LENGTH: 15
<212> TYPE: PRT
<213> ORGANISM: Artificial Sequence
<220> FEATURE:
<223> OTHER INFORMATION: Synthetic

<400> SEQUENCE: 255

Thr Val Glu Arg Leu Leu Gln Ala His Arg Gln Ala Glu Glu Arg
1               5                   10                  15

<210> SEQ ID NO 256
<211> LENGTH: 15
<212> TYPE: PRT
<213> ORGANISM: Artificial Sequence
<220> FEATURE:
<223> OTHER INFORMATION: Synthetic

<400> SEQUENCE: 256

Thr Val Glu Arg Leu Leu Gln Ala His Arg Gln Leu Ala Glu Arg
1               5                   10                  15

<210> SEQ ID NO 257
<211> LENGTH: 15
<212> TYPE: PRT
<213> ORGANISM: Artificial Sequence
<220> FEATURE:
<223> OTHER INFORMATION: Synthetic

<400> SEQUENCE: 257

Thr Val Glu Arg Leu Leu Gln Ala His Arg Gln Leu Glu Glu Ala
1               5                   10                  15

<210> SEQ ID NO 258
<211> LENGTH: 18
<212> TYPE: PRT
<213> ORGANISM: Artificial Sequence
<220> FEATURE:
<223> OTHER INFORMATION: Synthetic

<400> SEQUENCE: 258

Phe Val Gly Tyr His Gly Thr Phe Leu Glu Ala Ala Gln Ser Ile Val
1               5                   10                  15

Phe Gly

<210> SEQ ID NO 259
<211> LENGTH: 18
<212> TYPE: PRT
<213> ORGANISM: Artificial Sequence
<220> FEATURE:
<223> OTHER INFORMATION: Synthetic

<400> SEQUENCE: 259

Ala Val Gly Tyr His Gly Thr Phe Leu Glu Ala Ala Gln Ser Ile Val
1               5                   10                  15

Phe Gly

<210> SEQ ID NO 260
```

```
<211> LENGTH: 18
<212> TYPE: PRT
<213> ORGANISM: Artificial Sequence
<220> FEATURE:
<223> OTHER INFORMATION: Synthetic

<400> SEQUENCE: 260

Phe Ala Gly Tyr His Gly Thr Phe Leu Glu Ala Ala Gln Ser Ile Val
1               5                   10                  15

Phe Gly

<210> SEQ ID NO 261
<211> LENGTH: 18
<212> TYPE: PRT
<213> ORGANISM: Artificial Sequence
<220> FEATURE:
<223> OTHER INFORMATION: Synthetic

<400> SEQUENCE: 261

Phe Val Ala Tyr His Gly Thr Phe Leu Glu Ala Ala Gln Ser Ile Val
1               5                   10                  15

Phe Gly

<210> SEQ ID NO 262
<211> LENGTH: 18
<212> TYPE: PRT
<213> ORGANISM: Artificial Sequence
<220> FEATURE:
<223> OTHER INFORMATION: Synthetic

<400> SEQUENCE: 262

Phe Val Gly Ala His Gly Thr Phe Leu Glu Ala Ala Gln Ser Ile Val
1               5                   10                  15

Phe Gly

<210> SEQ ID NO 263
<211> LENGTH: 18
<212> TYPE: PRT
<213> ORGANISM: Artificial Sequence
<220> FEATURE:
<223> OTHER INFORMATION: Synthetic

<400> SEQUENCE: 263

Phe Val Gly Tyr Ala Gly Thr Phe Leu Glu Ala Ala Gln Ser Ile Val
1               5                   10                  15

Phe Gly

<210> SEQ ID NO 264
<211> LENGTH: 18
<212> TYPE: PRT
<213> ORGANISM: Artificial Sequence
<220> FEATURE:
<223> OTHER INFORMATION: Synthetic

<400> SEQUENCE: 264

Phe Val Gly Tyr His Gly Ala Phe Leu Glu Ala Ala Gln Ser Ile Val
1               5                   10                  15

Phe Gly

<210> SEQ ID NO 265
<211> LENGTH: 18
<212> TYPE: PRT
<213> ORGANISM: Artificial Sequence
<220> FEATURE:
```

<223> OTHER INFORMATION: Synthetic

<400> SEQUENCE: 265

Phe Val Gly Tyr His Gly Thr Ala Leu Glu Ala Ala Gln Ser Ile Val
1               5                   10                  15

Phe Gly

<210> SEQ ID NO 266
<211> LENGTH: 18
<212> TYPE: PRT
<213> ORGANISM: Artificial Sequence
<220> FEATURE:
<223> OTHER INFORMATION: Synthetic

<400> SEQUENCE: 266

Phe Val Gly Tyr His Gly Thr Phe Ala Glu Ala Ala Gln Ser Ile Val
1               5                   10                  15

Phe Gly

<210> SEQ ID NO 267
<211> LENGTH: 18
<212> TYPE: PRT
<213> ORGANISM: Artificial Sequence
<220> FEATURE:
<223> OTHER INFORMATION: Synthetic

<400> SEQUENCE: 267

Phe Val Gly Tyr His Gly Thr Phe Leu Glu Gly Ala Gln Ser Ile Val
1               5                   10                  15

Phe Gly

<210> SEQ ID NO 268
<211> LENGTH: 18
<212> TYPE: PRT
<213> ORGANISM: Artificial Sequence
<220> FEATURE:
<223> OTHER INFORMATION: Synthetic

<400> SEQUENCE: 268

Phe Val Gly Tyr His Gly Thr Phe Leu Glu Ala Gly Gln Ser Ile Val
1               5                   10                  15

Phe Gly

<210> SEQ ID NO 269
<211> LENGTH: 18
<212> TYPE: PRT
<213> ORGANISM: Artificial Sequence
<220> FEATURE:
<223> OTHER INFORMATION: Synthetic

<400> SEQUENCE: 269

Phe Val Gly Tyr His Gly Thr Phe Leu Glu Ala Ala Gln Ala Ile Val
1               5                   10                  15

Phe Gly

<210> SEQ ID NO 270
<211> LENGTH: 18
<212> TYPE: PRT
<213> ORGANISM: Artificial Sequence
<220> FEATURE:
<223> OTHER INFORMATION: Synthetic

<400> SEQUENCE: 270

-continued

Phe Val Gly Tyr His Gly Thr Phe Leu Glu Ala Ala Gln Ser Ala Val
1               5                   10                  15

Phe Gly

<210> SEQ ID NO 271
<211> LENGTH: 18
<212> TYPE: PRT
<213> ORGANISM: Artificial Sequence
<220> FEATURE:
<223> OTHER INFORMATION: Synthetic

<400> SEQUENCE: 271

Phe Val Gly Tyr His Gly Thr Phe Leu Glu Ala Ala Gln Ser Ile Ala
1               5                   10                  15

Phe Gly

<210> SEQ ID NO 272
<211> LENGTH: 18
<212> TYPE: PRT
<213> ORGANISM: Artificial Sequence
<220> FEATURE:
<223> OTHER INFORMATION: Synthetic

<400> SEQUENCE: 272

Phe Val Gly Tyr His Gly Thr Phe Leu Glu Ala Ala Gln Ser Ile Val
1               5                   10                  15

Ala Gly

<210> SEQ ID NO 273
<211> LENGTH: 42
<212> TYPE: PRT
<213> ORGANISM: Artificial Sequence
<220> FEATURE:
<223> OTHER INFORMATION: Synthetic

<400> SEQUENCE: 273

Asn Thr Lys Val Asp Lys Lys Val Glu Pro Lys Ser Cys Lys Ala Ser
1               5                   10                  15

Gly Gly Arg His Arg Gln Pro Arg Gly Trp Glu Gln Leu Gly Gly Ser
            20                  25                  30

Pro Thr Gly Ala Glu Phe Leu Gly Asp Gly
        35                  40

<210> SEQ ID NO 274
<211> LENGTH: 9
<212> TYPE: PRT
<213> ORGANISM: Artificial Sequence
<220> FEATURE:
<223> OTHER INFORMATION: Synthetic

<400> SEQUENCE: 274

Trp Glu Gln Leu Gly Gly Ser Pro Thr
1               5

<210> SEQ ID NO 275
<211> LENGTH: 9
<212> TYPE: PRT
<213> ORGANISM: Artificial Sequence
<220> FEATURE:
<223> OTHER INFORMATION: Synthetic

<400> SEQUENCE: 275

Val Glu Pro Lys Ser Cys Lys Ala Ser
1               5

<210> SEQ ID NO 276
<211> LENGTH: 4
<212> TYPE: PRT
<213> ORGANISM: Artificial Sequence
<220> FEATURE:
<223> OTHER INFORMATION: Synthetic

<400> SEQUENCE: 276

Asp Lys Thr His
1

<210> SEQ ID NO 277
<211> LENGTH: 3
<212> TYPE: PRT
<213> ORGANISM: Artificial Sequence
<220> FEATURE:
<223> OTHER INFORMATION: Synthetic

<400> SEQUENCE: 277

Gly Gly Gly
1

<210> SEQ ID NO 278
<211> LENGTH: 49
<212> TYPE: PRT
<213> ORGANISM: Artificial Sequence
<220> FEATURE:
<223> OTHER INFORMATION: Synthetic

<400> SEQUENCE: 278

Asn Thr Lys Val Asp Lys Lys Val Glu Pro Lys Ser Cys Asp Lys Thr
1               5                   10                  15

His Lys Ala Ser Gly Gly Arg His Arg Gln Pro Arg Gly Trp Glu Gln
            20                  25                  30

Leu Gly Gly Gly Gly Gly Ser Pro Thr Gly Ala Glu Phe Leu Gly Asp
        35                  40                  45

Gly

<210> SEQ ID NO 279
<211> LENGTH: 9
<212> TYPE: PRT
<213> ORGANISM: Artificial Sequence
<220> FEATURE:
<223> OTHER INFORMATION: Synthetic

<400> SEQUENCE: 279

Trp Glu Gln Leu Gly Gly Gly Gly Gly
1               5

<210> SEQ ID NO 280
<211> LENGTH: 9
<212> TYPE: PRT
<213> ORGANISM: Artificial Sequence
<220> FEATURE:
<223> OTHER INFORMATION: Synthetic

<400> SEQUENCE: 280

Leu Gly Gly Gly Gly Gly Ser Pro Thr
1               5

<210> SEQ ID NO 281
<211> LENGTH: 19
<212> TYPE: PRT
<213> ORGANISM: Artificial Sequence
<220> FEATURE:
<223> OTHER INFORMATION: Synthetic

<400> SEQUENCE: 281

Lys Ala Ser Gly Gly Arg His Arg Gln Pro Arg Gly Trp Glu Gln Leu
1               5                   10                  15
Gly Gly Ser

<210> SEQ ID NO 282
<211> LENGTH: 9
<212> TYPE: PRT
<213> ORGANISM: Artificial Sequence
<220> FEATURE:
<223> OTHER INFORMATION: Synthetic

<400> SEQUENCE: 282

Asp Lys Thr His Lys Ala Ser Gly Gly
1               5

<210> SEQ ID NO 283
<211> LENGTH: 3
<212> TYPE: PRT
<213> ORGANISM: Artificial Sequence
<220> FEATURE:
<223> OTHER INFORMATION: Synthetic

<400> SEQUENCE: 283

Gly Gly Ser
1

<210> SEQ ID NO 284
<211> LENGTH: 6
<212> TYPE: PRT
<213> ORGANISM: Artificial Sequence
<220> FEATURE:
<223> OTHER INFORMATION: Synthetic

<400> SEQUENCE: 284

Gly Gly Gly Gly Gly Ser
1               5

<210> SEQ ID NO 285
<211> LENGTH: 219
<212> TYPE: PRT
<213> ORGANISM: Artificial Sequence
<220> FEATURE:
<223> OTHER INFORMATION: Synthetic

<400> SEQUENCE: 285

Pro Thr Gly Ala Glu Phe Leu Gly Asp Gly Gly Asp Val Ser Phe Ser
1               5                   10                  15

Thr Arg Gly Thr Gln Asn Trp Thr Val Glu Arg Leu Leu Gln Ala His
            20                  25                  30

Ala Gln Leu Glu Glu Arg Gly Tyr Val Phe Val Gly Tyr His Gly Thr
        35                  40                  45

Ala Leu Glu Ala Ala Gln Ser Ile Val Phe Gly Gly Val Ala Ala Arg
    50                  55                  60

Ser Gln Asp Leu Ala Ala Ile Trp Ala Gly Phe Tyr Ile Ala Gly Asp
65                  70                  75                  80

Pro Ala His Ala Tyr Gly Tyr Ala Gln Asp Gln Glu Pro Asp Ala Ala
                85                  90                  95

Gly Arg Ile Ala Asn Gly Ala Leu Leu Arg Val Tyr Val Pro Ala Ser
            100                 105                 110

Ser Leu Pro Gly Phe Tyr Arg Thr Ser Leu Thr Leu Ala Ala Pro Glu
        115                 120                 125

Ala Ala Gly Glu Val Glu Arg Leu Ile Gly His Pro Leu Pro Leu Ala
        130                 135                 140

Leu Asp Ala Ile Thr Gly Pro Glu Glu Gly Gly Arg Glu Thr
145                 150                 155                 160

Ile Leu Gly Trp Pro Leu Ala Glu Arg Thr Val Val Ile Pro Ser Ala
                165                 170                 175

Ile Pro Thr Asp Pro Arg Asn Val Gly Gly Asp Leu Asp Pro Ser Ser
                180                 185                 190

Ile Pro Asp Lys Glu Gln Ala Ile Ser Ala Leu Pro Asp Tyr Ala Ser
            195                 200                 205

Gln Pro Gly Lys Pro Pro Arg Glu Asp Leu Lys
        210                 215

<210> SEQ ID NO 286
<211> LENGTH: 219
<212> TYPE: PRT
<213> ORGANISM: Artificial Sequence
<220> FEATURE:
<223> OTHER INFORMATION: Synthetic

<400> SEQUENCE: 286

Pro Thr Gly Ala Glu Phe Leu Gly Asp Gly Asp Val Ser Phe Ser
1               5                   10                  15

Thr Arg Gly Thr Gln Asn Trp Thr Val Glu Arg Leu Leu Gln Ala His
            20                  25                  30

Ala Gln Leu Glu Glu Arg Gly Tyr Val Phe Val Gly Tyr His Gly Thr
        35                  40                  45

Ala Leu Glu Ala Ala Gln Ser Ile Val Phe Gly Val Ala Ala Arg
    50                  55                  60

Ser Gln Asp Leu Ala Ala Ile Trp Ala Gly Phe Tyr Ile Ala Gly Asp
65                  70                  75                  80

Pro Ala His Ala Tyr Gly Tyr Ala Gln Asp Gln Glu Pro Asp Ala Ala
                85                  90                  95

Gly Arg Ile Ala Asn Gly Ala Leu Leu Arg Val Tyr Val Pro Ala Ser
            100                 105                 110

Ser Leu Pro Gly Phe Tyr Arg Thr Ser Leu Thr Leu Ala Ala Pro Glu
        115                 120                 125

Ala Ala Gly Glu Val Glu Arg Leu Ile Gly His Pro Leu Pro Leu Ala
        130                 135                 140

Leu Asp Ala Ile Thr Gly Pro Glu Glu Gly Gly Arg Asn Glu Thr
145                 150                 155                 160

Ile Leu Gly Trp Pro Leu Ala Glu Arg Thr Val Val Ile Pro Ser Ala
                165                 170                 175

Ile Pro Thr Asp Pro Arg Asn Val Gly Gly Asp Leu Asp Pro Ser Ser
                180                 185                 190

Ile Pro Asp Lys Glu Gln Ala Ile Ser Ala Leu Pro Asp Tyr Ala Ser
            195                 200                 205

Gln Pro Gly Lys Pro Pro Arg Glu Asp Leu Lys
        210                 215

<210> SEQ ID NO 287
<211> LENGTH: 219
<212> TYPE: PRT
<213> ORGANISM: Artificial Sequence

```
<220> FEATURE:
<223> OTHER INFORMATION: Synthetic

<400> SEQUENCE: 287

Pro Thr Gly Ala Glu Phe Leu Gly Asp Gly Asp Val Ser Phe Ser
1               5                   10                  15

Thr Arg Gly Thr Gln Asn Trp Thr Val Glu Arg Leu Leu Gln Ala His
                20                  25                  30

Ala Gln Leu Glu Glu Arg Gly Tyr Val Phe Val Gly Tyr His Gly Thr
            35                  40                  45

Ala Leu Glu Ala Ala Gln Ser Ile Val Phe Gly Gly Val Arg Ala Arg
        50                  55                  60

Ser Gln Asp Leu Ala Ala Ile Trp Ala Gly Phe Tyr Ile Ala Gly Asp
65                  70                  75                  80

Pro Ala His Ala Tyr Gly Tyr Ala Gln Asp Gln Glu Pro Asp Ala Ala
                85                  90                  95

Gly Arg Ile Ala Asn Gly Ala Leu Leu Arg Val Tyr Val Pro Ala Ser
            100                 105                 110

Ser Leu Pro Gly Phe Tyr Arg Thr Ser Leu Thr Leu Ala Ala Pro Glu
        115                 120                 125

Ala Ala Gly Glu Val Glu Arg Leu Ile Gly His Pro Leu Pro Leu Ala
130                 135                 140

Leu Asp Ala Ile Thr Gly Pro Glu Glu Gly Gly Arg Glu Thr
145                 150                 155                 160

Ile Leu Gly Trp Pro Leu Ala Glu Arg Thr Val Val Ile Pro Ser Ala
                165                 170                 175

Ile Pro Thr Asp Pro Arg Asn Val Gly Gly Asp Leu Asp Pro Ser Ser
            180                 185                 190

Ile Pro Asp Lys Glu Gln Ala Ile Ser Ala Leu Pro Tyr Ala Ser
        195                 200                 205

Gln Pro Gly Lys Pro Pro Arg Glu Asp Leu Lys
    210                 215

<210> SEQ ID NO 288
<211> LENGTH: 219
<212> TYPE: PRT
<213> ORGANISM: Artificial Sequence
<220> FEATURE:
<223> OTHER INFORMATION: Synthetic

<400> SEQUENCE: 288

Pro Thr Gly Ala Glu Phe Leu Gly Asp Gly Asp Val Ser Phe Ser
1               5                   10                  15

Thr Arg Gly Thr Gln Asn Trp Thr Val Glu Arg Leu Leu Gln Ala His
                20                  25                  30

Ala Gln Leu Glu Glu Arg Gly Tyr Val Phe Val Gly Tyr His Gly Thr
            35                  40                  45

Ala Leu Glu Ala Ala Gln Ser Ile Val Phe Gly Gly Val Arg Ala Arg
        50                  55                  60

Ser Gln Asp Leu Ala Ala Ile Trp Ala Gly Phe Tyr Ile Ala Gly Asp
65                  70                  75                  80

Pro Ala His Ala Tyr Gly Tyr Ala Gln Asp Gln Glu Pro Asp Ala Ala
                85                  90                  95

Gly Arg Ile Ala Asn Gly Ala Leu Leu Arg Val Tyr Val Pro Ala Ser
            100                 105                 110

Ser Leu Pro Gly Phe Tyr Arg Thr Ser Leu Thr Leu Ala Ala Pro Glu
```

Ala Ala Gly Glu Val Glu Arg Leu Ile Gly His Pro Leu Pro Leu Ala
130                 135                 140

Leu Asp Ala Ile Thr Gly Pro Glu Glu Gly Gly Arg Asn Glu Thr
145                 150                 155                 160

Ile Leu Gly Trp Pro Leu Ala Glu Arg Thr Val Val Ile Pro Ser Ala
                165                 170                 175

Ile Pro Thr Asp Pro Arg Asn Val Gly Gly Asp Leu Asp Pro Ser Ser
            180                 185                 190

Ile Pro Asp Lys Glu Gln Ala Ile Ser Ala Leu Pro Asp Tyr Ala Ser
            195                 200                 205

Gln Pro Gly Lys Pro Pro Arg Glu Asp Leu Lys
        210                 215

<210> SEQ ID NO 289
<211> LENGTH: 219
<212> TYPE: PRT
<213> ORGANISM: Artificial Sequence
<220> FEATURE:
<223> OTHER INFORMATION: Synthetic

<400> SEQUENCE: 289

Pro Thr Gly Ala Glu Phe Leu Gly Asp Gly Gly Asp Val Ser Phe Ser
1               5                   10                  15

Thr Arg Gly Thr Gln Asn Trp Thr Val Glu Arg Leu Leu Gln Ala His
                20                  25                  30

Ala Gln Leu Glu Glu Arg Gly Tyr Val Phe Val Gly Tyr His Gly Thr
            35                  40                  45

Ala Leu Glu Ala Ala Gln Ser Ile Val Phe Gly Gly Val Arg Ala Arg
        50                  55                  60

Ser Gln Asp Leu Asp Ala Ile Trp Arg Gly Phe Tyr Ile Ala Gly Asp
65                  70                  75                  80

Pro Ala His Ala Tyr Gly Tyr Ala Gln Asp Gln Glu Pro Asp Ala Arg
                85                  90                  95

Gly Arg Ile Ala Asn Gly Ala Leu Leu Arg Val Tyr Val Pro Ala Ser
            100                 105                 110

Ser Leu Pro Gly Phe Tyr Arg Thr Ser Leu Thr Leu Ala Ala Pro Glu
        115                 120                 125

Ala Ala Gly Glu Val Glu Arg Leu Ile Gly His Pro Leu Pro Leu Arg
130                 135                 140

Leu Asp Ala Ile Thr Gly Pro Glu Glu Gly Gly Arg Glu Glu Thr
145                 150                 155                 160

Ile Leu Gly Trp Pro Leu Ala Glu Arg Thr Val Val Ile Pro Ser Ala
                165                 170                 175

Ile Pro Thr Asp Pro Arg Asn Val Gly Gly Asp Leu Asp Pro Ser Ser
            180                 185                 190

Ile Pro Asp Lys Glu Gln Ala Ile Ser Ala Leu Pro Asp Tyr Ala Ser
            195                 200                 205

Gln Pro Gly Lys Pro Pro Arg Glu Asp Leu Lys
        210                 215

<210> SEQ ID NO 290
<211> LENGTH: 113
<212> TYPE: PRT
<213> ORGANISM: Artificial Sequence
<220> FEATURE:
<223> OTHER INFORMATION: Synthetic

<400> SEQUENCE: 290

```
Asp Ile Val Leu Thr Gln Ser Pro Asp Ser Leu Ala Val Ser Leu Gly
1               5                   10                  15
Glu Arg Ala Thr Ile Asn Cys Lys Ser Ser Gln Ser Leu Leu Tyr Ser
            20                  25                  30
Arg Asn Gln Lys Asn Tyr Leu Ala Trp Tyr Gln Gln Lys Pro Gly Gln
        35                  40                  45
Pro Pro Lys Leu Leu Ile Phe Trp Ala Ser Thr Arg Glu Ser Gly Val
    50                  55                  60
Pro Asp Arg Phe Ser Gly Ser Gly Phe Gly Thr Asp Phe Thr Leu Thr
65                  70                  75                  80
Ile Ser Ser Leu Gln Ala Glu Asp Val Ala Val Tyr Tyr Cys Gln Gln
                85                  90                  95
Tyr Phe Ser Tyr Pro Leu Thr Phe Gly Gln Gly Thr Lys Val Glu Ile
            100                 105                 110
Lys
```

<210> SEQ ID NO 291
<211> LENGTH: 473
<212> TYPE: PRT
<213> ORGANISM: Artificial Sequence
<220> FEATURE:
<223> OTHER INFORMATION: Synthetic

<400> SEQUENCE: 291

```
Met Gln Val Gln Leu Val Gln Ser Gly Ala Glu Val Lys Lys Pro Gly
1               5                   10                  15
Ala Ser Val Lys Val Ser Cys Lys Thr Ser Arg Tyr Thr Phe Thr Glu
            20                  25                  30
Tyr Thr Ile His Trp Val Arg Gln Ala Pro Gly Gln Arg Leu Glu Trp
        35                  40                  45
Ile Gly Gly Ile Asn Pro Asn Asn Gly Ile Pro Asn Tyr Asn Gln Lys
    50                  55                  60
Phe Lys Gly Arg Val Thr Ile Thr Val Asp Thr Ser Ala Ser Thr Ala
65                  70                  75                  80
Tyr Met Glu Leu Ser Ser Leu Arg Ser Glu Asp Thr Ala Val Tyr Tyr
                85                  90                  95
Cys Ala Arg Arg Ile Ala Tyr Gly Tyr Asp Glu Gly His Ala Met
            100                 105                 110
Asp Tyr Trp Gly Gln Gly Thr Leu Val Thr Val Ser Ser Ala Ser Thr
        115                 120                 125
Lys Gly Pro Ser Val Phe Pro Leu Ala Pro Ser Ser Lys Ser Thr Ser
    130                 135                 140
Gly Gly Thr Ala Ala Leu Gly Cys Leu Val Lys Asp Tyr Phe Pro Glu
145                 150                 155                 160
Pro Val Thr Val Ser Trp Asn Ser Gly Ala Leu Thr Ser Gly Val His
                165                 170                 175
Thr Phe Pro Ala Val Leu Gln Ser Ser Gly Leu Tyr Ser Leu Ser Ser
            180                 185                 190
Val Val Thr Val Pro Ser Ser Ser Leu Gly Thr Gln Thr Tyr Ile Cys
        195                 200                 205
Asn Val Asn His Lys Pro Ser Asn Thr Lys Val Asp Lys Lys Val Glu
    210                 215                 220
Pro Lys Ser Cys Asp Lys Thr His Lys Ala Ser Gly Gly Arg His Arg
```

```
                 225                 230                 235                 240
        Gln Pro Arg Gly Trp Glu Gln Leu Gly Gly Gly Ser Pro Thr
                        245                 250                 255
        Gly Ala Glu Phe Leu Gly Asp Gly Asp Val Ser Phe Ser Thr Arg
                        260                 265                 270
        Gly Thr Gln Asn Trp Thr Val Glu Arg Leu Leu Gln Ala His Ala Gln
                        275                 280                 285
        Leu Glu Glu Arg Gly Tyr Val Phe Val Gly Tyr His Gly Thr Phe Leu
                        290                 295                 300
        Glu Ala Ala Gln Ser Ile Val Phe Gly Val Ala Ala Arg Ser Gln
        305                 310                 315                 320
        Asp Leu Ala Ala Ile Trp Ala Gly Phe Tyr Ile Ala Gly Asp Pro Ala
                        325                 330                 335
        Leu Ala Tyr Gly Tyr Ala Gln Asp Gln Glu Pro Asp Ala Ala Gly Arg
                        340                 345                 350
        Ile Arg Asn Gly Ala Leu Leu Arg Val Tyr Val Pro Ala Ser Ser Leu
                        355                 360                 365
        Pro Gly Phe Tyr Arg Thr Ser Leu Thr Leu Ala Ala Pro Glu Ala Ala
                        370                 375                 380
        Gly Glu Val Glu Arg Leu Ile Gly His Pro Leu Pro Leu Ala Leu Asp
        385                 390                 395                 400
        Ala Ile Thr Gly Pro Glu Glu Glu Gly Gly Arg Leu Glu Thr Ile Leu
                        405                 410                 415
        Gly Trp Pro Leu Ala Glu Arg Thr Val Val Ile Pro Ser Ala Ile Pro
                        420                 425                 430
        Thr Asp Pro Arg Asn Val Gly Gly Asp Leu Asp Pro Ser Ser Ile Pro
                        435                 440                 445
        Asp Lys Glu Gln Ala Ile Ser Ala Leu Pro Asp Tyr Ala Ser Gln Pro
                        450                 455                 460
        Gly Lys Pro Pro Arg Glu Asp Leu Lys
        465                 470

<210> SEQ ID NO 292
<211> LENGTH: 473
<212> TYPE: PRT
<213> ORGANISM: Artificial Sequence
<220> FEATURE:
<223> OTHER INFORMATION: Synthetic

<400> SEQUENCE: 292

Met Gln Val Gln Leu Val Gln Ser Gly Ala Glu Val Lys Lys Pro Gly
        1               5                   10                  15
        Ala Ser Val Lys Val Ser Cys Lys Thr Ser Arg Tyr Thr Phe Thr Glu
                        20                  25                  30
        Tyr Thr Ile His Trp Val Arg Gln Ala Pro Gly Gln Arg Leu Glu Trp
                        35                  40                  45
        Ile Gly Gly Ile Asn Pro Asn Asn Gly Ile Pro Asn Tyr Asn Gln Lys
                        50                  55                  60
        Phe Lys Gly Arg Val Thr Ile Thr Val Asp Thr Ser Ala Ser Thr Ala
        65                  70                  75                  80
        Tyr Met Glu Leu Ser Ser Leu Arg Ser Glu Asp Thr Ala Val Tyr Tyr
                        85                  90                  95
        Cys Ala Arg Arg Arg Ile Ala Tyr Gly Tyr Asp Glu Gly His Ala Met
                        100                 105                 110
        Asp Tyr Trp Gly Gln Gly Thr Leu Val Thr Val Ser Ser Ala Ser Thr
```

```
                115                 120                 125
Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Lys Ala Ser Gly Gly Arg His Arg
225                 230                 235                 240

Gln Pro Arg Gly Trp Glu Gln Leu Gly Gly Gly Gly Ser Pro Thr
                245                 250                 255

Gly Ala Glu Phe Leu Gly Asp Gly Gly Asp Val Ser Phe Ser Thr Arg
            260                 265                 270

Gly Thr Gln Asn Trp Thr Val Glu Arg Leu Leu Gln Ala His Ala Gln
        275                 280                 285

Leu Glu Glu Arg Gly Tyr Val Phe Val Gly Tyr His Gly Thr Ala Leu
    290                 295                 300

Glu Ala Ala Gln Ser Ile Val Phe Gly Gly Val Arg Ala Arg Ser Gln
305                 310                 315                 320

Asp Leu Asp Ala Ile Trp Arg Gly Phe Tyr Ile Ala Gly Asp Pro Ala
                325                 330                 335

His Ala Tyr Gly Tyr Ala Gln Asp Gln Glu Pro Asp Ala Arg Gly Arg
            340                 345                 350

Ile Ala Asn Gly Ala Leu Leu Arg Val Tyr Val Pro Ala Ser Ser Leu
        355                 360                 365

Pro Gly Phe Tyr Arg Thr Ser Leu Thr Leu Ala Ala Pro Glu Ala Ala
    370                 375                 380

Gly Glu Val Glu Arg Leu Ile Gly His Pro Leu Pro Leu Arg Leu Asp
385                 390                 395                 400

Ala Ile Thr Gly Pro Glu Glu Gly Gly Arg Glu Glu Thr Ile Leu
                405                 410                 415

Gly Trp Pro Leu Ala Glu Arg Thr Val Val Ile Pro Ser Ala Ile Pro
            420                 425                 430

Thr Asp Pro Arg Asn Val Gly Gly Asp Leu Asp Pro Ser Ile Pro
        435                 440                 445

Asp Lys Glu Gln Ala Ile Ser Ala Leu Pro Asp Tyr Ala Ser Gln Pro
    450                 455                 460

Gly Lys Pro Pro Arg Glu Asp Leu Lys
465                 470

<210> SEQ ID NO 293
<211> LENGTH: 221
<212> TYPE: PRT
<213> ORGANISM: Artificial Sequence
<220> FEATURE:
<223> OTHER INFORMATION: Synthetic

<400> SEQUENCE: 293

Met Asp Ile Val Met Thr Gln Ser Pro Asp Ser Leu Ala Val Ser Leu
```

```
            1               5                  10                 15
          Gly Glu Arg Ala Thr Ile Asn Cys Lys Ser Ser Gln Ser Leu Leu Tyr
                          20                  25                 30

Ser Arg Asn Gln Lys Asn Tyr Leu Ala Trp Tyr Gln Gln Lys Pro Gly
                          35                  40              45

Gln Pro Pro Lys Leu Leu Ile Phe Trp Ala Ser Thr Arg Glu Ser Gly
                     50                  55                  60

Val Pro Asp Arg Phe Ser Gly Ser Gly Phe Gly Thr Asp Phe Thr Leu
           65                  70                  75                  80

Thr Ile Ser Ser Leu Gln Ala Glu Asp Val Ala Val Tyr Tyr Cys Gln
                              85                  90                  95

Gln Tyr Phe Ser Tyr Pro Leu Thr Phe Gly Gln Gly Thr Lys Val Glu
                              100                 105                 110

Ile Lys Arg Thr Val Ala Ala Pro Ser Val Phe Ile Phe Pro Pro Ser
                              115                 120                 125

Asp Glu Gln Leu Lys Ser Gly Thr Ala Ser Val Val Cys Leu Leu Asn
           130                 135                 140

Asn Phe Tyr Pro Arg Glu Ala Lys Val Gln Trp Lys Val Asp Asn Ala
          145                 150                 155                 160

Leu Gln Ser Gly Asn Ser Gln Glu Ser Val Thr Glu Gln Asp Ser Lys
                              165                 170                 175

Asp Ser Thr Tyr Ser Leu Ser Ser Thr Leu Thr Leu Ser Lys Ala Asp
                          180                 185                 190

Tyr Glu Lys His Lys Val Tyr Ala Cys Glu Val Thr His Gln Gly Leu
                          195                 200                 205

Ser Ser Pro Val Thr Lys Ser Phe Asn Arg Gly Glu Cys
                      210                 215                 220

<210> SEQ ID NO 294
<211> LENGTH: 221
<212> TYPE: PRT
<213> ORGANISM: Artificial Sequence
<220> FEATURE:
<223> OTHER INFORMATION: Synthetic

<400> SEQUENCE: 294

Met Asp Ile Val Leu Thr Gln Ser Pro Asp Ser Leu Ala Val Ser Leu
           1               5                   10                  15

Gly Glu Arg Ala Thr Ile Asn Cys Lys Ser Ser Gln Ser Leu Leu Tyr
                          20                  25                  30

Ser Arg Asn Gln Lys Asn Tyr Leu Ala Trp Tyr Gln Gln Lys Pro Gly
                          35                  40                  45

Gln Pro Pro Lys Leu Leu Ile Phe Trp Ala Ser Thr Arg Glu Ser Gly
                      50                  55                  60

Val Pro Asp Arg Phe Ser Gly Ser Gly Phe Gly Thr Asp Phe Thr Leu
           65                  70                  75                  80

Thr Ile Ser Ser Leu Gln Ala Glu Asp Val Ala Val Tyr Tyr Cys Gln
                              85                  90                  95

Gln Tyr Phe Ser Tyr Pro Leu Thr Phe Gly Gln Gly Thr Lys Val Glu
                              100                 105                 110

Ile Lys Arg Thr Val Ala Ala Pro Ser Val Phe Ile Phe Pro Pro Ser
                              115                 120                 125

Asp Glu Gln Leu Lys Ser Gly Thr Ala Ser Val Val Cys Leu Leu Asn
           130                 135                 140

Asn Phe Tyr Pro Arg Glu Ala Lys Val Gln Trp Lys Val Asp Asn Ala
```

```
                    145                 150                 155                 160
Leu Gln Ser Gly Asn Ser Gln Glu Ser Val Thr Glu Gln Asp Ser Lys
                165                 170                 175
Asp Ser Thr Tyr Ser Leu Ser Ser Thr Leu Thr Leu Ser Lys Ala Asp
                180                 185                 190
Tyr Glu Lys His Lys Val Tyr Ala Cys Glu Val Thr His Gln Gly Leu
                195                 200                 205
Ser Ser Pro Val Thr Lys Ser Phe Asn Arg Gly Glu Cys
                210                 215                 220

<210> SEQ ID NO 295
<211> LENGTH: 464
<212> TYPE: PRT
<213> ORGANISM: Artificial Sequence
<220> FEATURE:
<223> OTHER INFORMATION: Synthetic

<400> SEQUENCE: 295

Met Asp Val Lys Leu Val Glu Ser Gly Gly Gly Leu Val Lys Leu Gly
1               5                   10                  15
Gly Ser Leu Lys Leu Ser Cys Ala Ala Ser Gly Phe Thr Phe Ser Asn
                20                  25                  30
Tyr Tyr Met Ser Trp Val Arg Gln Thr Pro Glu Lys Arg Leu Glu Leu
            35                  40                  45
Val Ala Ala Ile Asn Ser Asp Gly Gly Ile Thr Tyr Tyr Leu Asp Thr
        50                  55                  60
Val Lys Gly Arg Phe Thr Ile Ser Arg Asp Asn Ala Lys Asn Thr Leu
65                  70                  75                  80
Tyr Leu Gln Met Ser Ser Leu Lys Ser Glu Asp Thr Ala Leu Phe Tyr
                85                  90                  95
Cys Ala Arg His Arg Ser Gly Tyr Phe Ser Met Asp Tyr Trp Gly Gln
                100                 105                 110
Gly Thr Ser Val Thr Val Ser Ser Ala Ser Thr Lys Gly Pro Ser Val
            115                 120                 125
Phe Pro Leu Ala Pro Ser Ser Lys Ser Thr Ser Gly Gly Thr Ala Ala
        130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
        195                 200                 205
Pro Ser Asn Thr Lys Val Asp Lys Lys Val Glu Pro Lys Ser Cys Lys
        210                 215                 220
Ala Ser Gly Gly Arg His Arg Gln Pro Arg Gly Trp Glu Gln Leu Gly
225                 230                 235                 240
Gly Gly Gly Gly Ser Pro Thr Gly Ala Glu Phe Leu Gly Asp Gly Gly
                245                 250                 255
Asp Val Ser Phe Ser Thr Arg Gly Thr Gln Asn Trp Thr Val Glu Arg
            260                 265                 270
Leu Leu Gln Ala His Ala Gln Leu Glu Glu Arg Gly Tyr Val Phe Val
        275                 280                 285
Gly Tyr His Gly Thr Phe Leu Glu Ala Ala Gln Ser Ile Val Phe Gly
```

```
                290                 295                 300
Gly Val Ala Ala Arg Ser Gln Asp Leu Ala Ala Ile Trp Ala Gly Phe
305                 310                 315                 320

Tyr Ile Ala Gly Asp Pro Ala Leu Ala Tyr Gly Tyr Ala Gln Asp Gln
                325                 330                 335

Glu Pro Asp Ala Ala Gly Arg Ile Arg Asn Gly Ala Leu Leu Arg Val
            340                 345                 350

Tyr Val Pro Ala Ser Ser Leu Pro Gly Phe Tyr Arg Thr Ser Leu Thr
            355                 360                 365

Leu Ala Ala Pro Glu Ala Ala Gly Glu Val Glu Arg Leu Ile Gly His
        370                 375                 380

Pro Leu Pro Leu Ala Leu Asp Ala Ile Thr Gly Pro Glu Glu Glu Gly
385                 390                 395                 400

Gly Arg Leu Glu Thr Ile Leu Gly Trp Pro Leu Ala Glu Arg Thr Val
                405                 410                 415

Val Ile Pro Ser Ala Ile Pro Thr Asp Pro Arg Asn Val Gly Gly Asp
            420                 425                 430

Leu Asp Pro Ser Ser Ile Pro Asp Lys Glu Gln Ala Ile Ser Ala Leu
        435                 440                 445

Pro Asp Tyr Ala Ser Gln Pro Gly Lys Pro Pro Arg Glu Asp Leu Lys
    450                 455                 460

<210> SEQ ID NO 296
<211> LENGTH: 464
<212> TYPE: PRT
<213> ORGANISM: Artificial Sequence
<220> FEATURE:
<223> OTHER INFORMATION: Synthetic

<400> SEQUENCE: 296

Met Asp Val Lys Leu Val Glu Ser Gly Gly Gly Leu Val Lys Leu Gly
1               5                   10                  15

Gly Ser Leu Lys Leu Ser Cys Ala Ala Ser Gly Phe Thr Phe Ser Asn
            20                  25                  30

Tyr Tyr Met Ser Trp Val Arg Gln Thr Pro Glu Lys Arg Leu Glu Leu
        35                  40                  45

Val Ala Ala Ile Asn Ser Asp Gly Gly Ile Thr Tyr Tyr Leu Asp Thr
    50                  55                  60

Val Lys Gly Arg Phe Thr Ile Ser Arg Asp Asn Ala Lys Asn Thr Leu
65                  70                  75                  80

Tyr Leu Gln Met Ser Ser Leu Lys Ser Glu Asp Thr Ala Leu Phe Tyr
                85                  90                  95

Cys Ala Arg His Arg Ser Gly Tyr Phe Ser Met Asp Tyr Trp Gly Gln
            100                 105                 110

Gly Thr Ser Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
```

```
                195                 200                 205

Pro Ser Asn Thr Lys Val Asp Lys Val Glu Pro Lys Ser Cys Lys
    210                 215                 220

Ala Ser Gly Gly Arg His Arg Gln Pro Arg Gly Trp Glu Gln Leu Gly
225                 230                 235                 240

Gly Gly Gly Gly Ser Pro Thr Gly Ala Glu Phe Leu Gly Asp Gly Gly
                245                 250                 255

Asp Val Ser Phe Ser Thr Arg Gly Thr Gln Asn Trp Thr Val Glu Arg
                260                 265                 270

Leu Leu Gln Ala His Ala Gln Leu Glu Glu Arg Gly Tyr Val Phe Val
            275                 280                 285

Gly Tyr His Gly Thr Ala Leu Glu Ala Ala Gln Ser Ile Val Phe Gly
            290                 295                 300

Gly Val Arg Ala Arg Ser Gln Asp Leu Asp Ala Ile Trp Arg Gly Phe
305                 310                 315                 320

Tyr Ile Ala Gly Asp Pro Ala His Ala Tyr Gly Tyr Ala Gln Asp Gln
                325                 330                 335

Glu Pro Asp Ala Arg Gly Arg Ile Ala Asn Gly Ala Leu Leu Arg Val
                340                 345                 350

Tyr Val Pro Ala Ser Ser Leu Pro Gly Phe Tyr Arg Thr Ser Leu Thr
            355                 360                 365

Leu Ala Ala Pro Glu Ala Ala Gly Glu Val Glu Arg Leu Ile Gly His
            370                 375                 380

Pro Leu Pro Leu Arg Leu Asp Ala Ile Thr Gly Pro Glu Glu Glu Gly
385                 390                 395                 400

Gly Arg Glu Glu Thr Ile Leu Gly Trp Pro Leu Ala Glu Arg Thr Val
                405                 410                 415

Val Ile Pro Ser Ala Ile Pro Thr Asp Pro Arg Asn Val Gly Gly Asp
                420                 425                 430

Leu Asp Pro Ser Ser Ile Pro Asp Lys Glu Gln Ala Ile Ser Ala Leu
            435                 440                 445

Pro Asp Tyr Ala Ser Gln Pro Gly Lys Pro Pro Arg Glu Asp Leu Lys
450                 455                 460

<210> SEQ ID NO 297
<211> LENGTH: 215
<212> TYPE: PRT
<213> ORGANISM: Artificial Sequence
<220> FEATURE:
<223> OTHER INFORMATION: Synthetic

<400> SEQUENCE: 297

Met Asp Ile Val Met Thr Gln Ser Gln Arg Phe Met Ser Thr Thr Val
1               5                   10                  15

Gly Asp Arg Val Ser Ile Thr Cys Lys Ala Ser Gln Asn Val Val Ser
                20                  25                  30

Ala Val Ala Trp Tyr Gln Gln Lys Pro Gly Ser Pro Lys Leu Leu
            35                  40                  45

Ile Tyr Ser Ala Ser Asn Arg Tyr Thr Gly Val Pro Asp Arg Phe Thr
        50                  55                  60

Gly Ser Gly Ser Gly Thr Asp Phe Thr Leu Thr Ile Ser Asn Met Gln
65                  70                  75                  80

Ser Glu Asp Leu Ala Asp Phe Phe Cys Gln Gln Tyr Ser Asn Tyr Pro
                85                  90                  95

Trp Thr Phe Gly Gly Gly Thr Lys Leu Glu Ile Lys Arg Thr Val Ala
```

-continued

```
        100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```